United States Patent
Schlessinger et al.

(10) Patent No.: US 9,273,134 B2
(45) Date of Patent: Mar. 1, 2016

(54) INHIBITORS OF RECEPTOR TYROSINE KINASES AND METHODS OF USE THEREOF

(75) Inventors: Joseph Schlessinger, Woodbridge, CT (US); Irit Lax, Woodbridge, CT (US); Satoru Yuzawa, Fukuoka (JP); Yarden Opatowsky, Raa'nana (IL); Yan Yang, Hamden, CT (US)

(73) Assignee: Yale University, New Haven, CT (US)

( * ) Notice: Subject to any disclaimer, the term of this patent is extended or adjusted under 35 U.S.C. 154(b) by 1352 days.

(21) Appl. No.: 12/602,235

(22) PCT Filed: Jun. 5, 2008

(86) PCT No.: PCT/US2008/007104
§ 371 (c)(1),
(2), (4) Date: Aug. 29, 2011

(87) PCT Pub. No.: WO2008/153926
PCT Pub. Date: Dec. 18, 2008

(65) Prior Publication Data
US 2011/0311538 A1    Dec. 22, 2011

Related U.S. Application Data

(60) Provisional application No. 60/933,238, filed on Jun. 5, 2007, provisional application No. 61/009,482, filed on Dec. 28, 2007, provisional application No. 61/070,506, filed on Mar. 24, 2008.

(51) Int. Cl.
*C07K 16/28* (2006.01)
*A61K 39/00* (2006.01)

(52) U.S. Cl.
CPC ......... *C07K 16/2803* (2013.01); *C07K 2316/96* (2013.01); *C07K 2317/34* (2013.01); *C07K 2317/77* (2013.01)

(58) Field of Classification Search
CPC ........... C07K 16/2863; C07K 2316/96; C07K 2317/77; C07K 2317/34
See application file for complete search history.

(56) References Cited

U.S. PATENT DOCUMENTS

| | | |
|---|---|---|
| 5,268,358 A | 12/1993 | Fretto |
| 5,686,572 A | 11/1997 | Wolf et al. |
| 5,817,310 A | 10/1998 | Ramakrishnan et al. |
| 5,882,644 A | 3/1999 | Chang et al. |
| 5,891,652 A | 4/1999 | Wolf et al. |
| 2005/0004066 A1 | 1/2005 | Rockwell |
| 2005/0261175 A1 | 11/2005 | Zsebo |
| 2007/0225202 A1 | 9/2007 | Andreev et al. |
| 2009/0192133 A1 | 7/2009 | Horton |
| 2012/0328599 A1 | 12/2012 | Bae et al. |
| 2013/0071397 A1 | 3/2013 | Schlessinger et al. |

FOREIGN PATENT DOCUMENTS

| | | |
|---|---|---|
| EP | 0548867 A2 | 7/1995 |
| EP | 0586445 B1 | 9/2004 |
| EP | 0889125 B1 | 8/2008 |
| WO | WO93/10805 A1 | 6/1993 |
| WO | WO9841090 A1 | 9/1998 |
| WO | WO03/091437 | 11/2003 |
| WO | WO 2007/004060 | 1/2007 |
| WO | WO2008153926 | 12/2008 |
| WO | WO2015/050959 | 4/2015 |

OTHER PUBLICATIONS

Lemmon, M.A., et al., Kit receptor dimerization is driven by bivalent binding of stem cell factor, J. Biol. Chem. 272(10):6311-6317 (1997).
Philo, J.S., et al., Human stem cell factor dimer forms a complex with two molecules of the extracellular domain of its receptor, Kit, J. Biol. Chem. 271(12):3895-3902 (1996).
Baselga et al., Critical update and emerging trends in epidermal growth factor receptor targeting in cancer, J. Clin. Oncol., 23(11):2445-2459 (2005).
http://en.wikipedia.org/wiki/Humanized_antibody.
Micke et al., Characterization of c-kit expression in small cell lung cancer: prognostic and therapeutic implications, Clin. Cancer Res., 9:188-194 (2003).
Roskoski, The ErbB/HER receptor protein-tyrosine kinases and cancer, Biochem. and Biophys. Res. Com., 319(1):1-11 (2004).
Shen W., Protein Kinase Inhibitors for Treatment of Cancer, Trends in Biopharmaceutical Industry, 1(3):15-19 (2005).
Adams et al., Humanization of a Recombinant Monoclonal Antibody to produce a therapeutic HER dimerization inhibitor, Pertuzumab, Cancer Immunol. Immunother., 55:717-727 (2005).
Bae D., et al., Arginine-rich anti-vascular endothelial growth factor peptides inhibit tumor growth and metastasis by blocking angiogenesis, J. Biol. Chem., 275(18):13588-13596 (2000).
Bae et al., Asymmetric receptor contact is required for tyrosine autophosphorylation of fibroblast growth factor receptor in living cells, PNAS, 107(7):2866-2867 (2010).
Berezov A. et al., Disabling receptor ensembles with rationally designed interface peptidomimetics, J. Biol. Chem., 277(31):28330-28339 (2002).
Binetruy-Tournaire R., et al., Identification of a peptide blocking vascular endothelial growth factor (VEGF)-mediated angiogenesis, EMBO J., 19(7):1525-1533 (2000).
Chen et al., A crystallographic snapshot of tyrosine trans-phosphorylation in action, PNAS 105(50):19660-19665 (2008).
Hubbard S.R., et al., EGF receptor inhibition: attacks on multiple fronts, Cancer Cell, 7(4):287-288 (2005).

(Continued)

*Primary Examiner* — Ruixiang Li
(74) *Attorney, Agent, or Firm* — McCarter & English, LLP; Maria Laccotripe Zacharakis; Marcie B. Clarke

(57) ABSTRACT

The present invention provides moieties that bind to an Ig-like domain, e.g., D4 or D5, of a human receptor tyrosine kinase, e.g., the human Kit RTK or the PDGFR RTK, or the D7 domain of a type V receptor tyrosine kinase wherein the moieties lock the ectodomain of the receptor tyrosine kinase in an inactive state thereby antagonizing the activity of the receptor tyrosine kinase.

9 Claims, 53 Drawing Sheets

(56) References Cited

OTHER PUBLICATIONS

Ruch et al., Structure of a VEGF-VEGF receptor complex determined by electron microscopy. Nat. Struct. Mol. Biol., 2007, 14(3):249-250.
Tamura Teruko et al., Tyrosine kinases as targets for anti-inflammatory therapy, Anti-Inflammatory & Anti-Allergy Agents in Medicinal Chemistry, 6(1):47-60 (2007).
Yang et al., Direct contacts between extracellular membrane-proximal domains are required for VEGF receptor activation and cell signaling, Proc. Nat'l. Acad. Sci. USA, 2010, 107(5):1906-1911.
Yoo Seung-ah et al., Arginine-rich anti-vascular endothelial growth factor (anti_VEGF) hexapeptide inhibits collagen-induced arthritis and VEGF-stimulated productions of TNF-alpha and IL-6 by human monocytes, J. Immunol., 174(9):5846-5855 (2005).
Yuzawa et al., Structural basis for activation of the receptor tyrosine kinase KIT by stem cell factor, Cell, 2007, 13(2):323-334.
Zhang et al., An allosteric mechanism for activation of kinase domain of epidermal growth factor receptor, Cell, 125:1137-1149 (2006).
Zhang et al., Targeting cancer with small molecule kinase inhibitors, Nature Reviews Cancer, 9:28-39 (2009).
Lennartsson, J., et al., Synergistic growth of stem cell factor and granulocyte macrophage colony-stimulating factor involves kinase-dependent and -independent contributions from c-kit, J. Biol. Chem. 279(43):44544-44553 (2004).
Wiesmann, C., et al., Ligand-binding sites in Ig-like domains of receptor tyrosine kinases, J. Molec. Med. 78(5):247-260 (2000).
Zhang, Z., et al., Crystal structure of human stem cell factor: Implication for stem cell factor receptor dimerization and activation, PNAS, 97(14):7732-7737.
Amir-Zaltsman et al., "Inhibitors of protein tyrosine phosphorylation: preliminary assessment of activity by time-resolved fluorescence" Luminescence, 15:377-380, 2000.
Atienza et al., "Label-free and real-time cell-based kinase assay for screening selective and potent receptor tyrosine kinase . . . " J. Biomolec. Screening, 11(6):634-643, 2006.
Besmer et al., "A new acute transforming feline retrovirus and relationship of its oncogene v-kit . . . " Nature, 320:415-421, 1986.
Blechman et al., "The Fourth Immunoglobulin Domain of the Stem Cell Factor Receptor Couples Ligand Binding to Signal Transduction," Cell, 80:103-113, 1995.
Blechman et al., "Soluble c-Kit proteins and antireceptor monoclonal antibodies confine the binding site of Stem Cell Factor" J. Biol. Chem., 268(6):4399-4406, 1993.
Carlberg and Rohrschneider, "The effect of activating mutations on dimerization, tyrosine phosphorylation and internalization of the macrophage colony stimulating factor receptor", Molec. Biol. Cell., 5(1):81-95, 1994.
GenBank Accession No. P05532, May 1, 2007.
GenBank Accession No. AAC50968, Feb. 6, 1997.
Granier et al., "Structure and Conformational Changes in the C-terminal domain of the beta2-Adrenoceptor" J. Biol. Chem., 282(18):13895-13905, 2007.
Jiang et al., "Structure of the Active Core of Human Stem Cell Factor and Analysis of Binding to its Receptor Kit", The EMBO Journal, 19(13):3192-3203, 2000.
Lev et al., "A Recombinant Ectodomain of the Receptor for the Stem Cell Factor (SCF) Retains Ligand Induced Dimerization . . . " J. Biol. Chem., 267(15):10866-10873, 1992.
Liu et al., "Structural basis for stem cell factor:KIT signaling and activation of class III receptor tyrosine kinases", The EMBO Journal, 26(3):891-901, 2007.
Lokker et al., "Functional importance of platelet-derived growth factor (PDGF) receptor extracellular immunoglobulin-like domains" J. Biol. Chem., 272(52):33037-33044, 1997.
Matthews et al., "A receptor tyrosine kinase cDNA isolated from a population of enriched primitive hematopoietic cells . . . " Proc. Natl. Acad. Sci. USA, 88:9026-9030, 1991.
Nakayama and Parandoosh, "An immunoassay for assessment of receptor tyrosine kinase autophosphorylation" J. Immunol. Methods, 225:67-74, 1999.
Omura et al., "Immunoglobulin-like domain 4-mediated receptor-receptor interactions contribute to platelet-derived growth factor . . . " J. Biol. Chem., 272(19):12676-12682, 1997.
Sakai et al., "Pertuzumab, a novel HER dimerization inhibitor, inhibits the growth of human lung cancer cells mediated by the HER3 signaling pathway", Cancer Sci., 98(9):1498-1503, 2007.
Sequence Alignment, GenBank Accession No. P05532.7 (KIT_MOUSE) May 1, 2007 and GenBank Accession No. AAC50968.1 (KIT protein, *Homo sapiens*) Feb. 6, 1997.
Shulman et al., "An antibody reactive with domain 4 of the platelet-derived growth factor beta receptor allows BB binding while inhibiting proliferation by impairing receptor dimerization" J. Biol. Chem., 272(28):17400-17404, 1997.
Tan et al., "Monitoring interactions between receptor tyrosine kinases and their downstream effector proteins in living cells . . . " Molec. Pharmacology, 72:1440-1446, 2008.
Tao et al., "Kinase Insert Domain Receptor (KDR) Extracellular Immunoglobulin-like Domains 4-7 Contain Structural Features . . . " J. Biol. Chem., 276(24):21916-21923, 2001.
Yarden et al., "Human proto-oncogene c-kit: a new cell surface receptor tyrosine kinase for an unidentified ligand" EMBO J., 6(11):3341-3351, 1987.
International Search Report from WO08/153926.
Written Opinion from WO08/153926.
International Preliminary Report on Patentability from WO08/153926.
Protein Knowledgebase (UniProtKB), P10721 (KIT_HUMAN) [online] [retrieved on May 19, 2014]. Retrieved from the Internet http://www.uniprot.org/uniprot/P10721#ref 1, pp. 1-25.
Japanese Society for Bioinformatics (ed.), Encyoclopedia of Bioinformatics, Jul. 1, 2006, pp. 462-463.
Kazuhisa Sugimura, Human-Anitbody Engineering (Review), Bioventure, Jul. 1, 2002, vol. 2, No. 4, pp. 30-33.
U.S. Appl. No. 61/960,939, Joseph Schlessinger et al.
U.S. Appl. No. 61/977,888, Joseph Schlessinger et al.

```
KIT
human             NIRYVSELHLTRLKGTEGGTYTFLVSNSD  398
mouse             NIRYVNQLRLTRLKGTEGGTYTFLVSNSD  401
chicken           NNSYTSELHLTRLKGTEGGIYTFFVSNSD  384
xenopus           NNRYVSELHLIRLKGTEKGIYTFYSSNSD  390
salamander        NSRYISELHLIRLKGAERGIYTFHVDNSD  394
zebrafish type A  N-SYTSELKLVRLKVSESGIYTFSCLNRD  392
zebrafish type B  Y-RYISELRLVRVHGSEGGIYTFSANHKY  456

CSF1R
human             TYRHTFTLSLPRLKPSEAGRYSFLARNPG  387
mouse             IYRYTFKLFLNRVKASEAGQYFLMAQNKA  385
torafugu type A   --IYHARLQLKRNNAQEQGQYTFYAKSNL  397
torafugu type B   --RSEASLLLRRVRQEDHGSYTFHFSNSF  462

PDGFRα
human             EIRYRSKLKLIRAKEEDSGGHYTIVAQNE  399
mouse             ETRYQSKLKLIRAKEEDSGGHYTIIVQNE  399

PDGFRβ
human             ETRYVSELTLVRVKVAEAGHYTMRAFHED  402
mouse             ETRYVSELILVRVKVSEAGYYTMRAFHED  401

VEGFR (7th domain)
human type 1      LGPGSSTLFIERVTEEDEGVYHCKATNQK  737
human type 2      LKDGNRNLTIRRVRKEDEGLYTCQACSVL  743
human type 3      LADSNQKLSIQRVREEDAGRYLCSVCNAK  754
```

*Fig. 6B*

*Oncogenic D5 repeat of A502/Y503

```
                            SEQUENCE LISTING

<160> NUMBER OF SEQ ID NOS: 159

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu, Arg or Gln
<220> FEATURE:
<221> NAME/KEY: MOD_RES
<222> LOCATION: (5)..(5)
<223> OTHER INFORMATION: Arg or Thr
<220> FEATURE:
<221> NAME/KEY: MOD_RES
<222> LOCATION: (6)..(6)
<223> OTHER INFORMATION: Glu or Lys
<220> FEATURE:
<221> NAME/KEY: MOD_RES
<222> LOCATION: (9)..(9)
<223> OTHER INFORMATION: Glu or Ala

<400> SEQUENCE: 1

Ile Xaa Arg Val Xaa Xaa Glu Asp Xaa Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Val Val Asp Lys Gly Phe Ile Asn
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Tyr Leu
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Leu Glu Val Val
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Tyr Leu Thr Leu Glu Val Val
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Lys Gly Arg Glu Gly
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Val Ser Val Ser Lys Ala Ser Tyr Leu Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Thr Thr Thr Leu Glu Val Val Asp
1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Glu Gly Glu Glu Phe Thr Val Thr Cys Thr Ile
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Thr Thr Leu Glu
1

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Thr Leu Glu Ala Ser Tyr Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ser Glu Asn Glu Ser Asn Ile Arg
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Glu Ser Asn
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Lys Ala Ser Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Glu Ser Asn Ser Lys Ala Ser Tyr
1               5

<210> SEQ ID NO 16
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 16

Ala Phe Pro Lys Pro
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Ser Asp Val
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Phe Pro Lys Pro Asn Ser Asp Val
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Ser Asn Ile Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Phe Pro Lys Pro Glu Ser Asn Ile Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Lys Trp Glu Asp Tyr Pro Lys Ser Glu
1               5                   10
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Arg Tyr Val Ser Glu Leu His Leu
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Thr Arg Leu Lys Gly Thr Glu Gly Gly Thr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Glu Asn Val Asp Leu Ile Val Glu Tyr Glu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Asn Arg Thr Phe Thr Asp Lys Trp Glu
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Trp Glu Asp Tyr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Val Ser Glu Leu His
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Trp Glu Asp Tyr Val Ser Glu Leu His
1               5                   10

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Lys Trp Glu
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu His Leu Thr
1

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Lys Trp Glu Leu His Leu Thr
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Leu Thr Arg Leu Lys Gly Thr Glu Gly Gly Thr
1               5                   10

<210> SEQ ID NO 33
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Asn Arg Thr Phe Thr Asp Lys Trp Glu His Leu Thr Arg Leu Lys
1               5                   10                  15

Gly Thr Glu Gly Gly Thr
            20

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Phe Val Asn Asp Gly Glu Asn Val Asp
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Asn Thr Lys Pro Glu Ile
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Tyr Asn Asp Val Gly Lys Thr
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Asn Thr Lys Pro Glu Ile Ala Tyr Asn Asp Val Gly Lys Thr
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Ala Gly Phe Pro Glu Pro Thr
1               5

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Asn Thr Lys Pro Glu Ile Ala Gly Phe Pro Glu Pro Thr
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Gly Lys Leu Val
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Asn Thr Lys Pro Glu Ile Phe Gly Lys Leu Val
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Asn Asp Gly Glu Asn
1               5

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Asn Thr Lys Pro Glu Ile Val Asn Asp Gly Glu Asn
1               5                   10

<210> SEQ ID NO 44
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 44

Arg Leu Lys Gly Thr Glu Gly
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Asn Thr Lys Pro Glu Ile Arg Leu Lys Gly Thr Glu Gly
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Pro Pro Phe Gly Lys Leu
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Thr Glu Gly Gly
1               5

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Pro Phe Gly Lys Leu Gly Thr Glu Gly Gly
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Asn Asp Gly Glu
1               5
```

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Asn Asp Val Gly Lys
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Asn Asp Gly Glu Tyr Asn Asp Val Gly Lys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Lys Pro Glu Ile Leu Thr Tyr Asp Arg Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Leu Val Asn Gly Met Leu Gln Cys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Lys Thr Ser Ala Tyr Phe Asn Phe Ala Phe Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Pro Gly Thr Glu Gln Arg Cys Ser Ala Ser
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ser Ala Ser Val Leu Pro Val Asp Val Gln
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ser Ser Ala Phe Lys His Asn Gly Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Thr Val Glu Cys Lys Ala Tyr Asn Asp
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Asn Ser Ser Gly Pro Pro Phe Gly Lys Leu
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe Ala Phe Lys Gly Asn Asn Lys Glu Gln Ile
1               5                   10

<210> SEQ ID NO 61
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Lys Pro Glu Ile Leu
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Gly Lys Thr Ser Ala
1               5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Lys Pro Glu Ile Leu Val Gly Lys Thr Ser Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Leu Thr Tyr Asp Arg Leu
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Tyr Phe Asn Phe Ala
1               5

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Leu Thr Tyr Asp Arg Leu Ala Tyr Phe Asn Phe Ala
```

```
1               5               10

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys His Asn Gly Thr
1               5

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Tyr Phe Asn Phe Ala Lys His Asn Gly Thr
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Thr Glu Gln Arg Cys
1               5

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Tyr Phe Asn Phe Ala Gly Thr Glu Gln Arg Cys
1               5                   10

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr His Arg Lys Val Arg Pro Val Ser Ser His Gly Asp Phe Asn Tyr
1               5                   10                  15

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Phe Val Ser
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ala Phe Thr
1

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ala Phe Lys Glu Ser Asn Ile Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Leu Glu Val Phe Glu Phe Ile
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Val Lys Gly Phe Pro Asp
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ala Ser Asn Glu Ser
1               5

<210> SEQ ID NO 78
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Ala Glu Ser
1

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Thr Thr Lys Glu Lys
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Phe Gly Lys Leu
1               5

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Val Asn Asn
1

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Asn Thr Lys Val
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Gly Gly Val Lys
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Gly Val Val
1

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Gly His Arg Lys Val Arg Pro Phe Val Ser Ser Ser His Gly Asp
1               5                   10                  15

Phe Asn Tyr

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ser Tyr Leu Phe Pro Lys Asn Glu Ser Asn Ile Tyr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Gly Tyr Val Thr Phe Phe Gly Lys
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Thr Lys Glu Ala Gly Lys
1               5

<210> SEQ ID NO 89
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 89

Tyr Phe Lys Leu Thr Arg Leu Glu Thr
1               5

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Gly Phe Pro
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Tyr Phe Pro
1

<210> SEQ ID NO 92
<211> LENGTH: 976
<212> TYPE: PRT
<213> ORGANISM: Homo sapiens

<400> SEQUENCE: 92

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175
```

```
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
        195                 200                 205
Lys Ala Val Pro Val Val Ser Val Ser Lys Ala Ser Tyr Leu Leu Arg
    210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
        515                 520                 525
Phe Val Ile Val Ala Gly Met Met Cys Ile Ile Val Met Ile Leu Thr
    530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
Lys Thr Leu Gly Ala Gly Ala Phe Gly Lys Val Val Glu Ala Thr Ala
```

```
                    595                 600                 605
Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
            930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 93
<211> LENGTH: 972
<212> TYPE: PRT
<213> ORGANISM: Homo sapiens

<400> SEQUENCE: 93
```

Met Arg Gly Ala Arg Gly Ala Trp Asp Phe Leu Cys Val Leu Leu Leu
1               5                   10                  15
Leu Leu Arg Val Gln Thr Gly Ser Ser Gln Pro Ser Val Ser Pro Gly
            20                  25                  30
Glu Pro Ser Pro Ser Ile His Pro Gly Lys Ser Asp Leu Ile Val
        35                  40                  45
Arg Val Gly Asp Glu Ile Arg Leu Leu Cys Thr Asp Pro Gly Phe Val
    50                  55                  60
Lys Trp Thr Phe Glu Ile Leu Asp Glu Thr Asn Glu Asn Lys Gln Asn
65                  70                  75                  80
Glu Trp Ile Thr Glu Lys Ala Glu Ala Thr Asn Thr Gly Lys Tyr Thr
                85                  90                  95
Cys Thr Asn Lys His Gly Leu Ser Asn Ser Ile Tyr Val Phe Val Arg
            100                 105                 110
Asp Pro Ala Lys Leu Phe Leu Val Asp Arg Ser Leu Tyr Gly Lys Glu
        115                 120                 125
Asp Asn Asp Thr Leu Val Arg Cys Pro Leu Thr Asp Pro Glu Val Thr
    130                 135                 140
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                165                 170                 175
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
        195                 200                 205
Lys Ala Val Pro Val Val Ser Val Ser Lys Ala Ser Tyr Leu Leu Arg
    210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly

-continued

```
            420                 425                 430
Phe Pro Glu Pro Thr Ile Asp Trp Tyr Phe Cys Pro Gly Thr Glu Gln
            435                 440                 445
Arg Cys Ser Ala Ser Val Leu Pro Val Asp Val Gln Thr Leu Asn Ser
450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
            485                 490                 495
Val Gly Lys Thr Ser Ala Tyr Phe Asn Phe Ala Phe Lys Glu Gln Ile
            500                 505                 510
His Pro His Thr Leu Phe Thr Pro Leu Leu Ile Gly Phe Val Ile Val
            515                 520                 525
Ala Gly Met Met Cys Ile Ile Val Met Ile Leu Thr Tyr Lys Tyr Leu
            530                 535                 540
Gln Lys Pro Met Tyr Glu Val Gln Trp Lys Val Val Glu Glu Ile Asn
545                 550                 555                 560
Gly Asn Asn Tyr Val Tyr Ile Asp Pro Thr Gln Leu Pro Tyr Asp His
                565                 570                 575
Lys Trp Glu Phe Pro Arg Asn Arg Leu Ser Phe Gly Lys Thr Leu Gly
            580                 585                 590
Ala Gly Ala Phe Gly Lys Val Val Glu Ala Thr Ala Tyr Gly Leu Ile
            595                 600                 605
Lys Ser Asp Ala Ala Met Thr Val Ala Val Lys Met Leu Lys Pro Ser
            610                 615                 620
Ala His Leu Thr Glu Arg Glu Ala Leu Met Ser Glu Leu Lys Val Leu
625                 630                 635                 640
Ser Tyr Leu Gly Asn His Met Asn Ile Val Asn Leu Leu Gly Ala Cys
                645                 650                 655
Thr Ile Gly Gly Pro Thr Leu Val Ile Thr Glu Tyr Cys Cys Tyr Gly
                660                 665                 670
Asp Leu Leu Asn Phe Leu Arg Arg Lys Arg Asp Ser Phe Ile Cys Ser
            675                 680                 685
Lys Gln Glu Asp His Ala Glu Ala Leu Tyr Lys Asn Leu Leu His
            690                 695                 700
Ser Lys Glu Ser Ser Cys Ser Asp Ser Thr Asn Glu Tyr Met Asp Met
705                 710                 715                 720
Lys Pro Gly Val Ser Tyr Val Val Pro Thr Lys Ala Asp Lys Arg Arg
            725                 730                 735
Ser Val Arg Ile Gly Ser Tyr Ile Glu Arg Asp Val Thr Pro Ala Ile
            740                 745                 750
Met Glu Asp Asp Glu Leu Ala Leu Asp Leu Glu Asp Leu Leu Ser Phe
            755                 760                 765
Ser Tyr Gln Val Ala Lys Gly Met Ala Phe Leu Ala Ser Lys Asn Cys
            770                 775                 780
Ile His Arg Asp Leu Ala Ala Arg Asn Ile Leu Leu Thr His Gly Arg
785                 790                 795                 800
Ile Thr Lys Ile Cys Asp Phe Gly Leu Ala Arg Asp Ile Lys Asn Asp
            805                 810                 815
Ser Asn Tyr Val Val Lys Gly Asn Ala Arg Leu Pro Val Lys Trp Met
            820                 825                 830
Ala Pro Glu Ser Ile Phe Asn Cys Val Tyr Thr Phe Glu Ser Asp Val
            835                 840                 845
```

```
Trp Ser Tyr Gly Ile Phe Leu Trp Glu Leu Phe Ser Leu Gly Ser Ser
            850                 855                 860
Pro Tyr Pro Gly Met Pro Val Asp Ser Lys Phe Tyr Lys Met Ile Lys
865                 870                 875                 880
Glu Gly Phe Arg Met Leu Ser Pro Glu His Ala Pro Ala Glu Met Tyr
                885                 890                 895
Asp Ile Met Lys Thr Cys Trp Asp Ala Asp Pro Leu Lys Arg Pro Thr
            900                 905                 910
Phe Lys Gln Ile Val Gln Leu Ile Glu Lys Gln Ile Ser Glu Ser Thr
            915                 920                 925
Asn His Ile Tyr Ser Asn Leu Ala Asn Cys Ser Pro Asn Arg Gln Lys
            930                 935                 940
Pro Val Val Asp His Ser Val Arg Ile Asn Ser Val Gly Ser Thr Ala
945                 950                 955                 960
Ser Ser Ser Gln Pro Leu Leu Val His Asp Asp Val
                965                 970
```

<210> SEQ ID NO 94
<211> LENGTH: 29
<212> TYPE: PRT
<213> ORGANISM: Homo sapiens

<400> SEQUENCE: 94

```
Asn Ile Arg Tyr Val Ser Glu Leu His Leu Thr Arg Leu Lys Gly Thr
1               5                   10                  15
Glu Gly Gly Thr Tyr Thr Phe Leu Val Ser Asn Ser Asp
            20                  25
```

<210> SEQ ID NO 95
<211> LENGTH: 29
<212> TYPE: PRT
<213> ORGANISM: Mus musculus

<400> SEQUENCE: 95

```
Asn Ile Arg Tyr Val Asn Gln Leu Arg Leu Thr Arg Leu Lys Gly Thr
1               5                   10                  15
Glu Gly Gly Thr Tyr Thr Phe Leu Val Ser Asn Ser Asp
            20                  25
```

<210> SEQ ID NO 96
<211> LENGTH: 29
<212> TYPE: PRT
<213> ORGANISM: Gallus gallus

<400> SEQUENCE: 96

```
Asn Asn Ser Tyr Thr Ser Glu Leu His Leu Thr Arg Leu Lys Gly Thr
1               5                   10                  15
Glu Gly Gly Ile Tyr Thr Phe Phe Val Ser Asn Ser Asp
            20                  25
```

<210> SEQ ID NO 97
<211> LENGTH: 29
<212> TYPE: PRT
<213> ORGANISM: Xenopus laevis

<400> SEQUENCE: 97

```
Asn Asn Arg Tyr Val Ser Glu Leu His Leu Ile Arg Leu Lys Gly Thr
1               5                   10                  15
Glu Lys Gly Ile Tyr Thr Phe Tyr Ser Ser Asn Ser Asp
```

```
                        20                  25

<210> SEQ ID NO 98
<211> LENGTH: 29
<212> TYPE: PRT
<213> ORGANISM: Ambystoma mexicanum

<400> SEQUENCE: 98

Asn Ser Arg Tyr Ile Ser Glu Leu His Leu Ile Arg Leu Lys Gly Ala
1               5                   10                  15

Glu Arg Gly Ile Tyr Thr Phe His Val Asp Asn Ser Asp
            20                  25

<210> SEQ ID NO 99
<211> LENGTH: 28
<212> TYPE: PRT
<213> ORGANISM: Danio rerio

<400> SEQUENCE: 99

Asn Ser Tyr Thr Ser Glu Leu Lys Leu Val Arg Leu Lys Val Ser Glu
1               5                   10                  15

Ser Gly Ile Tyr Thr Phe Ser Cys Leu Asn Arg Asp
            20                  25

<210> SEQ ID NO 100
<211> LENGTH: 28
<212> TYPE: PRT
<213> ORGANISM: Danio rerio

<400> SEQUENCE: 100

Tyr Arg Tyr Ile Ser Glu Leu Arg Leu Val Arg Val His Gly Ser Glu
1               5                   10                  15

Gly Gly Ile Tyr Thr Phe Ser Ala Asn His Lys Tyr
            20                  25

<210> SEQ ID NO 101
<211> LENGTH: 29
<212> TYPE: PRT
<213> ORGANISM: Homo sapiens

<400> SEQUENCE: 101

Thr Tyr Arg His Thr Phe Thr Leu Ser Leu Pro Arg Leu Lys Pro Ser
1               5                   10                  15

Glu Ala Gly Arg Tyr Ser Phe Leu Ala Arg Asn Pro Gly
            20                  25

<210> SEQ ID NO 102
<211> LENGTH: 29
<212> TYPE: PRT
<213> ORGANISM: Mus musculus

<400> SEQUENCE: 102

Ile Tyr Arg Tyr Thr Phe Lys Leu Phe Leu Asn Arg Val Lys Ala Ser
1               5                   10                  15

Glu Ala Gly Gln Tyr Phe Leu Asn Ala Gln Asn Lys Ala
            20                  25

<210> SEQ ID NO 103
<211> LENGTH: 27
<212> TYPE: PRT
<213> ORGANISM: Takifugu rubripes

<400> SEQUENCE: 103
```

```
Ile Tyr His Ala Arg Leu Gln Leu Lys Arg Asn Asn Ala Gln Glu Gln
1               5                   10                  15

Gly Gln Tyr Thr Phe Tyr Ala Lys Ser Asn Leu
            20                  25
```

<210> SEQ ID NO 104
<211> LENGTH: 27
<212> TYPE: PRT
<213> ORGANISM: Takifugu rubripes

<400> SEQUENCE: 104

```
Arg Ser Glu Ala Ser Leu Leu Leu Arg Arg Val Arg Gln Glu Asp His
1               5                   10                  15

Gly Ser Tyr Thr Phe His Phe Ser Asn Ser Phe
            20                  25
```

<210> SEQ ID NO 105
<211> LENGTH: 29
<212> TYPE: PRT
<213> ORGANISM: Homo sapiens

<400> SEQUENCE: 105

```
Glu Ile Arg Tyr Arg Ser Lys Leu Lys Leu Ile Arg Ala Lys Glu Glu
1               5                   10                  15

Asp Ser Gly Gly His Tyr Thr Ile Val Ala Gln Asn Glu
            20                  25
```

<210> SEQ ID NO 106
<211> LENGTH: 29
<212> TYPE: PRT
<213> ORGANISM: Mus musculus

<400> SEQUENCE: 106

```
Glu Thr Arg Tyr Gln Ser Lys Leu Lys Leu Ile Arg Ala Lys Glu Glu
1               5                   10                  15

Asp Ser Gly Gly His Tyr Thr Ile Ile Val Gln Asn Glu
            20                  25
```

<210> SEQ ID NO 107
<211> LENGTH: 29
<212> TYPE: PRT
<213> ORGANISM: Homo sapiens

<400> SEQUENCE: 107

```
Glu Thr Arg Tyr Val Ser Glu Leu Thr Leu Val Arg Val Lys Val Ala
1               5                   10                  15

Glu Ala Gly His Tyr Thr Met Arg Ala Phe His Glu Asp
            20                  25
```

<210> SEQ ID NO 108
<211> LENGTH: 29
<212> TYPE: PRT
<213> ORGANISM: Mus musculus

<400> SEQUENCE: 108

```
Glu Thr Arg Tyr Val Ser Glu Leu Ile Leu Val Arg Val Lys Val Ser
1               5                   10                  15

Glu Ala Gly Tyr Tyr Thr Met Arg Ala Phe His Glu Asp
            20                  25
```

<210> SEQ ID NO 109

```
<211> LENGTH: 29
<212> TYPE: PRT
<213> ORGANISM: Homo sapiens

<400> SEQUENCE: 109

Leu Gly Pro Gly Ser Ser Thr Leu Phe Ile Glu Arg Val Thr Glu Glu
1               5                   10                  15

Asp Glu Gly Val Tyr His Cys Lys Ala Thr Asn Gln Lys
            20                  25

<210> SEQ ID NO 110
<211> LENGTH: 29
<212> TYPE: PRT
<213> ORGANISM: Homo sapiens

<400> SEQUENCE: 110

Leu Lys Asp Gly Asn Arg Asn Leu Thr Ile Arg Arg Val Arg Lys Glu
1               5                   10                  15

Asp Glu Gly Leu Tyr Thr Cys Gln Ala Cys Ser Val Leu
            20                  25

<210> SEQ ID NO 111
<211> LENGTH: 29
<212> TYPE: PRT
<213> ORGANISM: Homo sapiens

<400> SEQUENCE: 111

Leu Ala Asp Ser Asn Gln Lys Leu Ser Ile Gln Arg Val Arg Glu Glu
1               5                   10                  15

Asp Ala Gly Arg Tyr Leu Cys Ser Val Cys Asn Ala Lys
            20                  25

<210> SEQ ID NO 112
<211> LENGTH: 79
<212> TYPE: PRT
<213> ORGANISM: Homo sapiens

<400> SEQUENCE: 112

Pro Ser Pro Ser Ile His Pro Gly Lys Ser Asp Leu Ile Val Arg
1               5                   10                  15

Val Gly Asp Glu Ile Arg Leu Leu Cys Thr Asp Pro Gly Phe Val Lys
            20                  25                  30

Trp Thr Phe Glu Ile Leu Asp Glu Thr Asn Glu Asn Lys Gln Asn Glu
        35                  40                  45

Trp Ile Thr Glu Lys Ala Glu Ala Thr Asn Thr Gly Lys Tyr Thr Cys
    50                  55                  60

Thr Asn Lys His Gly Leu Ser Asn Ser Ile Tyr Val Phe Val Arg
65                  70                  75

<210> SEQ ID NO 113
<211> LENGTH: 80
<212> TYPE: PRT
<213> ORGANISM: Mus musculus

<400> SEQUENCE: 113

Pro Ser Pro Pro Ser Ile His Pro Ala Gln Ser Glu Leu Ile Val Glu
1               5                   10                  15

Ala Gly Asp Thr Leu Ser Leu Thr Cys Ile Asp Pro Asp Phe Val Arg
            20                  25                  30

Trp Thr Phe Lys Thr Tyr Phe Asn Glu Met Val Glu Asn Lys Lys Asn
        35                  40                  45
```

```
Glu Trp Ile Gln Glu Lys Ala Glu Ala Thr Arg Thr Gly Thr Tyr Thr
        50                  55                  60
Cys Ser Asn Ser Asn Gly Leu Thr Ser Ser Ile Tyr Val Phe Val Arg
 65                  70                  75                  80

<210> SEQ ID NO 114
<211> LENGTH: 85
<212> TYPE: PRT
<213> ORGANISM: Homo sapiens

<400> SEQUENCE: 114

Gln Gly Ile Pro Val Ile Glu Pro Ser Val Pro Glu Leu Val Val Lys
  1               5                  10                  15
Pro Gly Ala Thr Val Thr Leu Arg Cys Val Gly Asn Gly Ser Val Glu
                 20                  25                  30
Trp Asp Gly Pro Pro Ser Pro His Trp Thr Leu Tyr Ser Asp Gly Ser
             35                  40                  45
Ser Ser Ile Leu Ser Thr Asn Asn Ala Thr Phe Gln Asn Thr Gly Thr
        50                  55                  60
Tyr Arg Cys Thr Glu Pro Gly Asp Pro Leu Gly Gly Ser Ala Ala Ile
 65                  70                  75                  80
His Leu Tyr Val Lys
                 85

<210> SEQ ID NO 115
<211> LENGTH: 97
<212> TYPE: PRT
<213> ORGANISM: Homo sapiens

<400> SEQUENCE: 115

Ser Leu Pro Ser Ile Leu Pro Asn Glu Asn Glu Lys Val Val Gln Leu
  1               5                  10                  15
Asn Ser Ser Phe Ser Leu Arg Cys Phe Gly Glu Ser Glu Val Ser Trp
                 20                  25                  30
Gln Tyr Pro Met Ser Glu Glu Glu Ser Ser Asp Val Glu Ile Arg Asn
             35                  40                  45
Glu Glu Asn Asn Ser Gly Leu Phe Val Thr Val Leu Glu Val Ser Ser
        50                  55                  60
Ala Ser Ala Ala His Thr Gly Leu Tyr Thr Cys Tyr Tyr Asn His Thr
 65                  70                  75                  80
Gln Thr Glu Glu Asn Glu Leu Glu Gly Arg His Ile Tyr Ile Tyr Val
                 85                  90                  95
Pro

<210> SEQ ID NO 116
<211> LENGTH: 91
<212> TYPE: PRT
<213> ORGANISM: Homo sapiens

<400> SEQUENCE: 116

Gln Gly Leu Val Val Thr Pro Pro Gly Pro Glu Leu Val Leu Asn Val
  1               5                  10                  15
Ser Ser Thr Phe Val Leu Thr Cys Ser Gly Ser Ala Pro Val Val Trp
                 20                  25                  30
Glu Arg Met Ser Gln Glu Pro Pro Gln Glu Met Ala Lys Ala Gln Asp
             35                  40                  45
Gly Thr Phe Ser Ser Val Leu Thr Leu Thr Asn Leu Thr Gly Leu Asp
```

```
                   50                  55                  60
Thr Gly Glu Tyr Phe Cys Thr His Asn Asp Ser Arg Gly Leu Glu Thr
 65                  70                  75                  80

Asp Glu Arg Lys Arg Leu Tyr Ile Phe Val Pro
                 85                  90
```

<210> SEQ ID NO 117
<211> LENGTH: 94
<212> TYPE: PRT
<213> ORGANISM: Homo sapiens

<400> SEQUENCE: 117

```
Asp Pro Ala Lys Leu Phe Leu Val Asp Arg Ser Leu Tyr Gly Lys Glu
 1               5                  10                  15

Asp Asn Asp Thr Leu Val Arg Cys Pro Leu Thr Asp Pro Glu Val Thr
                20                  25                  30

Asn Tyr Ser Leu Lys Gly Cys Gln Gly Lys Pro Leu Pro Lys Asp Leu
             35                  40                  45

Arg Phe Ile Pro Asp Pro Lys Ala Gly Ile Met Ile Lys Ser Val Lys
     50                  55                  60

Arg Ala Tyr His Arg Leu Cys Leu His Cys Ser Val Asp Gln Glu Gly
 65                  70                  75                  80

Lys Ser Val Leu Ser Glu Lys Phe Ile Leu Lys Val Arg Pro
                 85                  90
```

<210> SEQ ID NO 118
<211> LENGTH: 94
<212> TYPE: PRT
<213> ORGANISM: Mus musculus

<400> SEQUENCE: 118

```
Asp Pro Ala Lys Leu Phe Leu Val Gly Leu Pro Leu Phe Gly Lys Glu
 1               5                  10                  15

Asp Ser Asp Ala Leu Val Arg Cys Pro Leu Thr Asp Pro Gln Val Ser
                20                  25                  30

Asn Tyr Ser Leu Ile Glu Cys Asp Gly Lys Ser Leu Pro Thr Asp Leu
             35                  40                  45

Thr Phe Val Pro Asn Pro Lys Ala Gly Ile Thr Ile Lys Asn Val Lys
     50                  55                  60

Arg Ala Tyr His Arg Leu Cys Val Arg Cys Ala Ala Gln Arg Asp Gly
 65                  70                  75                  80

Thr Trp Leu His Ser Asp Lys Phe Thr Leu Lys Val Arg Ala
                 85                  90
```

<210> SEQ ID NO 119
<211> LENGTH: 95
<212> TYPE: PRT
<213> ORGANISM: Homo sapiens

<400> SEQUENCE: 119

```
Asp Pro Ala Arg Pro Trp Asn Val Leu Ala Gln Glu Val Val Val Phe
 1               5                  10                  15

Glu Asp Gln Asp Ala Leu Leu Pro Cys Leu Leu Thr Asp Pro Val Leu
                20                  25                  30

Glu Ala Gly Val Ser Leu Val Arg Val Arg Gly Arg Pro Leu Met Arg
             35                  40                  45

His Thr Asn Tyr Ser Phe Ser Pro Trp His Gly Phe Thr Ile His Arg
     50                  55                  60
```

```
Ala Lys Phe Ile Gln Ser Gln Asp Tyr Gln Cys Ser Ala Leu Met Gly
 65                  70                  75                  80

Gly Arg Lys Val Met Ser Ile Ser Ile Arg Leu Lys Val Gln Lys
                 85                  90                  95
```

<210> SEQ ID NO 120
<211> LENGTH: 87
<212> TYPE: PRT
<213> ORGANISM: Homo sapiens

<400> SEQUENCE: 120

```
Asp Pro Asp Val Ala Phe Val Pro Leu Gly Met Thr Asp Tyr Leu Val
  1               5                  10                  15

Ile Val Glu Asp Asp Ser Ala Ile Ile Pro Cys Arg Thr Thr Asp
                 20                  25                  30

Pro Glu Thr Pro Val Thr Leu His Asn Ser Glu Gly Val Val Pro Ala
                 35                  40                  45

Ser Tyr Asp Ser Arg Gln Gly Phe Asn Gly Thr Phe Thr Val Gly Pro
 50                  55                  60

Tyr Ile Cys Glu Ala Thr Val Lys Gly Lys Lys Phe Gln Thr Ile Pro
 65                  70                  75                  80

Phe Asn Val Tyr Ala Leu Lys
                 85
```

<210> SEQ ID NO 121
<211> LENGTH: 95
<212> TYPE: PRT
<213> ORGANISM: Homo sapiens

<400> SEQUENCE: 121

```
Asp Pro Thr Val Gly Phe Leu Pro Asn Asp Ala Glu Glu Leu Phe Ile
  1               5                  10                  15

Phe Leu Thr Glu Ile Thr Glu Ile Thr Glu Ile Thr Pro Cys Arg
                 20                  25                  30

Val Thr Asp Pro Gln Leu Val Val Thr Leu His Glu Lys Lys Gly Asp
                 35                  40                  45

Val Ala Leu Pro Val Pro Tyr Asp His Gln Arg Gly Phe Ser Gly Ile
 50                  55                  60

Phe Glu Gly Ile Phe Glu Asp Arg Ser Tyr Ile Cys Lys Thr Thr Ile
 65                  70                  75                  80

Gly Asp Arg Glu Val Asp Ser Asp Ala Tyr Tyr Val Tyr Arg Leu
                 85                  90                  95
```

<210> SEQ ID NO 122
<211> LENGTH: 90
<212> TYPE: PRT
<213> ORGANISM: Homo sapiens

<400> SEQUENCE: 122

```
Arg Asn Thr Leu Leu Tyr Thr Leu Arg Arg Pro Tyr Phe Arg Lys Met
  1               5                  10                  15

Glu Asn Gln Asp Ala Leu Val Cys Ile Ser Glu Ser Val Pro Glu Pro
                 20                  25                  30

Ile Val Glu Trp Val Leu Cys Asp Ser Gln Gly Glu Ser Cys Lys Glu
                 35                  40                  45

Glu Ser Pro Ala Val Val Lys Lys Glu Glu Lys Val Leu His Glu Leu
 50                  55                  60
```

```
Phe Gly Thr Asp Ile Arg Cys Cys Ala Arg Asn Glu Leu Gly Arg Glu
 65                  70                  75                  80

Cys Thr Arg Leu Phe Thr Ile Asp Leu Asn
                 85                  90

<210> SEQ ID NO 123
<211> LENGTH: 103
<212> TYPE: PRT
<213> ORGANISM: Homo sapiens

<400> SEQUENCE: 123

Ala Phe Lys Ala Val Pro Val Val Ser Val Ser Lys Ala Ser Tyr Leu
  1               5                  10                  15

Leu Arg Glu Gly Glu Phe Thr Val Thr Cys Thr Ile Lys Asp Val
                 20                  25                  30

Ser Ser Ser Val Tyr Ser Thr Trp Lys Arg Glu Asn Ser Gln Thr Lys
             35                  40                  45

Leu Gln Glu Lys Tyr Asn Ser Trp His His Gly Asp Phe Asn Tyr Glu
 50                  55                  60

Arg Gln Ala Thr Leu Thr Ile Ser Ser Ala Arg Val Asn Asp Ser Gly
 65                  70                  75                  80

Val Phe Met Cys Tyr Ala Asn Asn Thr Phe Gly Ser Ala Asn Val Thr
                 85                  90                  95

Thr Thr Leu Glu Val Val Asp
            100

<210> SEQ ID NO 124
<211> LENGTH: 105
<212> TYPE: PRT
<213> ORGANISM: Mus musculus

<400> SEQUENCE: 124

Ala Ile Lys Ala Ile Pro Val Val Ser Val Pro Glu Thr Ser His Leu
  1               5                  10                  15

Leu Lys Lys Gly Asp Thr Phe Thr Val Val Cys Thr Ile Lys Asp Val
                 20                  25                  30

Ser Thr Ser Val Asn Ser Met Trp Leu Lys Met Asn Pro Gln Pro Gln
             35                  40                  45

His Ile Ala Gln Val Lys His Asn Ser Trp His Arg Gly Asp Phe Asn
 50                  55                  60

Tyr Glu Arg Gln Glu Thr Leu Thr Ile Ser Ser Ala Arg Val Asp Asp
 65                  70                  75                  80

Ser Gly Val Phe Met Cys Tyr Ala Asn Asn Thr Phe Gly Ser Ala Asn
                 85                  90                  95

Val Thr Thr Thr Leu Lys Val Val Glu
            100                 105

<210> SEQ ID NO 125
<211> LENGTH: 100
<212> TYPE: PRT
<213> ORGANISM: Homo sapiens

<400> SEQUENCE: 125

Val Ile Pro Gly Pro Pro Ala Leu Thr Leu Val Pro Ala Glu Leu Val
  1               5                  10                  15

Arg Ile Arg Gly Glu Ala Ala Gln Ile Val Cys Ser Ala Ser Ser Val
                 20                  25                  30

Asp Val Asn Phe Asp Val Phe Leu Gln His Asn Asn Thr Lys Leu Ala
```

```
            35                  40                  45
Ile Pro Gln Gln Ser Asp Phe His Asn Asn Arg Tyr Gln Lys Val Leu
 50                  55                  60

Thr Leu Asn Leu Asp Gln Val Asp Phe Gln His Ala Gly Asn Tyr Ser
 65                  70                  75                  80

Cys Val Ala Ser Asn Val Gln Gly Lys His Ser Thr Ser Met Phe Phe
                 85                  90                  95

Arg Val Val Glu
            100

<210> SEQ ID NO 126
<211> LENGTH: 102
<212> TYPE: PRT
<213> ORGANISM: Homo sapiens

<400> SEQUENCE: 126

Ala Thr Ser Glu Leu Asp Leu Glu Met Glu Ala Leu Lys Thr Val Tyr
 1               5                  10                  15

Lys Ser Gly Glu Thr Ile Val Val Thr Cys Ala Val Phe Asn Asn Glu
                 20                  25                  30

Val Val Asp Leu Gln Trp Thr Tyr Pro Gly Glu Val Lys Gly Lys Gly
            35                  40                  45

Ile Thr Met Leu Glu Glu Ile Lys Val Pro Ser Ile Lys Leu Val Tyr
 50                  55                  60

Thr Leu Thr Val Pro Glu Ala Thr Val Lys Asp Ser Gly Asp Tyr Glu
 65                  70                  75                  80

Cys Ala Ala Arg Gln Ala Thr Arg Glu Val Lys Glu Met Lys Lys Val
                 85                  90                  95

Thr Ile Ser Val His Glu
            100

<210> SEQ ID NO 127
<211> LENGTH: 103
<212> TYPE: PRT
<213> ORGANISM: Homo sapiens

<400> SEQUENCE: 127

Gln Val Ser Ser Ile Asn Val Ser Val Asn Ala Val Gln Thr Val Val
 1               5                  10                  15

Arg Gln Gly Glu Asn Ile Thr Leu Met Cys Ile Val Ile Gly Asn Glu
                 20                  25                  30

Val Val Asn Phe Glu Trp Thr Tyr Pro Arg Lys Glu Ser Gly Arg Leu
            35                  40                  45

Val Glu Pro Val Thr Asp Phe Leu Leu Asp Met Pro Tyr His Ile Arg
 50                  55                  60

Ser Ile Leu His Ile Pro Ser Ala Glu Leu Glu Asp Ser Gly Thr Tyr
 65                  70                  75                  80

Thr Cys Asn Val Thr Glu Ser Val Asn Asp His Gln Asp Glu Lys Ala
                 85                  90                  95

Ile Asn Ile Thr Val Val Glu
            100

<210> SEQ ID NO 128
<211> LENGTH: 100
<212> TYPE: PRT
<213> ORGANISM: Homo sapiens

<400> SEQUENCE: 128
```

```
Gln Thr Pro Gln Thr Thr Leu Pro Gln Leu Phe Leu Lys Val Gly Glu
1               5                   10                  15

Pro Leu Trp Ile Arg Cys Lys Ala Val His Val Asn His Gly Phe Gly
            20                  25                  30

Leu Thr Trp Glu Leu Glu Asn Lys Ala Leu Glu Gly Asn Tyr Phe
        35                  40                  45

Glu Met Ser Thr Tyr Ser Thr Asn Arg Thr Met Ile Arg Ile Leu Phe
50                  55                  60

Ala Phe Val Ser Ser Val Ala Arg Asn Asp Thr Gly Tyr Tyr Thr Cys
65                  70                  75                  80

Ser Ser Ser Lys His Pro Ser Gln Ser Ala Leu Val Thr Ile Val Gly
            85                  90                  95

Lys Gly Phe Ile
            100

<210> SEQ ID NO 129
<211> LENGTH: 101
<212> TYPE: PRT
<213> ORGANISM: Homo sapiens

<400> SEQUENCE: 129

Lys Gly Phe Ile Asn Ile Phe Pro Met Ile Asn Thr Thr Val Phe Val
1               5                   10                  15

Asn Asp Gly Glu Asn Val Asp Leu Ile Val Glu Tyr Glu Ala Phe Pro
            20                  25                  30

Lys Pro Glu His Gln Gln Trp Ile Tyr Met Asn Arg Thr Phe Thr Asp
        35                  40                  45

Lys Trp Glu Asp Tyr Pro Lys Ser Glu Asn Glu Ser Asn Ile Arg Tyr
50                  55                  60

Val Ser Glu Leu His Leu Thr Arg Leu Lys Gly Thr Glu Gly Gly Thr
65                  70                  75                  80

Tyr Thr Phe Leu Val Ser Asn Ser Asp Val Asn Ala Ala Ile Ala Phe
            85                  90                  95

Asn Val Tyr Val Asn
            100

<210> SEQ ID NO 130
<211> LENGTH: 101
<212> TYPE: PRT
<213> ORGANISM: Mus musculus

<400> SEQUENCE: 130

Lys Gly Phe Ile Asn Ile Ser Pro Val Lys Asn Thr Thr Val Phe Val
1               5                   10                  15

Thr Asp Gly Glu Asn Val Asp Leu Val Val Glu Tyr Glu Ala Tyr Pro
            20                  25                  30

Lys Pro Glu His Gln Gln Trp Ile Tyr Met Asn Arg Thr Ser Ala Asn
        35                  40                  45

Lys Gly Lys Asp Tyr Val Lys Ser Asp Asn Lys Ser Asn Ile Arg Tyr
50                  55                  60

Val Asn Gln Leu Arg Leu Thr Arg Leu Lys Gly Thr Glu Gly Gly Thr
65                  70                  75                  80

Tyr Thr Phe Leu Val Ser Asn Ser Asp Ala Ser Ala Ser Val Thr Phe
            85                  90                  95

Asn Val Tyr Val Asn
            100
```

<210> SEQ ID NO 131
<211> LENGTH: 102
<212> TYPE: PRT
<213> ORGANISM: Homo sapiens

<400> SEQUENCE: 131

Ser Ala Tyr Leu Asn Leu Ser Ser Glu Gln Asn Leu Ile Gln Glu Val
1               5                   10                  15

Thr Val Gly Glu Gly Leu Asn Leu Lys Val Met Val Glu Ala Tyr Pro
            20                  25                  30

Gly Leu Gln Gly Phe Asn Trp Thr Tyr Leu Gly Pro Phe Ser Asp His
        35                  40                  45

Gln Pro Glu Pro Lys Leu Ala Asn Ala Thr Thr Lys Asp Thr Tyr Arg
    50                  55                  60

His Thr Phe Thr Leu Ser Leu Pro Arg Leu Lys Pro Ser Glu Ala Gly
65                  70                  75                  80

Arg Tyr Ser Phe Leu Ala Arg Asn Pro Gly Gly Trp Arg Ala Leu Thr
                85                  90                  95

Phe Glu Leu Thr Leu Arg
            100

<210> SEQ ID NO 132
<211> LENGTH: 100
<212> TYPE: PRT
<213> ORGANISM: Homo sapiens

<400> SEQUENCE: 132

Lys Gly Phe Ile Glu Ile Lys Pro Thr Phe Ser Gln Leu Glu Ala Val
1               5                   10                  15

Asn Leu His Glu Val Lys His Phe Val Val Glu Val Arg Ala Tyr Pro
            20                  25                  30

Pro Pro Arg Ile Ser Trp Leu Lys Asn Asn Leu Thr Leu Ile Glu Asn
        35                  40                  45

Leu Thr Glu Ile Thr Thr Asp Val Glu Lys Ile Gln Glu Ile Arg Tyr
    50                  55                  60

Arg Ser Lys Leu Lys Ile Arg Ala Lys Glu Glu Asp Ser Gly His Tyr
65                  70                  75                  80

Thr Ile Val Ala Gln Asn Glu Asp Ala Val Lys Ser Tyr Thr Phe Glu
                85                  90                  95

Leu Leu Thr Gln
            100

<210> SEQ ID NO 133
<211> LENGTH: 102
<212> TYPE: PRT
<213> ORGANISM: Homo sapiens

<400> SEQUENCE: 133

Ser Gly Tyr Val Arg Leu Leu Gly Glu Val Gly Thr Leu Gln Phe Ala
1               5                   10                  15

Glu Leu His Arg Ser Arg Thr Leu Gln Val Val Phe Glu Ala Tyr Pro
            20                  25                  30

Pro Pro Thr Val Leu Trp Phe Lys Asp Asn Arg Thr Leu Gly Asp Ser
        35                  40                  45

Ser Ala Gly Glu Ile Ala Leu Ser Thr Arg Asn Val Ser Glu Thr Arg
    50                  55                  60

Tyr Val Ser Glu Leu Thr Leu Val Arg Val Lys Val Ala Glu Ala Gly
65                  70                  75                  80

His Tyr Thr Met Arg Ala Phe His Glu Asp Ala Glu Val Gln Leu Ser
                85                  90                  95

Phe Gln Leu Gln Ile Asn
            100

<210> SEQ ID NO 134
<211> LENGTH: 99
<212> TYPE: PRT
<213> ORGANISM: Homo sapiens

<400> SEQUENCE: 134

Thr Lys Pro Glu Ile Leu Thr Tyr Asp Arg Leu Val Asn Gly Met Leu
1               5                   10                  15

Gln Cys Val Ala Ala Gly Phe Pro Glu Pro Thr Ile Asp Trp Tyr Phe
                20                  25                  30

Cys Pro Gly Thr Glu Gln Arg Cys Ser Ala Ser Val Leu Pro Val Asp
            35                  40                  45

Val Gln Thr Leu Asn Ser Ser Gly Pro Pro Phe Gly Lys Leu Val Val
        50                  55                  60

Gln Ser Ser Ile Asp Ser Ser Ala Phe Lys His Asn Gly Thr Val Glu
65                  70                  75                  80

Cys Lys Ala Tyr Asn Asp Val Gly Lys Thr Ser Ala Tyr Phe Asn Phe
                85                  90                  95

Ala Phe Lys

<210> SEQ ID NO 135
<211> LENGTH: 99
<212> TYPE: PRT
<213> ORGANISM: Mus musculus

<400> SEQUENCE: 135

Thr Lys Pro Glu Ile Leu Thr Tyr Asp Arg Leu Ile Asn Gly Met Leu
1               5                   10                  15

Gln Cys Val Ala Glu Gly Phe Pro Glu Pro Thr Ile Asp Trp Tyr Phe
                20                  25                  30

Cys Thr Gly Ala Glu Gln Arg Cys Thr Thr Pro Val Ser Pro Val Asp
            35                  40                  45

Val Gln Val Gln Asn Val Ser Val Ser Pro Phe Gly Lys Leu Val Val
        50                  55                  60

Gln Ser Ser Ile Asp Ser Ser Val Phe Arg His Asn Gly Thr Val Glu
65                  70                  75                  80

Cys Lys Ala Ser Asn Asp Val Gly Lys Ser Ser Ala Phe Phe Asn Phe
                85                  90                  95

Ala Phe Lys

<210> SEQ ID NO 136
<211> LENGTH: 104
<212> TYPE: PRT
<213> ORGANISM: Homo sapiens

<400> SEQUENCE: 136

Tyr Pro Pro Glu Val Ser Val Ile Trp Thr Phe Ile Asn Gly Ser Gly
1               5                   10                  15

Thr Leu Leu Cys Ala Ala Ser Gly Tyr Pro Gln Pro Asn Val Thr Trp
                20                  25                  30

-continued

```
Leu Gln Cys Ser Gly His Thr Asp Arg Cys Asp Glu Ala Gln Val Leu
         35                  40                  45

Gln Val Trp Asp Asp Pro Tyr Pro Glu Val Leu Ser Gln Glu Pro Phe
 50                      55                  60

His Lys Val Thr Val Gln Ser Leu Leu Thr Val Glu Thr Leu Glu His
 65                  70                  75                  80

Asn Gln Thr Tyr Glu Cys Arg Ala His Asn Ser Val Gly Ser Gly Ser
             85                  90                  95

Trp Ala Phe Ile Pro Ile Ser Ala
            100

<210> SEQ ID NO 137
<211> LENGTH: 106
<212> TYPE: PRT
<213> ORGANISM: Homo sapiens

<400> SEQUENCE: 137

Val Pro Ser Ser Ile Leu Asp Leu Val Asp Glu Glu Gly Ser Thr
 1               5                  10                  15

Gly Gly Gln Thr Val Arg Cys Thr Ala Glu Gly Thr Pro Leu Pro Asp
             20                  25                  30

Ile Glu Trp Met Ile Cys Lys Asp Ile Lys Lys Cys Asn Asn Glu Thr
         35                  40                  45

Ser Trp Thr Ile Leu Ala Asn Asn Val Ser Asn Ile Ile Thr Glu Ile
     50                  55                  60

Glu Ser Arg Asp Arg Ser Thr Val Glu Gly Arg Val Thr Phe Ala Lys
 65                  70                  75                  80

Val Glu Glu Thr Ile Ala Val Arg Cys Leu Ala Lys Asn Leu Leu Gly
             85                  90                  95

Ala Glu Asn Arg Glu Leu Lys Leu Val Ala
            100                 105

<210> SEQ ID NO 138
<211> LENGTH: 111
<212> TYPE: PRT
<213> ORGANISM: Homo sapiens

<400> SEQUENCE: 138

Val Pro Val Arg Val Leu Glu Leu Ser Glu Ser His Pro Asp Ser Gly
 1               5                  10                  15

Glu Gln Thr Val Arg Cys Arg Gly Arg Gly Met Pro Gln Pro Asn Ile
             20                  25                  30

Ile Trp Ser Ala Cys Arg Asp Leu Lys Arg Cys Pro Arg Glu Leu Pro
         35                  40                  45

Pro Thr Leu Leu Gly Asn Ser Ser Glu Glu Glu Ser Gln Leu Glu Thr
     50                  55                  60

Asn Val Thr Tyr Trp Glu Glu Glu Gln Glu Phe Glu Val Val Ser Thr
 65                  70                  75                  80

Leu Arg Leu Gln His Val Asp Arg Pro Leu Ser Val Arg Cys Thr Leu
             85                  90                  95

Arg Asn Ala Val Gly Gln Asp Thr Gln Glu Val Ile Val Val Pro
            100                 105                 110

<210> SEQ ID NO 139
<211> LENGTH: 96
<212> TYPE: PRT
<213> ORGANISM: Homo sapiens
```

```
<400> SEQUENCE: 139

Arg Lys Pro Gln Val Leu Ala Glu Ala Ser Ala Ser Gln Ala Ser Cys
1               5                   10                  15

Phe Ser Asp Gly Tyr Pro Leu Pro Ser Trp Thr Trp Lys Lys Cys Ser
            20                  25                  30

Asp Lys Ser Pro Asn Cys Thr Glu Glu Ile Thr Glu Gly Val Trp Asn
        35                  40                  45

Arg Lys Ala Asn Arg Lys Val Phe Gly Gln Trp Val Ser Ser Ser Thr
    50                  55                  60

Leu Asn Met Ser Glu Ala Ile Lys Gly Phe Leu Val Lys Cys Cys Ala
65                  70                  75                  80

Tyr Asn Ser Leu Gly Thr Ser Cys Glu Thr Ile Leu Leu Asn Ser Pro
                85                  90                  95

<210> SEQ ID NO 140
<211> LENGTH: 70
<212> TYPE: PRT
<213> ORGANISM: Homo sapiens

<400> SEQUENCE: 140

Ile Cys Arg Asn Arg Val Thr Asn Asn Val Lys Asp Val Thr Lys Leu
1               5                   10                  15

Val Ala Asn Leu Pro Lys Asp Tyr Met Ile Thr Leu Lys Tyr Val Pro
            20                  25                  30

Gly Met Asp Val Leu Pro Ser His Cys Trp Ile Ser Glu Met Val Val
        35                  40                  45

Gln Leu Ser Asp Ser Leu Thr Asp Leu Leu Asp Lys Phe Ser Asn Ile
    50                  55                  60

Ser Glu Gly Leu Ser Asn
65                  70

<210> SEQ ID NO 141
<211> LENGTH: 70
<212> TYPE: PRT
<213> ORGANISM: Mus musculus

<400> SEQUENCE: 141

Ile Cys Gly Asn Pro Val Thr Asp Asn Val Lys Asp Ile Thr Lys Leu
1               5                   10                  15

Val Ala Asn Leu Pro Asn Asp Tyr Met Ile Thr Leu Asn Tyr Val Ala
            20                  25                  30

Gly Met Asp Val Leu Pro Ser His Cys Trp Leu Arg Asp Met Val Ile
        35                  40                  45

Gln Leu Ser Leu Ser Leu Thr Thr Leu Leu Asp Lys Phe Ser Asn Ile
    50                  55                  60

Ser Glu Gly Leu Ser Asn
65                  70

<210> SEQ ID NO 142
<211> LENGTH: 68
<212> TYPE: PRT
<213> ORGANISM: Homo sapiens

<400> SEQUENCE: 142

Tyr Cys Ser His Met Ile Gly Ser Gly His Leu Gln Ser Leu Gln Arg
1               5                   10                  15

Leu Ile Asp Ser Gln Met Glu Thr Ser Cys Gln Ile Thr Phe Glu Phe
            20                  25                  30
```

Val Asp Gln Glu Gln Leu Ala Asp Pro Val Cys Tyr Leu Lys Lys Ala
         35                    40                    45

Phe Leu Leu Val Gln Asp Ile Met Glu Asp Thr Met Arg Phe Arg Asp
 50                    55                    60

Asn Thr Pro Asn
65

<210> SEQ ID NO 143
<211> LENGTH: 60
<212> TYPE: PRT
<213> ORGANISM: Homo sapiens

<400> SEQUENCE: 143

Ser Pro Ile Ser Ser Asp Phe Ala Val Lys Ile Arg Glu Leu Ser Asp
1               5                   10                 15

Tyr Leu Leu Gln Asp Tyr Pro Val Thr Val Ala Ser Asn Leu Gln Asp
             20                   25                  30

Asp Glu Leu Cys Gly Gly Leu Trp Arg Leu Val Leu Ala Gln Arg Trp
         35                    40                    45

Met Glu Arg Leu Lys Thr Val Ala Gly Ser Lys Met
 50                    55                    60

<210> SEQ ID NO 144
<211> LENGTH: 69
<212> TYPE: PRT
<213> ORGANISM: Homo sapiens

<400> SEQUENCE: 144

Tyr Ser Ile Ile Asp Lys Leu Val Asn Ile Val Asp Asp Leu Val Glu
1               5                   10                 15

Cys Val Lys Glu Asn Ser Ser Lys Asp Leu Lys Lys Ser Phe Lys Ser
             20                   25                  30

Pro Glu Pro Arg Leu Phe Thr Pro Glu Glu Phe Phe Arg Ile Phe Asn
         35                    40                    45

Arg Ser Ile Asp Ala Phe Lys Asp Phe Val Val Ala Ser Glu Thr Ser
 50                    55                    60

Asp Cys Val Val Ser
65

<210> SEQ ID NO 145
<211> LENGTH: 69
<212> TYPE: PRT
<213> ORGANISM: Mus musculus

<400> SEQUENCE: 145

Tyr Ser Ile Ile Asp Lys Leu Gly Lys Ile Val Asp Asp Leu Val Leu
1               5                   10                 15

Cys Met Glu Glu Asn Ala Pro Lys Asn Ile Lys Glu Ser Pro Lys Arg
             20                   25                  30

Pro Glu Thr Arg Ser Phe Thr Pro Glu Glu Phe Phe Ser Ile Phe Asn
         35                    40                    45

Arg Ser Ile Asp Ala Phe Lys Asp Phe Met Val Ala Ser Asp Thr Ser
 50                    55                    60

Asp Cys Val Leu Ser
65

<210> SEQ ID NO 146
<211> LENGTH: 69

```
<212> TYPE: PRT
<213> ORGANISM: Homo sapiens

<400> SEQUENCE: 146

Ala Ile Ala Ile Val Gln Leu Gln Glu Leu Ser Leu Arg Leu Lys Ser
1               5                   10                  15

Cys Phe Thr Lys Asp Tyr Glu Glu His Asp Ala Ala Cys Val Arg Thr
            20                  25                  30

Phe Tyr Glu Thr Pro Leu Gln Leu Leu Glu Lys Val Lys Asn Val Phe
        35                  40                  45

Asn Glu Thr Lys Asn Leu Leu Asp Lys Asp Ala Asn Ile Phe Ser Lys
    50                  55                  60

Asn Cys Asn Asn Ser
65

<210> SEQ ID NO 147
<211> LENGTH: 65
<212> TYPE: PRT
<213> ORGANISM: Homo sapiens

<400> SEQUENCE: 147

Gln Gly Leu Leu Glu Arg Val Asn Thr Glu Ile His Phe Val Thr Lys
1               5                   10                  15

Cys Ala Phe Gln Pro Pro Pro Ser Cys Leu Arg Phe Val Gln Thr Asn
            20                  25                  30

Ile Ser Arg Leu Leu Gln Glu Thr Ser Glu Gln Leu Val Ala Leu Lys
        35                  40                  45

Pro Trp Ile Thr Arg Gln Asn Phe Ser Arg Cys Leu Glu Leu Gln Cys
    50                  55                  60

Gln
65

<210> SEQ ID NO 148
<211> LENGTH: 101
<212> TYPE: PRT
<213> ORGANISM: Homo sapiens

<400> SEQUENCE: 148

Lys Gly Phe Ile Glu Ile Lys Pro Thr Phe Ser Gln Leu Glu Ala Val
1               5                   10                  15

Asn Leu His Glu Val Lys His Phe Val Val Glu Val Arg Ala Tyr Pro
            20                  25                  30

Pro Pro Arg Ile Ser Trp Leu Lys Asn Asn Leu Thr Leu Ile Glu Asn
        35                  40                  45

Leu Thr Glu Ile Thr Thr Asp Val Glu Lys Ile Gln Glu Thr Arg Tyr
    50                  55                  60

Gln Ser Lys Leu Lys Leu Ile Arg Ala Lys Glu Glu Asp Ser Gly His
65                  70                  75                  80

Tyr Thr Ile Val Ala Gln Asn Glu Asp Ala Val Lys Ser Tyr Thr Phe
                85                  90                  95

Glu Leu Leu Thr Gln
            100

<210> SEQ ID NO 149
<211> LENGTH: 101
<212> TYPE: PRT
<213> ORGANISM: Mus musculus

<400> SEQUENCE: 149
```

```
Lys Gly Phe Val Glu Ile Glu Pro Thr Phe Gly Gln Leu Glu Ala Val
1               5                   10                  15

Asn Leu His Glu Val Arg Glu Phe Val Glu Val Gln Ala Tyr Pro
            20                  25                  30

Thr Pro Arg Ile Ser Trp Leu Lys Asp Asn Leu Thr Leu Ile Glu Asn
            35                  40                  45

Leu Thr Glu Ile Thr Thr Asp Val Gln Lys Ser Gln Glu Thr Arg Tyr
        50                  55                  60

Gln Ser Lys Leu Lys Leu Ile Arg Ala Lys Glu Asp Ser Gly His
65              70                  75                  80

Tyr Thr Ile Ile Val Gln Asn Glu Asp Asp Val Lys Ser Tyr Thr Phe
                85                  90                  95

Glu Leu Ser Thr Leu
            100
```

<210> SEQ ID NO 150
<211> LENGTH: 101
<212> TYPE: PRT
<213> ORGANISM: Gallus gallus

<400> SEQUENCE: 150

```
His Gly Phe Ile His Leu Glu Pro Gln Phe Ser Pro Leu Glu Ala Val
1               5                   10                  15

Asn Leu His Glu Val Lys Asn Phe Val Asp Val Gln Ala Tyr Pro
            20                  25                  30

Ala Pro Lys Met Tyr Trp Leu Lys Asp Asn Val Thr Leu Ile Glu Asn
            35                  40                  45

Leu Thr Glu Ile Val Thr Ser Ser Asn Arg Val Gln Glu Thr Arg Phe
        50                  55                  60

Gln Ser Val Leu Lys Leu Ile Arg Ala Lys Glu Asp Ser Gly Thr
65              70                  75                  80

Ile Leu Trp Leu Leu Lys Asn Glu Asp Glu Ile Lys Arg Tyr Thr Phe
                85                  90                  95

Ser Leu Leu Ile Gln
            100
```

<210> SEQ ID NO 151
<211> LENGTH: 101
<212> TYPE: PRT
<213> ORGANISM: Rana sp.

<400> SEQUENCE: 151

```
Lys Gly Phe Ile Asp Leu Glu Pro Met Phe Gly Ser Glu Glu Phe Ala
1               5                   10                  15

Asn Leu His Glu Val Lys Ser Phe Ile Val Asn Leu His Ala Tyr Pro
            20                  25                  30

Thr Pro Gly Leu Phe Trp Leu Lys Asp Asn Arg Thr Leu Ser Glu Asn
            35                  40                  45

Leu Thr Glu Ile Thr Thr Ser Ile Val Thr Thr Lys Glu Thr Arg Phe
        50                  55                  60

Gln Ser Lys Leu Lys Leu Ile Arg Ala Lys Glu Glu Asp Ser Gly Leu
65              70                  75                  80

Tyr Thr Leu Val Ala Gln Asn Asp Arg Glu Thr Lys Ser Tyr Ser Phe
                85                  90                  95

Ile Leu Gln Ile Lys
            100
```

<210> SEQ ID NO 152
<211> LENGTH: 101
<212> TYPE: PRT
<213> ORGANISM: Takifugu rubripes

<400> SEQUENCE: 152

Ser Glu Phe Met Ser Ile Gln Pro Lys Phe Gly Glu Tyr Glu Ser Ala
1               5                   10                  15

Glu Leu Asp Glu Val Cys Glu Phe Arg Ala Glu Ile Thr Ser Phe Pro
            20                  25                  30

Thr Ala Ser Val Thr Trp Phe Lys Asp Ser Val Pro Leu Ser Asn Val
        35                  40                  45

Thr Ala Glu Ile Ser Thr Ser Leu Gln Lys Leu Ser Glu Thr Ser Tyr
    50                  55                  60

Met Ser Val Leu Thr Leu Ile Arg Ala Lys Glu Glu Asp Ser Gly Asn
65                  70                  75                  80

Tyr Thr Met Arg Val Lys Asn Gly Asp Gln Ser Arg Thr Val Ser Leu
                85                  90                  95

Ile Leu Glu Val Lys
            100

<210> SEQ ID NO 153
<211> LENGTH: 102
<212> TYPE: PRT
<213> ORGANISM: Homo sapiens

<400> SEQUENCE: 153

Ser Gly Tyr Val Arg Leu Leu Gly Glu Val Gly Thr Leu Gln Phe Ala
1               5                   10                  15

Glu Leu His Arg Ser Arg Thr Leu Gln Val Val Phe Glu Ala Tyr Pro
            20                  25                  30

Pro Pro Thr Val Leu Trp Phe Lys Asp Asn Arg Thr Leu Gly Asp Ser
        35                  40                  45

Ser Ala Gly Glu Ile Ala Leu Ser Thr Arg Asn Val Ser Glu Thr Arg
    50                  55                  60

Tyr Val Ser Glu Leu Thr Leu Val Arg Val Lys Val Ala Glu Ala Gly
65                  70                  75                  80

His Tyr Thr Met Arg Ala Phe His Glu Asp Ala Glu Val Gln Leu Ser
                85                  90                  95

Phe Gln Leu Gln Ile Asn
            100

<210> SEQ ID NO 154
<211> LENGTH: 102
<212> TYPE: PRT
<213> ORGANISM: Canis familiaris

<400> SEQUENCE: 154

Ser Gly Tyr Val Arg Leu Leu Gly Glu Leu Asp Ala Val Gln Phe Ala
1               5                   10                  15

Glu Leu His Arg Ser Arg Ala Leu Gln Val Val Phe Glu Ala Tyr Pro
            20                  25                  30

Pro Pro Thr Val Val Trp Phe Lys Asp Asn Arg Thr Leu Gly Asp Ser
        35                  40                  45

Ser Ala Gly Glu Ile Ala Leu Ser Thr Arg Asn Val Ser Glu Thr Arg
    50                  55                  60

```
Tyr Val Ser Glu Leu Thr Leu Val Arg Val Lys Val Ala Glu Ala Gly
65                  70                  75                  80

Tyr Tyr Thr Met Arg Ala Phe His Glu Asp Ala Glu Gln Leu Ser
                85                  90                  95

Phe Gln Leu Gln Val Asn
            100
```

<210> SEQ ID NO 155
<211> LENGTH: 102
<212> TYPE: PRT
<213> ORGANISM: Mus musculus

<400> SEQUENCE: 155

```
Asn Gly Tyr Val Arg Leu Leu Glu Thr Leu Gly Asp Val Glu Ile Ala
1               5                   10                  15

Glu Leu His Arg Ser Arg Thr Leu Arg Val Val Phe Glu Ala Tyr Pro
                20                  25                  30

Met Pro Ser Val Leu Trp Leu Lys Asp Asn Arg Thr Leu Gly Asp Ser
            35                  40                  45

Gly Ala Gly Glu Leu Val Leu Ser Thr Arg Asn Met Ser Glu Thr Arg
50                  55                  60

Tyr Val Ser Glu Leu Ile Leu Val Arg Val Lys Val Ser Glu Ala Gly
65                  70                  75                  80

Tyr Tyr Thr Met Arg Ala Phe His Glu Asp Asp Glu Val Gln Leu Ser
                85                  90                  95

Phe Lys Leu Gln Val Asn
            100
```

<210> SEQ ID NO 156
<211> LENGTH: 98
<212> TYPE: PRT
<213> ORGANISM: Takifugu rubripes

<400> SEQUENCE: 156

```
Arg Gly Phe Val Ala Val Lys Ser Thr Arg Lys Gln Asn Ile Thr Ala
1               5                   10                  15

Glu Leu Gln Glu Asn Val Glu Leu Arg Val Ile Glu Ala Tyr Pro
                20                  25                  30

Pro Pro Gln Ile Arg Trp Lys Lys Asp Gly Ala Pro Val Arg Gly Asp
            35                  40                  45

Lys Thr Ile Ile Ile Arg Gln Glu His Glu Ile Arg Tyr Val Thr Ile
50                  55                  60

Leu Thr Leu Val Arg Val Arg Thr Glu Gln Lys Gly Leu Tyr Thr Ala
65                  70                  75                  80

Leu Ile Thr Asn Glu Asp Asp Val Lys Glu Val Thr Phe Ala Leu Glu
                85                  90                  95

Val Gln
```

<210> SEQ ID NO 157
<211> LENGTH: 101
<212> TYPE: PRT
<213> ORGANISM: Homo sapiens

<400> SEQUENCE: 157

```
Lys Gly Phe Ile Asn Ile Phe Pro Met Ile Asn Thr Thr Val Phe Val
1               5                   10                  15

Asn Asp Gly Glu Asn Val Asp Leu Ile Val Glu Tyr Glu Ala Phe Pro
                20                  25                  30
```

```
Lys Pro Glu His Gln Gln Trp Ile Tyr Met Asn Arg Thr Phe Thr Asp
        35                  40                  45

Lys Trp Glu Asp Tyr Pro Lys Ser Glu Asn Glu Ser Asn Ile Arg Tyr
 50                  55                  60

Val Ser Glu Leu His Leu Thr Arg Leu Lys Gly Thr Glu Gly Gly Thr
 65                  70                  75                  80

Tyr Thr Phe Leu Val Ser Asn Ser Asp Val Asn Ala Ala Ile Ala Phe
                85                  90                  95

Asn Val Tyr Val Asn
            100

<210> SEQ ID NO 158
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Threonine, Isoleucine, Valine, Proline,
      Asparagine, or Lysine
<220> FEATURE:
<221> NAME/KEY: misc_feature
<222> LOCATION: (4)..(4)
<223> OTHER INFORMATION: Xaa is Leucine, Valine, Alanine, or Methionine
<220> FEATURE:
<221> NAME/KEY: misc_feature
<222> LOCATION: (5)..(5)
<223> OTHER INFORMATION: Xaa is Lysine, Histidine, Asparagine, or
      Arginine
<220> FEATURE:
<221> NAME/KEY: misc_feature
<222> LOCATION: (6)..(6)
<223> OTHER INFORMATION: Xaa is Glycine, Valine, Alanine, Glutamic Acid,
      Proline, or Methionine
<220> FEATURE:
<221> NAME/KEY: misc_feature
<222> LOCATION: (7)..(7)
<223> OTHER INFORMATION: Xaa is Threonine, Serine, Glutamic Acid,
      Alanine, Glutamine, or Aspartic acid
<220> FEATURE:
<221> NAME/KEY: misc_feature
<222> LOCATION: (8)..(8)
<223> OTHER INFORMATION: Xaa is Glutamic Acid, Aspartic acid, or
      Glutamine
<220> FEATURE:
<221> NAME/KEY: misc_feature
<222> LOCATION: (9)..(9)
<223> OTHER INFORMATION: Xaa is Glycine, Serine, Alanine, Lysine,
      Arginine, Glutamine, or Threonine

<400> SEQUENCE: 158

Leu Xaa Arg Xaa Xaa Xaa Xaa Xaa Xaa Gly
 1               5                  10

<210> SEQ ID NO 159
<211> LENGTH: 17
<212> TYPE: PRT
<213> ORGANISM: Artificial Sequence
<220> FEATURE:
<223> OTHER INFORMATION: Synthetic peptide

<400> SEQUENCE: 159

Ser Glu Leu His Leu Thr Arg Leu Lys Gly Thr Glu Gly Gly Thr Tyr
 1               5                  10                  15

Thr
```

INHIBITORS OF RECEPTOR TYROSINE KINASES AND METHODS OF USE THEREOF

CROSS-REFERENCE TO RELATED APPLICATIONS

This application is a 35 U.S.C. §371 national stage filing of International Application No. PCT/US2008/007104, filed Jun. 5, 2008, which is related and claims priority to U.S. provisional application Ser. No. 61/070,506 filed Mar. 24, 2008; U.S. provisional application Ser. No. 61/009,482 filed Dec. 28, 2007 and U.S. provisional application Ser. No. 60/933,238, filed Jun. 5, 2007. The entire contents of each of the foregoing applications are incorporated herein by this reference.

STATEMENT REGARDING FEDERALLY SPONSORED RESEARCH OR DEVELOPMENT

This invention was made with Government support under contract R01-AR 051448, R01-AR 051886, and P50 AR054086 awarded by the National Institutes of Health. The government has certain rights in the invention.

BACKGROUND OF THE INVENTION

Stem cell factor (SCF) is a cytokine that mediates its diverse cellular responses by binding to and activating the receptor tyrosine kinase Kit (also known as SCF-receptor). Kit was initially discovered as an oncogene in a feline retrovirus that captured an activated and truncated form of the surface receptor (Besmer et al. (1986) J Virol 60: 194-203). SCF is encoded by the murine steel (Sl) locus while Kit is encoded by the dominant white spotting (W) locus in the mouse (Copeland et al. (1990) Cell 63: 175-183; Huang et al. (1990) Cell 63: 225-233; Flanagan and Leder (1990) Cell 63: 185-194; Tan et al. (1990) Science 247: 209-212; Bernstein et al. (1990) Ciba Found Symp 148: 158-166; discussion 166-172). SCF functions as a non-covalent homodimer and both membrane-anchored and soluble forms of SCF generated by alternative RNA splicing and by proteolytic processing have been described (reviewed in Ashman (1999) Int J Biochem Cell Biol 31:1037-1051). Kit is a member of type-III family of receptor tyrosine kinases (RTK), which also includes PDGF-receptor-α, and β, CSF-1-receptor (also known as M-CSF-receptor or Fms), and the Flt3-receptor (also known as Flk2) (reviewed in Ullrich and Schlessinger (1990) Cell 61: 203-212; Blume-Jensen et al. (2001) Nature 411: 355-365). Kit is composed of a glycosylated extracellular ligand binding domain (ectodomain) that is connected to a cytoplasmic region by means of a single transmembrane (TM) domain (reviewed in Schlessinger (2000) Cell 103: 211-225). The ectodomain of Kit and other members of type-III RTKs all contain five Ig-like domains, in which the second and third membrane distal domains were shown to play a role in ligand recognition (reviewed in Ullrich and Schlessinger (1990) Cell 61: 203-212). Other RTKs whose extracellular ligand binding domains are composed exclusively of multiple Ig-like repeats include members of the VEGF-receptor family (7Ig-like), CCK4-receptor (7Ig-like) and FGF-receptors (3Ig-like). The cytoplasmic region of Kit contains a protein tyrosine kinase (PTK) domain with a large kinase-insert region; another hallmark of type-III RTKs. Binding of SCF to Kit leads to receptor dimerization, intermolecular autophosphorylation and PTK activation. It was proposed that the fourth Ig-like domain of Kit is responsible for Kit dimerization in response to either monovalent or bivalent SCF binding (Lev et al. (1992b) J Biol Chem 267: 15970-15977; Blechman et al. (1995) Cell 80: 103-113). However, other studies have demonstrated that ligand induced dimerization of Kit is driven by bivalent binding of SCF (Philo et al. (1996) J Biol Chem 271: 6895-6902; Lemmon et al. (1997) J Biol Chem 272: 6311-6317).

Characterization of mice mutated at the SCF or Kit loci has shown that SCF and Kit are required for development of hematopoietic cells, melanocytes, germ cells and intestinal pacemaker cells (reviewed in Ashman (1999) Int J Biochem Cell Biol 31:1037-1051). In humans, loss of function mutations in Kit cause the piebald trait that is characterized by de-pigmentation of the ventral chest and abdomen, white fareflock of hair, deafness and constipation (Fleischman et al. (1991) Proc Natl Acad Sci USA 88: 10885-10889). A variety of gain-of-function mutations in Kit were found in different types of human cancers. Activating Kit mutations were found in gastro-intestinal-stromal tumors (GIST), acute myeloid leukemia (AML) and mast cell leukemia (MCL) among other cancers. Mutations were identified in the membrane proximal Ig-like domain (D5) (exon 8 and 9), in the juxtamembrane (JM) domain (exon 11), and in the tyrosine kinase (PTK) domain (exon 17) (see Forbes et al. (2006) COSMIC 2005. BR J. CANCER, 94: 318-22. Somatic mutation database: Catalogue of Somatic Mutations in Cancer http://www.sangerac.uk/genetics/CGP/cosmic/). While there is good evidence that the gain of function mutations in the JM and the PTK domains lead to constitutive activation of Kit, by relieving autoinhibitory constraints (Mol et al., (2004) J Biol. Chem. 279: 31655-31663), the molecular mechanism underlying the gain of function mutations in D5 of the ectodomain is not understood. There is a need to better characterize the structures of RTKs such as Kit and PDGFR, as well as SCF, PDGFα/β, and the bound Kit/SCFcomplex. Such a characterization will lead to the informed identification of regions which may be targeted with drugs, pharmaceuticals, or other biologics.

SUMMARY OF THE INVENTION

The present invention provides moieties, e.g., antibodies or antigen binding portions thereof, small molecules, peptidic molecules, aptamers, and adnectins, that bind to the ectodomain, e.g., an Ig-like domain or a hinge between Ig-like domains, of a human receptor tyrosine kinase, e.g., a type III or type V receptor tyrosine kinase, such as the human Kit (also known as the SCF receptor) or PDGFRα/β. The moieties of the present invention lock the ectodomain of the receptor tyrosine kinase in an inactive state thereby inhibiting the activity of the receptor tyrosine kinase. In one embodiment of the invention, the moiety locks the ectodomain of the receptor tyrosine kinase to a monomeric state. In another embodiment of the invention, the moiety allows the ectodomain of the receptor tyrosine kinase to dimerize but affects the positioning, orientation and/or distance between the Ig-like domains of the two monomers (e.g., the D4-D4 or D5-D5 domains of a type III receptor tyrosine kinase or the D7-D7 domains of a type V receptor tyrosine kinase), thereby inhibiting the activity of the receptor tyrosine kinase. In other words, the moiety may allow ligand induced dimerization of the receptor tyrosine kinase ectodomains, but affect the positioning of the two ectodomains at the cell surface interface or alter or prevent conformational changes in the receptor tyrosine kinases, thereby inhibiting the activity of the receptor tyrosine kinase (e.g., inhibiting receptor internalization and/or inhibiting tyrosine autophosphorylation of the receptor and/or inhibiting the ability of the receptor to activate a downstream signaling pathway). The present invention is based, at least in part, on the deciphering of the crystal structures of the entire ectodomain of the receptor tyrosine kinase Kit both in the monomeric, as well as the ligand induced homodimeric forms. The deciphering of these crystal structures has allowed for the identification of epitopes, e.g., conformational epitopes, which the moieties of the invention may target.

The present invention is also based, at least in part on the discovery that, rather than playing a role in receptor dimerization, the homotypic D4 (and also homotypic D5) interactions between neighboring receptors are required for precise positioning of the membrane proximal regions of two receptors at a distance and orientation that enable interactions between their cytoplasmic domains resulting in tyrosine kinase activation.

Accordingly, in one aspect, the present invention provides a moiety that binds to the ectodomain, e.g., an Ig-like domain or a hinge region, of a human receptor tyrosine kinase, wherein the moiety locks the ectodomain of the receptor tyrosine kinase in an inactive state, thereby antagonizing the activity of the receptor tyrosine kinase. In one embodiment, the Ig-like domain may or may not responsible for the binding of a ligand to the receptor tyrosine kinase. In another embodiment, the moiety may or may not block the interaction between the receptor tyrosine kinase and a ligand for the receptor tyrosine kinase. In yet another embodiment, the moiety of the invention may or may not prevent dimerization of the receptor tyrosine kinase. In a further embodiment, the moiety of the invention may not prevent ligand induced receptor dimerzation but will prevent the homotypic or heterotypic interactions between membrane proximal regions that are required for receptor tyrosine kinase activation.

In some embodiments, a moiety of the invention prevents a homotypic or heterotypic interaction between a membrane proximal region of the ectodomain from each protomer of the receptor tyrosine kinase. For example, a moiety of the invention may cause the termini of the ectodomain (the ends of the ectodomain closest to the plasma membrane) from each protomer of the receptor tyrosine kinase to be separated by a distance greater than about 15 Å, about 20 Å, about 25 Å, about 30 Å, about 35 Å or about 40 Å.

In preferred embodiments, the receptor tyrosine kinase is a type III receptor tyrosine kinase, e.g., Kit, PDGFRα, PDGFRβ, CSF1R, Fms, Flt3 or Flk2.

In other embodiments, the Ig-like domain which is bound by a moiety of the present invention is a D4 domain of a type III receptor tyrosine kinase. In one specific embodiment, the moiety binds to the following consensus sequence for the D4 interaction site: $LX_1RX_2X_3X_4X_5X_6X_7G$ (SEQ ID NO: 158) wherein L is Leucine, R is Arginine, G is Glycine; $X_1$ is selected from the group consisting of Threonine, iso leucine, Valine. Proline, Asparagine, or Lysine; X2 is selected from the group consisting of Leucine, Valine, Alanine, and Methionine; $X_3$ is selected from the group consisting of Lysine, Histidine, Asparagine, and Arginine; $X_4$ is selected from the group consisting of Glycine, Valine, alanine, Glutamic Acid, Proline, and Methionine; $X_5$ is selected from the group consisting of Threonine. Serine, Glutamic Acid, Alanine, Glutamine, and Aspartic acid; $X_6$ is selected from the group consisting of Glutamic Acid, Aspartic acid, and Glutamine; and $X_7$ is selected from the group consisting of Glycine, Serine, Alanine, Lysine, Arginine, Glutamine, and Threonine, In another embodiment, the Ig-like domain which is bound by a moiety of the present invention is a D5 domain of a type III receptor tyrosine kinase, e.g., amino acid residues 309-413 or 410-519 of the human Kit. In a specific embodiment, a moiety of the present invention may bind to a consensus sequence of conserved amino acids from the D5 interaction site.

In another embodiment, the moiety of the present invention binds to mutants of the type III receptor tyrosine kinase D4 or D5 domain or to mutants of the type V receptor tyrosine kinase D7 domain. In a specific embodiment, the moiety binds a point mutation in a mutant D5 domain of human Kit, wherein the mutation is selected from the group consisting of Thr417, Tyr418, Asp419, Leu421, Arg420, Tyr503, and Ala502.

In some embodiments, the type III receptor tyrosine kinase is human Kit and the moiety of the invention binds to one or more amino acid residues, e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or 18 or more amino acid residues, selected from the group consisting of those amino acid residues shown in Table 4 below. For example, moieties of the invention may bind one or more of the following residues: Y125, G126, H180, R181, K203, V204, R205, P206, P206, F208, K127, A207, V238, S239, S240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F355, G311, G384, G387, G388, I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432. In specific embodiments, the moiety of the invention binds at least one of the amino acid residues in the Kit receptor selected from the group consisting of K218, S220, Y221, L222, F340, P341, K342, N367, E368, S369, N370, I371, and Y373 or at least one of the amino acid residues in the Kit receptor selected from the group consisting of Y350, R353, F355, K358, L379, T380, R381, L382, E386, and T390. The moieties of the invention may bind to all of the residues forming a pocket or a cavity identified in Table 4 or they may bind to a subset of the residues forming the pocket or the cavity. One of skill in the art will appreciate that, in some embodiments, moieties of the invention may be easily targeted to the residues corresponding to those listed above in other type III RTKs, e.g., those residues that form similar pockets or cavities or those in the same position by structural alignment or sequence alignment.

In another embodiment, a moiety of the invention binds to amino acid residues [381]Arg and [386]Glu of human Kit. In yet another embodiment, a moiety of the invention binds to amino acid residues [418]Tyr and/or [505]Asn of human Kit.

In a further embodiment, the moiety of the invention binds to the PDGFRα or PDGFRβ receptor. In a similar embodiment, a moiety of the invention binds to amino acid residues [385]Arg and/or [390]Glu of human PDGFRβ, or the corresponding residues in PDGFRα.

In yet another embodiment, a moiety of the invention binds to a conformational epitope on a type III RTK. In specific embodiments, the conformational epitope is composed of two or more residues from the D3, D4, or D5 domain or hinge regions from a type III RTK, e.g., the human Kit receptor or the PDGF receptor. In further specific embodiments, moieties of the invention may bind to conformational epitopes in the human Kit receptor composed of two or more residues, e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or 18 or more amino acid residues, selected from the group consisting of those amino acid residues listed in Table 4. In a particular embodiment, a moiety of the invention binds to a conformational epitope composed of 2 or more amino acids selected from the group consisting of Y125, H180, R181, K203, V204, R205, P206. V238, S239, S240, H263, G265, D266, F267, N268, and Y269. In similar embodiments, a moiety of the invention may bind to a conformational epitope composed of 2 or more amino acids selected from one of the following groups of amino acids: P206, F208, V238, and S239; K127, A207, F208, and T295; L222, A339, F340, K342, E368, S369, N370, I371, and Y373; L222, L223, E306, V308, F312, E338, F340, and I371; R224, V308, K310, G311, F340, P341, and D398; K218, A219, 5220, N367, E368, and S369; K218, A220, E368, and S369; G384, T385, T411, K412, E414, and K471; Y408, F433, G470, K471, and L472; F324, V325, N326, and N410; D327, N410, T411, K412, and V497; G384, G387, V409, and K471; L382, G387, V407, and V409; Y125, G126, H180, R181, K203, V204, R205, P206, F208, V238, 5239, S240, 5241, H263, G265, D266, F267, N268, and Y269; P206, F208, V238, and 5239; K218, S220, Y221, L222, F340, P341, K342, N367, E368, S369, N370, I371, and Y373; G384, G387, G388, Y408, V409, T411, F433, F469, G470, and K471; D327, T411, K412, E414, A431, G432, and K471; Y350, F355, K358, L379, T380, R381, L382, E386, and T390; Y350, R353, and F355. As indicated above, the moieties of the invention may bind to all of the amino acid residues forming a pocket or a cavity identified in Table 4 or they may bind to a subset of the residues forming the pocket or the cavity.

In a further embodiment, a moiety of the invention binds to a conformational epitope wherein the conformational epitope is composed of two or more amino acid residues selected from the peptides listed in Table 5. In a specific embodiment, the conformational epitope is composed of one or more amino acid residues selected from a first peptide and one or more amino acid residues selected from a second peptide, wherein the first and second peptides are selected from the group of peptides listed in Table 5. As such, a moiety of the invention may bind a conformational epitope wherein the first and second peptide groups are as follows: Ala219-Leu222 and Thr304-Val308; Asp309-Gly311 and Arg224-Gly226; Thr303-Glu306 and Ala219-Leu222; Asn367-Asn370 and Ser217-Tyr221; Ala339-Pro343 and Asn396-Val399; Ala339-Pro343 and Glu368-Arg372; Lys358-Tyr362 and Val374-His378; Asp357-Glu360 and Leu377-Thr380; Met351-Glu360 and His378-Thr389; His378-Thr389 and Val323-Asp332; Val409-Ile415 and Ala493-Thr500; Val409-Ile415 and Ala431-Thr437; Val409-Ile415 and Phe469-Val473; Val409-Ile415 and Val325-Asn330; Val409-Ile415 and Arg381-Gly387; Gly466-Leu472 and Gly384-Gly388; Val325-Glu329 and Tyr494-Lys499; Thr411-leu416 and Val497-Ala502; Ile415-Leu421 and Ala502-Ala507; Ala502-Ala507 and Lys484-Thr488; and Ala502-Ala507 and Gly445-Cys450. The moieties of the invention may bind to all of the amino acid residues forming the foregoing first and second peptide groups or they may bind to a subset of the residues forming the first and second peptide groups.

In other embodiments, moieties of the present invention bind to receptor tyrosine kinases which are members of the VEGF receptor family (type V receptor tyrosine kinases), e.g., VEGFR-1 (Flt1), VEGFR-2(Flk1) and VEGFR-3(Flt4). The Ig-like domain bound by moieties of the present invention may, in some embodiments, be the D7 domain of a member of the VEGF receptor family. In a specific embodiment, the moiety binds to the following consensus sequence for the D7 domain of a member of the VEGF receptor family: IX$_1$RVX$_2$X$_3$EDX$_4$G (SEQ ID NO: 1) wherein I is Isoleucine, R is Arginine, E is Glutamic Acid, D is Aspartic Acid, G is Glycine; X$_1$ is selected from the group consisting of Glutamic Acid, Arginine, and Glutamine; X2 is selected from the group consisting of Arginine and Threonine; X$_3$ is selected from the group consisting of Glutamic Acid and Lysine; and X$_4$ is selected from the group consisting of Glutamic Acid and Alanine.

In some embodiments, the moiety of the present invention is an isolated antibody, or an antigen-binding portion thereof. The antibody or antigen-binding portion thereof, may be a human antibody, a humanized antibody, a bispecific antibody, or a chimeric antibody. In some embodiments, the antibody, or antigen-binding portion thereof, comprises a heavy chain constant region selected from the group consisting of IgG1, IgG2, IgG3, IgG4, IgM, IgA and IgE constant regions. In a preferred embodiment the antibody heavy chain constant region is IgG1. Additionally, the moiety of the present invention may be an antibody, or antigen binding portion thereof, wherein the antibody, or antigen-binding portion thereof, is selected from the group consisting of a Fab fragment, a F(ab')2 fragment, a single chain Fv fragment, an SMIP, an affibody, an avimer, a nanobody, and a single domain antibody. In particular embodiments, an antibody, or antigen-binding portion thereof, of the present invention binds to an Ig-like domain of a receptor tyrosine kinase with a $K_D$ of $1\times10^{-7}$ M or less, more preferably $5\times10^{-8}$ M or less, more preferably $1\times10^{-8}$ M or less, more preferably $5\times10^{-9}$ M or less.

In some embodiments, the isolated antibody, or an antigen-binding portion thereof, of the present invention binds to amino acid residues 309-413 and/or 410-519 of the human Kit, thereby locking the ectodomain of the human Kit in an inactive state and antagonizing the activity of human Kit.

In further embodiments, the present invention includes a hybridoma which produces the antibody, or antigen binding portion thereof, of the present invention.

In another preferred embodiment, the moiety of the present invention is a small molecule.

In some preferred embodiments, the small molecule of the invention binds to one or more amino acid residues selected from the group consisting of those amino acid residues shown in Table 4. For example, small molecules of the invention may bind one or more of the following residues: Y125, G126, H180, R181, K203, V204, R205, P206, P206, F208, K127, A207, V238, S239, S240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F355, G311, G384, G387, G388, I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432. In a specific embodiment, the small molecule of the invention binds at least one of the amino acid residues in the Kit receptor selected from the group consisting of K218, S220, Y221, L222, F340, P341, K342, N367, E368, S369, N370, I371, and Y373. In a related embodiment, the small molecule of the invention binds at least one of the amino acid residues in the Kit receptor selected from the group consisting of Y350, R353, F355, K358, L379, T380, R381, L382, E386, and T390. One of skill in the art will appreciate that, in some embodiments, small molecules of the invention may be easily targeted to the residues corresponding to those listed above in other type III RTKs, e.g., those residues that form similar pockets or cavities or those in the same position by structural alignment or sequence alignment.

In a further embodiment, the moiety of the present invention is a peptidic molecule. In some embodiments, the peptidic molecule is designed based on an Ig-like domain of a receptor tyrosine kinase. In a specific embodiment, the peptidic molecule of the present invention is designed based on the D4 domain of Kit. The peptidic molecule of the present invention may comprise a conserved D4 interaction site, e.g., the D4 consensus sequence described above LX$_1$RX$_2$X$_3$X$_4$X$_5$X$_6$X$_7$G (SEQ NO: 158), or others generated by aligning or comparing D4 domains of type III receptor tyrosine kinases. In additional embodiments, a peptidic molecule of the present invention comprises a structure which is at least 80% identical to amino acid residues 309-413 of human Kit or a structure which is at least 80% identical to amino acid residues 410-519 of human Kit. The peptidic moities may also be designed based on the D5 domain of Kit, and, in further preferred embodiments, may comprise a consensus sequence generated by aligning or comparing D5 domains of type III receptor tyrosine kinases. In alternative embodiments, the peptidic molecule may be designed based on the sequence or consensus sequence of mutant D5 domains.

The peptidic moieties of the invention may be peptides comprising or consisting of any of the amino acid sequences identified herein (e.g., SEQ ID NOs: 1-89, 92, 93, and 105-157).

In some embodiments, the peptidic molecule of the present invention comprises at least one D-amino acid residue.

In another preferred embodiment, the moiety of the present invention is an adnectin.

In addition, in some embodiments the small molecules and peptidic molecules of the invention bind to conformational epitopes in the target RTKs. In other embodiments, the small molecules and peptidic molecules of the invention bind to epitopes in the target RTKs which are not conformational epitopes.

In another aspect, the present invention provides pharmaceutical compositions comprising any of the moieties of the present invention and a pharmaceutically acceptable carrier.

In additional aspects, the invention provides methods of treating or preventing a receptor tyrosine kinase associated disease in a subject. The methods include administering to the subject an effective amount of a moiety of the present invention (e.g., a moiety which binds the D4 or D5 domain of a type III receptor tyrosine kinase, or a D7 domain of a type V receptor tyrosine kinase), thereby treating or preventing the disease. In preferred embodiments, the receptor tyrosine kinase associated disease is cancer, e.g., GIST, AML, and SCLC.

In another aspect, the invention provides methods of treating or preventing a receptor tyrosine kinase associated disease in a subject, by administering to the subject an effective amount of a moiety which binds the D3-D4 and/or a D4-D5 hinge region of a human type III receptor tyrosine kinase, thereby treating or preventing the disease. In specific embodiments, the receptor tyrosine kinase associated disease is cancer, e.g., GIST, AML, and SCLC.

In another aspect, the invention provides methods for identifying a moiety that binds to an Ig-like domain of a receptor tyrosine kinase and locks the ectodomain of the receptor tyrosine kinase to an inactive state. The methods include contacting a receptor tyrosine kinase with a candidate moiety; simultaneously or sequentially contacting the receptor tyrosine kinase with a ligand for the receptor tyrosine kinase; and determining whether the moiety affects the positioning, orientation and/or distance between the Ig-like domains of the ligand induced dimeric receptor tyrosine kinase, thereby identifying a moiety that binds to an Ig-like domain of a receptor tyrosine kinase and locks the ectodomain of the receptor tyrosine kinase to an inactive state.

In a further aspect, the invention provides methods for identifying a moiety that locks the ectodomain of a type III receptor tyrosine kinase to an inactive state. The methods include contacting a type III receptor tyrosine kinase with a candidate moiety; simultaneously or sequentially contacting the receptor tyrosine kinase with a ligand for the receptor tyrosine kinase; and determining whether the moiety affects the positioning, orientation and/or distance between the D4-D4 or D5-D5 domains of the ligand induced dimeric receptor tyrosine kinase, thereby identifying a moiety that locks the ectodomain of the type III receptor tyrosine kinase to an inactive state.

Other features and advantages of the invention will be apparent from the following detailed description and claims.

BRIEF DESCRIPTION OF THE DRAWINGS

FIG. 1A shows a ribbon diagram (left) and surface representation (right) of Kit ectodomain monomer. Right panel shows a view following 90° rotation along the vertical axis of the view shown in the left panel. D1 is colored in blue, D2 in green, D3 in yellow, D4 in orange and D5 in pink, N and C termini are labeled. Disulfide bonds in D1 and D5 are shown in ball-and-stick rendering with sulfur atoms colored in orange. Asparagine-linked carbohydrates are shown in a stick model. FIG. 1B-E provides detailed views of the D1-D2 (B), D2-D3 (C), D3-D4 (D), and D4-D5 (E) interfaces. Color coding is the same as in FIG. 1A. Amino acids that participate in domain-domain interactions are labeled and hydrogen bonds are drawn as dashed yellow lines. Secondary structure elements are designated according to IgSF nomenclature.

FIG. 2A shows a ribbon diagram of SCF-Kit 2:2 complex. Color coding of D1 to D5 is the same as in FIG. 1 and SCF is colored in magenta. N and C termini of Kit and SCF are labeled. Disulfide bonds in D1 and D5 are shown in ball-and-stick rendering with sulfur atoms colored in orange. Asparagine-linked carbohydrates are represented in a stick model. Arrow marks a large cavity in the SCF-Kit 2:2 complex. FIG. 2B shows surface representations of SCF-Kit ectodomain 2:2 complex. The figure shows a top view (top), face view (center left), side view (center right) and bottom view (low). Color coding is the same as in A. The views show that a SCF dimer interacts symmetrically with D1, D2 and D3 of two corresponding Kit ectodomains. In addition, Kit ectodomains form homophylic interactions through lateral contacts between D4 (orange) and between D5 (pink) of two neighboring receptors.

FIG. 3A shows views of the SCF-Kit interface. Amino acids in the buried surfaces in SCF and Kit ectodomain are visualized by pulling apart the two molecules. The figure shows the molecular surface of Kit D1-D2-D3 (left) and SCF (right). Acidic amino acids are shown in red, basic amino acids in blue, polar amino acids in orange and hydrophobic amino acids in yellow. SCF binding site-I, site-II and site-III on Kit are circled. FIG. 3B depicts complementarity in the electrostatic potential in the ligand-receptor interface. The right panel shows a view following a rotation of 180° along the vertical axis of the electrostatic surface presented in the left panel. Electrostatic surface potential of D1-D2-D3 superimposed on the molecular surfaces with an imprint of a cartoon diagram of bound SCF that is colored in green. Right panel depicts the electrostatic surface potential of SCF-bound Kit colored in blue (positive)

and red (negative). Kit is shown in a form of ribbon diagram colored in cyan. FIGS. 3C-E show close-up views of site-I (C), site-II (D) and site-III (E) of SCF-Kit interface. SCF is colored in green and Kit in cyan. Interacting amino acids are labeled, hydrogen bonds are drawn as dashed yellow lines and secondary structure elements are marked on the ribbons and strands.

FIG. 4A shows that the angle between the two SCF protomers is altered upon Kit binding. The view shows a cartoon diagram of free SCF (green) and SCF bound to Kit (magenta). Superimposition of the one SCF protomer (left) reveals an angular movement of approximately 5° of the second protomer (right), as measured for helix αC. Helices are labeled and shown as cylinders. FIG. 4B depicts the conformational change in the N-terminus of SCF upon Kit binding. Site-III of Kit is shown as a molecular surface (gray), the N-terminus of free SCF is shown in green and of SCF bound to Kit in magenta. Disulfide bond between Cys4' and Cys89' is shown as yellow spheres. Key amino acids are labeled and shown as a stick model. FIG. 4C depicts the conformational change in the αC-β2 loop of SCF upon binding to site-I of Kit. Color coding is the same as in B.

FIG. 5A shows the reconfiguration of D4 and D5 in the SCF-Kit complex. Superimposition of D3 from Kit monomer with D3 of Kit-bound to SCF (both colored blue) shows that D4 of the bound form (red) moves by 22° relative to the position of D4 of the free form (green). Superimposition (right panel) of D4 of the two forms (both in blue) shows that D5 of the SCF-bound form (red) moves by 27° relative to the positions of D5 of the free form (green). The two bottom panels show close views of the hinge regions of D3-D4 and D4-D5 interfaces of the monomeric (green) and homodimeric (red) forms. FIG. 5B shows a surface representation of D4 and D5 of SCF occupied Kit (top panel), viewed in the same orientation as in FIG. 2. The black outline shows the location of D4 and D5 of Kit ectodomain monomers bridged by SCF binding to the ligand binding region. Reconfiguration of D4 and D5 leads to a movement of the C-termini of two neighboring ectodomains from 75 Å to 15 Å from each other. Lower panel shows a view from the cell membrane (bottom view) of SCF-Kit complex. Note a 90° rotation along the x-axis. Color coding of D1 to D5 is the same as in FIG. 1.

FIGS. 6A-D depict views of the D4-D4 and the D5-D5 interfaces. FIG. 6A (top panel) shows a 2Fo-Fc electron density map contoured at 1.1σ level showing a view of the D4-D4 interface. The backbones of Kit protomers are represented as pink and yellow tubes, respectively. A close view (bottom panel) of the D4-D4 interface of two neighboring ectodomains. Interchain hydrogen bonds formed between Arg381 and Glu386, of two adjacent D4 are colored in yellow. Key amino acids are labeled and shown as a stick model. Secondary structure elements are labeled according to the IgSF nomenclature. FIG. 6B depicts the conservation of the D4-D4 dimerization motif across member of type-III and type-V RTK families. Residues 370-398 of human Kit (AAC50969.1) (SEQ ID NO: 94) aligned with sequences of, mouse (AAH75716.1) (SEQ ID NO: 95), chicken (NP_989692.1) (SEQ ID NO: 96), xenopus laevis (AAH61947) (SEQ ID NO: 97), salamander (AAS91161.1) (SEQ ID NO: 98) and zebrafish (type A (SEQ ID NO: 99) and B (SEQ ID NO: 100) (NP_571128, XP_691901) homologs. Also shown amino-acid sequences of CSF1R from human (P07333) (SEQ ID NO: 101), mouse (P09581) (SEQ ID NO: 102) and torafugu type A (SEQ ID NO: 103) and B (SEQ ID NO: 104) (P79750, Q8UVR8), and sequences from PDGFRα and PDGFRβ from human (SEQ ID NOS 105 and 107, respectively) (P16234, P09619) and mouse (SEQ ID NOs: 106 and 108, respectively) (NP_035188, P05622). Amino acid sequences of type-V RTKs of human VEGFR type 1-3 (SEQ ID NOS:109-111, respectively, in order of appearance) (7th Ig-like domain) (P17948, P35968 and P35916) are also presented. Secondary structure elements on Kit are labeled on the top of the sequence alignment. The conserved residues of Arg381 and Lys383, Leu382 and Leu379, Glu386 and Gly388 are colored in blue, yellow, red and green, respectively. FIG. 6C depicts a ribbon diagram of a D5-D5 interface. Strands A and G of two adjacent Kit protomers participate in formation of the D5-D5 interface. The D5-D5 interface is maintained by lateral interactions between Tyr418 and Asn505 of two neighboring receptors probably through ion(s) or water molecule(s). FIG. 6D depicts the electrostatic potential surfaces of D4 and D5 of Kit. The figures show a face view of the D4-D4 interacting surface (right) and a view following 90° rotation along the vertical axis (left). The position of acidic patch and the D4-D4 interfaces are circled and the interacting residue Arg381 and Glu386 are labeled.

FIG. 7A depicts loss-of-function mutations responsible for the piebald trait are shown in the left panel. A ribbon diagrams of D1 (blue), D2 (green) and D3 (yellow) and surface representation of SCF (gray). Mutated amino acids are colored in red. Gain of function mutations responsible for GIST, SCLC and AML are shown in the right panel. Surface representation of D4 and D5 in the homodimeric form is colored in gray. Ala502 and Tyr503 that are duplicated in GIST are shown in blue and deletions and insertional mutations in proximity to Asp419 (AML and NCLL) are shown in green. Note that the activating Kit mutations are confined to the D5-D5 interface. FIG. 7B shows that Kit activation is compromised by point mutants in D4-D4 interface. HEK293 cells transiently expressing wild type Kit (WT), R381A or E386A point mutations in D4 were stimulated with 10 ng/ml SCF for six minutes at 37° C. as indicated (upper left panel). Lysates of unstimulated or SCF stimulated cells were subjected to immunoprecipitation (IP) with anti-Kit antibodies followed by SDS-PAGE and immunoblotting (IB) with either anti-Kit or anti phosphotyrosine (p-Tyr) antibodies. Densitometric quantitation of tyrosine autophosphorylation of Kit from anti-p-Tyr immunoblots (upper right panel). 3T3 cells stably expressing wild type Kit (WT) or the R381A mutant were treated with different concentrations of SCF. Lysates from unstimulated or SCF stimulated cells were subjected to immunoprecipitation with anti-Kit antibodies followed by SDS-PAGE and immunoblotting with anti-Kit or anti-p-Tyr antibodies (lower left panel). Displacement assay of cell bound 125I-SCF using native SCF. 3T3 cells expressing WT (■), R381A (▼), R381A/E386A (♦), or a kinase negative Kit (▲) were treated with 125I-SCF in the presence of increasing concentrations of native SCF. The EC50 (ligand concentration that displaces 50% of $^{125}$I-SCF bound to c-Kit) of SCF towards WT Kit (1.1 nM) is comparable to the EC50 of SCF towards R381A (1.0 nM), R381A1E386A (0.8 nM) or the kinase negative Kit mutant (1.4 nM). FIG. 7C shows models for Kit and other RTK activation driven by soluble (left panel) or membrane anchored (right panel) SCF molecules expressed on the cell surface of a neighboring cell. SCF binding to the D1-D2-D3 ligand binding module brings the C-termini of the two bound Kit ectodomain monomers within of 75 Å from each other. The flexibility of the D3-D4 and D4-D5 hinges enable lateral D4-D4 and D5-D5 interactions that bring the C-termini of two neighboring ectodomains within 15 Å from each other. Consequently, the increased proximity and local concentration of Kit cytoplasmic domains leads to autophosphorylation of regulatory tyrosine residues in the kinase domain resulting in PTK activation. (Note that PTK activation is not drawn in the model.) Recruitment and activation of a complement of cell signaling molecules will proceed following phosphorylation of key tyrosines in the cytoplasmic domain. The model is based on free SCF structure, ligand-free Kit, SCF-Kit complex and Kit PTK structure (PDB entries 1QZJ, 1R01 and 1T45). Regions whose structures have not been determined were modeled using secondary structure prediction (green helices and black loops). SCF is colored in magenta, Kit ectodomain in blue and kit PTK is light blue.

FIG. 10A shows the color-coded conservation pattern of the SCF-Kit crystal structure complex. Cyan through maroon are used for labeling from variable to conserved amino acids. FIG. 10B shows a visualization of SCF and Kit by pulling away the two molecules from each other. Site I, Site II, and Site III and the D4-D4 interacting region (D4-D4 interface) are circled.

FIG. 11A shows a partial view of site-II of the 2:2 SCF-Kit complex with a 2Fo-Fc electron-density map drawn around Kit at 2σ level. Kit main chain is drawn in yellow tubes except for labeled side chains. FIG. 11B depicts the electron densities of the SCF-Kit interface, showing a partial view of free Kit with an experimental map drawn around Kit at 1.5σ level. Orientation and color code are the same as in FIG. 12A.

Shown are structures of pairs of Ig-like domains (A) D1 and D2, (B) D2 and D3, (C) D3 and D4 and (D) D4 and D5 in which the superimposed Ig-like domain in each pair is colored in blue and the second (not superimposed) Ig-like domain is colored in green for free ectodomain and in red for SCFbound ectodomain. These figures show that virtually no changes take place in the structures of each of the five individual Kit Ig-like domains upon SCF binding and that D1-D2-D3 function as a ligand binding unit poised towards SCF binding. By contrast, large rearrangements take place in D3-D4 and D4-D5 interfaces in SCF bound Kit.

FIGS. 13A-B depict the electrostatic surface potential of the SCF-Kit complex structure. FIG. 13A specifically shows the SCF-Kit 2:2 complex. FIG. 13B depicts the electrostatic surface potential of the SCF-Kit complex structure, specifically a visualization of the electrostatic surface potential of Kit after SCF was pulled away from the SCF-Kit 2:2 complex. Positively and negatively charged surfaces are colored in blue and red, respectively. The SCF binding region and the D4-D4 interface are circled.

Figure 14:
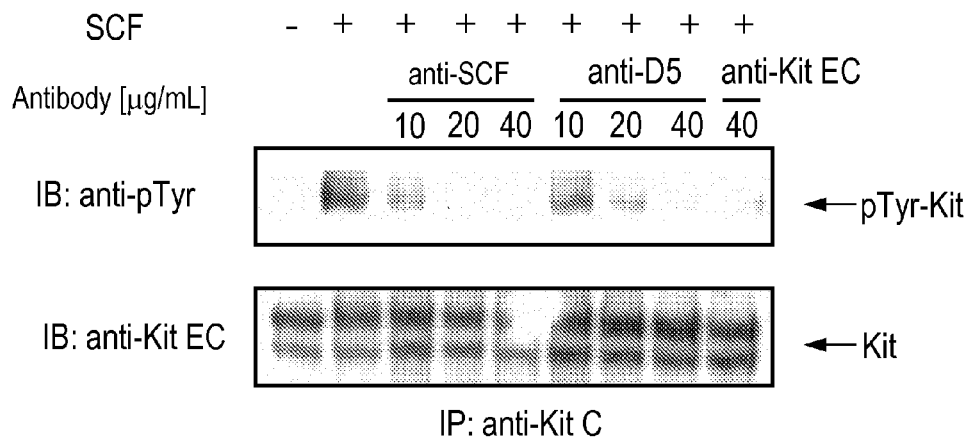

FIG. 14 depicts the inhibition of SCF-induced Kit activation by anti Kit-D5 antibodies. 3T3 cells expressing Kit were incubated with increasing concentrations of anti-Kit D5 (directed against fifth Ig-like domain of Kit) or as controls with anti-SCF (directed against the SCF ligand), or anti-Kit ectodomain (directed against the entire Kit ectodomain).

Figure 15:
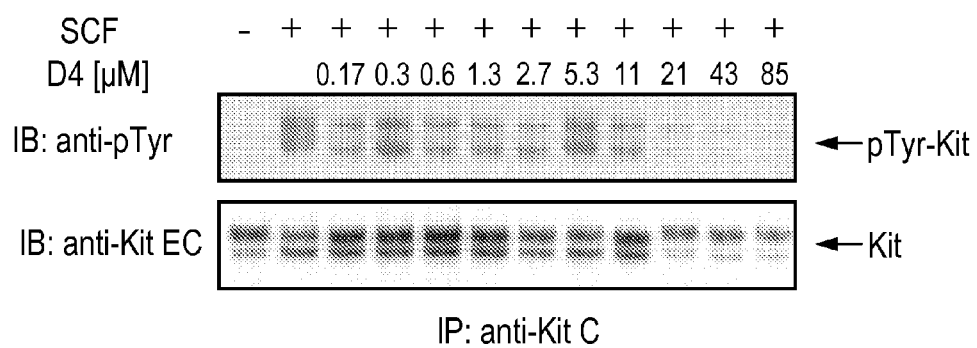

FIG. 15 depicts the inhibition of SCF induced Kit activation using recombinant Kit D4. 3T3 cells expressing Kit were incubated with increasing concentrations of recombinant Kit-D4 for 10 minutes at room temperature followed by 10 minutes SCF stimulation.

Figure 16A:
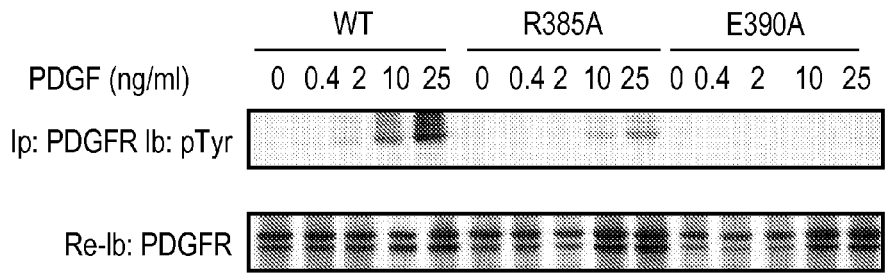

FIG. 16A demonstrates that PDGF-induced PDGFR activation is prevented by point mutations in D4. PDGFR−/− MEFs expressing WT PDGFR or D4 mutants (R385A and E390A) were serum starved overnight and stimulated with the indicated concentrations of PDGF BB for 5 minutes. Cell lysates were immunoprecipitated with anti-PDGFR antibodies, followed by SDS-PAGE and immunoblotting with anti-phosphotyrosine antibody 4G10. Membranes were stripped off, and re-blotted with anti-flag tag antibodies to determine total PDGFR levels.

Figure 16B:
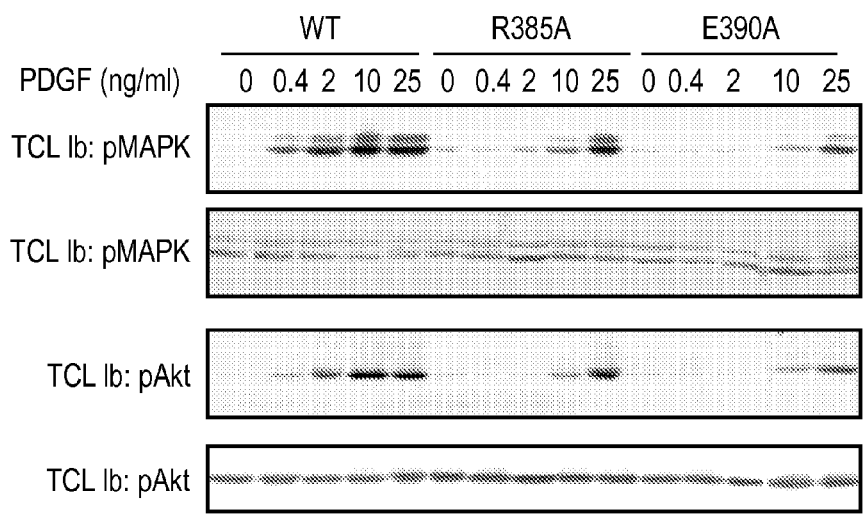

FIG. 16B demonstrates that signaling via PDGFR is prevented by point mutations in D4. PDGFR−/− MEFs expressing WT PDGFR and D4 mutants (R385A and E390A) were serum starved overnight and stimulated with indicated concentrations of PDGF BB for 5 minutes at 23 C.°. Equal amounts of total cell lysates (TCL) were subjected to SDS-PAGE and analyzed by immunoblotting with anti-phospho-MAPK, MAPK, phospho-Akt and Akt, respectively. This experiment shows that both MAPK response and Akt activation are prevented by point mutations in D4.

Figure 16C:
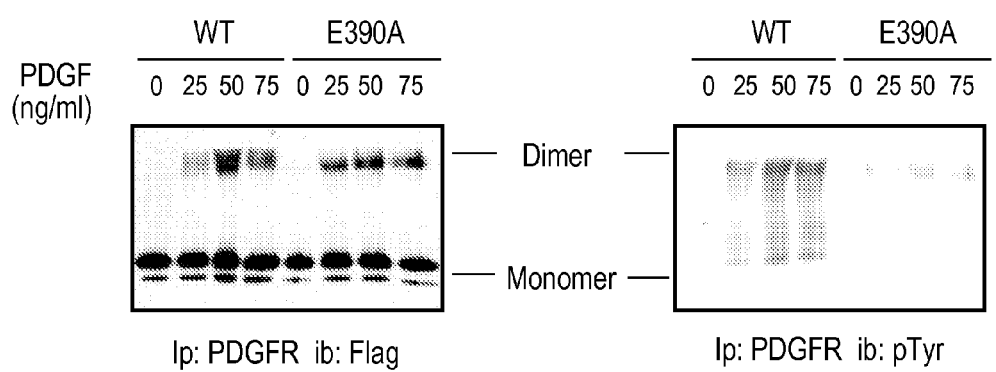

FIG. 16C demonstrates that point mutations in D4 that prevent PDGFR activation do not interfere with PDGF-induced PDGFR dimerization. PDGFR−/− MEFs expression WT or the E390A mutant were serum starved overnight, followed by incubation with the indicated amount of PDGF in DMEM/50 mM Hepes buffer (pH7.4) at 4° C. for 90 minutes. After removing unbound ligand, cells were incubated with 0.5 mM disuccinimidyl suberate (DSS) in PBS for 30 minutes. Lysates of unstimulated or stimulated cells were subjected to immunoprecipitation with anti-PDGFR antibodies followed by SDS-PAGE analysis and by immunoblotting with anti-flag antibodies (left panel) or anti-pTyr antibodies (right panel).

Figure 17A:
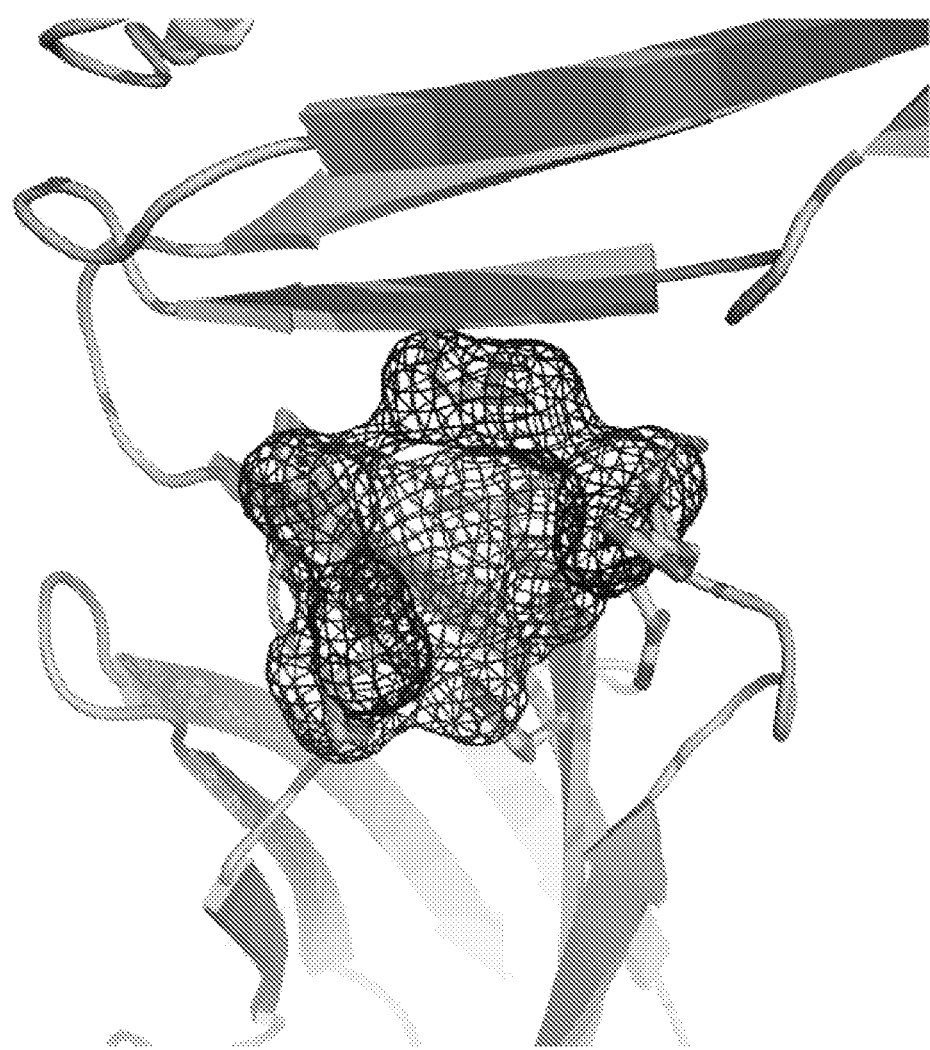
Figure 17B:
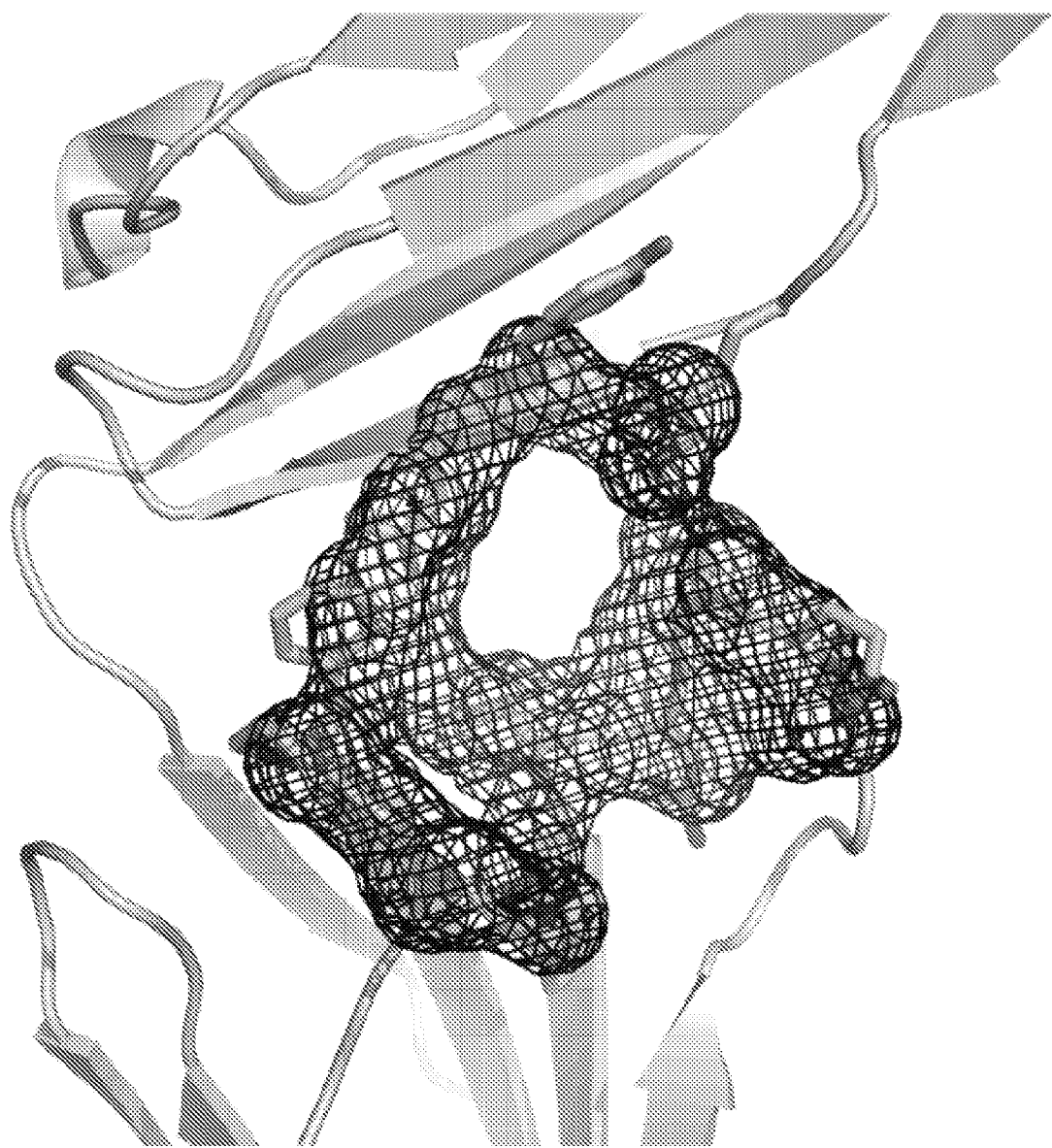

FIG. 17 shows cavities in the D3-D4 hinge region. Several cavities are scattered on the D3-D4 interface in the ectodomain monomer structure. The amino acids involved in defining the cavities are summarized in Table 4 (below). Upon formation of homotypic interaction between two Kit receptors, the D3-D4 hinge region is altered resulting in formation of a shallow cavity created by the following residues: K218, S220, Y221, L222 from D3 and F340, P341, K342, N367, E368, 5369, N370, I371, Y373 from D4. FIG. 17 shows a ribbon diagram of the D3-D4 hinge region of unoccupied monomers (A) and SCF-bound dimers (B) and a mesh representation of the D3-D4 pocket.

Figure 18A:
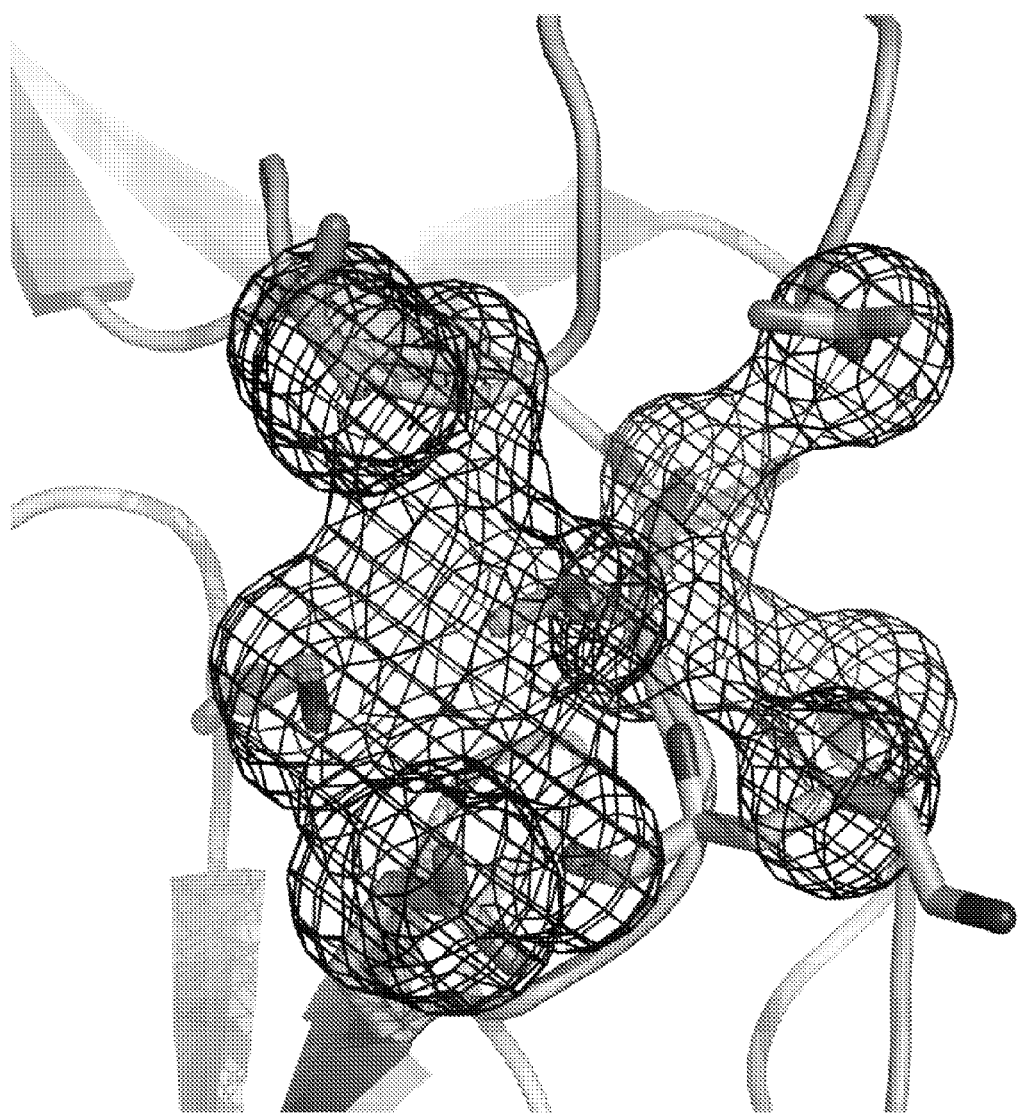
Figure 18B:
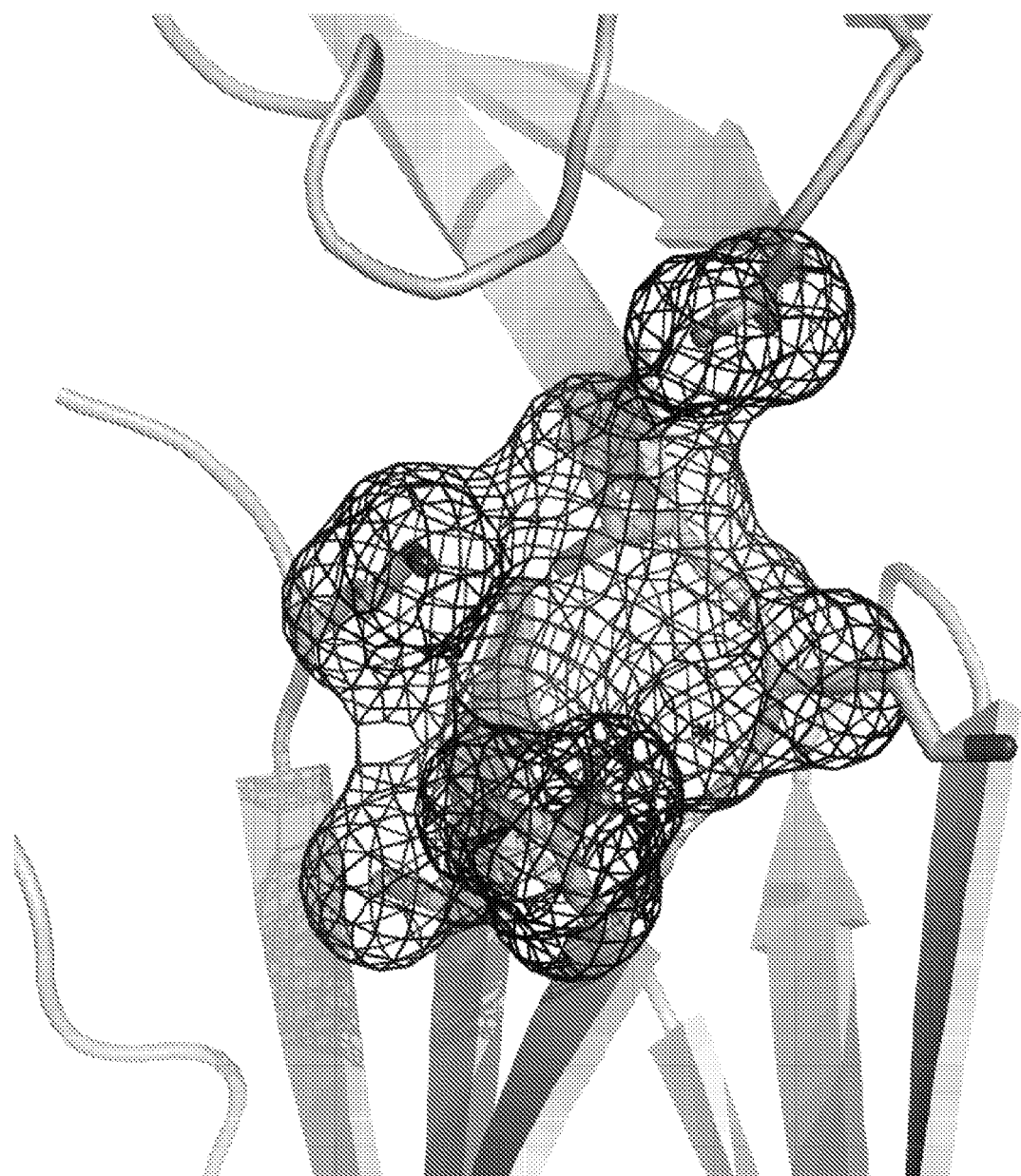

FIG. 18 shows cavities in the D4-D5 hinge region. A small cavity is formed by the AB loop and the EF loop of D4, the D4-D5 connecting linker and part of DE loop and FG loop of the D5 of Kit monomer. Residues defining the cavities are summarized in Table 4 (below). The shape and size of the cavities are changed in the Kit ectodomain dimeric structure. The major cavities formed by the EF loop and strand G of D4, the D4-D5 linker and strand B and DE loop of D5 are located beneath the EF loop of D4; a region critical for formation of the D4 homotypic interface. Note that the DE loop of D5 that is located close to the cavities may have higher flexibility as revealed by the lower quality of electron densities from both unbound and occupied Kit structures. FIG. 18 shows a ribbon diagram of unoccupied monomers (A) and SCF-dimers (B) and a mesh representation of a shallow cavity around the D4-D5 hinge region.

Figure 19A:
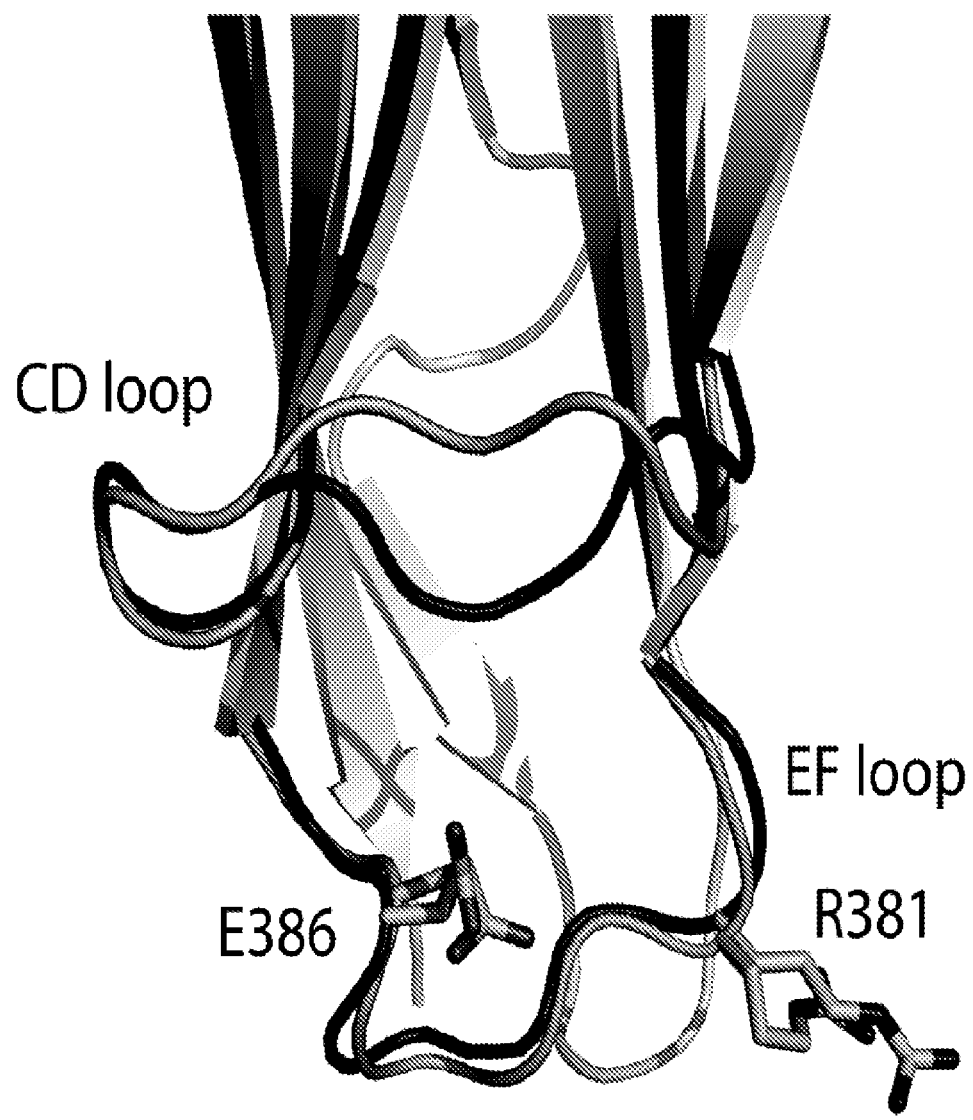
Figure 19B:
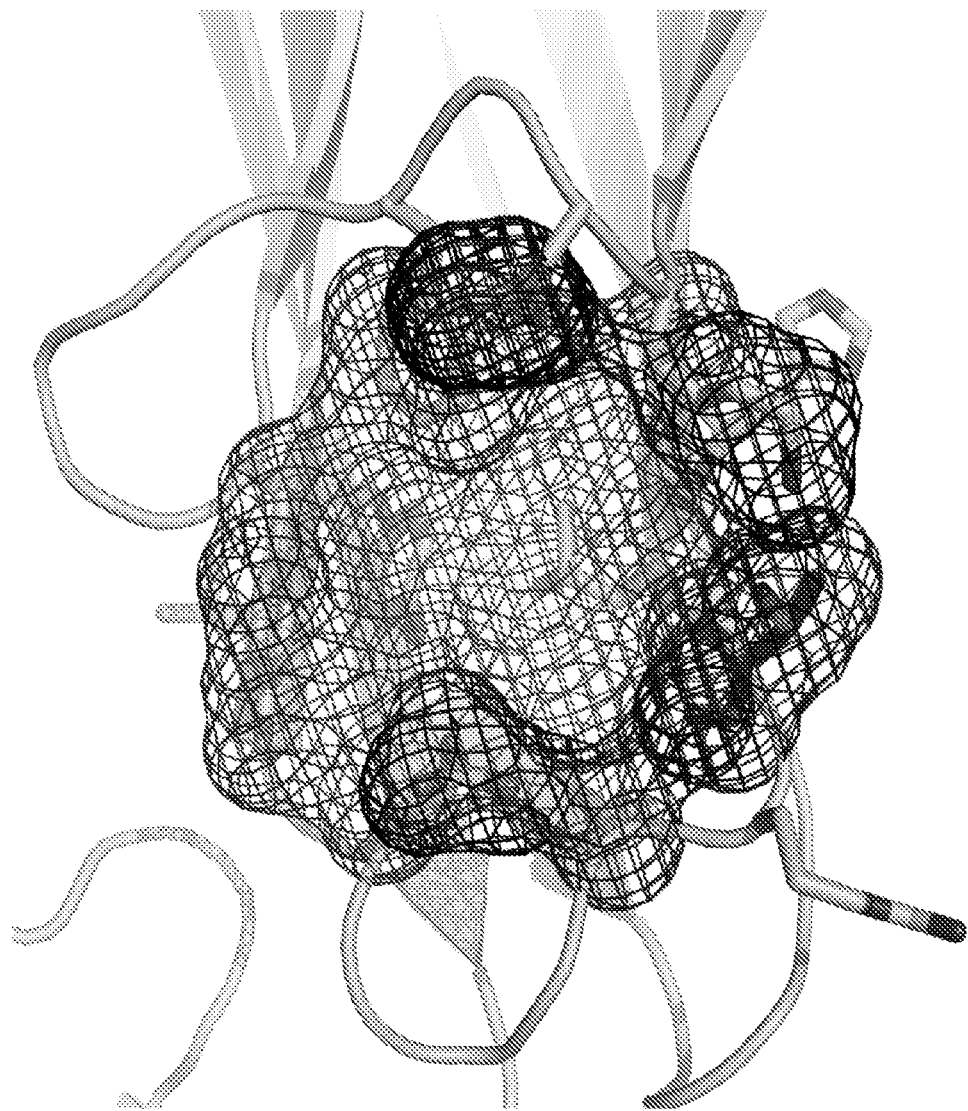
Figure 19C:
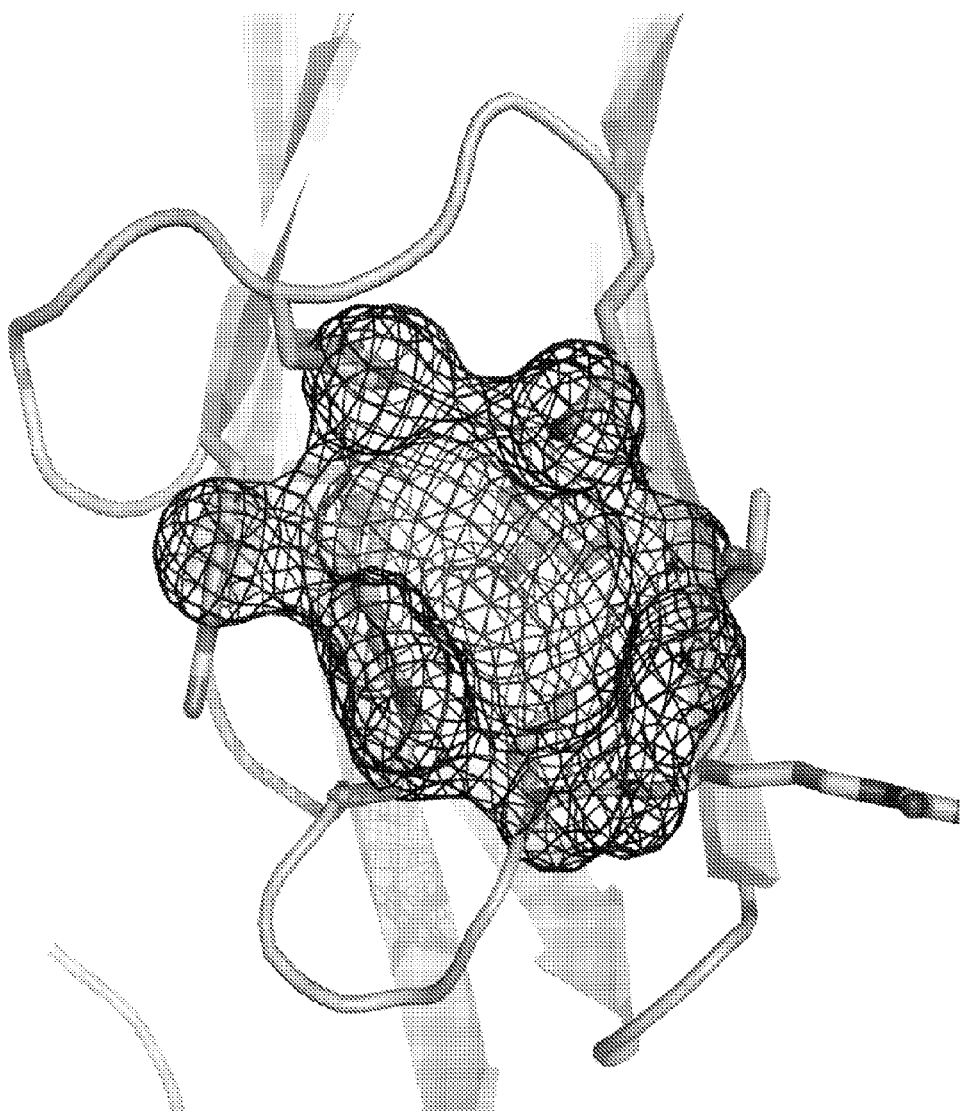

FIG. 19 shows a cavity at the region mediating D4 homotypic interactions. A concave surface formed by the CD loop and EF loop of Kit D4 is located right above the D4 homotypic interface. Residues, Y350, R353, F355, K358, L379, T380, R381, L382, E386 and T390 from D4 provide a surface area of approximately 130 A$^2$ for the concave surface in the ectodomain dimeric structure. The side chain of Glu386 that plays an important role in the D4 homotypic interface projects toward the center of the surface. A characteristic feature of the concave surface is a small hydrophobic patch surrounded by charged residues (Glu386 and Lys358). The size and accessibility of the surface is altered upon homotypic D4:D4 interactions with changes taking place in the conformation of the CD loop that becomes folded upwards to the top of the domain. Residues involved in the formation of a concave surface are summarized in Table 4 (below). Panel A in the figure below (FIG. 19A) shows a ribbon diagram of the unoccupied D4 domain of Kit (gold) overlaid onto the ligand-occupied Kit D4 (not shown) with different conformations of the CD and EF loops between ligand-occupied (green) and unoccupied ectodomain structures (red). The critical residues for the D4:D4 interactions are shown in a stick model format. Panels B and C show ribbon diagrams of unoccupied Kit (FIG. 19B) and SCF-occupied Kit structures (FIG. 19C) and a mesh presentation of shallow cavity above D4 homotypic interface.

Figure 20A:
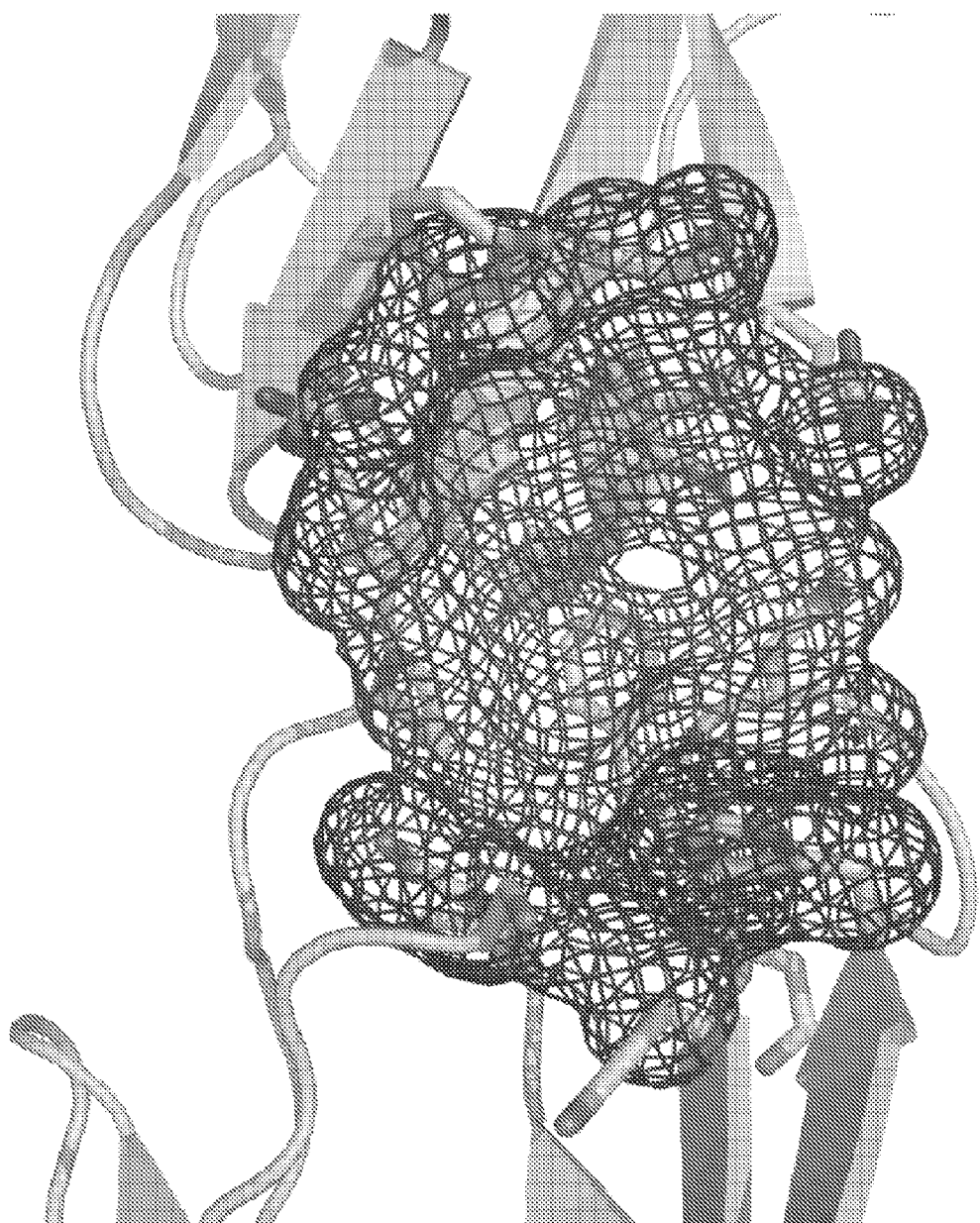
Figure 20B:
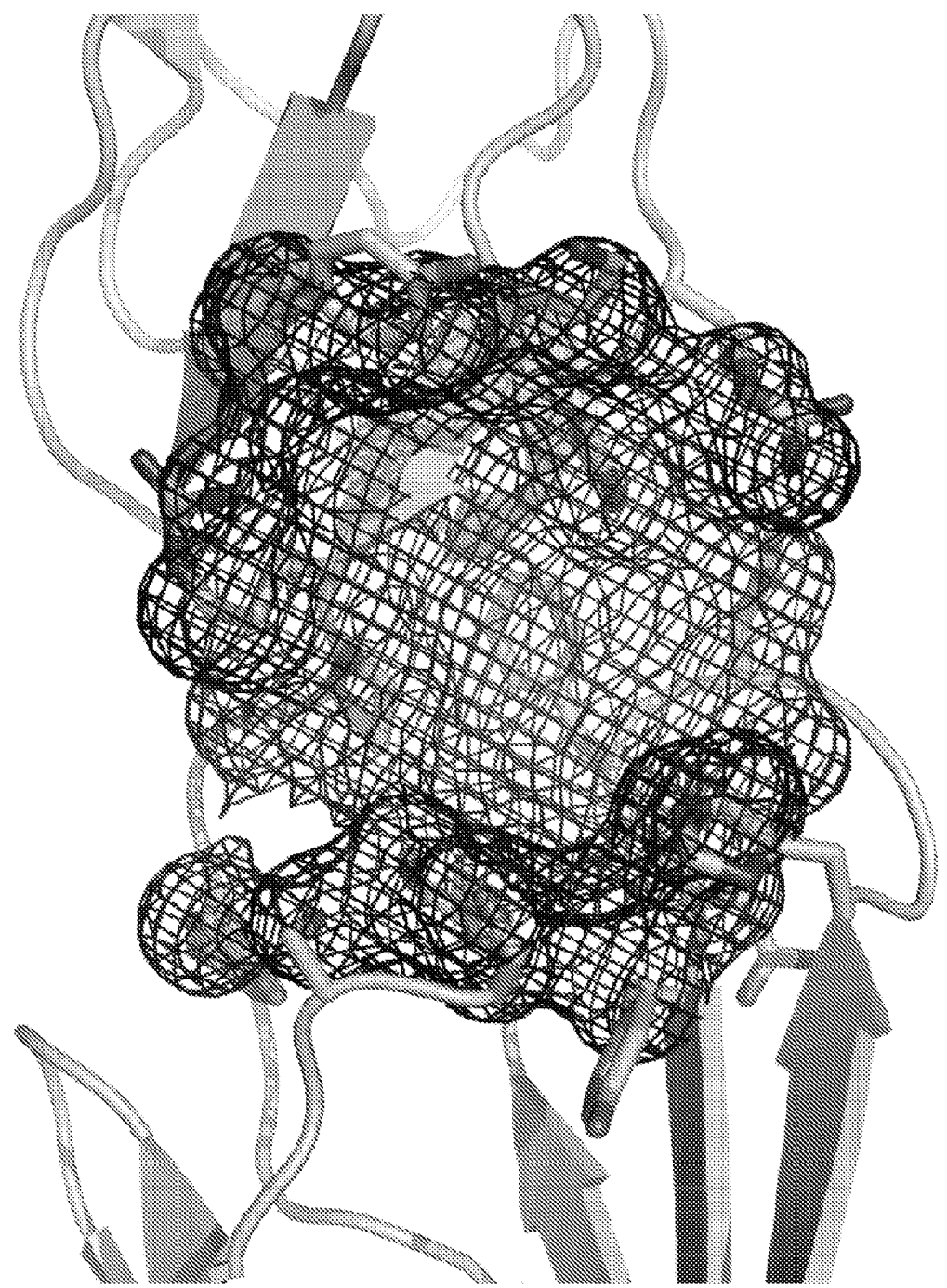

FIG. 20 shows a concave surface at the ligand-binding D2 and D3 regions. A shallow concave surface is located on part of the ligand-binding surface of D2 and D3. Residues involved in the small pocket are Y125, G126, H180, R181, K203, V204, R205, P206 and F208 from D2 and V238, 5239, 5240, 5241, H263, G265, D266, F267, N268 and Y269 from D3. The pocket is created by a small hydrophobic patch surrounded by hydrophilic residues. There is no major alteration between unoccupied and SCF-occupied Kit structures with an overall buried surface area of approximately 500 A$^2$. Figures A and B show ribbon diagrams of unoccupied Kit (A) and SCF-bound Kit (B) and a mesh presentation of the D2-D3 pocket.

Figure 21A:
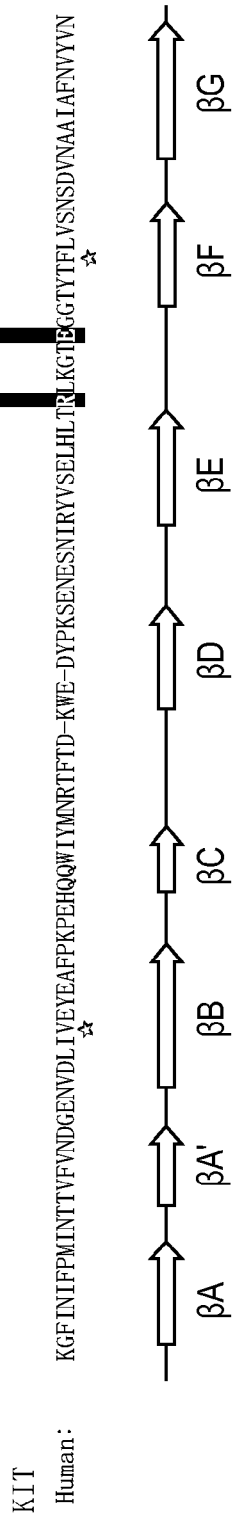
Figure 21B:
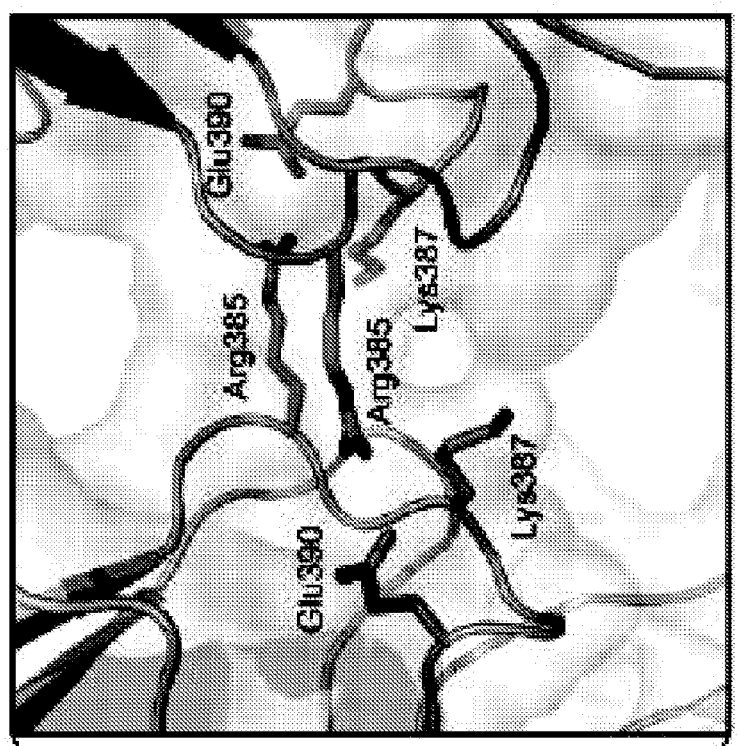
Figure 21B:
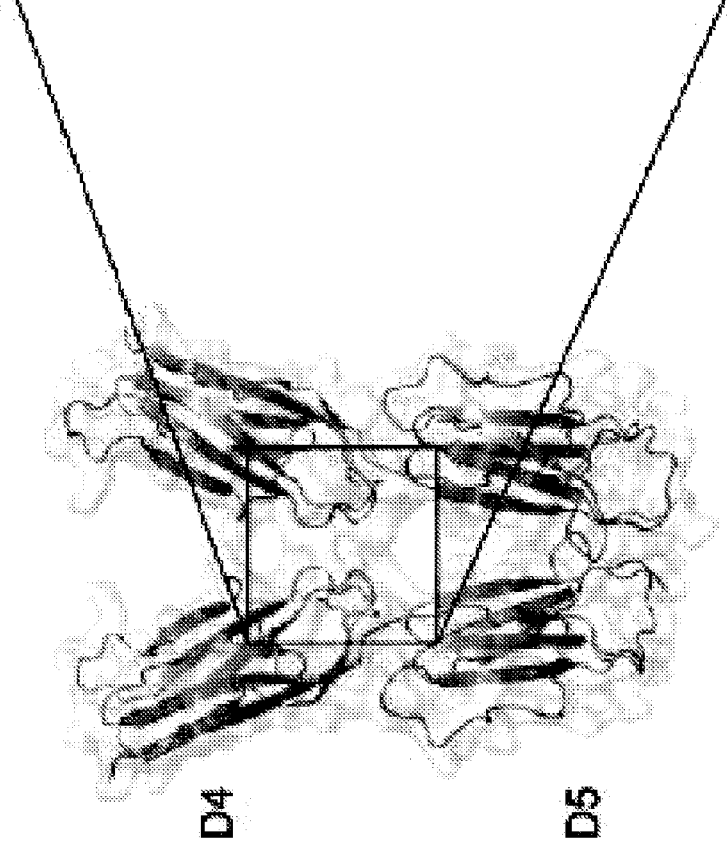

FIG. 21 depicts a structure-based sequence analysis and homology modeling of membrane proximal region of PDGF receptors. FIG. 21A depicts an alignment of amino acid sequences (SEQ ID NOS 148-157, respectively, in order of appearance) of D4 of PDGFRα, PDGFRβ, and Kit. The amino acids of key residues of the IgSF fold and the core residues of the Ig-fold of D4 of human Kit structure are colored in red and green, correspondingly. The two key basic and acidic residues responsible for D4 homotypic interaction are boxed in blue and red, respectively. Positions corresponding to the conserved disulfide bond-forming cysteine residues on the Ig-like domain (B5 and F5) are marked by asterisks. β-strands are labeled by arrows below the Kit sequence. Secondary structure elements are marked according to the IgSF nomenclature. FIG. 21B depicts a model of the membrane proximal region of extracellular domain of PDGFR. The membrane proximal region of PDGFRβ ectodomain is colored in white and shown as ribbons with a transparent molecular surface (D4 colored in orange, and D5 colored in pink; left panel). A closer view (right panel) of the D4-D4 interface of two neighboring PDGFRβ molecules demonstrates that interactions between D4 are mediated by residues Arg385 and Glu390 projected from two adjacent EF loop. Key amino acids are labeled and shown as a stick model.

Figure 22A:
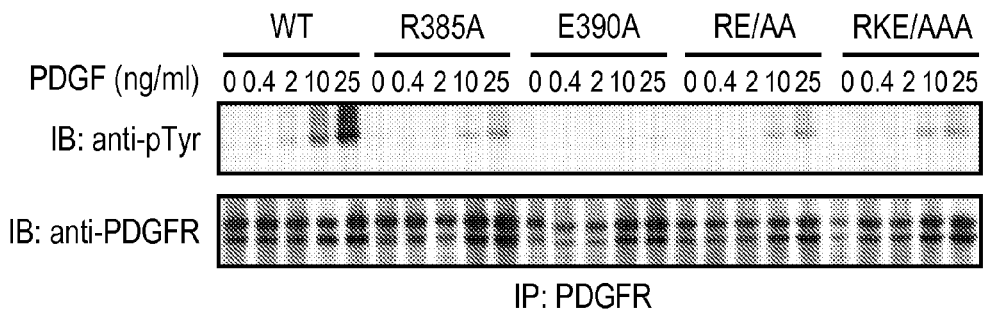
Figure 22B:
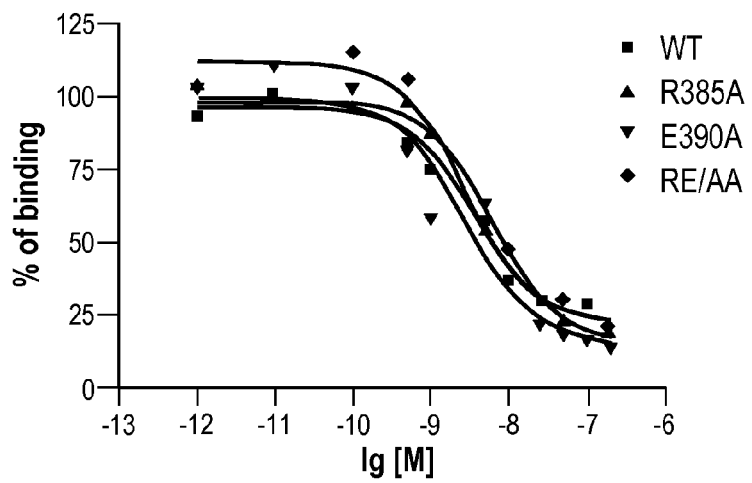
Figure 22C:
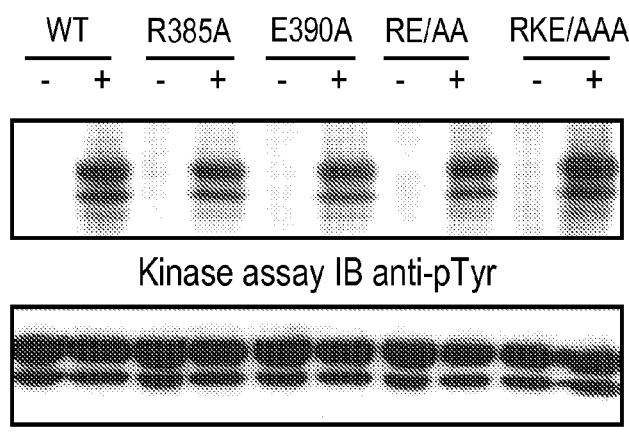

FIG. 22 depicts the results of experiments demonstrating that PDGF-induced PDGFR activation is compromised by mutations in D4. FIG. 22A shows the results of an experiment demonstrating that the PDGF-induced tyrosine autophosphorylation of PDGFRβ is strongly compromised in cells expressing the E390A, R385A, RE/AA, and RKE/AAA mutants of PDGFRβ. FIG. 22B is a graph showing the displacement curves of wild type and mutant PDGFRβs. The IC50 values were determined by curve fitting with Prism4. FIG. 22C depicts the results from an immunoblot demonstrating that the R385A, E390A or RE/AA mutations do not influence the intrinsic tyrosine kinase activity of PDGFR.

Figure 23:
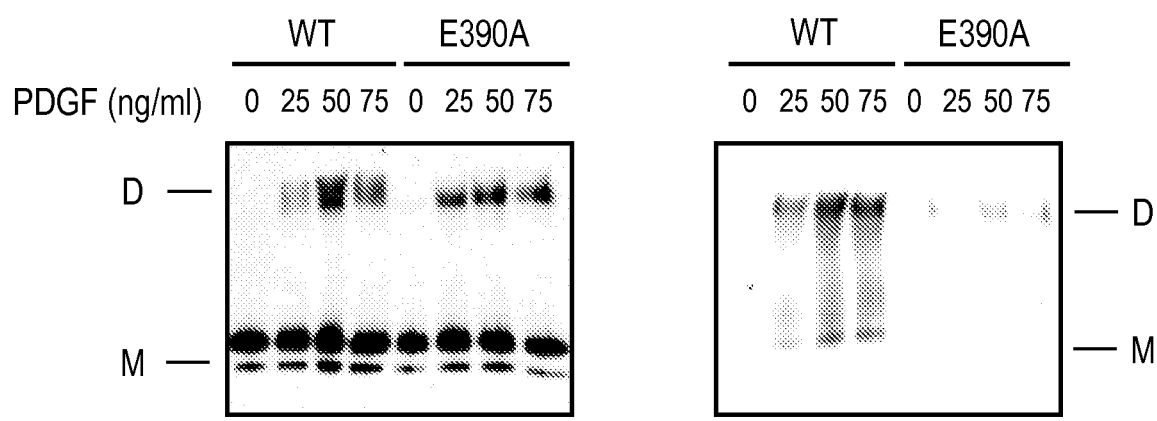

FIG. 23 depicts the results from an immunoprecipitation experiment demonstrating that PDGF-stimulated PDGFRβ mutated in the D4 domain are expressed on the cell surface in the form of inactive dimers. Cell lysates were immunoprecipitated with anti-PDGFR antibodies and immunopellees were analyzed by SDS-PAGE and immunoblotted with anti-flag antibodies (left panel) and antiphosphotyrosine antibodies (right panel) respectively.

FIG. 24 depicts the results from an immunoprecipitation experiment demonstrating that PDGF-induced cellular responses are compromised by mutations in the PDGFRβ D4 mutant.

Figure 25:
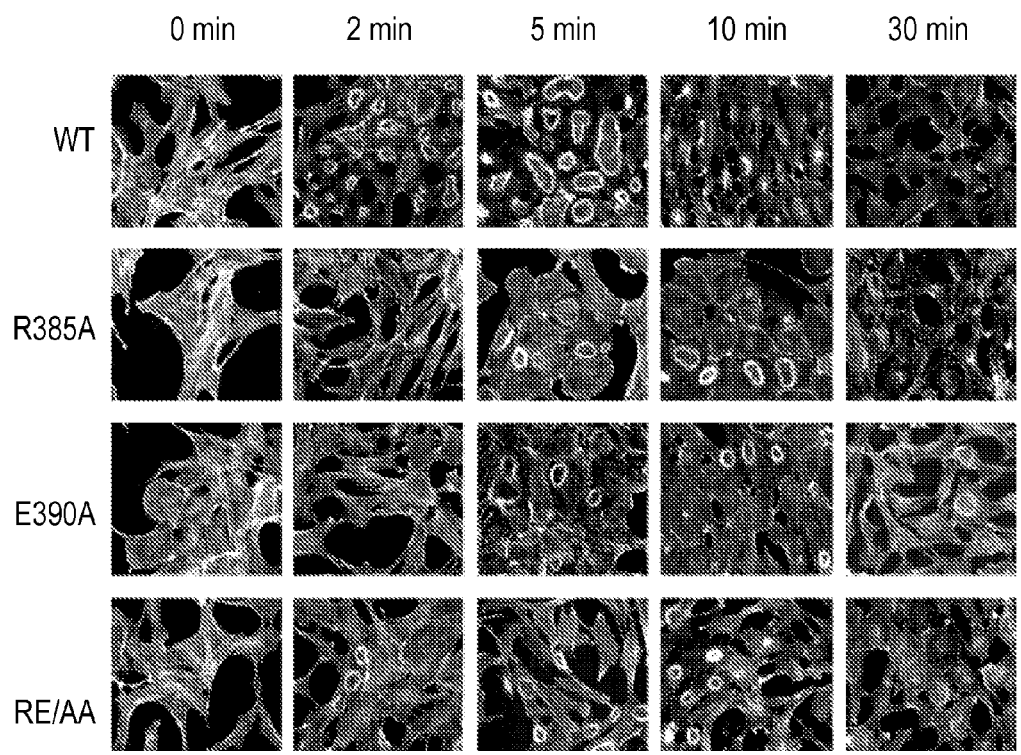
Figure 25:
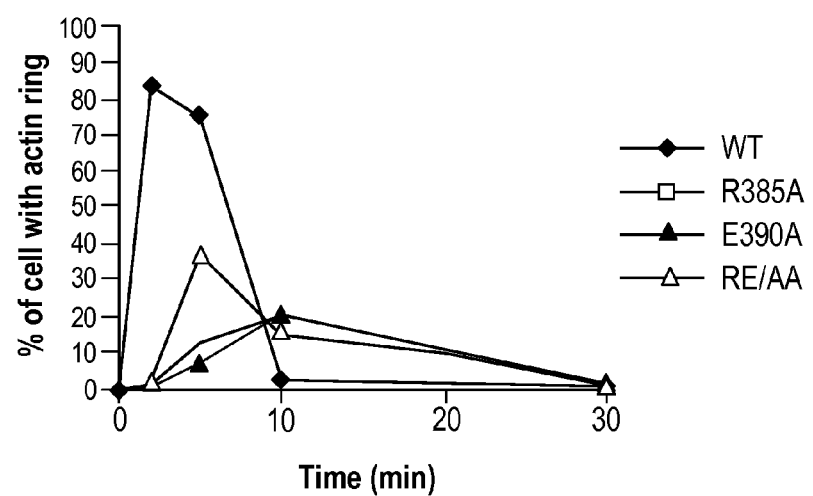

FIG. 25 depicts the results from an experiment demonstrating that PDGF stimulation of actin ring formation is compromised in MEFs expressing PDGFR D4 mutants. While approximately 83% of MEFs expressing WT PDGFR exhibited circular actin ring formation, only 5% of PDGFR D4 mutant cells showed similar circular actin ring formation after 2 minutes stimulation with 50 ng/ml of PDGF. Furthermore, the transient circular actin ring formation that peaks in MEFs expressing WT PDGFR after 2-5 minutes of PDGF stimulation was weakly detected in cells expressing the R385A, E390A or the RE/AA PDGFR mutants.

Figure 26A:
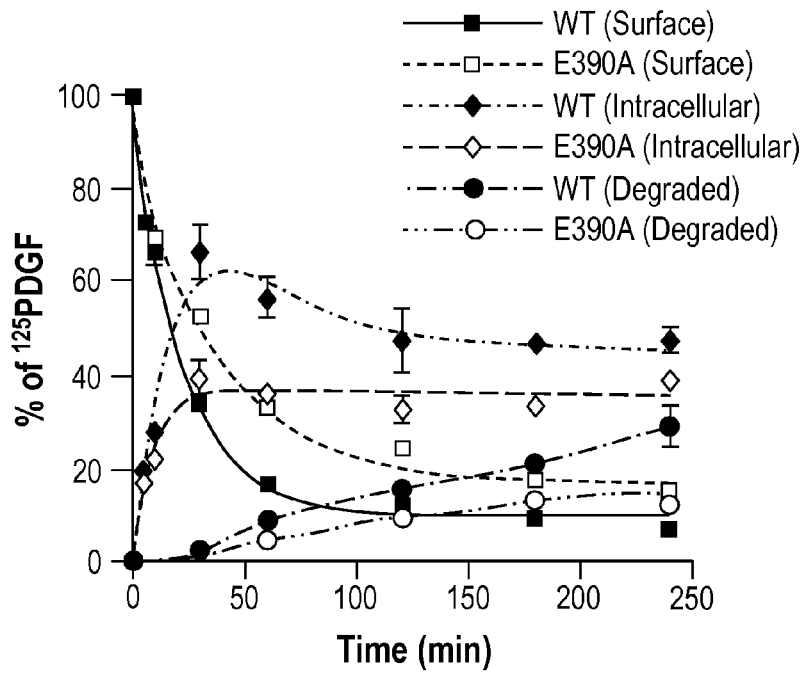
Figure 26B:
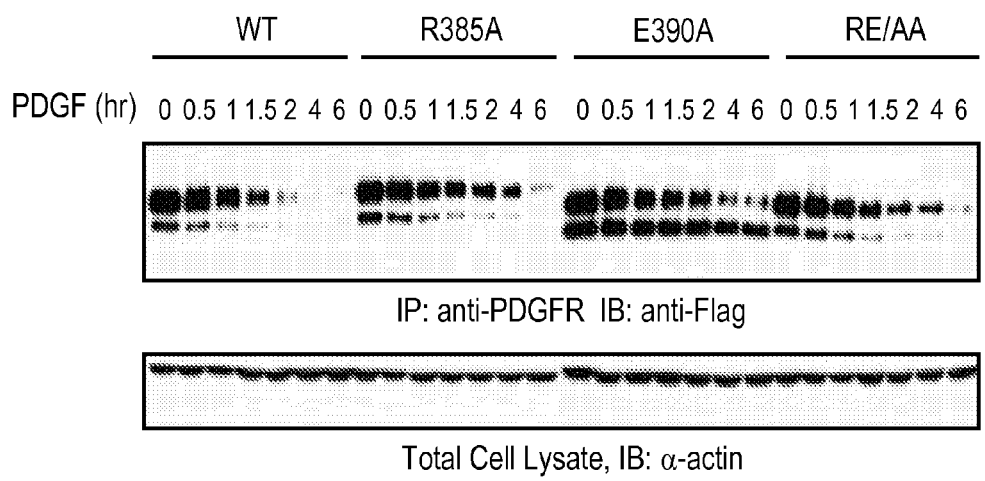
Figure 26C:
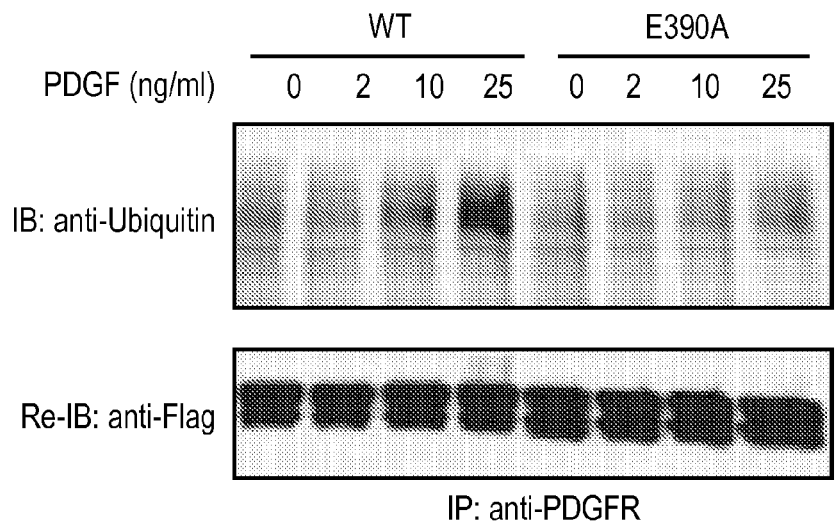

FIG. 26 depicts the results of experiments demonstrating that PDGFR internalization and ubiquitin-mediated PDGFR degradation are compromised by mutations in D4 of PDGFR. FIG. 26A is a graph demonstrating that the kinetics of internalization of $^{125}$I labeled PDGF bound to MEFs expressing WT PDGFR is much faster than the kinetics of internalization of $^{125}$I labeled PDGF bound to cells expressing the E390A, R385A or the RE/AA PDGFR. FIG. 26B shows that the kinetics of degradation of R385A, E390A or the RE/AA PDGFR mutants was strongly attenuated; and while half of WT PDGFRs were degraded within 1.5 hour of PDGF stimulation, the half-life for PDGFR D4 mutants was extended to approximately 4 to 6 hours. FIG. 26C depicts an experiment showing that PDGF induced stimulation of ubiquitination of the E390A PDGFR was also strongly reduced as compared to WT PDGFR under similar conditions.

Figure 27:
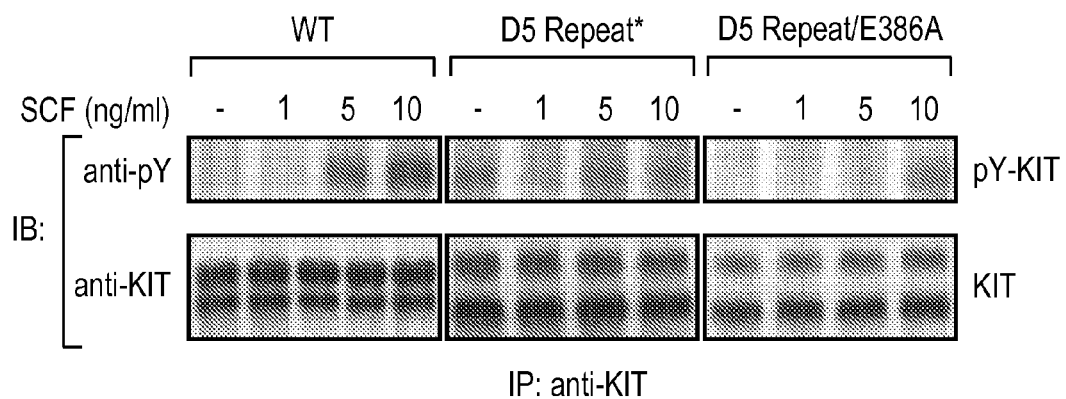

FIG. 27 depicts the results of experiments demonstrating that disruption of the D4 interface blocks oncogenic mutations in KIT. SCF stimulation of wild type KIT leads to enhancement of KIT activation revealed by enhanced tyrosine autophosphorylation of KIT. The experiment further shows that an oncogenic D5-Repeat mutant of KIT is constitutively tyrosine autophosphorylated. By contrast, the D5-Repeat/E386A mutant blocks constitutive tyrosine autophosphorylation of KIT mediated by the oncogenic D5-repeat mutation.

Figure 28:
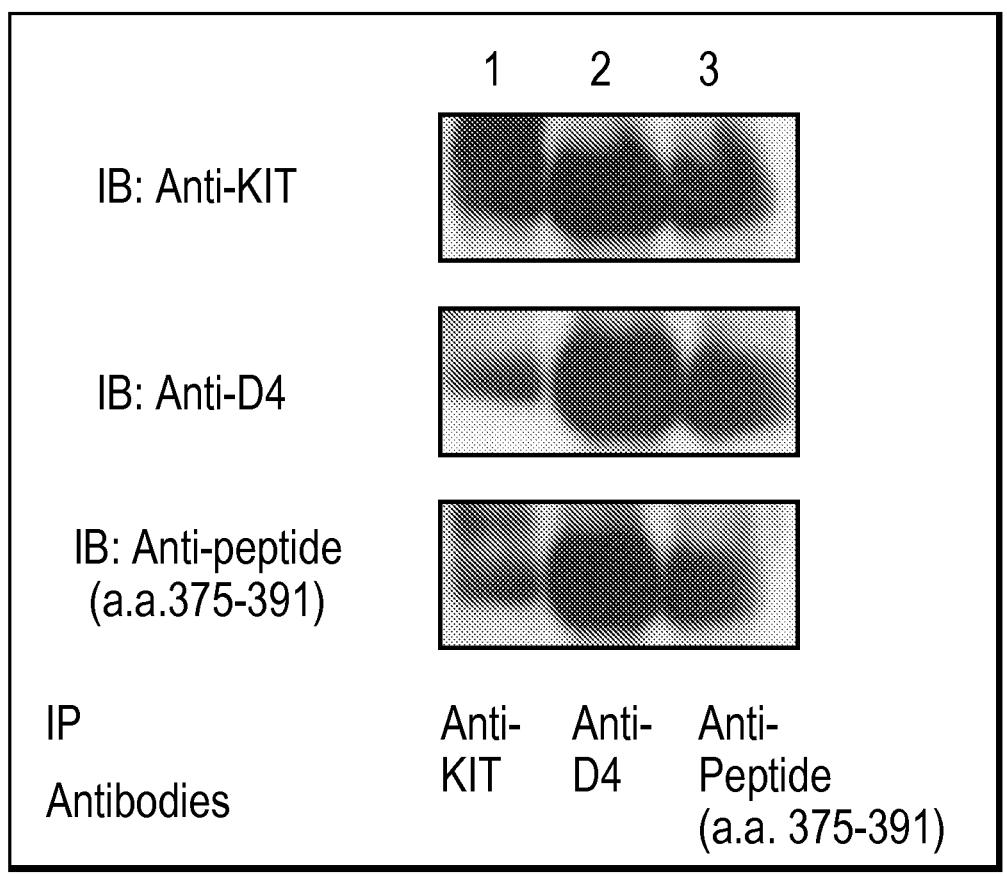

FIG. 28 depicts the results of an immunoblot experiment demonstrating that antibodies directed against a peptide corresponding to the homotypic interaction motif of KIT-D4, recognize the full length KIT receptor.

DETAILED DESCRIPTION OF THE INVENTION

The present invention provides moieties, e.g., antibodies or antigen binding portions thereof, small molecules, peptidic molecules, aptamers, and adnectins, that bind to the ectodomain, e.g., an Ig-like domain or a hinge between Ig-like domains, of a human receptor tyrosine kinase, e.g., a type III or type V receptor tyrosine kinase, such as the human Kit (also known as the SCF receptor) or PDGFRα or PDGFRβ. The moieties of the present invention lock the ectodomain of the receptor tyrosine kinase in an inactive state thereby inhibiting the activity of the receptor tyrosine kinase. In one embodiment of the invention, the moiety locks the ectodomain of the receptor tyrosine kinase to a monomeric state. In another embodiment of the invention, the moiety allows the ectodomain of the receptor tyrosine kinase to dimerize but affects the positioning, orientation and/or distance between the Ig-like domains of the two monomers (e.g., the D4-D4 or D5-D5 domains of a type III receptor tyrosine kinase or the D7-D7 domains of a type V receptor tyrosine kinase), thereby inhibiting the activity of the receptor tyrosine kinase. In other words, the moiety may allow ligand induced dimerization of the receptor tyrosine kinase ectodomains, but affect the positioning of the two ectodomains at the cell surface interface or alter or prevent conformational changes in the receptor tyrosine kinases, thereby inhibiting the activity of the receptor tyrosine kinase (e.g., inhibiting receptor internalization and/or inhibiting tyrosine autophosphorylation of the receptor and/or inhibiting the ability of the receptor to activate a downstream signaling pathway). The present invention is based, at least in part, on the deciphering of the crystal structures of the entire ectodomain of the receptor tyrosine kinase Kit both in the monomeric, as well as the ligand induced homodimeric forms. The deciphering of these crystal structures has allowed for the identification of epitopes, e.g., conformational epitopes, which the moieties of the invention may target.

As used herein, the term "moiety" is intended to include any moiety binds to the ectodomain, e.g., an Ig-like domain of a receptor tyrosine kinase, where the moiety locks the ectodomain of the receptor tyrosine kinase in an inactive state, e.g., a monomeric state, thereby antagonizing the activity of the receptor tyrosine kinase. The moiety can be an isolated antibody, or antigen binding portion thereof; a small molecule; a peptidic molecule (e.g., a peptidic molecule designed based on the structure of an Ig-like domain of a receptor tyrosine kinase); an aptamer or an adnectin. In some aspects, the moiety binds to the hinge regions connecting Ig-like domains of the receptor tyrosine kinase (e.g., the D3-D4 or the D4-D5 hinge regions of Type III RTKs).

In some embodiments, the moiety will bind to specific sequences of the human Kit receptor, for example, residues 309-413, residues 410-519, $^{381}$Arg and $^{386}$Glu, or $^{418}$Tyr and $^{505}$Asn of the human Kit. Residues 309-413 comprise the D4 domain and residues 410-519 comprise the D5 domain of the human Kit and are shown herein to be critical to Kit receptor dimerization. Residues $^{381}$Arg and $^{386}$Glu are residues in the D4 domain of Kit which are shown herein to be important for the non-covalent association of the D4 domain and, hence, the dimerization of the receptor. Similarly, residues $^{418}$Tyr and $^{505}$Asn are residues in the D5 domain of Kit which are shown herein to be important for dimerization of the receptor. One of skill in the art will appreciate that a moiety which specifically binds to the aforementioned residues can antagonize the activity of the receptor by, for example, preventing dimerization of the two monomeric Kit molecules.

In additional embodiments, the moiety binds to a mutated amino acid residue in the human Kit wherein the amino acid residue is at least one of $^{417}$Thr, $^{418}$Tyr, $^{419}$Asp, $^{421}$Leu, $^{420}$Arg, $^{503}$Tyr, or $^{502}$Ala.

In a preferred embodiment, moieties of the invention bind to one or more residues in the Kit receptor which make up the small cavities or pockets described in Table 4 (below). For example, moieties of the invention may bind to one or more of the following residues in the D3-D4 hinge region of the Kit receptor: K218, S220, Y221, L222 from the D3 domain and F340, P341, K342, N367, E368, S369, N370, I371, Y373 from the D4 domain. The moieties of the invention may also bind to one or more of the following residues which make up a concave surface in the D4 domain of the Kit receptor: Y350, R353, F355, K358, L379, T380, R381, L382, E386 and T390. In another embodiment, moieties of the invention bind to one or more of the following residues which form a pocket in the D2-D3 hinge region of the Kit receptor: Y125, G126, H180, R181, K203, V204, R205, P206 and F208 from the D2 domain and V238, S239, S240, S241, H263, G265, D266, F267, N268 and Y269 from the D3 domain.

Thus, in some embodiments, a moiety of the invention may bind to contiguous or non-contiguous amino acid residues and function as a molecular wedge that prevents the motion required for positioning of the membrane proximal region of the RTK at a distance and orientation that enables tyrosine kinase activation. The moieties of the invention may also act to prevent homotypic or heterotypic D4 or D5 receptor interactions or destabilize the ligand-receptor interaction site. In some preferred embodiments, moieties of the invention bind to one or more of the following residues on the Kit receptor: Y125, G126, H180, R181, K203, V204, R205, P206, P206, F208, K127, A207, V238, S239, S240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F355, G311, G384, G387, G388, I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432. One of skill in the art will appreciate that, in some embodiments, moieties of the invention may be easily targeted to the corresponding residues in other type III RTKs, e.g., those residues that form similar pockets or cavities or those in the same position by structural alignment or sequence alignment.

In a specific embodiment, a moiety of the invention binds to a conformational epitope or a discontinuous epitope on a type III RTK. The conformational or discontinuous epitope may be composed of two or more residues from the D3, D4, and/or D5 domain or the D4-D5 or D3-D4 hinge regions from a type III RTK, e.g., the human Kit receptor or the PDGF receptor. For example, the conformational or discontinuous epitope may be composed of two or more of the residues listed in Table 4.

In a particular embodiment, a moiety of the invention binds to a conformational epitope composed of 2 or more amino acids selected from the group consisting of Y125, H180, R181, K203, V204, R205, P206, V238, S239, S240, H263, G265, D266, F267, N268, and Y269. In similar embodiments, a moiety of the invention may bind to a conformational epitope composed of 2 or more amino acids selected from one of the following groups of amino acids: P206, F208, V238, and S239; K127, A207, F208, and T295; L222, A339, F340, K342, E368, S369, N370, I371, and Y373; L222, L223, E306, V308, F312, E338, F340, and I371; R224, V308, K310, G311, F340, P341, and D398; K218, A219, S220, N367, E368, and S369; K218, A220, E368, and S369; G384, T385, T411, K412, E414, and K471; Y408, F433, G470, K471, and L472; F324, V325, N326, and N410; D327, N410, T411, K412, and V497; G384, G387, V409, and K471; L382, G387, V407, and V409; Y125, G126, H180, R181, K203, V204, R205, P206, F208, V238, S239, S240, S241, H263, G265, D266, F267, N268, and Y269; P206, F208, V238, and S239; K218, S220, Y221, L222, F340, P341, K342, N367, E368, S369, N370, I371, and Y373; G384, G387, G388, Y408, V409, T411, F433, F469, G470, and K471; D327, T411, K412, E414, A431, G432, and K471; Y350, F355, K358, L379, T380, R381, L382, E386, and T390; Y350, 8353, and F355. As indicated above, the moieties of the invention may bind to all of the amino acid residues forming a pocket or a cavity identified in Table 4 or they may bind to a subset of the residues forming the pocket or the cavity. It is to be understood that, in certain embodiments, when reference is made to a moiety of the invention binding to an epitope, e.g., a conformational epitope, the intention is for the moiety to bind only to those specific residues that make up the epitope (e.g., the pocket or cavity identified in Table 4) and not other residues in the linear amino acid sequence of the receptor.

In a further embodiment, a moiety of the invention binds to a conformational epitope wherein said epitope is composed of two or more amino acid residues selected from the peptides listed in Table 5. In a specific embodiment, the conformational epitope is composed of one or more amino acid residues selected from a first peptide and one or more amino acid residues selected from a second peptide, wherein the first and second peptides are selected from the group of peptides listed in Table 5. As such, a moiety of the invention may bind a conformational epitope wherein the said first and second peptide groups from Table 5 are as follows: Ala219-Leu222 and Thr304-Val308; Asp309-Gly311 and Arg224-Gly226; Thr303-Glu306 and Ala219-Leu222; Asn367-Asn370 and Ser217-Tyr221; Ala339-Pro343 and Asn396-Val399; Ala339-Pro343 and Glu368-Arg372; Lys358-Tyr362 and Val374-His378; Asp357-Glu360 and Leu377-Thr380; Met351-Glu360 and His378-Thr389; His378-Thr389 and Val323-Asp332; Val409-Ile415 and Ala493-Thr500; Val409-Ile415 and Ala431-Thr437; Val409-Ile415 and Phe469-Val473; Val409-Ile415 and Val325-Asn330; Val409-Ile415 and Arg381-Gly387; Gly466-Leu472 and Gly384-Gly388; Val325-Glu329 and Tyr494-Lys499; Thr411-leu416 and Val497-Ala502; Ile415-Leu421 and Ala502-Ala507; Ala502-Ala507 and Lys484-Thr488; and Ala502-Ala507 and Gly445-Cys450. The moieties of the invention may bind to all of the amino acid residues forming the foregoing first and second peptide groups or they may bind to a subset of the residues forming the first and second peptide groups. It is to be understood that, in certain embodiments, when reference is made to a moiety of the invention binding to an epitope, e.g., a conformational epitope, the intention is for the moiety to bind only to those specific residues that make up the epitope (e.g., the specific peptides identified in Table 5) and not other residues in the linear amino acid sequence of the receptor.

In another embodiment, a moiety of the invention binds to a conformational or discontinuous epitope composed of 2 or more amino acids selected from the group consisting of E33, P34, D72, E76, N77; K78, Q79, K158, D159, N250, 5251, Q252, T253, K254, L255, N260, W262, H264, G265, E344, N352, R353, F355, T356, D357, Y362, 5365, E366, N367, N370, and G466.

In another embodiment, a moiety of the invention binds to amino acid residues $^{385}$Arg and $^{390}$Glu of human PDGFRβ, or the corresponding residues in PDGFRα. The residues $^{385}$Arg and $^{390}$Glu of human PDGFRβ are analogous to the residues $^{381}$Arg and $^{386}$Glu of the Kit receptor and mediate homotypic D4-D4 interactions of PDGFRβ. Moieties of the invention may exert their inhibitory effect on receptor activation by preventing critical homotypic interactions (such as salt bridges formed between $^{385}$Arg and $^{390}$Glu of human PDGFRβ) between membrane proximal regions of type-III RTKs that are essential for positioning the cytoplasmic domain at a distance and orientation essential for tyrosine kinase activation. Experiments discussed herein demonstrate that homotypic D4-D4 interactions are dispensable for PDGFRβ dimerization and that PDGFRβ dimerization is necessary but not sufficient for receptor activation. Thus, moieties of the invention may allow dimerization of PDGFRβ while preventing activation. Structure based sequence alignment has shown that the size of the EF loop, and the critical amino acids comprising the D4-D4 interface are conserved in Kit, PDGFRα, PDGFRβ, and CSF1R. Thus, in some embodiments, moieties of the invention may be targeted to the conserved regions of the D4 or D5 domains of type III RTKs. It will also be appreciated by one of skill in the art that a moiety of the invention may bind to sugar residues which may appear on a glycosylated form of an RTK. It is further possible that a moiety of the invention will bind an epitope that is composed of both amino acid residues and sugar residues.

The terms "receptor tyrosine kinase" and "RTK" are used interchangeably herein to refer to the well known family of membrane receptors that phosphorylate tyrosine residues. Many play significant roles in development or cell-division. Receptor tyrosine kinases possess an extracellular ligand binding domain, a transmembrane domain and an intracellular catalytic domain. The extracellular domains bind cytokines, growth factors or other ligands and are generally comprised of one or more identifiable structural motifs, including cysteine-rich regions, fibronectin III-like domains, immunoglobulin-like domains, EGF-like domains, cadherin-like domains, kringle-like domains, Factor VIII-like domains, glycine-rich regions, leucine-rich regions, acidic regions and discoidin-like domains. Activation of the intracellular kinase domain is achieved by ligand binding to the extracellular domain, which induces dimerization of the receptors. A receptor activated in this way is able to autophosphorylate tyrosine residues outside the catalytic domain, facilitating stabilization of the active receptor conformation. The phosphorylated residues also serve as binding sites for proteins which will then transduce signals within the cell. Examples of RTKs include, but are not limited to, Kit receptor (also known as Stem Cell Factor receptor or SCF receptor), fibroblast growth factor (FGF) receptors, hepatocyte growth factor (HGF) receptors, insulin receptor, insulin-like growth factor-1 (IGF-1) receptor, nerve growth factor (NGF) receptor, vascular endothelial growth factor (VEGF) receptor, PDGF-receptor-α, PDGF-receptor-β, CSF-1-receptor (also known as M-CSF-receptor or Fms), and the Flt3-receptor (also known as Flk2).

In a preferred embodiment of the invention, the RTK is a type III RTK. In another embodiment of the invention, the RTK is a type V RTK, i.e., a member of the VEGF receptor family.

As used herein the term "type III family of receptor tyrosine kinases" or "type III RTKs" is intended to include receptor tyrosine kinases which typically contain five immunoglobulin like domains, or Ig-like domains, in their ectodomains. Examples of type III RTKs include, but are not limited to PDGF receptors, the M-CSF receptor, the FGF receptor, the Flt3-receptor (also known as Flk2) and the Kit receptor. In a preferred embodiment of the invention, the type III RTK is Kit (also known in the art as the SCF receptor). Kit, like other type III RTKs is composed of a glycosylated extracellular ligand binding domain (ectodomain) that is connected to a cytoplasmic region by means of a single transmembrane (TM) domain (reviewed in Schlessinger (2000) Cell 103: 211-225). Another hallmark of the type III RTKs, e.g., Kit or PDGFR, is a cytoplasmic protein tyrosine kinase (PTK) domain with a large kinase-insert region. At least two splice isoforms of the Kit receptor are known to exist, the shorter making use of an in-frame splice site. All isoforms of Kit, and the other above described RTKs, are encompassed by the present invention.

As used herein, an "Ig-like domain" of a receptor tyrosine kinase (RTK) is intended to include the domains well known in the art to be present in the ectodomain of RTKs. In the ectodomain of the family of type III receptor tyrosine kinases (type III RTKs), e.g., Kit, there are five such domains, known as D1, D2, D3, D4 and D5. The D1, D2 and D3 domains of type III RTKs are responsible for binding the ligand of the RTK (reviewed in Ullrich and Schlessinger (1990) Cell 61: 203-212). Thus, in one embodiment of the invention the term "Ig-like domain" is not intended to include a domain of a RTK which is responsible for ligand binding. In a preferred embodiment of the invention, the Ig-like domain is a D4 and/or a D5 domain of a type III RTK. In the ectodomain of the VEGF receptor family, there are seven Ig-like domains, known as D1, D2, D3, D4, D5, D6 and D7. In one preferred embodiment of the invention, the Ig-like domain is a D7 domain of the VEGF receptor family.

As used herein the term "VEGF receptor family", also known as type V RTKs includes RTK receptors for the vascular endothelial growth factor. As described above, these RTKs have 7Ig-like domains in their ectodomains. Examples of VEGF family receptors are VEGFR-1 (also known as Flt-1), VEGFR-2 (also known as KDR or Flk-1), and VEGFR-3 (also known as Flt-4).

The term "ectodomain" of a receptor tyrosine kinase (RTK) is well known in the art and refers to the extracellular part of the RTK, i.e., the part of the RTK that is outside of the plasma membrane.

The term "a membrane proximal region" of the ectodomain of a receptor tyrosine kinase refers to an extracellular part of a RTK which is in proximity to the plasma membrane and which, preferably, is not directly responsible for the binding of a ligand to the RTK. Examples of membrane proximal regions include, but are not limited to, the D4 domain of a type III receptor tyrosine kinase, the D5 domain of a type III receptor tyrosine kinase, the D3-D4 hinge region of a type III receptor tyrosine kinase, the D4-D5 hinge region of a type III receptor tyrosine kinase, and the D7 domain of a type V receptor tyrosine kinase.

The term "homotypic interaction" as used herein, refers to the interaction between two identical membrane proximal regions from two monomeric receptors.

The term "heterotypic interaction" as used herein, refers to the interaction between two different membrane proximal regions from two monomeric receptors. A heterotypic interaction may be the result of dimerization of two different types of monomeric receptors or the result of dimerization of a wild type and a mutant form of the same monomeric receptor. For example, it is well known in the art that a cancer patient may carry a wild type allele and a mutant allele for a certain receptor.

The term "monomeric state" as used herein, refers to the state of a RTK wherein the RTK molecule is composed of a single polypeptide chain which is not associated with a second RTK polypeptide of the same or different type. RTK dimerization leads to autophosphorylation and receptor activation. Thus, a RTK in a monomeric state is in an inactive state. A monomeric state is also a state wherein the D4 or D5 domain of a single RTK is not associated with the D4 or D5 domain, respectively, of a second, RTK.

The phrase "locks the ectodomain of the receptor tyrosine kinase in an inactive state" refers to the ability of a moiety of the invention to inhibit the activity of the receptor tyrosine kinase. In other words, this phrase includes the ability of a moiety of the invention to shift the equilibrium towards formation of an inactive or inhibited receptor configuration. For example, a moiety of the invention may inhibit the activity of a receptor tyrosine kinase by at least 5%, 10%, 15%, 20%, 25%, 30%, 35%, 40%, 45%, 50%, 55%, 60%, 65%, 70%, 75%, 80%, 85%, 90% or 95% as compared to the activity of the receptor in the absence of the moiety.

The term "inactive state," as used herein, refers to the state of a RTK wherein the RTK molecule is unable to activate downstream signaling. An inactive state may be a state wherein the ectodomain of the receptor tyrosine kinase is allowed to dimerize but the positioning, orientation, conformation, and/or distance between the Ig-like domains of the two monomers (e.g., the D4-D4 or D5-D5 domains of a type III receptor tyrosine kinase or the D7-D7 domains of a type V receptor tyrosine kinase), is altered such that the activity of the receptor tyrosine kinase is inhibited (e.g., receptor internalization is inhibited and/or tyrosine autophosphorylation of the receptor is inhibited and/or the ability of the receptor to activate a downstream signaling pathway is inhibited). An inactive state also includes a monomeric state as described above. An inactive state may also be a state in which the ectodomain of the receptor tyrosine kinase is bound to a receptor ligand and is dimerized, but has not yet undergone the conformational change that allows for the activation of the receptor. Examples 22-25 further discuss experiments which show that there are specific conserved amino acid residues which are crucial for RTK activation (e.g., by mediating D4 or D5 homotypic interactions) but which are dispensable for receptor dimerization. The term "inactive state" includes a state in which a moiety of the invention may reduce or inhibit the activity of a receptor tyrosine kinase by at least 5%, 10%, 15%, 20%, 25%, 30%, 35%, 40%, 45%, 50%, 55%, 60%, 65%, 70%, 75%, 80%, 85%, 90% or 95% as compared to the activity of the receptor in the absence of the moiety. Any of the functional assays described herein may be used to determine the ability of a moiety of the invention to inhibit the activity of a receptor tyrosine kinase. In some embodiments, a moiety of the invention may exhibit a broad effect, e.g., when most or all target RTKs are inactivated. In other embodiments, a moiety of the invention may exhibit a narrower effect, e.g., when a portion of the target RTKs are inactivated. In such embodiments, at least 5%, 10%, 15%, 20%, 25%, 30%, 35%, 40%, 45%, 50%, 55%, 60%, 65%, 70%, 75%, 80%, 85%, 90% or 95% of the receptors are locked into an inactive state as compared to the receptors in the absence of said moiety.

As used herein, the terms "conformational epitope" or "non-linear epitope" or "discontinuous epitope" are used interchangeably to refer to an epitope which is composed of at least two amino acids which are not consecutive amino acids in a single protein chain. For example, a conformational epitope may be comprised of two or more amino acids which are separated by a strech of intervening amino acids but which are close enough to be recognized by a moiety of the invention as a single epitope. As a further example, amino acids which are separated by intervening amino acids on a single protein chain, or amino acids which exist on separate protein chains, may be brought into proximity due to the conformational shape of a protein structure or complex to become a conformational epitope which may be bound by a moiety of the invention. Particular discontinuous and conformation epitopes are described herein (see, for example, Tables 4 and 5).

It will be appreciated by one of skill in the art that, in general, a linear epitope bound by a moiety of the invention may or may not be dependent on the secondary, tertiary, or quaternary structure of the RTK. For example, in some embodiments, a moiety of the invention may bind to a group of amino acids regardless of whether they are folded in a natural three dimensional protein structure. In other embodiments, a moiety of the invention may not recognize the individual amino acid residues making up the epitope, and may require a particular conformation (bend, twist, turn or fold) in order to recognize and bind the epitope.

Various aspects of the invention are described in further detail in the following subsections:

I. Antibodies which Bind to the Ectodomain of a Human Receptor Tyrosine Kinase

In one aspect of the invention, the moiety that binds to the ectodomain, e.g., an Ig-like domain or a hinge region, of a human receptor tyrosine kinase is an antibody or an antigen binding fragment thereof.

The term "antibody" as referred to herein, includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., the D4 or D5 domains of Kit). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge, region; (iii) a Fab' fragment, which is essentially an Fab with part of the hinge region (see, FUNDAMENTAL IMMUNOLOGY (Paul ed., 3rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds to an Ig-like domain of an RTK is substantially free of antibodies that specifically bind antigens other than the Ig-like domain of an RTK). Moreover, an isolated antibody may be substantially free of other cellular material and/or chemicals. An "isolated antibody" may, however, include polyclonal antibodies which all bind specifically to, e.g., an Ig-like domain of an RTK.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$, regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences. It will be appreciated by one of skill in the art that when a sequence is "derived" from a particular species, said sequence may be a protein sequence, such as when variable region amino acids are taken from a murine antibody, or said sequence may be a DNA sequence, such as when variable region encoding nucleic acids are taken from murine DNA. A humanized antibody may also be designed based on the known sequences of human and non-human (e.g., murine or rabbit) antibodies. The designed antibodies, potentially incorporating both human and non-human residues, may be chemically synthesized. The sequences may also be synthesized at the DNA level and expressed in vitro or in vivo to generate the humanized antibodies.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "antibody mimetic" or "antibody mimic" is intended to refer to molecules capable of mimicking an antibody's ability to bind an antigen, but which are not limited to native antibody structures. Examples of such antibody mimetics include, but are not limited to, Adnectins (i.e., fibronectin based binding molecules), Affibodies, DARPins, Anticalins, Avimers, and Versabodies all of which employ binding structures that, while they mimic traditional antibody binding, are generated from and function via distinct mechanisms. The embodiments of the instant invention, as they are directed to antibodies, or antigen binding portions thereof, also apply to the antibody mimetics described above.

As used herein, an antibody that "specifically binds" to an Ig-like domain of a RTK is intended to refer to an antibody that binds to an Ig-like domain of a RTK with a $K_D$ of $1 \times 10^{-7}$ M or less, more preferably $5 \times 10^{-8}$ M or less, more preferably $1 \times 10^{-8}$ M or less, more preferably $5 \times 10^{-9}$ M or less The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ ($K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity", when referring an IgG type antibody, refers to an antibody having a $K_D$ of $10^{-8}$ M or less, more preferably $10^{-9}$ M or less and even more preferably $10^{-10}$ M or less for an Ig-like domain of a RTK. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

Antibodies

The antibodies of the invention bind specifically to an Ig-like domain of a RTK, e.g., member of the human type III family of receptor tyrosine kinases. In preferred embodiments, the binding of the antibodies, or antigen binding portions thereof, of the invention to an Ig-like domain of a RTK monomer locks the ectodomain in an inactive state, e.g., a monomeric state, and, thus, antagonizes the ability of the RTK to dimerize and activate a downstream signaling pathway. For example, the antibody may block a ligand induced tyrosine autophosphorylation of the receptor tyrosine kinase and/or receptor internalization.

The antibodies of the invention are selected or designed to bind to specific Ig-like domains of the RTK, for example, the D4 domain or the D5 domain of the human Kit or the D7 domain of a VEGF receptor. In other embodiments the antibodies, or antigen binding portions thereof, are selected or designed to bind proteins sharing homology to a domain of the RTK, e.g., the Kit, receptor. For example, an antibody may be selected or designed to bind a domain which is at least 50% identical, at least 60% identical, at least 70% identical, at least 80% identical, at least 90% identical, or at least 95%, 96%, 97%, 98% or 99% identical to a domain, e.g., the D4 or D5 domain, of the Kit receptor. Such an antibody, or antigen binding portion thereof, would be able to bind protein domains, possibly in Kit and other RTKs, which are functionally similar to the D4 or D5 domains of Kit.

The antibodies, or antigen binding portions thereof, of the present invention may also be selected or designed to bind a particular motif or consensus sequence derived from an Ig-like domain of a RTK, e.g., a human type III RTK, allowing the antibodies, or antigen binding portions thereof, to specifically bind epitopes or domains which are shared among members of the human type III family of RTKs and between the type III RTKs and other RTKs, e.g., type V RTKs. Such a linear consensus sequence may be found, for example, by using a sequence alignment algorithm to align domains of various RTKs, e.g., domains of D4 domains across RTK types or across species (see FIG. 6B). One of skill in the art may align the protein sequences of, for example, the Kit D4 domains from various species (e.g., human, mouse, rat) to determine which protein residues are conserved in at least 40%, at least 50%, at least 60%, at least 70%, at least 80%, at least 90%, or at least 100% of the sequences being aligned. Such a consensus sequence may then be used to generate antibodies or other moieties which specifically bind the consensus sequence and, thus, will bind the most conserved residues of the Kit RTK. Similarly, one may also align the protein sequences of the D7 domain of type V RTKs (see FIG. 6) to obtain a consensus sequence for which moieties of the present invention may be generated. One of skill in the art should appreciate that the most highly conserved residues are those which have been preserved through evolution and are most likely to be important for protein function. Alternatively, if the alignment is made across various classes of RTKs, antibodies generated toward such consensus sequences would allow the antibodies to bind a similar Ig-like domain in multiple RTK types.

In a specific embodiment a moiety of the present invention (e.g., antibodies or antigen binding portions thereof) binds to the following consensus sequence for the D4 interaction site: $LX_1RX_2X_3X_4X_5X_6X_7G$ (SEQ ID NO: 158) wherein L is Leucine, R is Arginine. G is Glycine; $X_1$ is selected from the group consisting of Threonine, Isoleucine, Valine, Proline, Asparagine, or Lysine; X2 is selected from the group consisting of Leucine, Valine, Alanine, and Methionine; $X_3$ is selected from the group consisting of Lysine, Histidine, Asparagine, and Arginine; $X_4$ is selected from the group consisting of Glycine, Alanine, Glutamic Acid, Proline, and Methionine; $X_5$ is selected from the group consisting of Threonine, Serine, Glutamic Acid, Alanine, Glutamine, and Aspartic acid; X5 is selected from the group consisting of Glutamic Acid, Aspartic acid, and Glutamine; and $X_7$ is selected from the group consisting of Glycine, Serine, Alanine, Lysine, Arginine, Glutamine, and Threonine.

In another embodiment, a moiety of the present invention (e.g., antibodies or antigen binding portions thereof) binds to the following consensus sequence for the D7 domain of a member of the VEGF receptor family: $IX_1RVX_2X_3EDX_4G$ (SEQ ID NO: 1) wherein I is Isoleucine, R is Arginine, E is Glutamic Acid, D is Aspartic Acid, G is Glycine; $X_1$ is selected from the group consisting of Glutamic Acid, Arginine, and Glutamine; X2 is selected from the group consisting of Arginine and Threonine; $X_3$ is selected from the group consisting of Glutamic Acid and Lysine; and $X_4$ is selected from the group consisting of Glutamic Acid and Alanine.

The antibodies of the present invention do not bind to the ligand binding site of the RTK, e.g., the SCF binding site of the Kit receptor. Therefore, the antibodies described herein do not antagonize the ability of the receptor to hind its target ligand.

In some embodiments the antibody or antigen binding portion thereof binds to specific sequences of the human Kit receptor, for example, residues 309-413, residues 410-519, $^{381}$Arg and $^{386}$Glu, or $^{418}$Tyr and $^{505}$Asn of the human Kit receptor.

In other embodiments, the antibodies, or antigen binding portions thereof, bind protein motifs or consensus sequences which represent a three dimensional structure in the protein. Such motifs or consensus sequences would not represent a contiguous string of amino acids, but a non-contiguous amino acid arrangement that results from the three-dimensional folding of the RTK (i.e., a "structural motif" or "non-linear epitope"). An example of such a motif would be the D4-D4 or the D5-D5 binding interface of a Kit receptor. In one embodiment, an antibody of the present invention binds to, for example, a non-linear epitope in the D4-D4 or D5-D5 interface, preventing the activation of the RTK.

In a preferred embodiment, an antibody or antigen binding portion thereof of the invention may bind to one or more residues in the Kit receptor which make up the small cavities or pockets described in Table 4 (below). For example, an antibody or antigen binding portion thereof of the invention may bind to one or more of the following residues in the D3-D4 hinge region of the Kit receptor: K218, S220, Y221, L222 from the D3 domain and F340, P341, K342, N367, E368, 5369, N370, I371, Y373 from the D4 domain. An antibody or antigen binding portion thereof of the invention may also bind to one or more of the following residues which make up a concave surface in the D4 domain of the Kit receptor: Y350, R353, F355, K358, L379, T380, R381, L382, E386 and T390. In another embodiment, an antibody or antigen binding portion thereof of the invention may bind to one or more of the following residues which form a pocket in the D2-D3 hinge region of the Kit receptor: Y125, G126, H180, R181, K203, V204, R205, P206 and F208 from the D2 domain and V238, 5239, S240, S241, H263, G265, D266, F267, N268 and Y269 from the D3 domain.

Thus, in some embodiments, an antibody or antigen binding portion thereof of the invention may bind to contiguous or non-contiguous amino acid residues and function as a molecular wedge that prevents the motion required for positioning of the membrane proximal region of the RTK at a distance and orientation that enables tyrosine kinase activation. An antibody or antigen binding portion thereof of the invention may also act to prevent homotypic D4 or D5 receptor interactions or destabilize the ligand-receptor interaction site. In some preferred embodiments, an antibody or antigen binding portion thereof of the invention may bind to one or more of the following residues on the Kit receptor: Y125, G126, H180, R181, K203, V204, R205, P206, P206, F208, K127, A207, V238, S239, S240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F355, G311, G384, G387, G388, I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432.

One of skill in the art will appreciate that, in some embodiments, an antibody or antigen binding portion thereof of the invention may be easily targeted to the corresponding residues in other type III RTKs, e.g., those residues that form similar pockets or cavities or those in the same position by structural alignment or sequence alignment.

In a specific embodiment, an antibody or antigen binding portion thereof of the invention binds to a conformational epitope or a discontinuous epitope on a type III RTK. The conformational or discontinuous epitope may be composed of two or more residues from the D3, D4, or D5 domain or the D4-D5 or D3-D4 hinge regions from a type III RTK, e.g., the human Kit receptor or the PDGF receptor. For example, the conformational or discontinuous epitope may be composed of two or more of the residues listed in Table 4 below.

In a particular embodiment, an antibody or antigen binding portion thereof, of the invention binds to a conformational epitope composed of 2 or more amino acids selected from the group consisting of Y125, H180, R181, K203, V204, R205, P206. V238, 5239, S240, H263, G265, D266, F267, N268, and Y269. In similar embodiments, an antibody or antigen binding portion thereof of the invention may bind to a conformational epitope composed of 2 or more amino acids selected from one of the following groups of amino acids: P206, F208, V238, and S239; K127, A207, F208, and T295; L222, A339, F340, K342, E368, S369, N370, I371, and Y373; L222, L223, E306, V308, F312, E338, F340, and I371; R224, V308, K310, G311, F340, P341, and D398; K218, A219, S220, N367, E368, and S369; K218, A220, E368, and S369; G384, T385, T411, K412, E414, and K471; Y408, F433, G470, K471, and L472; F324, V325, N326, and N410; D327, N410, T411, K412, and V497; G384, G387, V409, and K471; L382, G387, V407, and V409; Y125, G126, H180, R181, K203, V204, R205, P206, F208, V238, S239, 5240, S241, H263, G265, D266, F267, N268, and Y269; P206, F208, V238, and S239; K218, S220, Y221, L222, F340, P341, K342, N367, E368, 5369, N370, I371, and Y373; G384, G387, G388, Y408, V409, T411, F433, F469, G470, and K471; D327, T411, K412, E414, A431, G432, and K471; Y350, F355, K358, L379, T380, R381, L382, E386, and T390; Y350, R353, and F355. As indicated above, the antibodies of the invention may bind to all of the amino acid residues forming a pocket or a cavity identified in Table 4 or they may bind to a subset of the residues forming the pocket or the cavity. It is to be understood that, in certain embodiments, when reference is made to an antibody of the invention binding to an epitope, e.g., a conformational epitope, the intention is for the antibody to bind only to those specific residues that make up the epitope (e.g., the pocket or cavity identified in Table 4) and not other residues in the linear amino acid sequence of the receptor.

In a further embodiment, an antibody or antigen binding portion thereof of the invention binds to a conformational epitope wherein the conformational epitope is composed of two or more amino acid residues selected from the peptides listed in Table 5. In a specific embodiment, the conformational epitope is composed of one or more amino acid residues selected from a first peptide and one or more amino acid residues selected from a second peptide, wherein the first and second peptides are selected from the group of peptides listed in Table 5. As such, an antibody or antigen binding portion thereof of the invention binds a conformational epitope wherein the first and second peptide groups are as follows: Ala219-Leu222 and Thr304-Val308; Asp309-Gly311 and Arg224-Gly226; Thr303-Glu306 and Ala219-Leu222; Asn367-Asn370 and Ser217-Tyr221; Ala339-Pro343 and Asn396-Val399; Ala339-Pro343 and Glu368-Arg372; Lys358-Tyr362 and Val374-His378; Asp357-Glu360 and Leu377-Thr380; Met351-Glu360 and His378-Thr389; His378-Thr389 and Val323-Asp332; Val409-Ile415 and Ala493-Thr500; Val409-Ile415 and Ala431-Thr437; Val409-Ile415 and Phe469-Val473; Val409-Ile415 and Val325-Asn330; Val409-Ile415 and Arg381-Gly387; Gly466-Leu472 and Gly384-Gly388; Val325-Glu329 and Tyr494-Lys499; Thr411-leu416 and Val497-Ala502; Ile415-Leu421 and Ala502-Ala507; Ala502-Ala507 and Lys484-Thr488; and Ala502-Ala507 and Gly445-Cys450.

The antibodies of the invention may bind to all of the amino acid residues forming the foregoing first and second peptide groups or they may bind to a subset of the residues forming the first and second peptide groups. It is to be understood that, in certain embodiments, when reference is made to an antibody of the invention binding to an epitope, e.g., a conformational epitope, the intention is for the antibody to bind only to those specific residues that make up the epitope (e.g., the specific peptides identified in Table 5) and not other residues in the linear amino acid sequence of the receptor.

In another embodiment, an antibody or antigen binding portion thereof of the invention binds to a conformational or discontinuous epitope composed of 2 or more amino acids selected from the group consisting of E33, P34, D72, E76, N77, K78, Q79, K158, D159, N250, 5251, Q252, T253, K254, L255, N260, W262, H264, G265, E344, N352, R353, F355, T356, D357, Y362, 5365, E366, N367, N370, and G466.

In another embodiment, an antibody or antigen binding portion thereof of the invention binds to amino acid residues $^{385}$Arg and $^{390}$Glu of human PDGFRβ, or the corresponding residues in PDGFRα. The residues $^{385}$Arg and $^{390}$Glu of human PDGFRβ are analogous to the residues $^{381}$Arg and $^{386}$Glu of the Kit receptor and mediate homotypic D4-D4 interactions of PDGFRβ. Antibodies or antigen binding portions thereof of the invention may exert their inhibitory effect on receptor activation by preventing critical homotypic interactions (such as salt bridges formed between $^{385}$Arg and $^{390}$Glu of human PDGFRβ) between membrane proximal regions of type-III RTKs that are essential for positioning the cytoplasmic domain at a distance and orientation essential for tyrosine kinase activation. Experiments discussed herein demonstrate that homotypic D4-D4 interactions are dispensable for PDGFRβ dimerization and that PDGFRβ dimerization is necessary but not sufficient for receptor activation. Thus, antibodies or antigen binding portions thereof of the invention may allow dimerization of PDGFRβ while preventing activation. Structure based sequence alignment has shown that the size of the EF loop, and the critical amino acids comprising the D4-D4 interface are conserved in Kit, PDGFRα, PDGFRβ, and CSF1R. Thus in some embodiments, antibodies or antigen binding portions thereof of the invention may be targeted to the conserved regions of the D4 or D5 domains of type III RTKs.

In additional embodiments, the antibody, or antigen binding portion thereof, of the invention is selected or designed to bind specifically to a mutant RTK. In preferred embodiments, the mutant RTK is a tumorigenic or oncogenic mutant. In one specific embodiment, the antibody, or antigen binding portion thereof, is selected or designed to bind to an oncogenic Kit receptor mutant. Several Kit receptor mutants which may be targeted by the antibodies of the present invention are Kit receptors with mutations in one or more of the following amino acids: Thr417, Tyr418, Asp419, Leu421, Arg420, Tyr503, or Ala502. It should be appreciated by one of skill in the art that the methods of the invention would be applicable to other mutations in Kit or to mutations in other RTKs. One advantage of targeting a mutant RTK is that a therapeutic antibody may bind to only the RTKs on cells containing the mutation, leaving healthy cells largely or entirely unaffected.

Accordingly, in instances where the mutation is tumorigenic, only tumor cells would be targeted for therapy, potentially reducing side effects and dosage requirements.

Preferably, the antibody binds to an Ig-like domain of a human RTK with a $K_D$ of $5\times10^{-8}$ M or less, a $K_D$ of $1\times10^{-8}$ M or less, a $K_D$ of $5\times10^{-9}$ M or less, or a $K_D$ of between $1\times10^{-8}$ M and $1\times10^{-10}$ M or less. Standard assays to evaluate the binding ability of the antibodies toward an Ig-like domain of a RTK, e.g., Kit, are known in the art, including for example, ELISAs, Western blots and RIAs. The binding kinetics (e.g., binding affinity) of the antibodies also can be assessed by standard assays known in the art, such as by ELISA, Scatchard and Biacore analysis.

Engineered and Modified Antibodies

The $V_H$ and/or $V_L$, sequences of an antibody prepared according the methods of the present invention and may be used as starting material to engineer a modified antibody, which modified antibody may have altered properties from the starting antibody. An antibody can be engineered by modifying one or more residues within one or both of the original variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Framework sequences for antibodies can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database.

Antibody protein sequences are compared against a compiled protein sequence database using one of the sequence similarity searching methods called the Gapped BLAST (Altschul et al. (1997) Nucleic Acids *Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for the top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames. Other human germline sequence databases, such as that available from IMGT (http://imgt-.cines.fr), can be searched similarly to VBASE as described above.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Identified $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693, 762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays known in the art. For example, an antibody of the present invention may be mutated to create a library, which may then be screened for binding to an Ig-like domain of an RTK, e.g., a D4 or a D5 domain of the human Kit RTK. Preferably conservative modifications (as discussed above) are introduced. The mutations may be amino acid substitutions, additions or deletions, but are preferably substitutions. Moreover, typically no more than one, two, three, four or five residues within a CDR region are altered.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of $CH_1$ is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. These strategies will be effective as long as the binding of the antibody to the Ig-like domain of the RTK is not compromised.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the C-terminal end of an antibody of the present invention is modified by the introduction of a cysteine residue as is described in U.S. Provisional Application Ser. No. 60/957,271, which is hereby incorporated by reference in its entirety. Such modifications include, but are not limited to, the replacement of an existing amino acid residue at or near the C-terminus of a full-length heavy chain sequence, as well as the introduction of a cysteine-containing extension to the c-terminus of a full-length heavy chain sequence. In preferred embodiments, the cysteine-containing extension comprises the sequence alanine-alanine-cysteine (from N-terminal to C-terminal).

In preferred embodiments the presence of such C-terminal cysteine modifications provide a location for conjugation of a partner molecule, such as a therapeutic agent or a marker molecule. In particular, the presence of a reactive thiol group, due to the C-terminal cysteine modification, can be used to conjugate a partner molecule employing the disulfide linkers described in detail below. Conjugation of the antibody to a partner molecule in this manner allows for increased control over the specific site of attachment. Furthermore, by introducing the site of attachment at or near the C-terminus, conjugation can be optimized such that it reduces or eliminates interference with the antibody's functional properties, and allows for simplified analysis and quality control of conjugate preparations.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 to Co et al. Additional approaches for altering glycosylation are described in further detail in U.S. Pat. No. 7,214,775 to Hanai et al., U.S. Pat. No. 6,737,056 to Presta, U.S. Pub No. 20070020260 to Presta, PCT Publication No. WO/2007/084926 to Dickey et al., PCT Publication No. WO/2006/

089294 to Zhu et al., and PCT Publication No. WO/2007/055916 to Ravetch et al., each of which is hereby incorporated by reference in its entirety.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Additionally or alternatively, an antibody can be made that has an altered type of glycosylation, wherein that alteration relates to the level of sialyation of the antibody. Such alterations are described in PCT Publication No. WO/2007/084926 to Dickey et al, and PCT Publication No. WO/2007/055916 to Ravetch et al., both of which are incorporated by reference in their entirety. For example, one may employ an enzymatic reaction with sialidase, such as, for example, Arthrobacter ureafacens sialidase. The conditions of such a reaction are generally described in the U.S. Pat. No. 5,831,077, which is hereby incorporated by reference in its entirety. Other non-limiting examples of suitable enzymes are neuraminidase and N-Glycosidase F, as described in Schloemer et al. J. Virology, 15(4), 882-893 (1975) and in Leibiger et al., Biochem J., 338, 529-538 (1999), respectively. Desialylated antibodies may be further purified by using affinity chromatography. Alternatively, one may employ methods to increase the level of sialyation, such as by employing sialytransferase enzymes. Conditions of such a reaction are generally described in Basset et al., Scandinavian Journal of Immunology, 51(3), 307-311 (2000).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al. As such, the methods of pegylation described here also apply the peptidic molecules of the invention described below.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Adnectins, Affibodies, DARPins, Anticalins, Avimers, and Versabodies that employ binding structures that, while they mimic traditional antibody binding, are generated from and function via distinct mechanisms. Some of these alternative structures are reviewed in Gill and Damle (2006) 17: 653-658.

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see, e.g., WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts, e.g., E. coli (see, e.g., U.S. Pat. No. 6,765,087, which is herein incorporated by reference in its entirety), molds (for example Aspergillus or Trichoderma) and yeast (for example Saccharomyces, Kluyveromyces, Hansenula or Pichia) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see, e.g., WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent application WO2007/059782, which is herein incorporated by reference in its entirety.

Adnectin molecules are engineered binding proteins derived from one or more domains of the fibronectin protein. Fibronectin exists naturally in the human body. It is present in the extracellular matrix as an insoluble glycoprotein dimer and also serves as a linker protein. It is also present in soluable form in blood plasma as a disulphide linked dimer. The plasma form of fibronectin is synthesized by liver cells (hepatocytes), and the ECM form is made by chondrocytes, macrophages, endothelial cells, fibroblasts, and some cells of the epithelium (see Ward M., and Marcey, D., callutheran.edu/Academic_Programs/Departments/BioDev/omm/fibro/fibro.htm). As mentioned previously, fibronectin may function naturally as a cell adhesion molecule, or it may mediate the interaction of cells by making contacts in the extracellular matrix. Typically, fibronectin is made of three different protein modules, type I, type II, and type III modules. For a review of the structure of function of the fibronectin, see Pankov and Yamada (2002) J Cell Sci.; 115 (Pt 20):3861-3, Hohenester and Engel (2002) 21:115-128, and Lucena et al. (2007) Invest Clin. 48:249-262.

In a preferred embodiment, adnectin molecules are derived from the fibronectin type III domain by altering the native protein which is composed of multiple beta strands distributed between two beta sheets. Depending on the originating tissue, fibronecting may contain multiple type III domains which may be denoted, e.g., $^1$Fn3, $^2$Fn3, $^3$Fn3, etc. The $^{10}$Fn3 domain contains an integrin binding motif and further contains three loops which connect the beta strands. These loops may be thought of as corresponding to the antigen binding loops of the IgG heavy chain, and they may be altered by methods discussed below to specifically bind a target of interest, e.g., an Ig-like domain of a RTK, such as the D4 or D5 domain of human Kit RTK. Preferably, a fibronectin type III domain useful for the purposes of this invention is a sequence which exhibits a sequence identity of at least 30%, at least 40%, at least 50%, at least 60%, at least 70%, at least 80%, at least 90%, or at least 95% to the sequence encoding the structure of the fibronectin type III molecule which can be accessed from the Protein Data Bank (PDB, rcsb.org/pdb/home/home.do) with the accession code: 1 ttg. Adnectin molecules may also be derived from polymers of $^{10}$Fn3 related molecules rather than a simple monomeric $^{10}$Fn3 structure.

Although the native $^{10}$Fn3 domain typically binds to integrin, $^{10}$Fn3 proteins adapted to become adnectin molecules are altered so to bind antigens of interest, e.g., an Ig-like domain of a RTK, such as the D4 or D5 domain of human Kit. In one embodiment, the alteration to the $^{10}$Fn3 molecule comprises at least one mutation to a beta strand. In a preferred embodiment, the loop regions which connect the beta strands of the $^{10}$Fn3 molecule are altered to bind to an Ig-like domain of a human receptor tyrosine kinase, e.g., a type III receptor tyrosine kinase, such as the human Kit.

The alterations in the $^{10}$Fn3 may be made by any method known in the art including, but not limited to, error prone PCR, site-directed mutagenesis, DNA shuffling, or other types of recombinational mutagenesis which have been referenced herein. In one example, variants of the DNA encoding the $^{10}$Fn3 sequence may be directly synthesized in vitro, and later transcribed and translated in vitro or in vivo. Alternatively, a natural $^{10}$Fn3 sequence may be isolated or cloned from the genome using standard methods (as performed, e.g., in U.S. pat. application No. 20070082365), and then mutated using mutagenesis methods known in the art.

In one embodiment, a target protein, e.g., an Ig-like domain of a RTK, such as the D4 or D5 domain of the Kit RTK, may be immobilized on a solid support, such as a column resin or a well in a microtiter plate. The target is then contacted with a library of potential binding proteins. The library may comprise $^1$Fn3 clones or adnectin molecules derived from the wild type $^1$Fn3 by mutagenesis/randomization of the $^1$Fn3 sequence or by mutagenesis/randomization of the $^1$Fn3 loop regions (not the beta strands). In a preferred embodiment the library may be an RNA-protein fusion library generated by the techniques described in Szostak et al., U.S. Ser. No. 09/007,005 and 09/247,190; Szostak et al., WO989/31700; and Roberts & Szostak (1997) 94:12297-12302. The library may also be a DNA-protein library (e.g., as described in Lohse, U.S. Ser. No. 60/110,549, U.S. Ser. No. 09/459,190, and WO 00/32823). The fusion library is then incubated with the immobilized target (e.g., the D4 or D5 domain of human Kit RTK) and the solid support is washed to remove non-specific binding moieties. Tight binders are then eluted under stringent conditions and PCR is used to amply the genetic information or to create a new library of binding molecules to repeat the process (with or without additional mutagenesis). The selection/mutagenesis process may be repeated until binders with sufficient affinity to the target are obtained. Adnectin molecules for use in the present invention may be engineered using the PROfusion™ technology employed by Adnexus, a Briston-Myers Squibb company. The PROfusion technology was created based on the techniques referenced above (e.g., Roberts & Szostak (1997) 94:12297-12302). Methods of generating libraries of altered $^{10}$Fn3 domains and selecting appropriate binders which may be used with the present invention are described fully in the following U.S. patent and patent application documents and are incorporated herein by reference: U.S. Pat. Nos. 7,115,396; 6,818,418; 6,537,749; 6,660,473; 7,195,880; 6,416,950; 6,214,553; 6,623,926; 6,312,927; 6,602,685; 6,518,018; 6,207,446; 6,258,558; 6,436,665; 6,281,344; 7,270,950; 6,951,725; 6,846,655; 7,078,197; 6,429,300; 7,125,669; 6,537,749; 6,660,473; and U.S. pat. application Nos. 20070082365; 20050255548; 20050038229; 20030143616; 20020182597; 20020177158; 20040086980; 20040253612; 20030022236; 20030013160; 20030027194; 20030013110; 20040259155; 20020182687; 20060270604; 20060246059; 20030100004; 20030143616; and 20020182597. The generation of diversity in fibronectin type III domains, such as $^{10}$Fn3, followed by a selection step may be accomplished using other methods known in the art such as phage display, ribosome display, or yeast surface display, e.g., Lipovšek et al. (2007) Journal of Molecular Biology 368: 1024-1041; Sergeeva et al. (2006) Adv Drug Deliv Rev. 58:1622-1654; Petty et al. (2007) Trends Biotechnol. 25: 7-15; Rothe et al. (2006) Expert Opin Biol Ther. 6:177-187; and Hoogenboom (2005) Nat. Biotechnol. 23:1105-1116.

It should be appreciated by one of skill in the art that the methods references cited above may be used to derive antibody mimics from proteins other than the preferred $^{10}$Fn3 domain. Additional molecules which can be used to generate antibody mimics via the above referenced methods include, without limitation, human fibronectin modules $^{1}$Fn3-$^{9}$Fn3 and $^{11}$Fn3-$^{17}$Fn3 as well as related Fn3 modules from non-human animals and prokaryotes. In addition, Fn3 modules from other proteins with sequence homology to $^{10}$Fn3, such as tenascins and undulins, may also be used. Other exemplary proteins having immunoglobulin-like folds (but with sequences that are unrelated to the $V_H$ domain) include N-cadherin, ICAM-2, titin, GCSF receptor, cytokine receptor, glycosidase inhibitor, E-cadherin, and antibiotic chromoprotein. Further domains with related structures may be derived from myelin membrane adhesion molecule P0, CD8, CD4, CD2, class I MHC, T-cell antigen receptor, CD1, C2 and I-set domains of VCAM-1, I-set immunoglobulin fold of myosin-binding protein C, 1-set immunoglobulin fold of myosin-binding protein H, 1-set immunoglobulin-fold of telokin, telikin, NCAM, twitchin, neuroglian, growth hormone receptor, erythropoietin receptor, prolactin receptor, GC-SF receptor, interferon-gamma receptor, beta-galactosidase/glucuronidase, beta-glucuronidase, and transglutaminase. Alternatively, any other protein that includes one or more immunoglobulin-like folds may be utilized to create a adnecting like binding moiety. Such proteins may be identified, for example, using the program SCOP (Murzin et al., J. Mol. Biol. 247:536 (1995); Lo Conte et al., Nucleic Acids Res. 25:257 (2000).

An aptamer is another type of antibody-mimetic which is encompassed by the present invention. Aptamers are typically small nucleotide polymers that bind to specific molecular targets. Aptamers may be single or double stranded nucleic acid molecules (DNA or RNA), although DNA based aptamers are most commonly double stranded. There is no defined length for an aptamer nucleic acid; however, aptamer molecules are most commonly between 15 and 40 nucleotides long.

Aptamers often form complex three-dimensional structures which determine their affinity for target molecules. Aptamers can offer many advantages over simple antibodies, primarily because they can be engineered and amplified almost entirely in vitro. Furthermore, aptamers often induce little or no immune response.

Aptamers may be generated using a variety of techniques, but were originally developed using in vitro selection (Ellington and Szostak. (1990) Nature. 346(6287):818-22) and the SELEX method (systematic evolution of ligands by exponential enrichment) (Schneider et al. 1992. J Mol. Biol. 228(3): 862-9) the contents of which are incorporated herein by reference. Other methods to make and uses of aptamers have been published including Klussmann. The Aptamer Handbook: Functional Oligonucleotides and Their Applications. ISBN: 978-3-527-31059-3; Ulrich et al. 2006. Comb Chem High Throughput Screen 9(8):619-32; Cerchia and de Franciscis. 2007. Methods Mol. Biol. 361:187-200; Ireson and Kelland. 2006. Mol Cancer Ther. 2006 5(12):2957-62; U.S. Pat. Nos. 5,582,981; 5,840,867; 5,756,291; 6,261,783; 6,458, 559; 5,792,613; 6,111,095; and U.S. patent application Ser. Nos. 11/482,671; 11/102,428; 11/291,610; and 10/627,543 which are all incorporated herein by reference.

The SELEX method is clearly the most popular and is conducted in three fundamental steps. First, a library of candidate nucleic acid molecules is selected from for binding to specific molecular target. Second, nucleic acids with sufficient affinity for the target are separated from non-binders. Third, the bound nucleic acids are amplified, a second library is formed, and the process is repeated. At each repetition, aptamers are chosen which have higher and higher affinity for the target molecule. SELEX methods are described more fully in the following publications, which are incorporated herein by reference: Bugaut et al. 2006. 4(22):4082-8; Stoltenburg et al. 2007 Biomol Eng. 2007 24(4):381-403; and Gopinath. 2007. Anal Bioanal Chem. 2007. 387(1):171-82.

An "aptamer" of the invention also been includes aptamer molecules made from peptides instead of nucleotides. Peptide aptamers share many properties with nucleotide aptamers (e.g., small size and ability to bind target molecules with high affinity) and they may be generated by selection methods that have similar principles to those used to generate nucleotide aptamers, for example Baines and Colas. 2006. Drug Discov Today. 11(7-8):334-41; and Bickle et al. 2006. Nat. Protoc. 1(3):1066-91 which are incorporated herein by reference.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to abroad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in U.S. patent application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in U.S. patent application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in E. coli at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in U.S. patent application Publication No. 2007/0191272 which is hereby incorporated by reference in its entirety.

SMIPs™ (Small Modular ImmunoPharmaceuticals-Trubion Pharmaceuticals) engineered to maintain and optimize target binding, effector functions, in vivo half life, and expression levels. SMIPS consist of three distinct modular domains. First they contain a binding domain which may consist of any protein which confers specificity (e.g., cell surface receptors, single chain antibodies, soluble proteins, etc). Secondly, they contain a hinge domain which serves as a flexible linker between the binding domain and the effector domain, and also helps control multimerization of the SMIP drug. Finally, SMIPS contain an effector domain which may be derived from a variety of molecules including Fc domains or other specially designed proteins. The modularity of the design, which allows the simple construction of SMIPs with a variety of different binding, hinge, and effector domains, provides for rapid and customizable drug design.

More information on SMIPs, including examples of how to design them, may be found in Zhao et al. (2007) Blood 110: 2569-77 and the following U.S. pat. app. Nos. 20050238646; 20050202534; 20050202028; 20050202023; 20050202012; 20050186216; 20050180970; and 20050175614.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Antibody Physical Properties

The antibodies of the present invention, which bind to an Ig-like domain of a RTK, may be further characterized by the various physical properties. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) Annu Rev Biochem 41:673-702; Gala F A and Morrison S L (2004) J Immunol 172:5489-94; Wallick et al (1988) J Exp Med 168:1099-109; Spiro R G (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it may be preferred to have an antibody that does not contain variable region glycosylation. This can be achieved either by selecting antibodies that do not contain the glycosylation motif in the variable region or by mutating residues within the glycosylation motif using standard techniques well known in the art.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) Electrophoresis 23:1605-11; Ma et al. (2001) Chromatographia 53:S75-89; Hunt et al (1998) J Chromatogr A 800:355-67). In some instances, it is preferred to have an antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) Curr Pharm Biotechnol 3:361-71). A higher thermal stability indicates greater overall antibody stability in vivo. The melting point of an antibody may be measure using techniques such as differential scanning calorimetry (Chen et al (2003) Pharm Res 20:1952-60; Ghirlando et al (1999) Immunol Lett 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies that do not rapidly degrade may be desired. Fragmentation of an antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Production of Polyclonal Antibodies of the Invention

Polyclonal antibodies of the present invention can be produced by a variety of techniques that are well known in the art. Polyclonal antibodies are derived from different B-cell lines and thus may recognize multiple epitopes on the same antigen. Polyclonal antibodies are typically produced by immunization of a suitable mammal with the antigen of interest, e.g., an Ig-like domain of an RTK such as the D4 or D5 domain of human Kit or the D7 domain of human VEGF. Animals often used for production of polyclonal antibodies are chickens, goats, guinea pigs, hamsters, horses, mice, rats, sheep, and, most commonly, rabbit. In Example 14 below polyclonal anti-Kit antibodies were generated by immunizing rabbits with the fourth (D4) or fifth (D5) Ig-like domain of Kit or the entire ectodomain of Kit. Standard methods to produce polyclonal antibodies are widely known in the art and can be combined with the methods of the present invention (e.g., research.cm.utexas.edu/bkitto/Kittolabpage/Protocols/Immunology/PAb.html; U.S. Pat. Nos. 4,719,290, 6,335, 163, 5,789,208, 2,520,076, 2,543,215, and 3,597,409, the entire contents of which are incorporated herein by reference.

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes. It should be noted that antibodies (monoclonal or polyclonal) or antigen binding portions thereof, may be raised to any epitope on an Ig-like domain of a RTK, more preferably the D4 or D5 domains of the human Kit RTK or, to the concensus sequences discussed herein, or to any conformational, discontinuous, or linear epitopes described herein.

Several methods known in the art are useful for specifically selecting an antibody or antigen binding fragment thereof that specifically binds a discontinuous epitope of interest. For example, the techniques disclosed in U.S. Publication No. 2005/0169925, the entire contents of which are incorporated herein by reference, allow for the selection of an antibody which binds to two different peptides within a protein sequence. Such methods may be used in accordance with the present invention to specifically target the conformational and discontinuous epitopes disclosed herein. If the conformational epitope is a protein secondary structure, such structures often form easily in smaller peptides (e.g., <50 amino acids).

Thus, immunizing an animal with smaller peptides could capture some conformational epitopes. Alternatively, two small peptides which comprise a conformational epitope (e.g., the peptides identified in Table 5) may be connected via a flexible linker (e.g., polyglycol, or a stretch of polar, uncharged amino acids). The linker will allow the peptides to explore various interaction orientations. Immunizing with this construct, followed by appropriate screening could allow for identification of antibodies directed to a conformational epitope. In a preferred embodiment, peptides to specific conformational or linear epitopes may be generated by immunizing an animal with a particular domain of an RTK (e.g., domain 4 or domain 5 of the Kit ectodomain) and subsequently screening for antibodies which bind the epitope of interest. In one embodiment cryoelectron microscopy (Jiang et al. (2008) Nature 451, 1130-1134; Joachim (2006) *Oxford University Press*_ISBN:0195182189) may be used to identify the epitopes bound by an antibody or antigen binding fragment of the invention. In another embodiment, the RTK or a domain thereof may be crystallized with the bound antibody or antigen binding fragment thereof and analyzed by X-ray crystallography to determine the precise epitopes that are bound. In addition, epitopes may be mapped by replacing portions of an RTK sequence with the corresponding sequences from mouse or another species. Antibodies directed to epitopes of interest will selectively bind the human sequence regions and, thus, it is possible to sequentially map target epitopes. This technique of chimera based epitope mapping has been used successfully to identify epitopes in various settings (see Henriksson and Pettersson (1997) Journal of Autoimmunity. 10(6):559-568; Netzer et al. (1999) J Biol. Chem. 1999 Apr. 16; 274(16):11267-74; Hsia et al. (1996) *Mol. Microbiol.* 19, 53-63, the entire contents of which are incorporated herein by reference).

It is believed that the epitopes of interest in target RTKs (e.g., the Kit RTK) are not glycosylated. However, if an RTK of interest is glycosylated, antibodies or antigen binding portions thereof (and other moieties of the invention), may be raised such that they bind to the relevant amino acid and/or sugar residues. For example, it is known in the art that the Kit protein has at least 10 sites for potential N-linked glycosylation (Morstyn, Foote, Lieschke (2004) Hematopoietic Growth Factors in Oncology: Basic Science and Clinical Therapeutics. Humana Press. ISBN:1588293025). It is further thought that Kit may exhibit O-linked glycosylation as well as attachment to sialic acid residues (Wypych J, et al. (1995) Blood. 85(1):66-73). Thus, it is contemplated that antibodies or antigen binding portions thereof (and other moieties of the invention), may be raised such that they also bind to sugar residues which may be attached to any epitope identified herein. For this purpose, an antigenic peptide of interest may be produced in an animal cell such that it gets properly glycosylated and the glycosylated antigenic peptide may then be used to immunize an animal. Suitable cells and techniques for producing glycosylated peptides are known in the art and described further below (see, for example, the technologies available from GlycoFi, Inc., Lebanon, N.H. and BioWa; Princeton, N.J.). The proper glycosylation of a peptide may be tested using any standard methods such as isoelectric focusing (IEF), acid hydrolysis (to determine monosaccharide composition), chemical or enzymatic cleavage, and mass spectrometry (MS) to identify glycans. The technology offered by Procognia (procognia.com) which uses a lectin-based array to speed up glycan analysis may also be used. O-glycosylation specifically may be detected using techniques such as reductive alkaline cleavage or "beta elimination", peptide mapping, liquid chromatography, and mass spectrometry or any combination of these techniques.

The preferred animal system for preparing hybridomas is the murine system. Hybridoma production in the mouse is a very well-established procedure Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.). Alternatively, a humanized antibody may be designed at the DNA or protein level, given knowledge of human and non-human sequences. Such antibodies may be directly synthesized chemically, or the DNA may be synthesized and expressed in vitro or in vivo to produce a humanized antibody.

In a preferred embodiment, the antibodies of the invention are human monoclonal antibodies. Such human monoclonal antibodies directed against an Ig-like domain of an RTK, e.g. the D4 or D5 domain of Kit, can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368 (6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise the antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise the antibodies of the invention. For example, mice carrying both a human heavy chain transchromosome and a human light chain tranchromosome, referred to as "TC mice" can be used; such mice are described in Tomizuka et al. (2000)Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise the antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In another embodiment, antibodies of the invention may be raised using well known phage display techniques, as described in Marks, J. D., et al. ((1991). J. Mol. Biol. 222, 581), Nissim, A., et al. ((1994). EMBO J. 13, 692) and U.S. Pat. Nos. 6,794,132; 6,562,341; 6,057,098; 5,821,047; and 6512097.

In a further embodiment, antibodies of the present invention may be found using yeast cell surface display technology as described, for example, in U.S. Pat. Nos. 6,423,538; 6,300,065; 6,696,251; 6,699,658.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3x63-Ag8.653 nonsecreting mouse myeloma cells (ATCC, CRL 1580) with 50% PEG Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma (a type of hybridoma) using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the described antibodies can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin, signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR☐ promoter system, which contains sequences from the SV40 early promoter and the long terminal repeat of human T cell leukemia virus type 1 (Takebe, Y. et al. (1988)*Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982)*Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to an Ig-Like Domain of a RTK

Antibodies of the invention can be tested for binding to the ectodomain, e.g., an Ig-like domain of a RTK (or any chosen region such as the concensus sequences discussed herein) by, for example, standard ELISA. Briefly, microtiter plates are coated with the purified Ig-like domain (or a preferred receptor domain) at 0.25 µg/ml in PBS, and then blocked with 5% bovine serum albumin in PBS. Dilutions of antibody (e.g., dilutions of plasma from immunized mice, e.g., mice immunized with the D4 or D5 domain of human Kit) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with immunogen. Hybridomas that bind with high avidity to, e.g., an Ig-like domain of an RTK, are subcloned and further characterized. One clone from each hybridoma, which retains the reactivity of the parent cells (by ELISA), can be chosen for making a 5-10 vial cell bank stored at −140° C., and for antibody purification.

To purify anti-RTK antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected monoclonal antibodies bind to unique epitopes, each antibody can be biotinylated using commercially available reagents (Pierce, Rockford, IL). Competition studies using unlabeled monoclonal antibodies and biotinylated monoclonal antibodies can be performed using RTK coated ELISA plates coated with an Ig-like domain of a RTK (e.g., Kit-D4 domain, or Kit-D5 domain) as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-RTK human IgGs can be further tested for reactivity with an Ig-like domain of a RTK or a concensus sequence presented herein by Western blotting. Briefly, an Ig-like domain of a RTK, such as the D4 or D5 domain of the Kit RTK, can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Epitope mapping may be employed to determine the binding site of an antibody or antigen binding fragment thereof of the invention. Several methods are available which further allow the mapping of conformational epitopes. For example, the methods disclosed in Timmerman et al. (Mol. Divers. 2004; 8(2):61-77) may be used. Timmerman et al. were able to successfully map discontinuous/conformational epitopes using two novel techniques, Domain Scan and Matrix Scan. The techniques disclosed in Ansong et al. (J Thromb Haemost. 2006. 4(4):842-7) may also be used. Ansong et al. used affinity directed mass spectrometry to map the discontinuous epitope recognized by the antibody R8B12. In addition, imaging techniques such as Protein Tomography may be used to visualize antibody or peptide binding to target RTKs. Protein Tomography has been used previously to gain insight into molecular interactions, and was used to show that an inhibitory antibody acted by binding domain III of EGFR thereby locking EGFR into an inflexible and inactive conformation (Lammerts et al. Proc Natl Acad Sci USA. 2008. 105(16): 6109-14). More traditional methods such as site-directed mutagenesis may also be applied to map discontinuous epitopes. Amino acid regions thought to participate in a discontinuous epitope may be selectively mutated and assayed for binding to an antibody or antigen binding fragment thereof of the invention. The inability of the antibody to bind when either region is mutated may indicate that binding is dependent upon both amino acid segments. As noted above, some linear epitopes are characterized by particular three-dimensional structures which must be present in order to bind a moiety of the invention. Such epitopes may be discovered by assaying the binding of the antibody (or another moiety) when the RTK is in its native or folded state and again when the RTK is denatured. An observation that binding occurs only in the folded state would indicate that the epitope is either a linear epitope characterized by a particular folded structure or a discontinuous epitope only present in folded protein.

In addition to the activity assays described herein, Protein Tomography may be used to determine whether an antibody or antigen binding fragment thereof of the invention is able to bind and inactivate a receptor tyrosine kinase. Visualization of the binding interaction may indicate that binding of the antibody may affect the positioning of the two ectodomains at the cell surface interface or alter or prevent conformational changes in the receptor tyrosine kinase.

II. Small Molecules which Bind to an Ig-Like Domain or a Hinge Region of a Human Receptor Tyrosine Kinase In another aspect of the invention, the moiety that binds to the ectodomain, e.g., an Ig-like domain or a hinge region, of a human receptor tyrosine kinase is a small molecule.

The small molecules of the instant invention are characterized by particular functional features or properties. For example, the small molecules bind to an Ig-like domain of a RTK, e.g., the D4 or D5 domain of Kit RTK, or a hinge region of a RTK, e.g., the D3-D4 or D4-D5 hinge regions of the Kit RTK. In preferred embodiments, the binding of small molecule inhibitors to the D3-D4 or the D4-D5 hinge regions will prevent the movement that enables the membrane proximal D4 and D5 domains to be at a distance and orientation (position) that allows trans-autophosphorylation and activation of the tyrosine kinase domain followed by recruitment and activation of downstream signaling pathways. The small molecule binding may, in some embodiments, allow the ectodomain of the receptor tyrosine kinase to dimerize but affects the positioning, orientation and/or distance between the Ig-like domains of the two monomers (e.g., the D4-D4 or D5-D5 domains of a type III receptor tyrosine kinase or the D7-D7 domains of a type V receptor tyrosine kinase), thereby inhibiting the activity of the receptor tyrosine kinase. In other words, the moiety or small molecule may allow ligand induced dimerization of the receptor tyrosine kinase ectodomains, but affect the positioning of the two ectodomains at the cell surface interface, thereby inhibiting the activity of the receptor tyrosine kinase (e.g., inhibiting receptor internalization and/or inhibiting tyrosine autophosphorylation of the receptor and/or inhibiting the ability of the receptor to activate a downstream signaling pathway).

The terms "small molecule compounds", "small molecule drugs", "small molecules", or "small molecule inhibitors" are used interchangeably herein to refer to the compounds of the present invention screened for an effect on RTKs and their ability to inhibit the dimerization or activity of the RTK, e.g., the Kit RTK. These compounds may comprise compounds in PubChem database (pubchem.ncbi.nlm.nih.gov/), the Molecular Libraries Screening Center Network (MLSCN) database, compounds in related databases, or derivatives and/or functional analogues thereof.

As used herein, "analogue" or "functional analogue" refers to a chemical compound or small molecule inhibitor that is structurally similar to a parent compound, but differs slightly in composition (e.g., one or more atoms or functional groups are added, removed, or modified). The analogue may or may not have different chemical or physical properties than the original compound and may or may not have improved biological and/or chemical activity. For example, the analogue may be more hydrophobic or it may have altered activity (increased, decreased, or identical to parent compound) as compared to the parent compound. The analogue may be a naturally or non-naturally occurring (e.g., recombinant) variant of the original compound. Other types of analogues include isomers (enantiomers, diasteromers, and the like) and other types of chiral variants of a compound, as well as structural isomers. The analogue may be a branched or cyclic variant of a linear compound. For example, a linear compound may have an analogue that is branched or otherwise substituted to impart certain desirable properties (e.g., improve hydrophilicity or bioavailability).

As used herein, "derivative" refers to a chemically or biologically modified version of a chemical compound or small molecule inhibitor that is structurally similar to a parent compound and (actually or theoretically) derivable from that parent compound. A "derivative" differs from an "analogue" or "functional analogue" in that a parent compound may be the starting material to generate a "derivative," whereas the parent compound may not necessarily be used as the starting material to generate an "analogue" or "functional analogue." A derivative may or may not have different chemical or physical properties of the parent compound. For example, the derivative may be more hydrophilic or it may have altered reactivity as compared to the parent compound. Derivatization (i.e., modification by chemical or other means) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Bundgaard (ed.), Elsevier, 1985; and H. Bundgaard, Drugs of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups such as carboxylic acid groups can form alkali metal salts or alkaline earth metal salts (e.g., sodium salts, potassium salts, magnesium salts, calcium salts, and salts with physiologically tolerable quaternary ammonium ions and acid addition salts with ammonia and physiologically tolerable organic amines such as triethylamine, ethanolamine, or tris-(2-hydroxyethyl)amine). Basic groups can form acid addition salts, for example with inorganic acids such as hydrochloric acid ("HCl"), sulfuric acid, or phosphoric acid, or with organic carboxylic acids and sulfonic acids such as acetic acid, citric acid, benzoic acid, maleic acid, fumaric acid, tartaric acid, methanesulfonic acid, or p-toluenesulfonic acid. Compounds which simultaneously contain a basic group and an acidic group such as a carboxyl group in addition to basic nitrogen atoms can be present as zwitterions. Salts can be obtained by customary methods known to those skilled in the art, for example by combining a compound with an inorganic or organic acid or base in a solvent or diluent, or from other salts by cation exchange or anion exchange.

Small molecules are known to have molecular weights of 1200 or below, 1000 or below, 900 or below, 800 or below, 700 or below, 600 or below, 500 or below, 400 or below, 300 or below, 200 or below, 100 or below; 50 or below, 25 or below, or 10 or below.

The small molecule inhibitors of the present invention are selected or designed to bind to the ectodomain, e.g., an Ig-like domain or a hinge region, of a RTK. In some embodiments, the small molecule inhibitors are selected or designed to bind an Ig-like domain or a hinge region of human Kit or PDGFR, e.g., the D4 or D5 domain, or the D3-D4 and/or D4-D5 hinge regions of the human Kit receptor, thereby antagonizing the ability of the receptor to dimerize and become active, e.g., autophosphorylate and activate an intracellular signal transduction pathway. In other embodiments the small molecule inhibitors are selected to bind domains sharing homology to a domain of the Kit receptor. For example, a small molecule of the present invention may be directed toward a domain which is at least 50% identical, at least 60% identical, at least 70% identical, at least 80% identical, at least 90% identical, or at least 95% or 99% identical to an Ig-like domain of a RTK, e.g., the D4 or D5 domain of Kit; or a hinge region of a RTK, e.g., the D3-D4 or D4-D5 hinge regions, of the Kit or PDGFR receptor. Such a small molecule would be capable of binding protein domains, possibly in Kit and other RTKs, which are functionally similar to, for example, the D4 or D5 domains or the D3-D4 and/or D4-D5 hinge regions of the Kit or PDGF receptor.

The small molecule inhibitors of the present invention may also bind to a particular motif or consensus sequence derived from an Ig-like domain or a hinge region of a RTK, e.g., a human type III RTK, allowing the small molecule inhibitors to specifically bind domains which are shared among members of the RTK family, e.g., members of the human type III family of RTKs.

In a specific embodiment, a small molecule of the present invention binds to the following consensus sequence for the D4 interaction site: $LX_1RX_2X_3X_4X_5X_6X_7G$ (SEQ ID NO: 158) wherein L is Leucine, R is Arginine, G is Glycine; $X_1$, is selected from the group consisting of Threonine, Isoleucine, Valine, Proline, Asparagine, or Lysine: X2 is selected from the group consisting of Leucine, Valine, Alanine, and Methionine; $X_3$, is selected from the group consisting of Lysine. Histidine, Asparagine, and Arginine; $X_4$ is selected from the group consisting of Glycine, Valine, Alanine, Glutamic Acid, Proline, and Pviethionine; $X_5$ is selected from the group consisting of Threw)Me, Serine, Glutamic Acid, Alanine, Glutamine, and Aspartic acid; $X_6$ is selected from the group consisting of (ilutamic Acid, Aspartic acid. and Glutamine; and $X_7$ is selected from the group consisting of Glycine, Serine, Alanine, Lysine, Arginine, Glutamine, and Threonine.

In another embodiment a small molecule of the present invention binds to the following consensus sequence for the D7 domain of a member of the VEGF receptor family: $IX_1RVX_2X_3EDX_4G$ (SEQ ID NO: 1) wherein I is Isoleucine, R is Arginine, E is Glutamic Acid, D is Aspartic Acid, G is Glycine; $X_1$ is selected from the group consisting of Glutamic Acid, Arginine, and Glutamine; X2 is selected from the group consisting of Arginine and Threonine; $X_3$ is selected from the group consisting of Glutamic Acid and Lysine; and $X_4$ is selected from the group consisting of Glutamic Acid and Alanine.

In other embodiments, small molecule inhibitors bind protein motifs or consensus sequences which represent the three dimensional structure of the protein. Such motifs or consensus sequences would not represent a contiguous string of amino acids, but a non-linear amino acid arrangement that results from the three-dimensional folding of the RTK (i.e., a structural motif). An example of such a motif would be a motif designed based on the D3-D4 and/or D4-D5 hinge regions of the Kit receptor. Such motifs and consensus sequences may be designed according to the methods discussed in Section I regarding antibodies.

Importantly, a small molecule inhibitor of the invention does not bind to the ligand binding site of the RTK, e.g., the SCF binding site of the Kit receptor. In other words, the small molecule inhibitor does not bind to the Ig-like domains of a RTK responsible for ligand binding.

In additional embodiments, small molecule inhibitors of the invention are selected or designed to bind specifically to a mutant ectodomain, e.g., a mutant Ig-like domain or a mutant hinge region, of a RTK. In preferred embodiments, the mutant RTK is a tumorigenic or an oncogenic mutant. In one specific embodiment, the small molecule inhibitor is selected or designed to bind to an oncogenic Kit receptor mutant. Kit receptor mutants which may be targeted by the small molecules of the instant invention are Kit receptors with mutations in one or more of the following amino acids: Thr417, Tyr418, Asp419, Leu421, Arg420, Tyr503, or Ala502. It should be appreciated by one of skill in the art that the methods of the invention would be applicable to other mutations in Kit or to mutations in other RTKs. One advantage of targeting a mutant RTK is that a therapeutic small molecule may bind to only the RTKs on cells containing the mutation, leaving healthy cells largely or entirely unaffected. Accordingly, in instances where the mutation is tumorigenic, only tumor cells would be targeted for therapy, potentially reducing side effects and dosage requirements.

In some embodiments the small molecule binds to specific sequences of the human Kit receptor, for example, residues 309-413, residues 410-519, $^{381}$Arg and $^{386}$Glu, or $^{418}$Tyr and $^{505}$Asn of the human Kit receptor.

In a preferred embodiment, a small molecule of the invention may bind to one or more residues in the Kit receptor which make up the small cavities or pockets described in Table 4 (below). For example, a small molecule of the invention may bind to one or more of the following residues in the D3-D4 hinge region of the Kit receptor: K218, S220, Y221, L222 from the D3 domain and F340, P341, K342, N367, E368, 5369, N370, I371, Y373 from the D4 domain. A small molecule of the invention may also bind to one or more of the following residues which make up a concave surface in the D4 domain of the Kit receptor: Y350, R353, F355, K358, L379, T380, R381, L382, E386 and T390. In another embodiment, a small molecule of the invention may bind to one or more of the following residues which form a pocket in the D2-D3 hinge region of the Kit receptor: Y125, G126, H180, R181, K203, V204, R205, P206 and F208 from the D2 domain and V238, S239, S240, S241, H263, G265, D266, F267, N268 and Y269 from the D3 domain.

Thus, in some embodiments, a small molecule of the invention may bind to contiguous or non-contiguous amino acid residues and function as a molecular wedge that prevents the motion required for positioning of the membrane proximal region of the RTK at a distance and orientation that enables tyrosine kinase activation. A small molecule of the invention may also act to prevent homotypic D4 or D5 receptor interactions or destabilize the ligand-receptor interaction site. In some preferred embodiments, a small molecule of the invention may bind to one or more of the following residues on the Kit receptor: Y125, G126, H180, R181, K203, V204, R205, P206, P206, F208, K127, A207, V238, S239, 5240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F355, G311, G384, G387, G388,I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432. One of skill in the art will appreciate that, in some embodiments, a small molecule of the invention may be easily targeted to the corresponding residues in other type III RTKs, e.g., those residues that form similar pockets or cavities or those in the same position by structural alignment or sequence alignment.

In a specific embodiment, a small molecule of the invention binds to a conformational epitope or a discontinuous epitope on a type III RTK. The conformational or discontinuous epitope may be composed of two or more residues from the D3, D4, or D5 domain or the D4-D5 or D3-D4 hinge regions from a type III RTK, e.g., the human Kit receptor or the PDGF receptor. For example, the conformational or discontinuous epitope may be composed of two or more of the residues listed in Table 4 below. In a particular embodiment, a small molecule of the invention binds to a conformational epitope composed of 2 or more amino acids selected from the group consisting of Y125, H180, R181, K203, V204, R205, P206, V238, 5239, S240, H263, G265, D266, F267, N268, and Y269. In similar embodiments, a small molecule of the invention may bind to a conformational epitope composed of 2 or more amino acids selected from one of the following groups of amino acids: P206, F208, V238, and S239; K127, A207, F208, and T295; L222, A339, F340, K342, E368, S369, N370, I371, and Y373; L222, L223, E306, V308, F312, E338, F340, and I371; R224, V308, K310, G311, F340, P341, and D398; K218, A219, S220, N367, E368, and S369; K218, A220, E368, and S369; G384, T385, T411, K412, E414, and K471; Y408, F433, G470, K471, and L472; F324, V325, N326, and N410; D327, N410, T411, K412, and V497; G384, G387, V409, and K471; L382, G387, V407, and V409; Y125, G126, H180, R181, K203, V204, R205, P206, F208, V238, S239, S240, 5241, H263, G265, D266, F267, N268, and Y269; P206, F208, V238, and S239; K218, S220, Y221, L222, F340, P341, K342, N367, E368, S369, N370, I371, and Y373; G384, G387, G388, Y408, V409, T411, F433, F469, G470, and K471; D327, T411, K412, E414, A431, G432, and K471; Y350, F355, K358, L379, T380, R381, L382, E386, and T390; Y350, 8353, and F355. As indicated above, the small molecules of the invention may bind to all of the amino acid residues forming a pocket or a cavity identified in Table 4 or they may bind to a subset of the residues forming the pocket or the cavity. It is to be understood that, in certain embodiments, when reference is made to a small molecule of the invention binding to an epitope, e.g., a conformational epitope, the intention is for the small molecule to bind only to those specific residues that make up the epitope (e.g., the pocket or cavity identified in Table 4) and not other residues in the linear amino acid sequence of the receptor.

In a further embodiment, a small molecule of the invention binds to a conformational epitope wherein the conformational epitope is composed of two or more amino acid residues selected from the peptides listed in Table 5. In a specific embodiment, the conformational epitope is composed of one or more amino acid residues selected from a first peptide and one or more amino acid residues selected from a second peptide, wherein the first and second peptides are selected from the group of peptides listed in Table 5. As such, a small molecule of the invention binds a conformational epitope wherein the first and second peptide groups are as follows: Ala219-Leu222 and Thr304-Val308; Asp309-Gly311 and Arg224-Gly226; Thr303-Glu306 and Ala219-Leu222; Asn367-Asn370 and Ser217-Tyr221; Ala339-Pro343 and Asn396-Val399; Ala339-Pro343 and Glu368-Arg372; Lys358-Tyr362 and Val374-His378; Asp357-Glu360 and Leu377-Thr380; Met351-Glu360 and His378-Thr389; His378-Thr389 and Val323-Asp332; Val409-Ile415 and Ala493-Thr500; Val409-Ile415 and Ala431-Thr437; Val409-Ile415 and Phe469-Val473; Val409-Ile415 and Val325-Asn330; Val409-Ile415 and Arg381-Gly387; Gly466-Leu472 and Gly384-Gly388; Val325-Glu329 and Tyr494-Lys499; Thr411-leu416 and Val497-Ala502; Ile415-Leu421 and Ala502-Ala507; Ala502-Ala507 and Lys484-Thr488; and Ala502-Ala507 and Gly445-Cys450. The small molecules of the invention may bind to all of the amino acid residues forming the foregoing first and second peptide groups or they may bind to a subset of the residues forming the first and second peptide groups. It is to be understood that, in certain embodiments, when reference is made to a small molecule of the invention binding to an epitope, e.g., a conformational epitope, the intention is for the small molecule to bind only to those specific residues that make up the epitope (e.g., the specific peptides identified in Table 5) and not other residues in the linear amino acid sequence of the receptor.

In another embodiment, a small molecule of the invention binds to a conformational or discontinuous epitope composed of 2 or more amino acids selected from the group consisting of E33, P34, D72, E76, N77, K78, Q79, K158, D159, N250, S251, Q252, T253, K254, L255, N260, W262, H264, G265, E344, N352, R353, F355, T356, D357, Y362, S365, E366, N367, N370, and G466.

In another embodiment, a small molecule of the invention binds to amino acid residues $^{385}$Arg and $^{390}$Glu of human PDGFRβ, or the corresponding residues in PDGFRα. The residues $^{385}$Arg and $^{390}$Glu of human PDGFRβ are analogous to the residues $^{381}$Arg and $^{386}$Glu of the Kit receptor and mediate homotypic D4-D4 interactions of PDGFRβ. Small molecules of the invention may exert their inhibitory effect on receptor activation by preventing critical homotypic interactions (such as salt bridges formed between $^{385}$Arg and $^{390}$Glu of human PDGFRβ between membrane proximal regions of type-III RTKs that are essential for positioning the cytoplasmic domain at a distance and orientation essential for tyrosine kinase activation. Experiments discussed herein demonstrate that homotypic D4-D4 interactions are dispensable for PDGFRβ dimerization and that PDGFRβ dimerization is necessary but not sufficient for receptor activation. Thus, small molecules of the invention may allow dimerization of PDGFRβ while preventing activation. Structure based sequence alignment has shown that the size of the EF loop, and the critical amino acids comprising the D4-D4 interface are conserved in Kit, PDGFRα, PDGFRβ, and CSF1R. Thus in some embodiments, small molecules of the invention may be targeted to the conserved regions of the D4 or D5 domains of type III RTKs.

In preferred embodiments, a small molecule of the invention binds to an Ig-like domain or hinge region of Kit (e.g., the D3-D4 and/or D4-D5 hinge regions or the D4-D4 and/or D5-D5 interface binding site of the Kit receptor) with high affinity, for example, with an affinity of a $K_D$ of $1\times10^{-7}$ M or less, a $K_D$ of $5\times10^{-8}$ M or less, a $K_D$ of $1\times10^{-8}$ M or less, a $K_D$ of $5\times10^{-9}$ M or less, or a $K_D$ of between $1\times10^{-8}$ M and $1\times10^{-10}$ M or less.

Small molecule inhibitors of the invention may be made or selected by several methods known in the art. Screening procedures can be used to identify small molecules from libraries which bind desired Ig-like domains or hinge regions of a RTK, e.g., the D4 or D5 domain of human Kit RTK. One method, Chemetics® (Nuevolutions) uses DNA tags for each molecule in the library to facilitate selection. The Chemetics® system allows screening of millions of compounds for target binding. Patents related to small molecule libraries and tag based screening are U.S. pat. application Nos. 20070026397; 20060292603; 20060269920; 20060246450; 20060234231; 20060099592; 20040049008; 20030143561 which are incorporated herein by reference in their entirety.

Other well known methods that may be used to identify small molecules from libraries which bind desired Ig-like domains or hinge regions of a RTK, e.g., the D4 or D5 domain of human Kit RTK, include methods which utilize libraries in which the library members are tagged with an identifying label, that is, each label present in the library is associated with a discreet compound structure present in the library, such that identification of the label tells the structure of the tagged molecule. One approach to tagged libraries utilizes oligonucleotide tags, as described, for example, in PCT Publication No. WO 2005/058479 A2 (the Direct Select™ technology) and in U.S. Pat. Nos. 5,573,905; 5,708,153; 5,723,598, 6,060,596 published PCT applications WO 93/06121; WO 93/20242; WO 94/13623; WO 00/23458; WO 02/074929 and WO 02/103008, and by Brenner and Lerner (*Proc. Natl. Acad. Sci. USA* 89, 5381-5383 (1992); Nielsen and Janda (*Methods: A Companion to Methods in Enzymology* 6, 361-371 (1994); and Nielsen, Brenner and Janda (*J. Am. Chem. Soc.* 115, 9812-9813 (1993)), the entire contents of each of which are incorporated herein by reference in their entirety. Such tags can be amplified, using for example, polymerase chain reaction, to produce many copies of the tag and identify the tag by sequencing. The sequence of the tag then identifies the structure of the binding molecule, which can be synthesized in pure form and tested for activity.

Preparation and screening of combinatorial chemical libraries is well known to those skilled in the art. Such combinatorial chemical libraries which may be used to identify moieties of the invention include, but are not limited to, peptide libraries (see, e.g., U.S. Pat. No. 5,010,175, Furka, *Int. J. Pept. Prot. Res.* 37:487 493 (1991) and Houghton et al., Nature 354:84 88 (1991)). Other chemistries for generating chemical diversity libraries are well known in the art and can be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909 6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217 9218 (1992)), analogous organic syntheses of small compound libraries (Chen et al., *J. Amer. Chem. Soc.* 116:2661 (1994)), oligocarbamates (Cho et al., *Science* 261:1303 (1993)), and/ or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), carbohydrate libraries (see, e.g., Liang et al., *Science,* 274:1520 1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, 5,288,514, and the like). Each of the foregoing publications is incorporated herein by reference. Public databases are also available and are commonly used for small molecule screening, e.g., PubChem (pubchem.ncbi.nlm.nih-.gov), Zinc (Irwin and Shoichet (2005) J. Chem. Inf. Model. 45(1):177-82), and ChemBank (Seiler et al. (2008) Nucleic Acids Res. 36 (Database issue): D351-D359).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.). Moreover, since screening methodologies are so well defined, it is common to contract specialist firms to identify particular compounds for a target of interest (e.g., BioFocus DPI (biofocus.com), and Quantum Lead (q-lead.com)).

Other methods of selecting small molecules which are well known in the art, and may be applied to the methods of the present invention are Huang and Stuart L. Schreiber (1997) Proc Natl Acad Sci USA. 94(25): 13396-13401; Hung et al. (2005) *Science* 310:670-674; Zhang et al. (2007) Proc Natl Acad Sci 104: 4606-4611; or any of the methods reviewed in Gordon (2007) ACS Chem. Biol. 2:9-16, all of which are incorporated herein by reference in their entirety.

In addition to experimental screening methods, small molecules of the invention may be selected using virtual screening methods. Virtual screening technologies predict which small molecules from a library will bind to a protein, or a specific epitope therein, using statistical analysis and protein docking simulations. Most commonly, virtual screening methods compare the three-dimensional structure of a protein to those of small molecules in a library. Different strategies for modeling protein-molecule interactions are used, although it is common to employ algorithms which simulate binding energies between atoms, including hydrogen bonds, electrostatic forces, and van-der walls interactions. Typically, virtual screening methods can scan libraries of more than a million compounds and return a short list of small molecules which are likely to be strong binders. Several reviews of virtual screening methods are available, detailing the techniques which may be used to identify small molecules of the present invention (Engel et al. (2008) J. Am. Chem. Soc., 130 (15), 5115-5123; McInnes. (2007). Curr Opin Chem. Biol. October; 11(5):494-502; Reddy et al. (2007) Curr Protein Pept Sci. August; 8(4):329-51; Muegge and Oloff. (2006) Drug Discovery Today. 3(4): 405-411; Kitchen et al. (2004) Nature Reviews Drug Discovery 3, 935-949). Further examples of small molecule screening can be found in U.S. 2005/0124678, which is incorporated herein by reference.

Small molecules of the invention may contain one of the scaffold structures depicted in the table below. The references cited in the table are incorporated herein by reference in their entirety. The groups $R_1$, $R_2$, $R_3$ and $R_4$ are limited only in that they should not interfere with, or significantly inhibit, the indicated reaction, and can include hydrogen, alkyl, substituted alkyl, heteroalkyl, substituted heteroalkyl, cycloalkyl, heterocycloalkyl, substituted cycloalkyl, substituted heterocycloalkyl, aryl, substituted aryl, arylalkyl, heteroarylalkyl, substituted arylalkyl, substituted heteroarylalkyl, heteroaryl, substituted heteroaryl, halogen, alkoxy, aryloxy, amino, substituted amino and others as are known in the art. Suitable substituents include, but are not limited to, alkyl, alkoxy, thioalkoxy, nitro, hydroxyl, sulfhydryl, aryloxy, aryl-S—, halogen, carboxy, amino, alkylamino, dialkylamino, arylamino, cyano, cyanate, nitrile, isocyanate, thiocyanate, carbamyl, and substituted carbamyl.

TABLE 6
| Scaffolds | Amine | Aldehyde/Ketone | Carboxylic acid | Other | Reference |
|---|---|---|---|---|---|
| 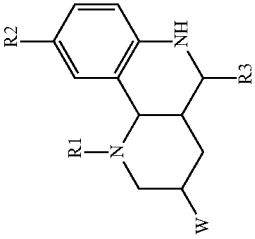 | 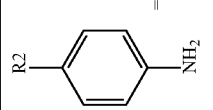 |  | 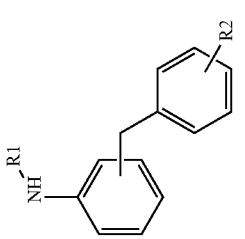 | 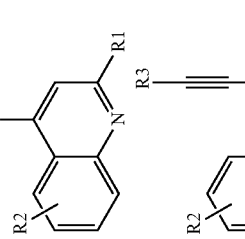 | Carranco, I., et al. (2005) J. Comb. Chem. 7:33-41 |
| 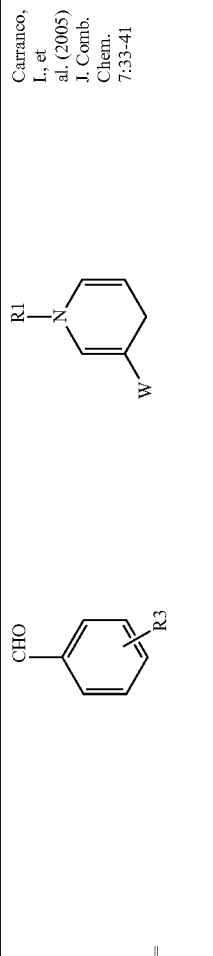 | amines | benzaldehydes and furfural |  | 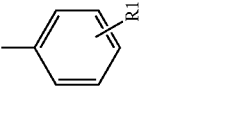 | Rosamilia, A. E., et al. (2005) Organic Letters 7:1525-1528 |
| 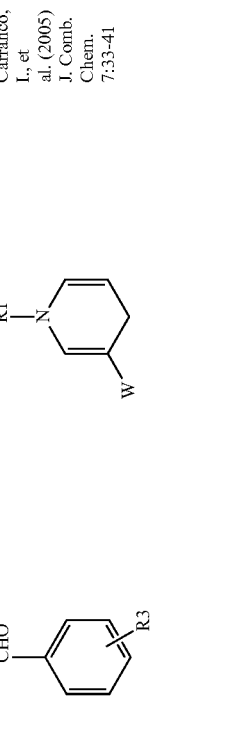 | 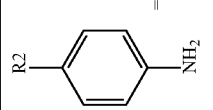 | 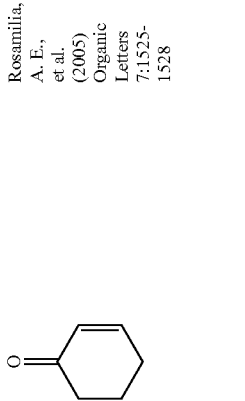 |  |  | Syeda Huma, H.Z., et al. (2002) Tet Lett 43:6485-6488 |
| 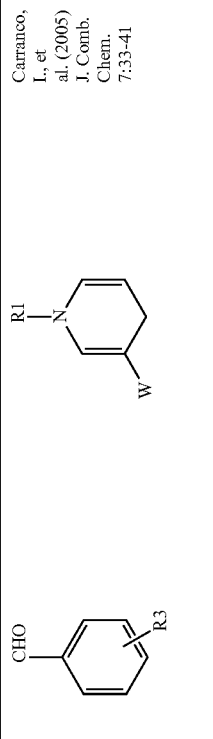 |  |  |  |  |  |

TABLE 6-continued

| Scaffolds | Amine | Aldehyde/Ketone | Carboxylic acid | Other | Reference |
|---|---|---|---|---|---|
| | H₂N–[phenyl]–NHBoc | R2—CHO | [phenyl with R1]—COOH | ≡N—R3 | Tempest, P., et al. (2001) Tet Lett 42:4959-4962 |
| | [benzyl]—NH₂ | [furan with R1]—CHO | COOH—[chain]—EWG | [benzyl]—C≡N | Paulvannan, K. (1999) Tet Lett 40:1851-1854 |
| | R2—NH₂ | R1—CHO | NO₂—[fluorophenyl]—COOH | ≡N—R4 | Tempest, P., et al. (2001) Tet Lett 42:4963-4968 |
| | | Boc–HN–CH(R1)–CHO | NO₂—[fluorophenyl]—COOH | ≡N—R3 | Tempest, P., et al. (2003) Tet Lett 44:1947-1950 |

TABLE 6-continued

| Scaffolds | Amine | Aldehyde/ Ketone | Carboxylic acid | Other | Reference |
|---|---|---|---|---|---|
| | | R1—CHO | R2—COOH | | |
| (scaffold structure) | | | | (Fmoc-Cys(S-Ar-NO2,COOMe)-OH structure) | Nefzi, A., et al. (1999) Tet Lett 40:4939-4942 |
| (dihydropyrimidinone scaffold) | | (ethyl acetoacetate); (ArCHO with R) | | (thiourea, H2N-C(=S)-NH2) | Bose, A.K., et al. (2005) Tet Lett 46:1901-1903 |
| (dihydropyrimidine scaffold) → (pyrimidine scaffold) | | R2-C(O)-CH2-EWG; R1—CHO | | (H2N-C(=S)-NH2); (R3-HN-C(=NZ)-NH2) | Stadler, A. and Kappe, C.O. (2001) J. Comb. Chem. 3:624-630; Lengar, A. and Kappe, C.O. (2004) Organic Letters 6:771-774 |

TABLE 6-continued

| Scaffolds | Amine | Aldehyde/Ketone | Carboxylic acid | Other | Reference |
|---|---|---|---|---|---|
| | wide range of primary aliphatic amines | | | R4-CH2-Cl | Ivachtchenko, A.V., et al. (2003) J. Comb. Chem. 5:775-788 |
| | | aryl ketone (R1), aryl CHO (R2) | CO2Me, NCS substituted toluene (R2) | SH, NH2 substituted benzene (R3) | Micheli, F., et al. (2001) J. Comb. Chem. 3:224-228 |
| | R1—HS, R1—NH2 | FMOC-protected aminomethyl aryl dimethyl acetal (R2) | R3-COOH | epoxide-containing benzyl alcohol, RAC | Sternson, S.M., et al. (2001) Org. Lett. 3:4239-4242 |

TABLE 6-continued
| Scaffolds | Amine | Aldehyde/Ketone | Carboxylic acid | Other | Reference |
|---|---|---|---|---|---|
| 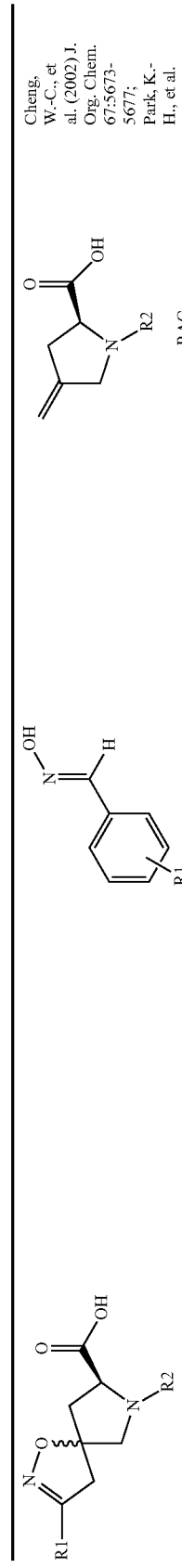 | | 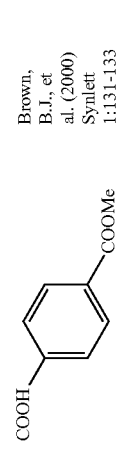 | | 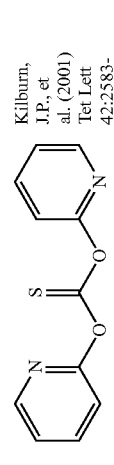 RAC | Cheng, W.-C., et al. (2002) J. Org. Chem. 67:5673-5677; Park, K.-H., et al. (2001) J Comb Chem 3:171-176 |
| 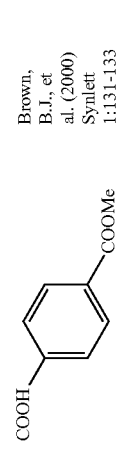 DIA | 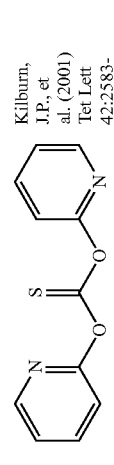 | | | 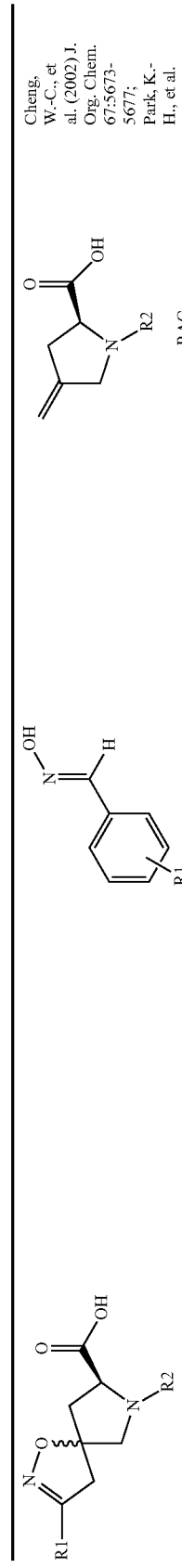 | Brown, B.J., et al. (2000) Synlett 1:131-133 |
| 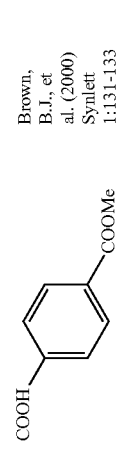 | R1—NH$_2$ | | 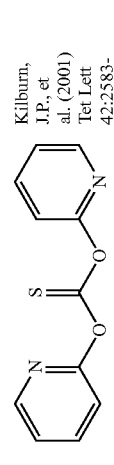 FMOC | 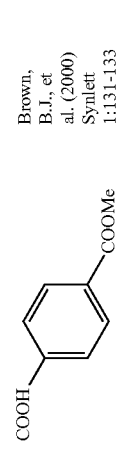 | Kilburn, J.P., et al. (2001) Tet Lett 42:2583-2586 |
| 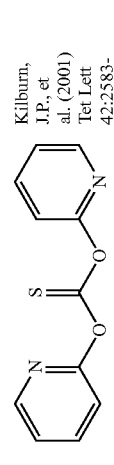 | amino acid | | amino acid ester | | del Fresno, M., et al. (1998) Tet Lett 39:2639-2642 |
| 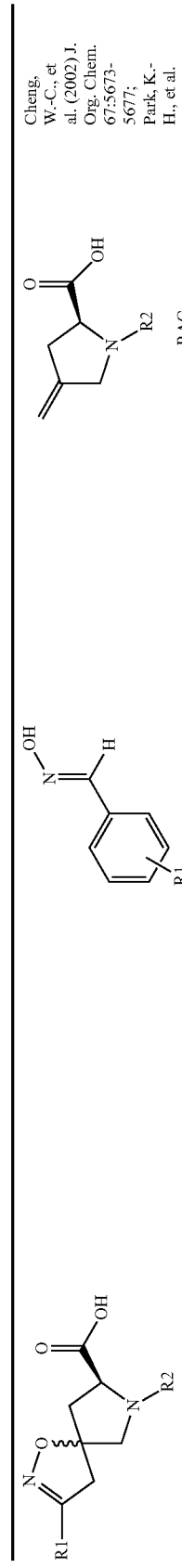 | amino acid | | carboxylic acids | | Alvarez-Gutierrez, J.M., et al. (2000) Tet Lett 41:609-612 |

TABLE 6-continued
| Scaffolds | Amine | Aldehyde/Ketone | Carboxylic acid | Other | Reference |
|---|---|---|---|---|---|
| 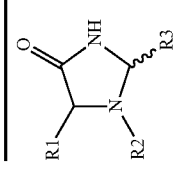 | | R2—CHO | 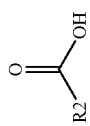 |  | Rinnová, M., et al. (2002) J. Comb. Chem 4:209-213 |
| 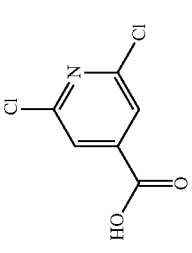 | R1—NH$_2$ | | 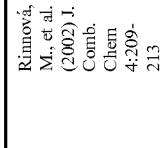 |  | Makara, G.M., et al. (2002) Organic Lett 4:1751-1754 |
|  | | | | 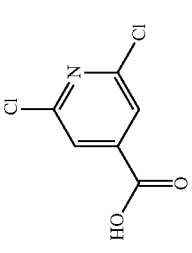 | Schell, P., et al. (2005) J. Comb. Chem 7:96-98 |
| | | | amino acids | | Feliu, L., et al. (2003) J. Comb. Chem. 5:356-361 |

TABLE 6-continued
| Scaffolds | Amine | Aldehyde/Ketone | Carboxylic acid | Other | Reference |
|---|---|---|---|---|---|
|  | Amines | Aldehydes | | | |
|  | | | amino acids | | Hiroshige, M., et al (1995) J. Am. Chem. Soc. 117: 11590-11591 |
|  | | | amino acids | | Bose, A.K., et al. (2005) Tet Lett 46:1901-1903 |

III. Peptidic Molecules Which Bind To An Ig-Like Domain Of A Human Receptor Tyrosine Kinase In another aspect of the invention, the moiety that binds to the ectodomain, e.g., an Ig-like domain or a hinge region, of a human receptor tyrosine kinase is a peptidic molecule.

The peptidic molecules may be designed based on an Ig-like domain of a RTK or a consensus sequence derived from such a domain.

In a specific embodiment, the peptidic molecules bind to the following consensus sequence for the D4 interaction site: $LX_1RX_2X_3X_4X_5X_6X_7G$ (SEQ ID NO: 158) wherein L is Leucine, R is Arginine, G is Glycine; $X_1$, is selected from the group consisting of Threonine, Isoleucine, Valine, Proline, Asparagine, or Lysine; X2 is selected from the group consisting of Leucine, Valine, Alanine, and Methionine; $X_3$ is selected from the group consisting of Lysine, Histidine, Asparagine, and Arginine; $X_4$ selected from the group consisting of Glycine, Valine, Alanine, Glutamic Acid, Proline, and Methionine; $X_5$ is selected from the group consisting of Threonine, Serine, Glutamic Acid, Alanine, Glutamine, and Aspartic acid; $X_6$ is selected from the group consisting of Glutamic Acid, Aspartic acid, and Glutamine; and $X_7$ is selected from the group consisting of Glycine, Serine, Alanine, Lysine, Arginine, Glutamine, and Threonine.

As such, in one embodiment, the peptidic molecules of the invention comprise or consist of a sequence matching the aforementioned consensus sequence $(LX_1RX_2X_3X_4X_5X_6X_7G)$ (SEQ ID NO: 158) wherein L is Leucine, R is Arginine, G is Glycine; $X_1$ is selected from the group consisting of Threonine, Isoleucine, Valine, Proline, Asparagine, or Lysine; X2 is selected from the group consisting of Leucine, Valine, Alanine, and Methionine; $X_3$ is selected from the group consisting of Lysine, Histidine, Asparagine, and Arginine; $X_4$ is selected from the group consisting of Glycine, Valine, Alanine, Glutamic Acid, Proline, and Methionine; $X_5$ is selected from the group consisting of Threonine, Serine, Glutamic Acid, Alanine, Glutamine, and Aspartic acid; $X_6$ is selected from the group consisting of Glutamic Acid, Aspartic acid, and Glutamine; and $X_7$ is selected from the group consisting of Glycine, Serine, Alanine, Lysine, Arginine, Glutamine, and Threonine.

In another embodiment, the peptidic molecules bind to the following consensus sequence for the D7 domain of a member of the VEGF receptor family: $IX_1RVX_2X_3EDX_4G$ (SEQ ID NO: 1) wherein I is Isoleucine, R is Arginine, E is Glutamic Acid, D is Aspartic Acid, G is Glycine; $X_1$ is selected from the group consisting of Glutamic Acid, Arginine, and Glutamine; X2 is selected from the group consisting of Arginine and Threonine; $X_3$ is selected from the group consisting of Glutamic Acid and Lysine; and $X_4$ is selected from the group consisting of Glutamic Acid and Alanine.

As such, in one embodiment, the peptidic moieties of the invention comprise or consist of a sequence matching the consensus sequence $IX_1RVX_2X_3EDX_4G$ (SEQ ID NO: 1) wherein I is Isoleucine, R is Arginine, E is Glutamic Acid, D is Aspartic Acid, G is Glycine; $X_1$ is selected from the group consisting of Glutamic Acid, Arginine, and Glutamine; X2 is selected from the group consisting of Arginine and Threonine; $X_3$ is selected from the group consisting of Glutamic Acid and Lysine; and $X_4$ is selected from the group consisting of Glutamic Acid and Alanine.

In one embodiment, the peptidic moieties of the invention may comprise an entire protein domain, for example, a D4 or a D5 domain such as the D4 domain (residues 309-413) or the D5 domain (residues 410-519) of human Kit. As a further example, the peptidic moieties of the invention may comprise a D7 domain (or fragment thereof) of a type V RTK, such as the D7 domain of VEGFR. Such a peptidic molecule binds the RTK and acts as an antagonist by preventing activation of RTK (see Example 16 below). In some embodiments, the peptidic moieties of the invention may have as little as 50% identity to a domain of a RTK, such as a Type III RTK, e.g., a peptidic moiety of the invention may be at least 50% identical, at least 60% identical, at least 70% identical, at least 80% identical, at least 90% identical, or at least 95%, 96%, 97%, or 98% identical to a D4 or a D5 domain of a RTK. In a specific embodiment, the peptidic moiety of the invention is at least 80% identical, at least 90% identical, or at least 95%, 96%, 97%, or 98% identical to amino acid residues 309-413 of human Kit RTK. In a similar embodiment, the peptidic moiety of the invention is at least 80% identical, at least 90% identical, or at least 95%, 96%, 97%, or 98% identical to amino acid residues 410-519 of human Kit RTK.

In some embodiments, the peptidic moiety of the invention binds to or comprises specific sequences of the human Kit receptor, for example, residues 309-413, residues 410-519, $^{381}$Arg and $^{386}$Glu, or $^{418}$Tyr and $^{505}$Asn of the human Kit receptor.

In a preferred embodiment, a peptidic moiety of the invention may bind to (or comprise or consist of) one or more residues in the Kit receptor which make up the small cavities or pockets described in Table 4 (below). For example, a peptidic molecule of the invention may bind to (or comprise or consist of) one or more of the following residues in the D3-D4 hinge region of the Kit receptor: K218, S220, Y221, L222 from the D3 domain and F340, P341, K342, N367, E368, 5369, N370, I371, Y373 from the D4 domain. A peptidic molecule of the invention may also bind to (or comprise or consist of) one or more of the following residues which make up a concave surface in the D4 domain of the Kit receptor: Y350, R353, F355, K358, L379, T380, R381, L382, E386 and T390. In another embodiment, a peptidic molecule of the invention may bind to (or comprise or consist of) one or more of the following residues which form a pocket in the D2-D3 hinge region of the Kit receptor: Y125, G126, H180, R181, K203, V204, R205, P206 and F208 from the D2 domain and V238, S239, 5240, S241, H263, G265, D266, F267, N268 and Y269 from the D3 domain.

A peptidic moiety of the invention may bind to contiguous or non-contiguous amino acid residues and function as a molecular wedge that prevents the motion required for positioning of the membrane proximal region of the RTK at a distance and orientation that enables tyrosine kinase activation. A peptidic molecule of the invention may also act to prevent homotypic D4 or D5 receptor interactions or destabilize the ligand-receptor interaction site. In some preferred embodiments, a peptidic molecule of the invention may bind to (or comprise or consist of) one or more of the following residues on the Kit receptor: Y125, G126, H180, R181, K203, V204, R205, P206, P206, F208, K127, A207, V238, S239, S240, S241, H263, G265, D266, F267, N268, Y269, T295, L222, L222, L223, E306, V308, R224, V308, K310, K218, A219, S220, K218, A220, Y221, A339, D327, D398, E338, E368, E386, F312, F324, F340, F3, G384, G387, G388, I371, K342, K358, L382, L379, N326, N367, N370, N410, P341, S369, T385, V325, V407, V409, Y373, Y350, Y408, T380, T390, R381, R353, T411, K412, E414, K471, F433, G470, L472, V497, F469, A431, or G432. The peptidic moieties of the invention may bind to (or comprise or consist of) all of the amino acid residues forming a pocket or a cavity identified in Table 4 or they may bind to (or comprise or consist of) a subset of the residues forming the pocket or the cavity. One of skill in the art will appreciate that, in some embodiments, a peptidic molecule of the invention may be easily targeted to the corresponding residues in other type III RTKs, e.g., those residues that form similar pockets or cavities or those in the same position by structural alignment or sequence alignment.

In a specific embodiment, a peptidic molecule of the invention binds to a conformational epitope or a discontinuous epitope on a type III RTK. The conformational or discontinuous epitope may be composed of two or more residues from the D3, D4, or D5 domain or the D4-D5 or D3-D4 hinge regions from a type III RTK, e.g., the human Kit receptor or the PDGF receptor. For example, the conformational or discontinuous epitope may be composed of two or more of the residues listed in Table 4 below. In a particular embodiment, a peptidic molecule of the invention binds to a conformational epitope composed of 2 or more amino acids selected from the group consisting of Y125, H180, R181, K203, V204, R205, P206, V238, S239, S240, H263, G265, D266, F267, N268, and Y269. In similar embodiments, a peptidic molecule of the invention may bind to a conformational epitope composed of 2 or more amino acids selected from one of the following groups of amino acids: P206, F208, V238, and 5239; K127, A207, F208, and T295; L222, A339, F340, K342, E368, S369, N370, I371, and Y373; L222, L223, E306, V308, F312, E338, F340, and I371; R224, V308, K310, G311, F340, P341, and D398; K218, A219, S220, N367, E368, and S369; K218, A220, E368, and S369; G384, T385, T411, K412, E414, and K471; Y408, F433, G470, K471, and L472; F324, V325, N326, and N410; D327, N410, T411, K412, and V497; G384, G387, V409, and K471; L382, G387, V407, and V409; Y125, G126, H180, R181, K203, V204, R205, P206, F208, V238, S239, S240, 5241, H263, G265, D266, F267, N268, and Y269; P206, F208, V238, and S239; K218, S220, Y221, L222, F340, P341, K342, N367, E368, S369, N370, I371, and Y373; G384, G387, G388, Y408, V409, T411, F433, F469, G470, and K471; D327, T411, K412, E414, A431, G432, and K471; Y350, F355, K358, L379, T380, R381, L382, E386, and T390; Y350, R353, and F355.

In a further embodiment, a peptidic molecule of the invention binds to a conformational epitope wherein the conformational epitope is composed of two or more amino acid residues selected from the peptides listed in Table 5. In a specific embodiment, the conformational epitope is composed of one or more amino acid residues selected from a first peptide and one or more amino acids selected from a second peptide, wherein the first and second peptides are selected from the group of peptides listed in Table 5. As such, a peptidic molecule of the invention binds a conformational epitope wherein the first and second peptide groups are as follows: Ala219-Leu222 and Thr304-Val308; Asp309-Gly311 and Arg224-Gly226; Thr303-Glu306 and Ala219-Leu222; Asn367-Asn370 and Ser217-Tyr221; Ala339-Pro343 and Asn396-Val399; Ala339-Pro343 and Glu368-Arg372; Lys358-Tyr362 and Val374-His378; Asp357-Glu360 and Leu377-Thr380; Met351-Glu360 and His378-Thr389; His 378-Thr389 and Val323-Asp332; Val409-Ile415 and Ala493-Thr500; Val409-Ile415 and Ala431-Thr437; Val409-Ile415 and Phe469-Val473; Val409-Ile415 and Val325-Asn330; Val409-Ile415 and Arg381-Gly387; Gly466-Leu472 and Gly384-Gly388; Val325-Glu329 and Tyr494-Lys499; Thr411-leu416 and Val497-Ala502; Ile415-Leu421 and Ala502-Ala507; Ala502-Ala507 and Lys484-Thr488; and Ala502-Ala507 and Gly445-Cys450. The peptidic moieties of the invention may bind to all of the amino acid residues forming the foregoing first and second peptide groups or they may bind to a subset of the residues forming the first and second peptide groups.

In another embodiment, a peptidic moiety of the invention may bind to (or comprise or consist of) 2 or more amino acids selected from the group consisting of E33, P34, D72, E76, N77, K78, Q79, K158, D159, N250, S251, Q252, T253, K254, L255, N260, W262, H264, G265, E344, N352, R353, F355, T356, D357, Y362, S365, E366, N367, N370, and G466.

In another embodiment, a peptidic molecule of the invention binds to, or comprises, amino acid residues $^{385}$Arg and $^{390}$Glu of human PDGFRβ, or the corresponding residues in PDGFRα. The residues $^{385}$Arg and $^{390}$Glu of human PDGFRβ are analogous to the residues $^{381}$Arg and $^{386}$Glu of the Kit receptor and mediate homotypic D4-D4 interactions of PDGFRβ. Peptidic molecules of the invention may exert their inhibitory effect on receptor activation by preventing critical homotypic interactions (such as salt bridges formed between $^{385}$Arg and $^{390}$Glu of human PDGFRβ between membrane regions of type-III RTKs that are essential for positioning the cytoplasmic domain at a distance and orientation essential for tyrosine kinase activation. Experiments discussed herein demonstrate that homotypic D4-D4 interactions are dispensable for PDGFRβ dimerization and that PDGFRβ dimerization is necessary but not sufficient for receptor activation. Thus, peptidic molecules of the invention may allow dimerization of PDGFRβ while preventing activation. Structure based sequence alignment has shown that the size of the EF loop, and the critical amino acids comprising the D4-D4 interface are conserved in Kit, PDGFRα, PDGFRβ, and CSF1R. Thus, in some embodiments, peptidic molecules of the invention may be targeted to the conserved regions of the D4 or D5 domains of type III RTKs.

The peptidic moieties of the invention may be peptides comprising or consisting of any of the amino acid sequences identified herein (e.g., SEQ ID NOs: 1-89, 92, 93, and 105-157). For example, peptidic moieties of the invention may be peptides comprising or consisting of any of the following amino acid sequences: EVVDKGFIN (SEQ ID NO: 2), ASYL (SEQ ID NO: 3), TLEVV (SEQ ID NO: 4), ASYLTLEVV (SEQ ID NO: 5), DKG, REG, DKGREG (SEQ ID NO: 6), VVSVSKASYLL (SEQ ID NO: 7), VTTTLEVVD (SEQ ID NO: 8), REGEEFTVTCTI (SEQ ID NO: 9), TTLE (SEQ ID NO: 10), TTLEASYL (SEQ ID NO: 11), KSENESNIR (SEQ ID NO: 12), NESN (SEQ ID NO: 13), SKASY (SEQ ID NO: 14), NESNSKASY (SEQ ID NO: 15), AFPKP (SEQ ID NO: 16), NSDV (SEQ ID NO: 17), AFPKPNSDV (SEQ ID NO: 18), ESNIR (SEQ ID NO: 19), AFPKPESNTR (SEQ ID NO: 20), DKWEDYPKSE (SEQ ID NO: 21), IRYVSELHL (SEQ ID NO: 22), LTRLKGTEGGT (SEQ ID NO: 23), GENVDLIVEYE (SEQ ID NO: 24), MNRTFTDKWE (SEQ ID NO: 25), KWEDY (SEQ ID NO: 26), VSELH (SEQ ID NO: 27), KWEDYVSELH (SEQ ID NO: 28), DKWE (SEQ ID NO: 29), LHLT (SEQ ID NO: 30), DKWELHLT (SEQ ID NO: 31), HLTRLKGTEGGT (SEQ ID NO: 32), MNRTFTDKWE (SEQ ID NO: 25), HLTRLKGTEGGT (SEQ ID NO: 32), MNRTFTDKWEHLTRLKGTEGGT (SEQ ID NO: 33), VFVNDGENVD (SEQ ID NO: 34), VNTKPEI (SEQ ID NO: 35), AYNDVGKT (SEQ ID NO: 36), VNTKPEIAYNDVGKT (SEQ ID NO: 37), AGFPEPT (SEQ ID NO: 38), VNTKPEIAGFPEPT (SEQ ID NO: 39), FGKLV (SEQ ID NO: 40), VNTKPEI FGKLV (SEQ ID NO: 41), VNDGEN (SEQ ID NO: 42), VNTKPEIVNDGEN (SEQ ID NO: 43), RLKGTEG (SEQ ID NO: 44), VNTKPEIRLKGTEG (SEQ ID NO: 45), GPPFGKL (SEQ ID NO: 46), GTEGG (SEQ. ID NO: 47), GPPFGKLGTEGG (SEQ ID NO: 48), VNDGE (SEQ ID NO: 49), YNDVGK (SEQ ID NO: 50), VNDGEYNDVGK (SEQ ID NO: 51), TKPEILTYDRL (SEQ ID NO: 52), DRLVNGMLQC (SEQ ID NO: 53), GKTSAYFNFAFK (SEQ ID NO: 54), CPGTEQRCSAS (SEQ ID NO: 55), CSASVLPVDVQ (SEQ ID NO: 56), DSSAFKHNGT (SEQ ID NO: 57), GTVECKAYND (SEQ ID NO: 58), LNSSGPPFGKL, (SEQ ID NO: 59), FAFKGNNKEQI (SEQ ID NO: 60), TKPEIL (SEQ ID NO: 61), VGKTSA (SEQ ID NO: 62), TKPEIL-VGKTSA (SEQ ID NO: 63), ILTYDRL (SEQ ID NO: 64), AYFNFA (SEQ ID NO: 65), ILTYDRLAYFNFA (SEQ ID NO: 66), KHNGT (SEQ ID NO: 67), AYFNFAKHNGT (SEQ ID NO: 68), GTEQRC (SEQ ID NO: 69), AYFNF-AGTEQRC (SEQ ID NO: 70), YHRKVRPVSSHGDFNY (SEQ ID NO: 71), PFVS (SEQ ID NO: 72), KAFT (SEQ ID NO: 73), LAFKESNIY (SEQ ID NO: 74), LLEVFEFI (SEQ ID NO: 75), RVKGFPD (SEQ ID NO: 76), KASNES (SEQ ID NO: 77), KAES (SEQ ID NO: 78), GTTKEK (SEQ ID NO: 79), YFGKL (SEQ ID NO: 80), FVNN (SEQ ID NO: 81), DNTKV (SEQ ID NO: 82), GGVK (SEQ ID NO: 83), LGVV (SEQ ID NO: 84), YGHRKVRPFVSSSHGDFNY (SEQ ID NO: 85), PFVS (SEQ ID NO: 72), KSYLFP-KNESNIY (SEQ ID NO: 86), GGGYVTFFGK (SEQ ID NO: 87), DTKEAGK (SEQ ID NO: 88), YFKLTRLET (SEQ ID NO: 89), and YRF.

A peptide molecule of the invention may be further modified to increase its stability, bioavailability or solubility. For example, one or more L-amino acid residues within the peptidic molecules may be replaced with a D-amino acid residue. The term "mimetic" as applied to the peptidic molecules of the present invention is intended to include molecules which mimic the chemical structure of a D-peptidic structure and retain the functional properties of the D-peptidic structure. The term "mimetic" is further intended to encompass an "analogue" and/or "derivative" of a peptide as described below. Approaches to designing peptide analogs, derivatives and mimetics are known in the art. For example, see Farmer, P.S. in Drug Design (E. J. Ariens, ed.) Academic Press, New York, 1980, vol. 10, pp. 119-143; Ball. J. B. and Alewood, P. F. (1990) *J. Mol. Recognition.* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113-11123; Smith, A. B. 3rd, et al. (1994) *J. Am. Chem. Soc.* 116:9947-9962; and Hirschman, R., et al. (1993) *J. Am. Chem. Soc.* 115:12550-12568.

As used herein, a "derivative" of a peptidic molecule of the invention refers to a form of the peptidic molecule in which one or more reaction groups on the molecule have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an "analogue" of a peptidic molecule of the invention to a peptidic molecule which retains chemical structures of the molecule necessary for functional activity of the molecule yet which also contains certain chemical structures which differ from the molecule. An example of an analogue of a naturally-occurring peptide is a peptide which includes one or more non-naturally-occurring amino acids. As used herein, a "mimetic" of a peptidic molecule of the invention refers to a peptidic molecule in which chemical structures of the molecule necessary for functional activity of the molecule have been replaced with other chemical structures which mimic the conformation of the molecule. Examples of peptidomimetics include peptidic compounds in which the peptide backbone is substituted with one or more benzodiazepine molecules (see e.g., James, G L. et al. (1993) *Science* 260:1937-1942).

Analogues of the peptidic molecules of the invention are intended to include molecules in which one or more L- or D-amino acids of the peptidic structure are substituted with a homologous amino acid such that the properties of the molecule are maintained. Preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-limiting examples of homologous substitutions that can be made in the structures of the peptidic molecules of the invention include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other possible modifications include an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

Peptidic molecules of the present invention may be made by standard methods known in the art. The peptidic molecule, e.g., D4 domain of the human Kit RTK, may be cloned from human cells using standard techniques, inserted in to a recombinant vector, and expressed in an in vitro cell system (e.g., by transfection of the vector into yeast cells). Alternatively, the peptidic molecules may be designed and synthesized de novo via known synthesis methods such as Atherton et al. (1989) Oxford, England: IRL Press. ISBN 0199630674; Stewart et al. (1984). 2nd edition, Rockford: Pierce Chemical Company, 91. ISBN 0935940030; Merrifield (1963) *J. Am. Chem. Soc.* 85: 2149-2154.

The peptidic molecules can then be tested for functional activity using any of the assays described herein, e.g., those described in the Examples section below.

IV. Screening Assays for Identifying Moieties of the Invention

The moieties of the invention may be screened for RTK inhibitory activity using any of the assays described herein and those assays that are well known in the art. For example, assays which may determine receptor internalization, receptor autophosphorylation, and/or kinase signaling may be used to identify moieties which prevent the activation of target RTKs, e.g., the Kit receptor. Screening for new inhibitor moieties may be accomplished by using standard methods known in the art, for example, by employing a phospho-ELISA™ procedure (available at Invitrogen) to determine the phosphorylation state of the RTK or a downstream molecule. The phosphorylation state of the receptor, e.g., the Kit receptor may be determined using commercially available kits such as, for example, C-Kit [pY823] ELISA KIT, HU (BioSource™; Catalog Number—KH00401); c-KIT [TOTAL] ELISA KIT, HU (BioSource™; Catalog Number—KH00391). Antibodies, small molecules, and other moieties of the invention may be screened using such kits to determine their RTK inhibitory activity. For example, after treatment with an appropriate ligand and a moiety of the invention, a phosphoELISA™ may be performed to determine the phosphorylation state and, thus, the activation state of a RTK of interest. Moieties of the invention could be identified as those which prevent RTK activation. Examples 15 and 16 below describe assays which involve the detection of RTK activation using anti-phosphotyrosine antibodies. Example 20 below describes one possible assay for detecting receptor activation using the phosphoELISA™ system. Examples 22-25 (including the methods and introduction related thereto) describe further methods used herein to determine the activation state of RTKs.

Since receptor activation may lead to endocytosis and receptor internalization, it is useful, in some embodiments, to determine the ability of moieties of the invention to inhibit target RTKs by measuring their ability to prevent receptor internalization. Example 25 below (and the methods related thereto) describes the measurement of the internalization and degradation of PDGF receptor mutants. Receptor internalization assays are well known in the art and described in, for example, Fukunaga et al. (2006) *Life Sciences.* 80(1). p. 17-23; Bernhagen et al. (2007) *Nature Medicine* 13, 587-596; natureprotocols.com/2007/04/18/receptor_internalization_assay.php), the entire contents of each of which are incorporated herein by reference. One well-known method to determine receptor internalization is to tag a ligand with a fluororecent protein, e.g., Green Fluorescent Protein (GFP), or other suitable labeling agent. Upon binding of the ligand to the receptor, fluororescence microscopy may be used to visualize receptor internalization. Similarly, a moiety of the invention may be tagged with a labeling agent and fluororescence microscopy may be used to visualize receptor internalization. If the moiety is able to inhibit the activity of the receptor, lessened internalization of fluororescence in the presence of ligand as compared to appropriate controls (e.g., fluorescence may be observed only at the periphery of the cell where the moity binds the receptor rather than in endosomes or vesicles).

In addition to those mentioned above, various other receptor activation assays are known in the art, any of which may be used to evaluate the function of the moieties of the invention. Further receptor activation assays which may be used in accordance with the present invention are described in U.S. Pat. Nos. 6,287,784; 6,025,145; 5,599,681; 5,766,863; 5,891,650; 5,914,237; 7,056,685; and many scientific publications including, but not limited to: Amir-Zaltsman et al. (2000) *Luminescence* 15(6):377-80; Nakayama and Parandoosh (1999) *Journal of Immunological Methods.* 225(1-2), 27, 67-74; Pike et al. (1987) *Methods of Enzymology* 146: 353-362; Atienza et al. (2005) *Journal of Biomolecular Screening.* 11(6): 634-643; Hunter et al. (1982). *Journal of Biological Chemistry* 257(9): 4843-4848; White and Backer (1991) *Methods in Enzymology* 201: 65-67; Madden et al. (1991) *Anal Biochem* 199: 210-215; Cleaveland et al. (1990) Analytical Biochemistry 190: 249-253; Lazaro et al. (1991) *Analytical Biochemistry* 192: 257-261; Hunter and Cooper (1985) *Ann Rev Biochem* 54: 897-930; Ullrich and Schlessinger (1990) Cell 61: 203-212; Knutson and Buck (1991) *Archives of Biochemistry and Biophysics* 285(2): 197-204); King et al. (1993) *Life Sciences* 53: 1465-1472; Wang. (1985) *Molecular and Cellular Biology* 5(12): 3640-3643; Glenney et al. (1988) *Journal of Immunological Methods* 109: 277-285; Kamps (1991) *Methods in Enzymology* 201: 101-110; Kozma et al. (1991) *Methods in Enzymology* 201: 28-43; Holmes et al. (1992) *Science* 256: 1205-10; and Corfas et al. (1993) *PNAS, USA* 90: 1624-1628.

Receptor activation by ligand binding typically initiates subsequent intracellular events, e.g., increases in secondary messengers such as $IP_3$ which, in turn, releases intracellular stores of calcium ions. Thus, receptor activity may be determined by measuring the quantity of secondary messengers such as $IP_3$, cyclic nucleotides, intracellular calcium, or phosphorylated signaling molecules such as STAT, PI3K, Grb2, or other possible targets known in the art. U.S. Pat. No. 7,056,685 describes and references several methods which may be used in accordance with the present invention to detect receptor activity and is incorporated herein by reference.

Many of the assays described above, such as receptor internalization assays or receptor activation assays may involve the detection or quantification of a target RTK using immunological binding assays (e.g., when using a radiolabeled antibody to detecting the amount of RTK on the cell surface during a receptor internalization assay). Immunological binding assays are widely described in the art (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Immunoassays such as may be employed in receptor internalization studies, receptor activation studies, or receptor detection assays often use a labeling agent to specifically bind to and label the complex formed by the detecting antibody and the RTK (see U.S. Pat. No. 7,056,685 which is incorporated herein by reference). The labeling agent may itself be the antibody used to detect the receptor (the antibody here may or may not be a moiety of the invention). Alternatively, the labeling agent may be a third agent, such as a secondary or tertiary antibody (e.g., and anti-mouse antibody binding to mouse monoclonal antibody specific for the target RTK). Other proteins capable of specifically binding immunoglobulin constant regions, such as protein A or protein G may also be used as the labeling agent in an immunological binding assay. These proteins exhibit a strong non-immunogenic reactivity with immunoglobulin constant regions from a variety of species (see, e.g., Kronval et al. (1973), *J. Immunol.* 111:1401-1406; Akerstrom et al. (1985), *J. Immunol.* 135: 2589 2542). The labeling agent can also be modified with a detectable agent, such as biotin, to which another molecule can specifically bind, such as streptavidin. A variety of detectable moieties are well known to those skilled in the art.

Commonly used assays include noncompetitive assays, e.g., sandwich assays, and competitive assays. Commonly used assay formats include Western blots (immunoblots), which are used to detect and quantify the presence of protein in a sample. The particular label or detectable group used in the assay is not a critical aspect of the invention, as long as it does not significantly interfere with the specific binding of the immunoglobulin used to detect the RTK or a moiety of the invention which is designed to bind and inactivate the RTK. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene or latex).

The label may be coupled directly or indirectly to the desired component of the assay according to methods well known in the art. The label can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, and the like. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

In a further aspect of the invention, the moieties of the present invention may bind to epitopes on a target RTK and still allow the ectodomain of the receptor tyrosine kinase to dimerize. In this embodiment, the binding of the moiety may affect the positioning, orientation and/or distance between the Ig-like domains of the two monomers (e.g., the D4-D4 or D5-D5 domains of a type III receptor tyrosine kinase or the D7-D7 domains of a type V receptor tyrosine kinase), thereby inhibiting the activity of the receptor tyrosine kinase. In other words, the moiety may allow ligand induced dimerization of the receptor tyrosine kinase ectodomains, but affect the positioning of the two ectodomains at the cell surface interface or alter or prevent conformational changes in the receptor tyrosine kinases, thereby inhibiting the activity of the receptor tyrosine kinase (e.g., inhibiting receptor internalization and/or inhibiting tyrosine autophosphorylation of the receptor and/or inhibiting the ability of the receptor to activate a downstream signaling pathway).

Thus, in some embodiments, it is useful to employ assays which are able to identify moieties that allow receptor dimerization, yet render the receptor inactive. Such assays are described below. For example, Example 18 describes experiments performed with the PDGF receptor whereby receptor dimerization is detected using cross linking, and receptor activation is determined using phosphotyrosine specific antibodies. Furthermore, Example 23 shows that a mutant of PDGFR has an impairment in ligand-induced tyrosine autophosphorylation which is not caused by a deficiency in ligand-induced receptor dimerization (see also the Methods and Introduction to Examples 22-25).

The conformational state, of the RTK may also be determined by Fluorescence Resonance Energy Transfer (FRET) analysis. A comprehensive review of fluorescence methodologies for determining protein conformations and interactions can be found in Johnson (2005) Traffic. 2005 December; 6(12):1078-92 which is incorporated herein by reference. In the FRET assay a RTK of interest is labeled with appropriate FRET fluorophores. After the RTK is labeled, cells expressing the labeled RTK are incubated with test moieties of the invention and the ligand of the RTK (e.g., SCF for the Kit RTK). FRET analysis will allow the observation of conformational changes in the RTK associated with ligand binding, RTK dimerization, and/or receptor activation. By this method one of skill in the art may directly assess a protein conformational change which indicates RTK dimerization without downstream activation. There are a number of methods available to perform FRET analysis, and a large portion of the variation arises from the use of different fluorophores or different techniques to incorporate those fluorophores into proteins of interest. FRET fluorophores and analysis methods are well known in the art, and a brief review of FRET technology is available in Heyduk. (2002) Current Opinion in Biotechnology. 13(4). 292-296 and references therein. The following publications expand on the FRET method and are incorporated herein by reference: Kajihara et al. (2006) *Nat. Methods.* 3(11):923-9; Biener-Ramanujan et al. (2006) Growth Horm IGF Res.16(4):247-57; Taniguchi et al. (2007) *Biochemistry.* 46(18):5349-57; U.S. Pat. Nos. 6,689,574; 5,891,646; and WIPO Publication No. WO/2002/033102. FRET fluorophores may be incorporated into any domain or hinge region of a RTK to detect conformational changes (e.g., the D4 or D5 domains of a Type III RTK or the D7 domain of a Type V RTK) provided that the fluorophores do not interfere with the function of the RTK or the ability of moieties of the invention to bind the RTK.

Fluorophores useful for FRET are often the same as those useful for Bioluminescence Resonance Energy Transfer (BRET) as discussed below. The most popular FRET method is to engineer reactive cystein residues into a protein of interest. Fluorophores can then easily react with the chosen cystein residues. Often fusion proteins are constructed, whereby a protein of interest is fused to Green Fluorescent Protein (see Neininger et al. (2001) *EMBO Reports.* 2(8):703-708). Additional methods and useful fluorophores for FRET are described in Huebsch and Mooney (2007) *Biomaterials.* 28(15):2424-37; Schmid and Birbach (2007) *Thromb Haemost.* 97(3):378-84; Jares-Erijman AND Jovin (2006) *Curr Opin Chem. Biol.* 10(5):409-16; Johansson (2006) *Methods Mol. Biol.* 335:17-29; Wallrabe and Periasamy (2005) *Curr Opin Biotechnol.* 16(1):19-27; and Clegg R M (1995) *Curr Opin Biotechnol.* 6(1):103-10 which are incorporated herein by reference.

In other embodiments, it may be unknown or difficult to determine (depending on the receptor) which RTK conformation is specifically indicative of dimerization without activation. In such cases, one of skill in the art may combine assays that determine receptor dimerization with those that determine receptor activation: For example, one may use traditional cross-linking studies (exemplified by Rodriguez et al. (1990) *Molecular Endocrinology*, 4(12), 1782-1790) to detect RTK dimerization in combination with any of the receptor activation assays discussed above. FRET and similar systems may also be used to directly measure receptor activation or dimerization. For example, by incorporating appropriate FRET fluorophores into the cytoplasmic domain of the RTK and into a phosphorylation target protein (i.e., a downstream signaling molecule), FRET would be capable of determining whether downstream signaling molecules were being recruited to the RTK. Therefore, in one embodiment a successful moiety of the invention is one which allows receptor dimerization, as measured by cross-linking or FRET, but which prevents receptor activation, detected as lack of fluorescence by FRET or BRET analysis or by other receptor activation assays (e.g., autophosphorylation assay employing anti-phosphotyrosine antibodies and Western Blot). Thus, using the techniques described herein, one of skill in the art can easily test moieties (e.g., small molecules, peptides, or antibodies.) to determine whether they inhibit RTK activity and whether they allow receptor dimerization.

In particular, Bioluminescence Resonance Energy Transfer (BRET) analysis may be used to identify moieties which inhibit the activity of RTKs. U.S. pat. Pub. No. 20060199226, WIPO Publication No. WO/2006/094073, and Tan et al. (2007. Molecular Pharmacology. 72:1440-1446) specifically describe methods to identify ligands which activate RTKs and are thus incorporated herein by reference. These techniques have been employed for determining protein interactions in vitro and in vivo (Pfleger et al. (2006) *Nature Protocols* 1 337-345; Kroeger et al. (2001), *J. Biol. Chem.*, 276(16):12736-43; and Harikumar, et al. (2004) *Mol Pharmacol* 65:28-35; which are all incorporated herein by reference).

BRET is useful for identifying moieties of the present invention from test compounds by screening for those moieties which prevent RTK activation.

As discussed in U.S. pat. Publication No. 2006/0199226 which is incorporated herein by reference, BRET based assays can be used to monitor the interaction of proteins having a bioluminescent donor molecule (DM) with proteins having a fluorescent acceptor moiety (AM). Briefly, cells expressing an RTK-DM fusion will convert the substrate's chemical energy into light. If there is an AM (e.g., a signaling protein-AM fusion) in close proximity to the RTK-DM fusion, then the cells will emit light at a certain wavelength. For example, BRET based assays can be used to assess the interaction between a RTK-luciferase fusion and a GFP-signalling protein fusion. This differs slightly from FRET analysis, where the donor molecule may be excited by light of a specific wavelength rather than by chemical energy conversion. Examples of bioluminescent proteins with luciferase activity that may be used in a BRET analysis may be found in U.S. Pat. Nos. 5,229,285, 5,219,737, 5,843,746, 5,196,524, 5,670,356. Alternative DMs include enzymes, which can act on suitable substrates to generate a luminescent signal. Specific examples of such enzymes are beta-galactosidase, alkaline phosphatase, beta-glucuronidase and beta-glucosidase. Synthetic luminescent substrates for these enzymes are well known in the art and are commercially available from companies, such as Tropix Inc. (Bedford, Mass., USA). DMs can also be isolated or engineered from insects (U.S. Pat. No. 5,670,356).

Depending on the substrate, DMs emit light at different wavelengths. Non-limiting examples of substrates for DMs include coelenterazine, benzothiazole, luciferin, enol formate, terpene, and aldehyde, and the like. The DM moiety can be fused to either the amino terminal or carboxyl terminal portion of the RTK protein. Preferably, the positioning of the BDM domain within the RTK-DM fusion does not alter the activity of the native protein or the binding of moieties of the present invention. RTK-DM fusion proteins can be tested to ensure that it retains biochemical properties, such as ligand binding and ability to interact with downstream signaling molecules of the native protein.

AMs in BRET analysis may re-emit the transferred energy as fluorescence. Examples of AMs include Green Fluorescent Protein (GFP), or isoforms and derivatives thereof such as YFP, EGFP, EYFP and the like (R. Y. Tsien, (1998) Ann. Rev. Biochem. 63:509-544). Preferably, the positioning of the AM domain within the AM-protein fusion does not alter the activity of the native protein. AM-second protein fusion proteins can be tested to ensure that it retains biochemical properties of the cognate native protein, such as interaction with RTKs. By way of example, an amino terminal fusion of the GFP protein to any substrate which is phosphorylated by or can bind to the target RTK can be used.

V. Pharmaceutical Compositions Containing the Moieties of the Invention

In another aspect, the present invention provides a composition, e.g., a pharmaceutical composition, containing one or a combination of the moieties of the invention (e.g., monoclonal antibodies, or antigen-binding portion(s) thereof, antibody mimetics, small molecules, or peptidic molecules of the present invention), formulated together with a pharmaceutically acceptable carrier. Such compositions may include one or a combination of (e.g., two or more different) antibodies, or immunoconjugates, small molecules, or peptidic molecules of the invention. For example, a pharmaceutical composition of the invention can comprise a combination of antibodies and small molecules that bind to different epitopes on the target RTK or that have complementary activities, e.g., a small molecule that binds to the D3-D4 hinge region of a type III RTK together with a monoclonal antibody that binds the D4 domain of a type III RTK.

Pharmaceutical compositions of the invention also can be administered in combination therapy, i.e., combined with other agents. For example, the combination therapy can include an anti-RTK antibody (or small molecule or peptidic molecule) of the present invention combined with at least one other anti-cancer agent. Examples of therapeutic agents that can be used in a combination therapy are described in greater detail below.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the moiety of the invention, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, small molecule, or peptidic molecule, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a moiety of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively, the antibody, small molecule, or peptidic molecule can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients and small molecules in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-RTK moiety of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

An anti-RTK moiety of the present invention may be tested to determine whether it is effective in antagonizing the RTK. One method of testing the anti-RTK moiety is to confirm that interaction occurs between the anti-RTK moiety and the RTK. For example, one of skill in the art may test whether an antibody, small molecule, or peptidic molecule of the invention binds to the D4 or D5 domain of human Kit RTK. Such tests for binding are well known in the art and may include labeling (e.g., radiolabeling) the anti-RTK moiety, incubating the anti-RTK moiety with an RTK under conditions in which binding may occur, and then isolating/visualizing the complex on a gel or phosphor screen. Similarly, the ELISA technique may be employed to determine binding.

Another method to determine whether the moiety of the invention is antagonizing a RTK is to test the phosphorylation state of the cytoplasmic domain of the RTK. In specific embodiments, effective antagonists will prevent activation and autophosphorylation of a RTK. Phosphorylation of the RTK may be tested using standard methods known in the art, for example, by using antibodies which specifically bind the phosphorylated residues of the RTK. Other methods to detect phosphorylation events include those described in U.S. Pat. Nos. 6,548,266; or Goshe et al. (2006) Brief Funct Genomic Proteomic. 4:363-76; de Graauw et al. (2006) Electrophoresis. 27:2676-86; Schmidt et al. (2007) J Chromatogr B Analyt Technol Biomed Life Sci. 849:154-62; or by the use of the FlashPlates (SMP200) protocol for the Kinase Phosphorylation Assay using [gamma-33P]ATP by PerkinElmer. One of skill in the art will appreciate that these methods, and those demonstrated in the Examples may also be used to determine the phosphorylation state of proteins which are phosphorylated by the RTK and are signal transducers within the cell. Detecing the phosphorylation state of such proteins will also indicate whether the RTK has been effectively antagonized by the moieties of the present invention.

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an anti-RTK binding moiety of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

V. Methods for Using the Moieties of the Invention

In another aspect, the present invention provides a method for treating a RTK associated disease in a subject, comprising administering to the subject a therapeutically effective amount of a moiety of the invention. The anti-RTK moieties, e.g., antibodies, small molecules, or peptidic molecules, of the present invention have numerous in vitro and in vivo diagnostic and therapeutic utilities involving the diagnosis and treatment of a receptor tyrosine kinase associated disease. The binding moieties of the present invention can be administered to cells in culture, in vitro or ex vivo, or to human subjects, e.g., in vivo, to treat, prevent and to diagnose a receptor tyrosine kinase associated disease.

As used herein "a receptor tyrosine kinase associated disease" is a disease or condition which is mediated by RTK activity or is associated with aberrant RTK expression or activation. Examples of receptor tyrosine kinase associated diseases include diseases or conditions that are associated with, for example, FGF receptors, HGF receptors, insulin receptors, IGF-1 receptors, NGF receptors, VEGF receptors, PDGF-receptor-α, PDGF-receptor-β, CSF-1-receptor, and Flt3-receptors, such as age-related macular degeneration (AMD), atherosclerosis, rheumatoid arthritis, diabetic retinopathy or pain associated diseases. Specific examples of receptor tyrosine kinase associated diseases include, but are not limited to, gastrointestinal stromal tumors (GIST), acute myelogenous leukemia (AML), small cell lung cancer (SCLC), breast cancer, bone metastatic breast cancer and tenosynovial giant cell tumors. Additional examples of receptor tyrosine kinase associated diseases include colon cancer (including small intestine cancer), lung cancer, breast cancer, pancreatic cancer, melanoma (e.g., metastatic malignant melanoma), acute myeloid leukemia, kidney cancer, bladder cancer, ovarian cancer and prostate cancer. Examples of other cancers that may be treated using the methods of the invention include renal cancer (e.g., renal cell carcinoma), glioblastoma, brain tumors, chronic or acute leukemias including acute lymphocytic leukemia (ALL), adult T-cell leukemia (TALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Furthermore, given the expression of type III or type V RTKs on various tumor cells, the binding moieties, compositions, and methods of the present invention can be used to treat a subject with a tumorigenic disorder, e.g., a disorder characterized by the presence of tumor cells expressing Kit including, for example, gastrointestinal stromal tumors, mast cell disease, and acute myelogenous lukemia. Examples of other subjects with a tumorigenic disorder include subjects having renal cancer (e.g., renal cell carcinoma), glioblastoma, brain tumors, chronic or acute leukemias including acute lymphocytic leukemia (ALL), adult T-cell leukemia (TALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles. Preferred subjects include human subjects having a receptor tyrosine kinase associated disease.

The moieties (e.g., antibodies, antigen binding portions thereof, small molecules, peptidic molecules, antibody mimetics, and compositions) of the invention have additional utility in therapy and diagnosis of a RTK associated disease. For example, the human monoclonal antibodies, the multi-specific or bispecific molecules, the small molecules, or the peptidic molecules can be used to elicit in vivo or in vitro one or more of the following biological activities: to inhibit the growth of and/or kill a cell expressing a RTK (e.g., Kit or PDGFR); to mediate phagocytosis or ADCC of a cell expressing a RTK (e.g., Kit or PDGFR) in the presence of human effector cells; or to lock the ectodomain of a RTK, e.g., member of the type III family of RTKs, to an inactive state and/or a monomeric state thereby antagonizing the activity of the receptor.

Suitable routes of administering the anti-RTK moieties of the invention in vivo and in vitro are well known in the art and can be selected by those of ordinary skill. For example, the anti-RTK moieties can be administered by injection (e.g., intravenous or subcutaneous). Suitable dosages of the molecules used will depend on the age and weight of the subject and the concentration and/or formulation of the binding moiety composition.

As previously described, the anti-RTK moieties of the invention can be co-administered with one or other more therapeutic agents, e.g., a cytotoxic agent, a radiotoxic agent or an immunosuppressive agent. The moiety can be linked to the agent or can be administered separate from the agent. In the latter case (separate administration), the binding moiety can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the anti-RTK binding moieties, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the binding moiety.

When administering anti-RTK moiety-partner molecule conjugates of the present invention for use in the prophylaxis and/or treatment of diseases related to abnormal cellular proliferation, a circulating concentration of administered compound of about 0.001 µM to 20 µM or about 0.01 µM to 5 µM may be used.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug). Preferably, the anti-RTK moiety-drug conjugate retards growth of the tumor when administered in the daily dosage amount over a period of at least five days.

In one embodiment, conjugates of the invention can be used to target compounds (e.g., therapeutic agents, labels, cytotoxins, radiotoxoins immunosuppressants, etc.) to cells which have RTK cell surface receptors by linking such compounds to the anti-RTK binding moiety. For example, an anti-RTK moiety can be conjugated to any of the toxin compounds described in U.S. Pat. Nos. 6,281,354 and 6,548,530, US patent publication Nos. 20030050331, 20030064984, 20030073852 and 20040087497 or published in WO 03/022806, which are hereby incorporated by reference in their entireties. Thus, the invention also provides methods for localizing ex vivo or in vivo cells expressing RTK (e.g., with a detectable label, such as a radioisotope, a fluorescent compound, an enzyme or an enzyme co-factor).

Target-specific effector cells, e.g., effector cells linked to compositions (e.g., antibodies, antigen binding portions thereof, small molecules, or peptidic molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing RTK and to effect cell killing by, e.g., phagocytosis. Routes of administration can also vary.

Therapy with target-specific effector cells can be performed in conjunction with other techniques for removal of targeted cells. For example, anti-tumor therapy using the moieties of the invention and/or effector cells armed with these compositions can be used in conjunction with chemotherapy.

The invention further provides methods for detecting the presence of a human RTK antigen in a sample, or measuring the amount of human RTK antigen (e.g., an Ig-like domain of human Kit RTK or PDGFR), comprising contacting the sample, and a control sample, with and RTK binding moiety, e.g., a human monoclonal antibody, or other binding moiety, which specifically binds to a human RTK, under conditions that allow for formation of a complex between the antibody or other moiety and a human RTK such as Kit. The formation of a complex is then detected, wherein a difference complex formation between the sample compared to the control sample is indicative the presence of RTK, e.g., human Kit RTK or the PDGFR RTK in the sample.

Also within the scope of the present invention are kits comprising the anti-RTK binding moieties (e.g., antibodies, antigen binding portions thereof, small molecules, or peptidic molecules) and instructions for use. The kit can further contain one more additional reagents, such as an immunosuppressive reagent, a cytotoxic agent or a radiotoxic agent or one or more additional anti-RTK moieties of the invention (e.g., an anti-RTK binding moiety having a complementary activity which binds to an epitope in the RTK antigen distinct from the first anti-RTK moiety). Kits typically include a label indicating the intended use of the contents of the kit. The term label includes any writing, or recorded material supplied on or with the kit, or which otherwise accompanies the kit.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Introduction to Examples 1-19

Stem Cell Factor (SCF) initiates its multiple cellular responses by binding to the ectodomain of Kit resulting in tyrosine kinase activation. In some of the examples below the crystal structure of the entire ectodomain of Kit before and after SCF stimulation is described. The structures show that Kit dimerization is driven by SCF binding whose sole role is to bring two Kit molecules together. Receptor dimerization is followed by conformational changes that enable lateral interactions between membrane proximal Ig-like domains D4 and D5 of two Kit molecules. Experiments with cultured cells show that Kit activation is compromised by point mutations in amino acids critical for D4-D4 interaction. Moreover, a variety of oncogenic mutations are mapped to the D5-D5 interface. Since key hallmarks of Kit structures, ligand-induced receptor dimerization and the critical residues in the D4-D4 interface are conserved in other receptors, the mechanism of Kit stimulation unveiled in this report may apply for other receptor activation. This indicates that drugs or biologics targeted to these interfaces can be used as therapeutics.

The elucidation of the X-ray crystal structure of the entire ectodomain of Kit before and after SCF stimulation described herein has provided valuable insights concerning the mechanism of SCF-induced Kit dimerization and activation. The structure shows that the first three Ig-like domains of Kit designated D1, D2 and D3 are responsible for SCF binding. The main role of SCF binding is to crosslink two Kit molecules to increase the local concentration of Kit on the cell membrane. This facilitates a large conformational change in the membrane-proximal regions of Kit resulting in homotypic interaction between D4 or D5 of neighboring Kit molecules. The lateral interactions between D4 of two neighboring Kit molecules occur via direct contacts through two pairs of salt bridges from the EF loops of each D4 protomer. The membrane proximal D5 domain provides additional indirect interactions between neighboring Kit molecules to further stabilize and position the membrane proximal part of the ectodomain at a distance and orientation that enables the activation of cytoplasmic tyrosine kinase.

In several of the examples below the crystal structures of the entire ectodomain of Kit in both monomeric and SCF-induced homodimeric (SCF-Kit 2:2 complex) forms is described. Detailed views of the unoccupied monomeric form at 3.0 Å resolution and SCF-induced homodimeric form at 3.5 Å resolution provide novel insights concerning the activation mechanism of Kit and other RTKs. It should be appreciated by one of skill in the art that the experiments described below may be performed with other RTKs. Example RTK sequences which may be used by methods of the present invention include, but are not limited to, the Genbank reference sequence for the Kit mRNA NM_000222.2 (encoding the protein NP_000213.1; MRGARGAWDFLCVLLLLL-RVQTGSSQPSVSPGEPSPPSIHPGKSDLIVRVGDEIRL-LCTDPGFVKWTFEILDETNENKQNEWITEKAEATN-TGKYTCTNKHGLSNSIYVFVRDPAKLFLVDRSLYG-KEDNDTLVRCPLTDPEVTNYSLKGCQGKPLPKD-LRFIPDPKAGIMIKSVKRAYHRLCLHCSVDQEGKSV-LSEKFILKVRPAFKAVPVVSVSKASYLLREGEEFTVT-CTIKDVSSSVYSTWKRENSQTKLQEKYNSWHHG-DFNYERQATLTISSARVNDSGVFMCYANNTFGSAN-VTTTLEVVDKGFINIFPMINTTVFVNDGENVDLIVE-YEAFPKPEHQQWIYMNRTFTDKWEDYPKSENES-NIRYVSELHLTRLKGTEGGTYTFLVSNSDVNAAIA-FNVYVNTKPEILTYDRLVNGMLQCVAAGFPEPTI-DWYFCPGTEQRCSASVLPVDVQTLNSSGPPFGKLV-VQSSIDSSAFKHNGTVECKAYNDVGKTSAYFNFA-FKGNNKEQIHPHTLFTPLLIGFVIVAGMMCIIVMIL-TYKYLQKPMYEVQWKVVEEINGNNYVYIDPTQL-PYDHKWEFPRNRLSFGKTLGAGAFGKVVEATAYG-LIKSDAAMTVAVKMLKPSAHLTEREALMSELKVLSY-LGNHMNIVNLLGACTIG GPTLVITEYCCYGDLLNFL-RRKRDSFICSKQEDHAEAALYKNLLHSKESSCSD-STNEYMDMKPGVSYVVPTKADKRRSVRIGSYIER-DVTPAIMEDDELALDLEDLLSFSYQVAKGMAFLAS-KNCIHRDLAARNILLTHGRITKICDFGLARDIKNDS-NYVVKGNARLPVKWMAPESIFNCVYTFESDVWSY-GIFLWELFSLGSSPYPGMPVDSKFYKMIKEGFRML-SPEHAPAEMYDIMKTCWDADPLKRPTFKQIVQL-IEKQISESTNHILYSNLANCSPNRQKPVVDHSVRI-NSVGSTASSSQPLLVHDDV (SEQ ID NO: 92)) or the Genbank reference sequence for variant 2 of the Kit mRNA NM_001093772.1 (encoding protein NP_001087241.1; MRGARGAWDFLCVLLLLLRVQTGSSQPSVSPGEPS-PPSIHPGKSDLIVRVGDEIRLLCTDPGFVKWTFEILD-ETNENKQNEWITEKAEATNTGKYTCTNKHGLSNSI-YVFVRDPAKLFLVDRSLYGKEDNDTLVRCPLTDPE-VTNYSLKGCQGKPLPKDLRFIPDPKAGIMIKSVKRA-YHRLCLHCSVDQEGKSVLSEKFILKVRPAFKAVP-VVSVSKASYLLREGEEFTVTCTIKDVSSSVYST-WKRENSQTKLQEKYNSWHHGDFNYERQATLTISS-ARVNDSGVFMCYANNTFGSANVTTTLEVVDKGFI-NIFPMENTTVFVNDGENVDLIVEYEAFPKPEHQQ-WIYMNRTFTDKWEDYPKSENESNIRYVSELHLTRL-KGTEGGTYTFLVSNSDVNAAIAFNVYVNTKPEIL-TYDRLVNGMLQCVAAGFPEPTIDWYFCPGTEQRC-SASVLPVDVQTLNSSGPPFGKLVVQSSIDSSAFKFIN-GTVECKAYNDVGKTSAYFNFAFKEQIHPHTLFT-PLLIGFVIVAGMMCIIVMILTYKYLQKPMYEVQ-WKVVEEINGNNYVYIDPTQLPYDHKWEFPRNRLS-FGKTLGAGAFGKVVEATAYGLIKSDAAMTVAVKM-LKPSAHLTEREALMSELKVLSYLGNHMNIVNLLGA-CTIGGPTLVITEYCCYGDLLNFLRRKRDSFICSK-QEDHAEAALYKNLLHSKESSCSDSTNEYMDMKPG-VSYVVPTKADKRRSVRIGSYIERDVTPAIMEDDEA-LDLEDLLSFSYQVAKGMAFLASKNCIHRDLAAR-NILLTHGRITKICDFGLARDIKNDSNYVVKGNA-RLPVKWMAPESIFNCVYTFESDVWSYGIFLWEL-FSLGSSPYPGMPVDSKFYKMIKEGF RMLSPEHAPAE-MYDIMKTCWDADPLKRPTFKQIVQLIEKQISES-TNHIYSNLANCSPNRQKPVVDHSVRINSVGSTASSS-QPLLVHDDV (SEQ ID NO: 93)), wherein the proteins are designated by the standard 1-letter amino acid code.

Example 1

Expression, Purification and Crystallization of SCF and Kit

The entire ectodomain of Kit composed of five Ig-like domains designated D1, D2, D3, D4 and D5 was expressed in insect cells using the baculovirus expression system. Purified Kit ectodomain monomers or SCF-induced Kit ectodomain homodimers (SCF-Kit 2:2 complex) were each subjected to extensive screening for crystal growth and optimization followed by determination of their crystal structures.

Protein Expression and Purification

A soluble Kit ectodomain (amino acids 1-519) containing a poly-histidine tag at the C-terminus was expressed in insect cells (Sf9) using the baculovirus expression system. Kit ectodomain was purified by Ni-chelate followed by size-exclusion chromatography (Superdex 200, GE Healthcare). After partial deglycosylation using endo-glycosidase F1, the ectodomain was further purified by anion exchange chromatography (MonoQ, GE Healthcare). SCF (1-141) was expressed, refolded and purified as previously described (Langley et al. (1994) Arch Biochem Biophys 311: 55-61; Zhang et al. (2000) Proc Natl Acad Sci U S A 97: 7732-7737).

Cell Lines and Expression Vectors

HEK and NIH3T3 cells were cultured in DMEM supplemented with 10% FCS and 10% CS, respectively. Prior to SCF stimulation, cells were starved overnight in serum free medium as previously described (Kouhara et al. (1997) Cell 30: 693-702). Transfection was performed with Lipofectamin (Invitrogen) according to the manufacturer instructions. The cDNA of full length Kit was subcloned into the RK5 expression vector for transient transfection and into the pBABE/puro vector for stable expression (Kouhara et al. (1997) Cell 30: 693-702). Anti-Kit antibodies were generated by immunizing rabbits with recombinant Kit ectodomain. Monoclonal anti-Kit antibodies (Santa Cruz) were used for immunoblotting. Anti-phosphotyrosine (anti-pTyr) antibodies were purchased from Upstate Biotechnology.

Crystallization and Data Collection

Samples of Kit ectodomain alone or in complex with SCF were subjected to extensive screening for crystal growth and optimization. Crystals of deglycosylated (ectodomain of approximate dimensions of 0.12×0.1×0.05 mm were obtained in phosphate buffer with polyethyleneglycol (PEG) as the precipitant (0.1 M Na-Pi buffer pH 6.0, 0.2 M KCl, 12% PEG 400) at 4°. All crystals were immersed in a reservoir solution supplemented with 5-18% glycerol for several seconds; flash cooled, and kept in a stream of nitrogen gas at 100° K during data collection. The crystals belonged to the rhomboidal space group R3 with unit cell dimensions of a=162.4 Å, and c=67.1 Å in hexagonal lattice setting, with one molecule per asymmetric unit. Platinum, bromine and iodine derivatives of Kit were prepared by soaking the crystals in a reservoir solution containing heavy atom reagents in concentration ranges of 0.1 mM to 50 mM at 277 K for few seconds to 10 days.

Crystals of the SCF-Kit complex were grown with polyethyleneglycol (PEG) as the precipitant (0.2 M ammonium sulfate, 8-12% PEG 8000, 5-8% ethylene glycol at pH 7.0-8.5) at 4° C. and diffraction data were collected to resolution of 3.5 Å with a ADSD quantum-210 CCD detector at the X25 beamline of NSLS, Brookhaven National Laboratory. The crystals belong to the monoclinic space group C2 with unit cell dimensions a=269.5 Å, b=52.1 Å, c=189.8 Å, β=108.2°, which is comprised of two sets of SCF and Kit molecules in the asymmetric unit. All data sets were processed and scaled using the DENZO and SCALEPACK and the HKL2000 program package (Otwinowski et al. (1997) Methods Enzymol. 276: 307-326). The data collection statistics are summarized in Table 1A.

Example 2

Structure Determination

The experimental phases were calculated by using multiple isomorphous replacement with anomalous scattering (MIRAS) and by multi-wavelength anomalous diffraction (MAD) to 3.0 Å resolution (Table 1A). The resulting electron-density maps showed continuous electron density of β sandwich structures, and clear solvent-protein boundaries. The molecular model of monomeric Kit ectodomain was built manually into the experimental electron density maps. The structure was refined to a 3.0 Å resolution using the native data set to a crystallographic R-factor of 25.4% and free R-factor of 29.6% (Table 1B). The structure of SCF-Kit 2:2 complex was solved by molecular replacement using the structure of the monomeric form described in this report and the structure of SCF (Zhang et al. (2000) Proc Natl Acad Sci USA 97: 7732-7737; retrievable from the Protein Data Bank with code: 1EXZ) as search models. The structure was refined to 3.5 Å resolution using the native data set to a crystallographic R-factor of 24.9% and free R-factor of 29.5% (Tables 1A and 1B). Molecular images were produced using Pymol (pymol.sourceforge.net) and CCP4MG (Potterton et al. (2004) Acta Crystallogr D Biol Crystallogr 60: 2288-2294) software. The atomic coordinates and structure factors of Kit monomer and SCF-Kit complex have been deposited in the Protein Data Bank (rcsb.org/pdb) with accession code 2EC8 and 2E9W, respectively.

TABLE 1A

Data collection and phasing statistics

| | Kit Native | $K_2Pt(NO_2)_4$ | $NaI_2$ | $K_2Pt(NO_2)_4$ (Peak) | $K_2Pt(NO_2)_4$ (inflection) | $K_2Pt(NO_2)_4$ (remote) | SCF-Kit Native |
|---|---|---|---|---|---|---|---|
| Data collection | | | | | | | |
| X-ray source | NSLS X26C | NSLS X6A | NSLS X6A | NSLS 6A | NSLS 6A | NSLS 6A | NSLS X25 |
| Date | 2006-Apr-3 | 2006-Jun-10 | 2006-Jun-12 | 2006-Jun-11 | 2006-Jun-11 | 2006-Jun-11 | 1999-Jun-29 |
| Wavelength (Å) | 1.1000 | 1.0716 | 1.6000 | 1.0716 | 1.0722 | 0.9600 | 1.2500 |
| Space group | R3 | R3 | R3 | R3 | R3 | R3 | C2 |
| Unit Cell dimensions | | | | | | | |
| a (Å) | 162.25 | 162.09 | 161.81 | 162.02 | 162.44 | 162.27 | 269.48 |
| b (Å) | 162.25 | 162.09 | 161.81 | 162.02 | 162.44 | 162.27 | 52.07 |
| c (Å) | 67.59 | 66.94 | 67.62 | 69.02 | 69.13 | 69.09 | 189.79 |
| β (°) | | | | | | | 108.24 |
| Resolution (Å) | 50-3.0 | 50-3.1 | 50-3.0 | 50-3.3 | 50-3.3 | 50-3.3 | 50-3.5 |
| | (3.11-3.0) | (3.2-3.1) | (3.11-3.00) | (3.42-3.3) | (3.42-3.3) | (3.42-3.3) | (3.63-3.50) |
| No. of total reflections | 156126 | 68961 | 120301 | 78599 | 79043 | 79258 | 113481 |

TABLE 1A-continued

Data collection and phasing statistics

| No. of unique reflections | 13342 | 23535 | 26281 | 19468 | 19550 | 19473 | 31962 |
|---|---|---|---|---|---|---|---|
| Completeness (%)[a] | 99.8 (100) | 99.2 (99.6) | 99.5 (97.1) | 95.4 (97.2) | 95.4 (97.0) | 95.0 (96.4) | 98.5 (91.4) |
| I/c (I) | 11.7 (7.5) | 11.3 (3.0) | 21.7 (9.5) | 13.0 (5.9) | 11.6 (4.8) | 11.2 (4.7) | 19.1 (6.6) |
| $R_{merge}$ (%)[b] | 7.6 (17.0) | 8.6 (32.1) | 8.5 (20.8) | 11.1 (22.8) | 10.7 (27.0) | 11.9 (27.5) | 6.1 (17.6) |

Phasing statistics

| | MIRAS | | | MAD | | |
|---|---|---|---|---|---|---|
| Resolution (Å) | 50-3.0 | 50-3.0 | 50-3.0 | 50-3.3 | 50-3.3 | 50-3.3 |
| No. of sites | | 3 | 6 | 3 | 3 | 3 |
| $R_{iso}^{(c)}$ (%) | | 22.0 | 11.6 | | | |
| $R_{cells}$ (iso/anom)[d] | | 0.85/0.68 | 0.80/0.81 | 0.79 | 0.74/0.81 | 0.81/0.98 |
| Phasing power (iso/anom)[e] | | 0.88/1.48 | 1.07/0.65 | 1.10 | 1.32/1.06 | 0.97/0.16 |
| <FOM>[f] | 0.50 | | | 0.48 | | |

Values in parentheses indicate statistics for the highest resolution shells.
[a]Completeness = (number of independent reflections)/(total theoretical reflections).
[b]$R_{merge} = \Sigma |Ii - <I>|/\Sigma Ii$, where Ii is the observed intensity and <Ii> is the averaged intensity obtained from multiple observations of symmetry related reflections.
[c]$R_{iso} = \Sigma ||Fph| - |Fp||/\Sigma |Fp|$,
[d]$R_{cells} = \Sigma |Fh - (Fph - Fp)|/\Sigma |Fph - Fp|$,
[e]Phasing power = r.m.s. (|Fh|/E), where Fph and Fp are the derivative and native structure-factor amplitudes, Fh is the heavy-atom structure amplitude, respectively. E is the residual lack of closure error.
[f]<FOM> is the mean figure of merit.

TABLE 1B

Refinement statistics

| | Kit | SCF-Kit |
|---|---|---|
| Resolution (Å) | 27.7-3.0 | 39.0-3.5 |
| No. of reflections (work/test) | 12521/650 | 30351/1594 |
| $R_{cryst}^{(a)}/R_{free}^{(b)}$ (%) | 25.4/29.6 | 24.9/29.5 |
| No. of atoms | | |
| Protein | 3498 | 9064 |
| Waters | 0 | 0 |
| Carbohydrate | 70 | 84 |
| Average B-factor (Å$^2$) | 31.6 | 75.2 |
| R.m.s.d. from ideal[c] | | |
| Bond lengths (Å) | 0.015 | 0.013 |
| Bond angles (°) | 1.8 | 1.9 |
| Ramachandran plot quality | | |
| Most favored (%) | 74.4 | 73.5 |
| Additionally favored (%) | 24.1 | 24.5 |
| Generously allowed (%) | 1.5 | 2.0 |
| Disallowed (%) | 0 | 0 |
| PDB code | 2EC8 | 2E9W |

[a]$R_{cryst} = \Sigma |F_{obs} - F_{calc}|/\Sigma |F_{obs}|$, where $F_{obs}$ and $F_{calc}$ are the observed and the calculated structure factors, respectively.
[b]$R_{free}$ is calculated from 5% of reflections removed before refinement.
[c]R.m.s.d., root mean square deviation.

Example 3

Analysis of the Structure of the Kit Ectodomain

General Analysis of Ectodomain Structure

Figure 1A:
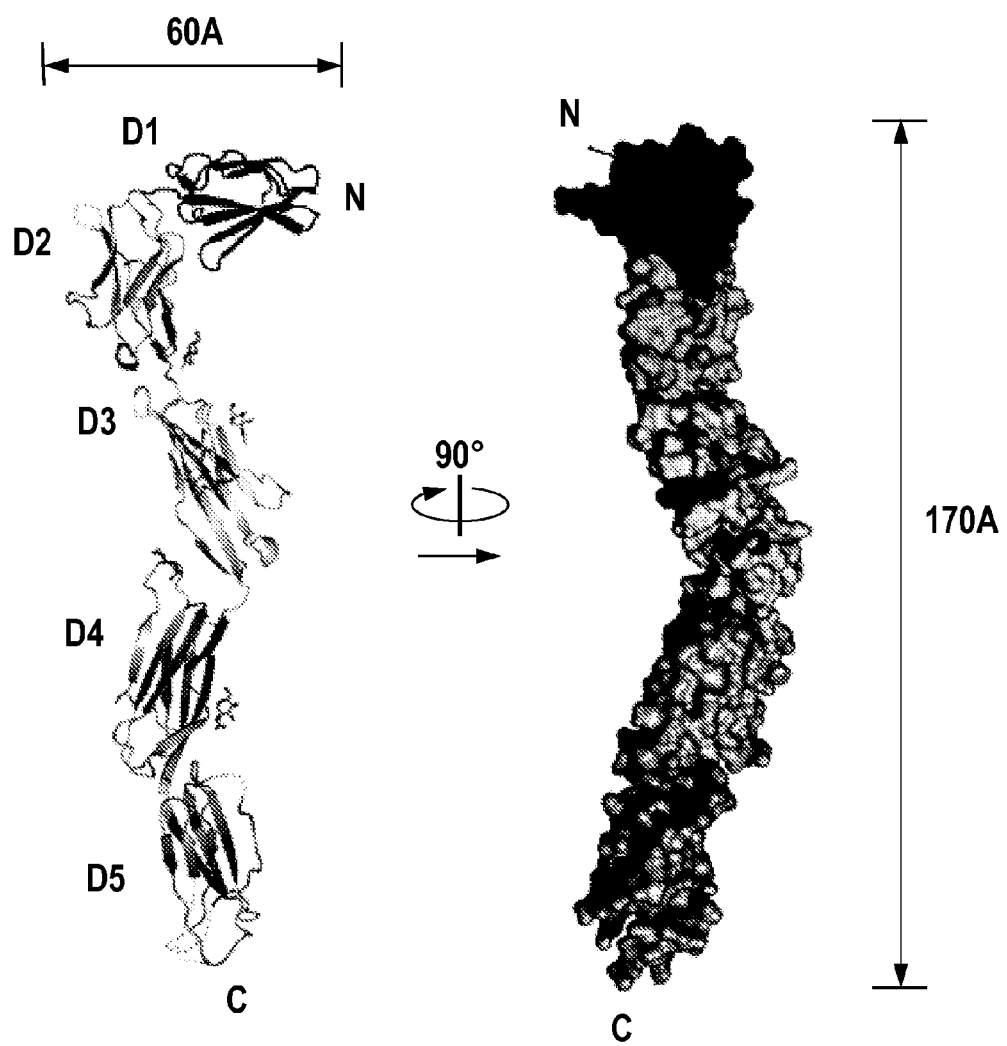
FIGS. 1A-E depict the crystal structure of Kit ectodomain.

Kit ectodomain shows an elongated serpentine shape with approximate dimensions of 170×60×50 Å (FIG. 1A). The D1, D2, D3, D4 and D5 domains of Kit exhibit a typical immunoglobulin super family (IgSF) fold, composed of eight β strands, designated ABCC'DEFG, assembled into a β sandwich consisting of two anti-parallel β sheets (FIG. 1A). D1, D2, D3 and D5 each contain a conserved disulfide bond connecting cysteine residues at B5 and F5 (Fifth amino acids of strand B and F, respectively); positions that bridge the two β sheets to form the center of the hydrophobic core of the Ig-like fold (Harpaz and Chothia (1994) J Mol Biol 238: 528-539). D2 and D5 contain two disulphide bonds and D4 does not contain any cysteine residue, nevertheless, the integrity of the Ig-like fold of D4 is maintained even though the conserved cysteine residues at B5 and F5 are replaced by a valine and phenylalanine residues, respectively.

The angle between D1 and D2 along the axis of the two domains is 76° (FIG. 1A, B) resembling the orientation between the first and second Ig-like domains of interleukin-1β receptor (Vigers et al. (1997) Nature, 386: 190-194). In contrast, the angle between D2 and D3 is 150°, between D3 and D4 is 119° and between D4 and D5 is 162°. The orientations between the ABED and A'GFC β-sheets for the different Ig-like domains are ~180° for D1-D2, ~180° for D2-D3, ~90° for D3-D4, and ~180° for D4-D5 (FIG. 1).

The superposition of all five Ig-like domains of the Kit ectodomain with telokin (Holden et al. (1992) J. Mol. Biol. 227: 840-851) used as a standard for Ig-folds reveals a root mean square (r.m.s.) deviation of 1.5-2.9 Å for equivalent Cα atoms. D2 is the most divergent among the five Kit Ig-like domains (FIG. 8) as revealed by its higher r.m.s.d. values when superimposed with telokin. Based on the structural conservation of key amino acids in Ig-like domains and their secondary structural topology (Harpaz et al., (1994) J Mol Biol 238: 528-539; Halaby et al. (1999) Protein Eng 12: 563-571), D1, D2, D3 and D4 belong to the I-subset and D5 is related to the C2 and IgCAM subsets of IgSF. Furthermore, among the structurally conserved 20 finger-print residues of IgSF (Harpaz et al. (1994) J Mol Biol 238: 528-539), 10-14 residues are conserved in the five Ig-like domains of Kit (Table 2).

TABLE 2

20 of key finger print residues of IgSF for Kit domains and Telokin (PDB code: 1TLK) as the typical I-set IgSF[1]

| Position | D1 | D2 | D3 | D4 | D5 | Telokin | Characteristic |
|---|---|---|---|---|---|---|---|
| A'B1 | Gly51 | Asp129 | Gly226 | Gly328 | Asn423 | Gly56 | Gly |
| B1 | Ile54 | Thr132 | Phe229 | Val331 | Gly424 | Ala59 | Aliphatic |
| B3 | Leu56 | Val134 | Val231 | Leu333 | Leu426 | Phe61 | large hydrophobic |
| B5 | Cys58 | Cys136 | Cys233 | Val335 | Cys428 | Cys63 | Cys |
| B7 | Asp60 | Leu138 | Ile235 | Tyr337 | Ala430 | Val65 | Neutral or hydrophobic |
| C2 | (Phe63) | Tyr146 | Ser244 | Gln346 | Ile438 | Val73 | Hydrophobic |
| C4 | Trp66 | Leu148 | Trp246 | Trp348 | Trp440 | Trp75 | Trp |
| CD | — | (Leu156) | (Leu253) | Phe355 | — | Val82 | large hydrophobic |
| D1 | — | (Asp159) | (Gln258) | (Lys358) | — | His87 | basic and form salt bridge |
| D2 | — | (Leu160) | (Glu257) | (Trp359) | — | Phe88 | Hydrophobic |
| E4 | Trp82 | Ile170 | Leu275 | Leu377 | Ile478 | Leu100 | Hydrophobic, almost Leu |
| E6 | Thr84 | Ile172 | Ile277 | Leu379 | Ser480 | Ile102 | Hydrophobic |
| EF2 | Ala87 | Val175 | Ala280 | Leu382 | — | Val105 | Hydrophobic |
| EF6 | Asn91 | Tyr179 | Asp284 | Glu386 | — | Asp109 | Asp |
| F1 | Gly93 | Leu182 | Gly286 | Gly388 | Gly487 | Ala111 | Gly or Ala or (Asp) |
| F3 | Tyr95 | Leu184 | Phe288 | Tyr390 | Val489 | Tyr113 | Tyr |
| F5 | Cys97 | Cys186 | Cys290 | Phe392 | Cys491 | Cys115 | Cys |
| G6 | Ile107 | Phe204 | Thr303 | Phe405 | Phe504 | Ala128 | Hydrophobic |
| G8 | Val109 | Leu202 | Leu305 | Val407 | Phe506 | Leu130 | Hydrophobic |
| G10 | Val111 | Val210 | Val307 | Val409 | — | Val132 | Hydrophobic |

[1]The positions of 20 of key finger print residues and typical characteristics of each of finger print residue are shown in the first and last column, which are defined by Harpaz and Chothia, 1994.

Detailed Analysis of the Structure of Kit Ig-Like Domains

Kit D1. The D1 fold is a β sandwich composed of two β sheets. One sheet is formed by the three-strands, A, B and E and the second sheet is composed of the five-strands, A', G, F, C and C'(ABE/A'GFCC'). The first strand, interrupted by a cis-conformation at Pro41, is split into two shorter strands of A and A' which pair with strands B and G, respectively. A disulfide bond connecting Cys58 of B5 with Cys97 of F5 bridges the two β sheets. A fairly long strand C', that interacts with strand C, directs the C-terminal end of the polypeptide chain toward the upper side of D1 which is directly connected to strand E. On the basis of the Ig-like domain nomenclature, D1 belongs to the I2-subset of IgSF (Casasnovas et al. (1998) Proc Natl Acad Sci USA 95: 4134-4139).

Kit D2. D2 consists of a small β-sheet formed by strands B, E, and D and a second β-sheet composed of strands A', G, F and C (BED/A'GFC), as well as an additional helix at the crossover between strands E and F (residues 177-179). Although 11 of 20 hallmark residues of I-set of IgSF are identified on D2, this Ig-like domain differs from a standard I1-set of IgSF in a number of ways. D2 has a Leu residue at the C4 position, while other I1-set of IgSF have a conserved Trp. The pattern of hydrogen bonds in strand B is altered due to formation of two short β strands, referred as strands B and B'. The additional B' strand is aligned to strand A, forming a short β sheet with an, AB' topology. The G strand is split into two short strands, G (bottom side) and G' (top side) because of an insert at amino acids 197-199, which results in formation of a β sheet with strand A'. Disruption of the hydrogen bond pattern caused by a "kink" in G strand at residues 197-199 is compensated by the hydrogen bonds between the side chains of Ser197 and the main chain amide of Cys186. Notably Ser197, is conserved as a Ser or Thr residue in Kit from different species and in other type-III RTKs. D2 contains an additional disulfide bond, between Cys151 and Cys183 bridging the CD loop with the end of the F strand to provide additional stability to strand C and the CD loop. The additional disulfide bridge may compensate for the reduced network of hydrogen bonds between strands C and F. These two Cys are highly conserved in Kit from zebrafish to humans.

Kit D3. D3 is composed of two sets of (3 sheets (ABED/A'GFC) belonging to the I1-subset of IgSF. The two β sheets are bridged by a disulfide bond between Cys233 on strand B and Cys290 on strand F. Comparison of telokin (PDB code: 1TLK) and D3 structures shows a Zscore of 10.4 and an r.m.s. deviation of 2.0 Å for the 98 aligned Cα residues of D3.

Kit D4. Although D4 lacks the characteristic disulfide bond between cysteines at B5 and F5, D4 maintains an IgSF topology. In addition, 13 out of 20 finger-print residues of 1-set IgSF are conserved in D4. The structural integrity of D4 is preserved by interactions between buried aliphatic (Val335) and aromatic (Phe392) residues present at B5 and F5, respectively, which constitute part of the hydrophobic core of the domain. Structural comparison using DALI shows that among Kit Ig-like domains D4 is most similar to telokin (retrieve with Protein Data Bank code: 1TLK), with a Z-score of 11.9 and an r.m.s.d. of 1.5 Å for the 89 aligned Cα residues. The distance of 8.6 Å between Cα-Cα of Val335 and Phe392 is within the distance range seen between similar positions in IgSF domains lacking a disulfide bond connecting B5 and F5. For example, Titin Ig-like domain M5 (Protein Data Bank code: 1TNM); also lacking a disulfide bond, superimposes with an r.m.s.d of 2 Å with D4 and has a distance of 8.9 Å between B5 and F5 positions. D4 is composed of two β sheets each containing four strands with the arrangement ABED/A'GFC. Thr321, the first residue of the A' strand, forms Van der Waals contacts with the aromatic ring of the highly conserved Phe405. Notably, the CD loop folded upwards to the top side of the domain is stabilized by three main interactions. Side chain of Thr354 forms hydrogen bonds with side chain of Gln347 and main chain carbonyl of Trp348. The hydrophobic residues (Trp348, Tyr350, Trp359 Val377, Leu379 and Tyr390), located at the edge of the hydrophobic core provide a hydrophobic environment for Phe355. Although the CD loop does not exhibit notable sequence conservation, this loop contains eight amino acids in all type-III family RTKs.

Kit D5. D5 belongs to C2 and IgCAM subset of IgSF and 10 out of 20 fingerprint residues are conserved in this module. D5 exhibits a ABED/CFG topology, a disulfide bond between Cys428 of B5 and Cys491 of F5 that bridges the two β sheets and a second disulfide bond bridging the C strand and the CD loop. The two disulfide bonds are conserved in all Kit and type-III RTKs. Notably, the top half of D5 resembles the third Ig of neuronal cell adhesion molecule Axonin-1/TAG-1 (Protein Data Bank code 1CS6). Several hallmarks can be identified, though to a lesser extent in Telokin (Protein Data Bank code 1FHG), FGFR (Protein Data Bank code 1CVS) and in the RTK Musk (Protein Data Bank code 21EP). These include two Ala residues (Ala430 and Ala493), in proximity to the disulfide bond connecting B5 with F5; the presence of small side chains in this region enables close packing at the top of the domain. The second hallmark is a ring arrangement of the Pro and Gly residues Pro413, Gly432, Pro436 and Gly498 in the A, B, C and G strands, respectively. The third hallmark is the presence of an Mn residue in F9 (Asn495) that forms hydrogen bonds with main chains of Val497 and Pro434 of FG and BC loop, respectively. Taken together, these three hallmarks at the top of D5 result in a tightly packed configuration similar to the configuration of Ig-like domains of cell adhesion proteins.

Example 4

Inter Ig-Like Domain Interactions in Kit Monomeric Form

The inter-domain interactions between the 5Ig-like domains of Kit are responsible for maintaining the overall topology of Kit ectodomain monomers (FIG. 1). The orientation of D1 relative to D2 is determined by the extensive buried surface area that is caused by the numerous interactions between the two Ig-like domains (FIG. 1B). The buried surface area of 1240 $Å^2$ in the D1-D2 interface is much larger than the buried surface areas of most inter Ig-like domain interfaces of rod-like multi-domain IgSF structures (Su et al. (1998) Science 281: 991-995) including the three other inter Ig-like interfaces in Kit ectodomain that range between 500 and 800 $Å^2$. This interface is formed primarily by hydrophobic and electrostatic interactions between strands A' and G, loops EF and CC' of D1 with the N-terminal region of strand A, the C-terminal end of strand B, loop BC and DE of D2 (FIG. 1B). Moreover, many residues in the D1-D2 interface including amino acids from strands G of D1, the linker region connecting D1 and D2 and the BC loop of D2 are conserved in Kit from different species (FIG. 1B).

Figure 1B:
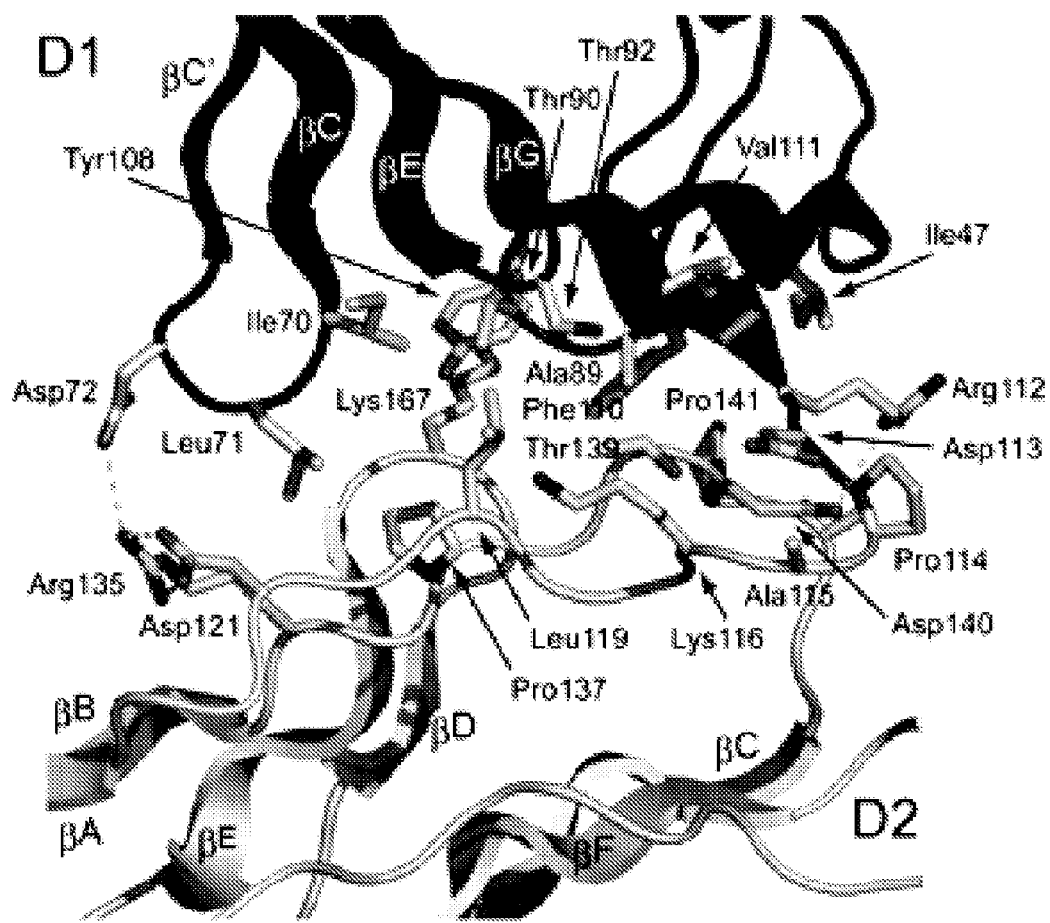
Figure 1C:
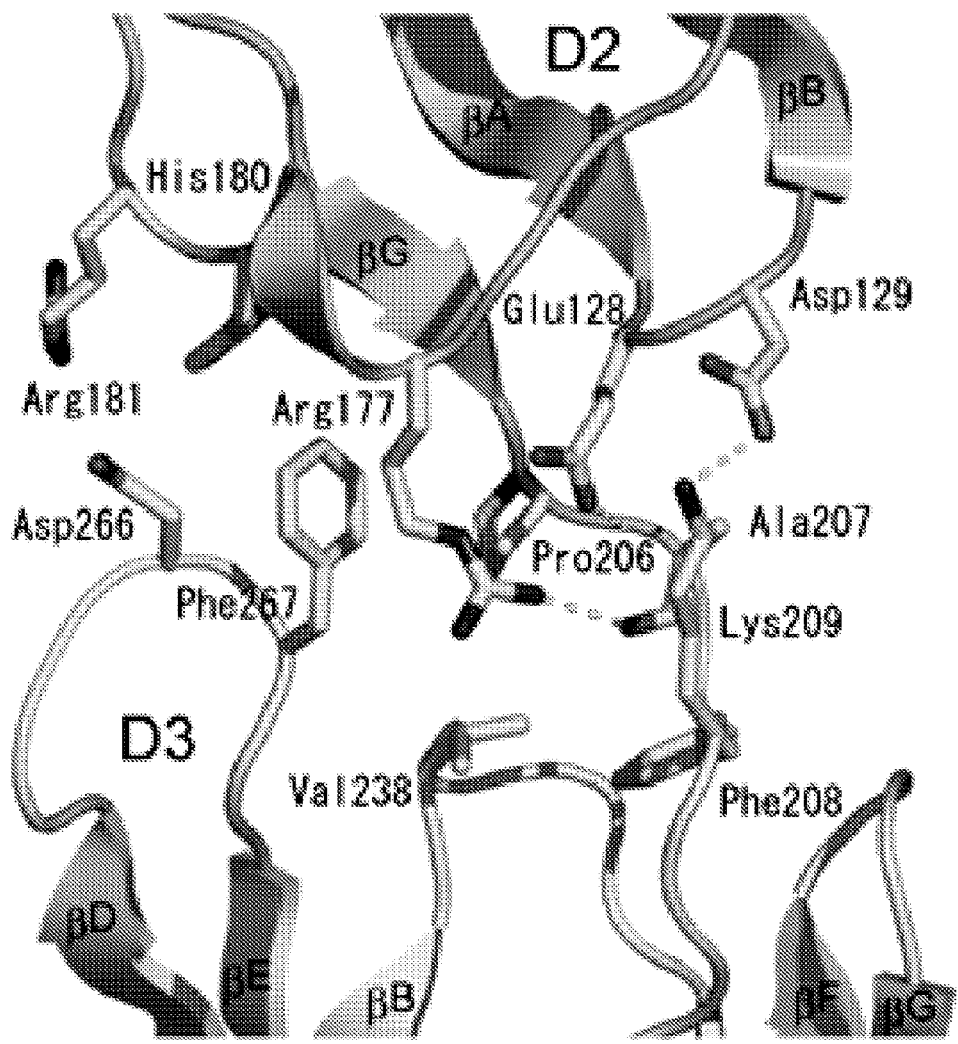
Figure 1D:
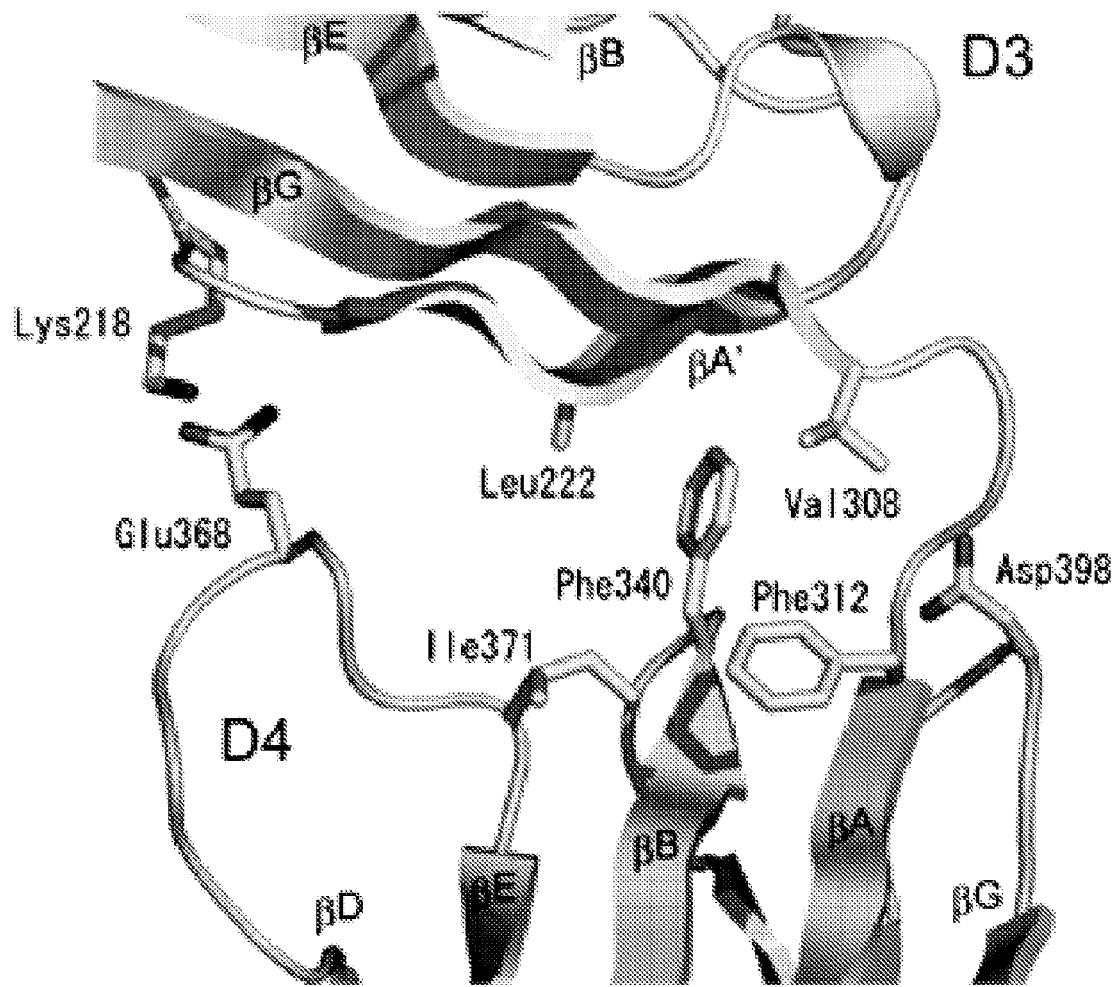
Figure 1E:
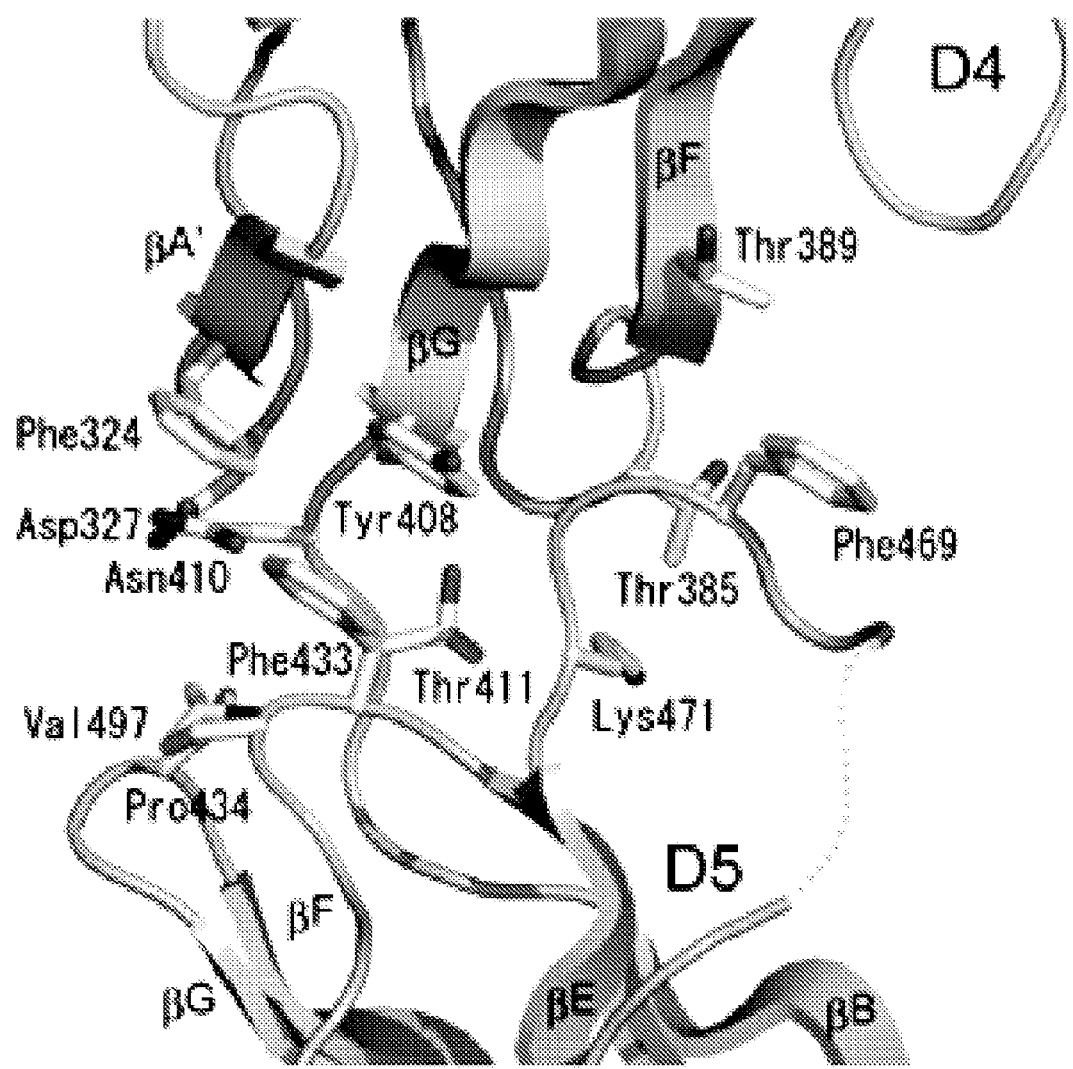

The buried surface area of the D2-D3 interface is approximately 780 $Å^2$. The D2-D3 interface is composed of a small hydrophobic patch surrounded by two electrostatic interactions. This interface is formed by an interaction between the EF loop of D2 and the DE loop of D3 and interactions between the D2-D3 linker region with the FG and BC loops of D3 (FIG. 1C). The buried surface area of D3-D4 interface is approximately 570 $A^2$. D3 and D4 interact primarily through strands A' and G of D3 with the BC and DE loops of D4 (FIG. 1D). The length of the D3-D4 interface is approximately 20 Å due to the angular arrangement of D4 relative to D3 with an angle of 119° along the long axis of the two Ig-like domains. The D4-D5 interface forms a buried surface area of 760 $Å^2$, mainly mediated by hydrophobic interactions (FIG. 1E). The interface is formed by interactions between strands A, G and F of D4, with the BC and DE loops of D5, as well as with the D4-D5 linker region (FIG. 1E)

Detailed Domain-by-Domain Information about Inter-Ig-Like Domain Interactions in Kit Monomers The D1-D2 interface. The hydrophobic interactions between residues Ile47, Ile70, Leu71, Ala89, Tyr108 and Phe110 of D1 and Leu119, Pro137, Leu138, Pro141, Pro166 and the side chain of Lys167 of D2 stabilize the interdomain interactions (FIG. 1B). There are two major electrostatic interactions in the region surrounding the hydrophobic patch including interaction between Arg 112 of D1 and Asp 140 of D2 and interactions between Asp72 of D1 and Arg135 of D2 (FIG. 1B).

The D2-D3 interface. The hydrophobic patch is composed of the aliphatic part of Arg177 and side chains of Pro206, Phe208, Val238 and Phe267. The electrostatic interaction involves hydrogen bonds between side chains of Glu128 and Asp129 of D2 with Lys209 of D3 (FIG. 1C). A salt bridge between the side chain of Arg177 and the side chain of Glu128 stabilize the position of the side chain of Arg177 and the side chain of Pro206 in D2 and Phe267 in D3 to create a hydrophobic environment for the aliphatic portion of the side chain of Arg177 in D2 (FIG. 1C). A second electrostatic interaction is mediated by the side chains of Arg 181 in D2 with the side chain of Asp266 of D3.

The D3-D4 interface. The hydrophobic interactions in D3-D4 interface include those between Val308 and Leu222 from D3 and Phe312, Phe340, and Ile371 from D4. The D3-D4 interface covers a smaller buried area than other inter Ig-like domain interfaces (FIG. 1D).

The D4-D5 interface. The hydrophobic patch on the D4-D5 interface includes Phe324 and Tyr408 from the A and G strands of D4 and Phe433 from the BC loop of D5, respectively. In addition, van-der-Waals contacts contribute to the stabilization of the interface surrounding the hydrophobic patch; Phe324, Gly384, Thr389, Tyr408, Asn410, Thr411 and Met351 of D4 interact with Val497, Phe433, Gly470, Phe649 and Lys471 of D5 (FIG. 1E).

Example 5

Analysis of the Overall Structure of the Bound SCF-Kit Complex

Figure 2A:
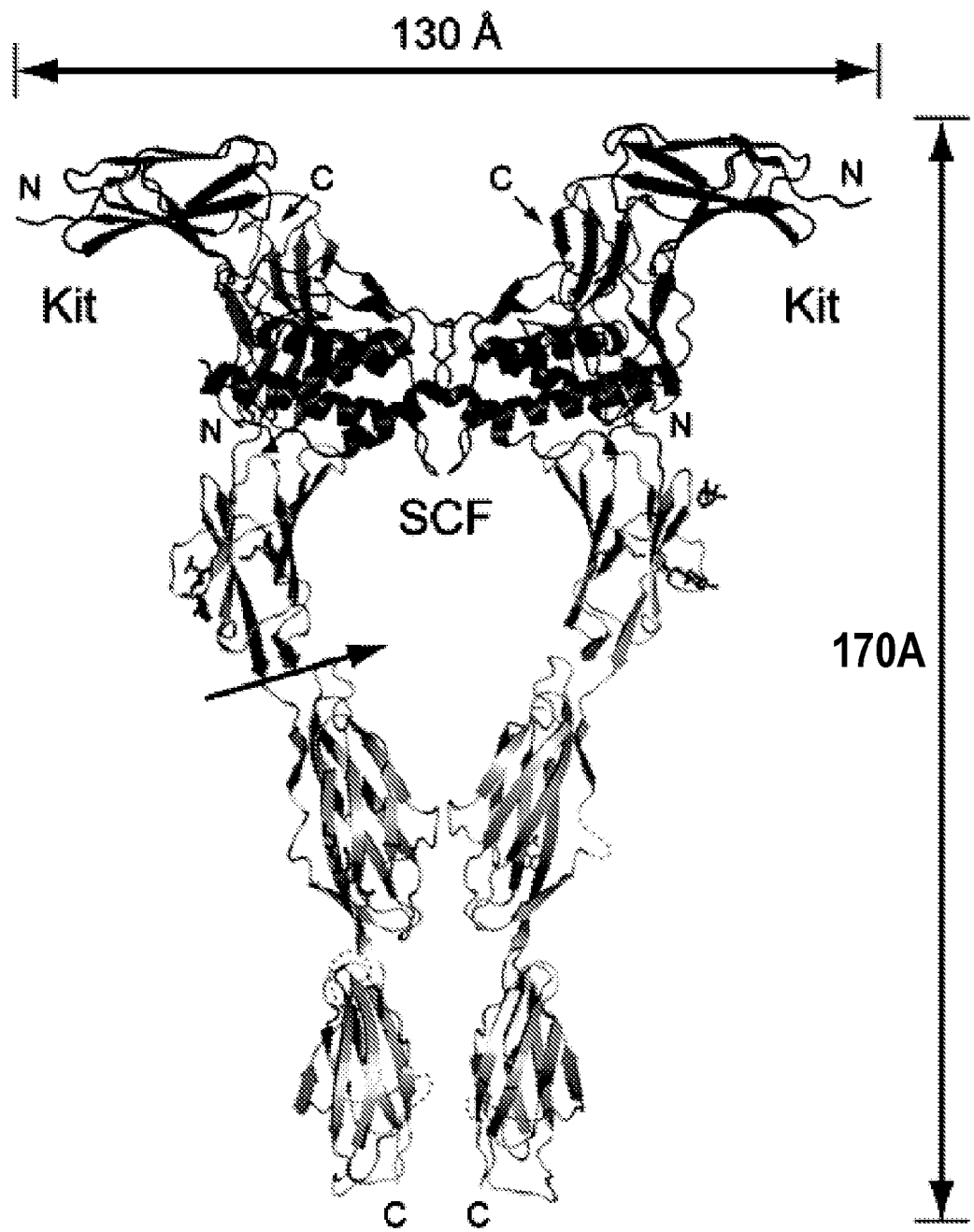
FIGS. 2A-B depict the crystal structure of the SCF-Kit ectodomain 2:2 complex.
Figure 9:
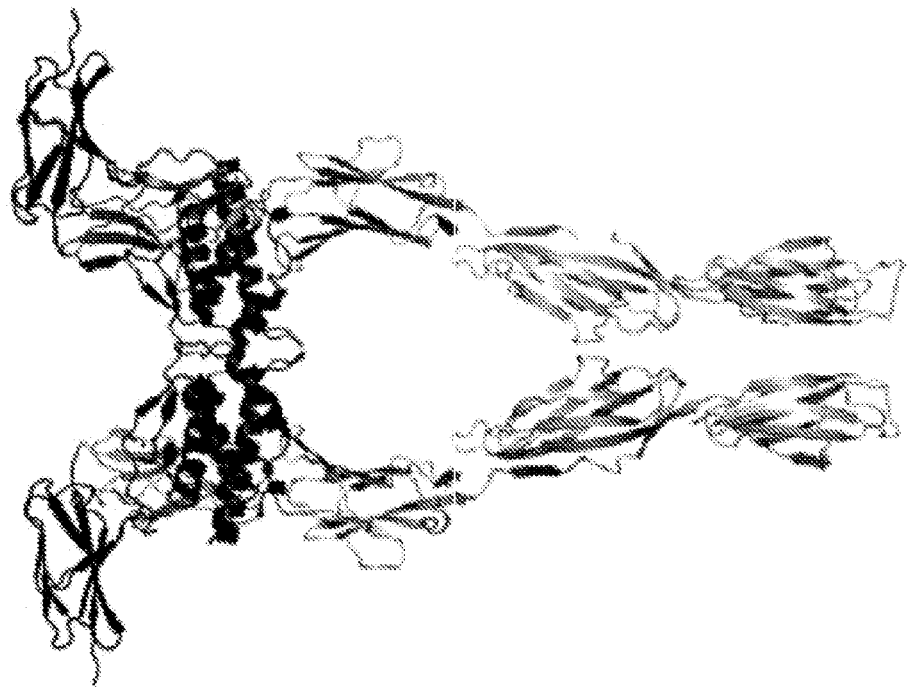
FIG. 9 provides a stereo view of overall structure of the 2:2 SCF-Kit complex. Ribbon model of the 2:2 SCF-Kit complex is shown in stereo representation. The view and the color code are the same as in FIG. 2A.
Figure 9:
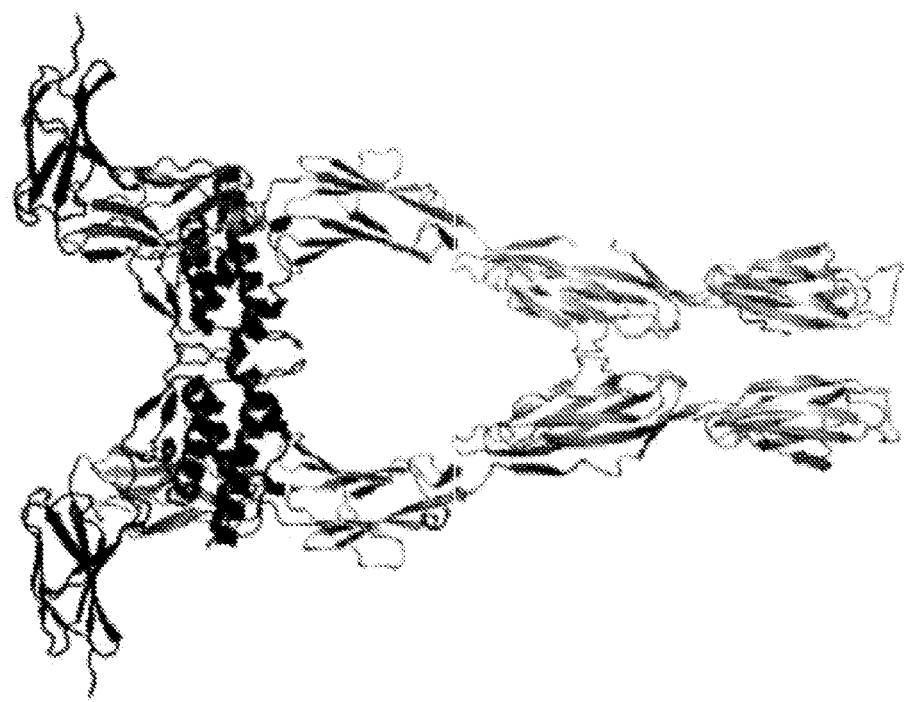

The structure of the SCF-Kit complex shows a 2:2 stoichiometry, in which two sets of 1:1 complexes in the asymmetric unit are related by a non-crystallographic twofold symmetry (FIG. 2). The observed SCF-Kit 2:2 complex in the crystal lattice is consistent with experiments demonstrating that Kit dimerization is driven by the dimeric SCF ligand (Philo et al. (1996) J Biol Chem 271: 6895-6902; Lemmon et al. (1997) J Biol Chem 272: 6311-6317). The two sets of Kit ectodomains and SCF molecules resemble an upside down "A" letter with approximate dimensions of 170×130×70 Å (FIG. 2A and FIG. 9).

Figure 2B:
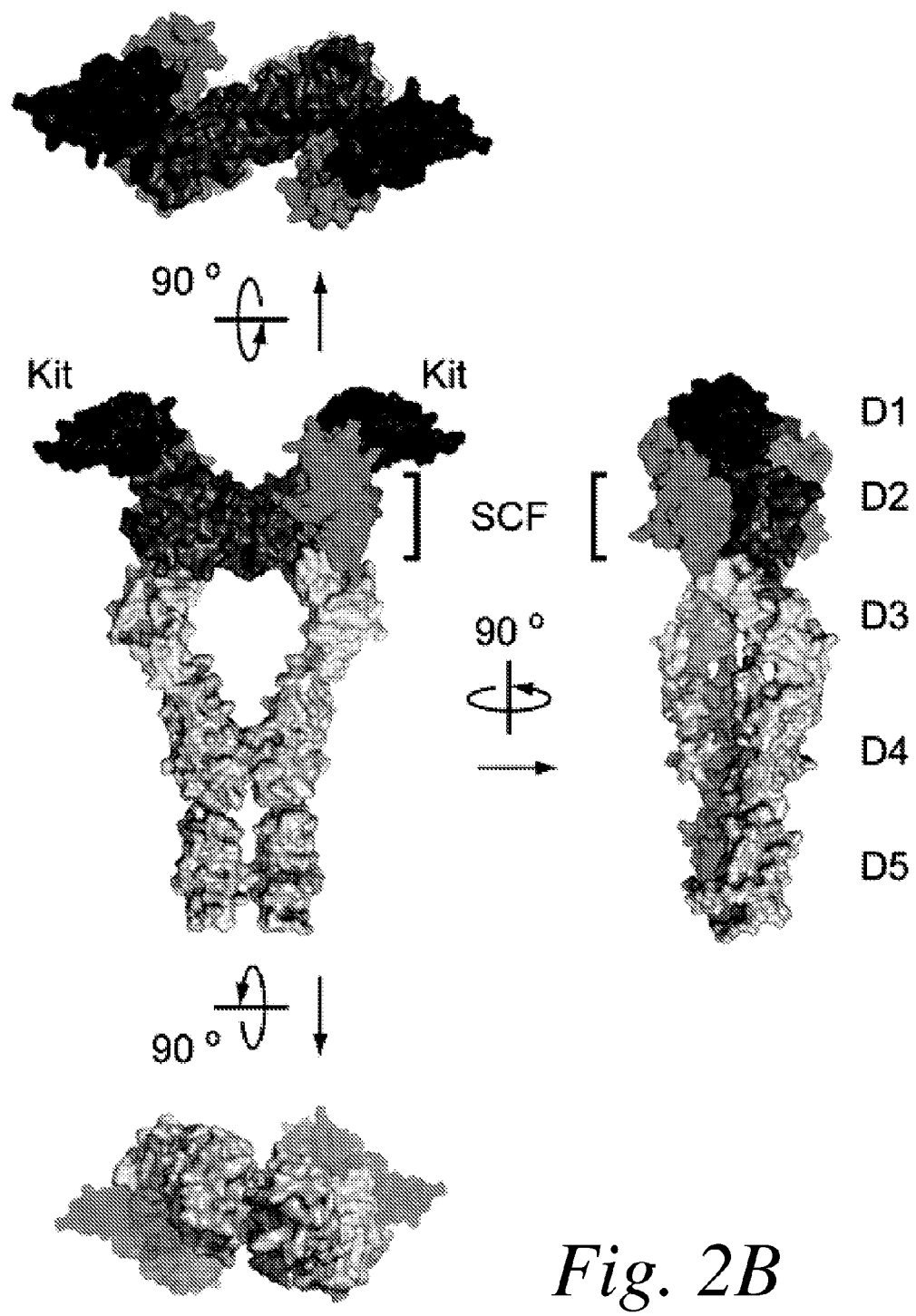

The overall structure of SCF bound to Kit is similar to the previously described structures of free SCF (Zhang et al., (2000) Proc Natl Acad Sci USA 97: 7732-7737; Jiang et al. (2000) Embo J 19: 3192-3203). The structure of SCF-Kit 2:2 complex shows that an individual SCF protomer binds directly to D1, D2 and D3 of an individual Kit protomer (FIG. 2B). Consequently, a single receptor protomer forms a symmetric complex with a similar two-fold related surface on an SCF protomer. Dimerization of Kit is also mediated by homotypic interactions between the two membrane proximal Ig-like domains of Kit, namely, by D4-D4 and D5-D5 interactions (FIG. 2B). This results in dramatically altered configurations of D4 and D5 relative to the rest of the molecule that brings the C-termini within 15 Å of each other close to the place where they connect to the transmembrane domain (FIG. 2B and FIG. 9). The structure is also characterized by the existence of a large cavity at the center of the complex with dimensions of ~50×50×15 Å (FIG. 2B). The crystal structure demonstrates that each protomer of SCF binds exclusively to a single Kit molecule and that receptor dimerization is driven by SCF dimers which facilitate additional receptor-receptor interactions.

Example 6

Analysis of the Scf Binding Region of Kit

SCF is bound to a concave surface formed by D1, D2 and D3 of Kit in a configuration in which the four helix bundle of SCF is oriented perpendicularly to the long axis of D1, D2 and D3 and the C-termini of SCF and Kit are facing opposite directions (FIG. 2, 3 and FIG. 9). The solvent-accessible surface area buried at the interface between Kit and each of the SCF protomers is approximately 2060 Å$^2$; a buried surface area that is within the range of known ligand receptor interfaces. It is possible to divide the SCF-Kit interface into three binding sites (FIG. 3A, B, Table 2, and Table 3). Site-I is located on D1, Site-II is located in D2 and in the D2-D3 linker region and Site-III is located in D3. The buried surface areas of Site I, II and III are approximately 280, 770 and 1010 Å$^2$, respectively.

Site-I

Figure 3A:
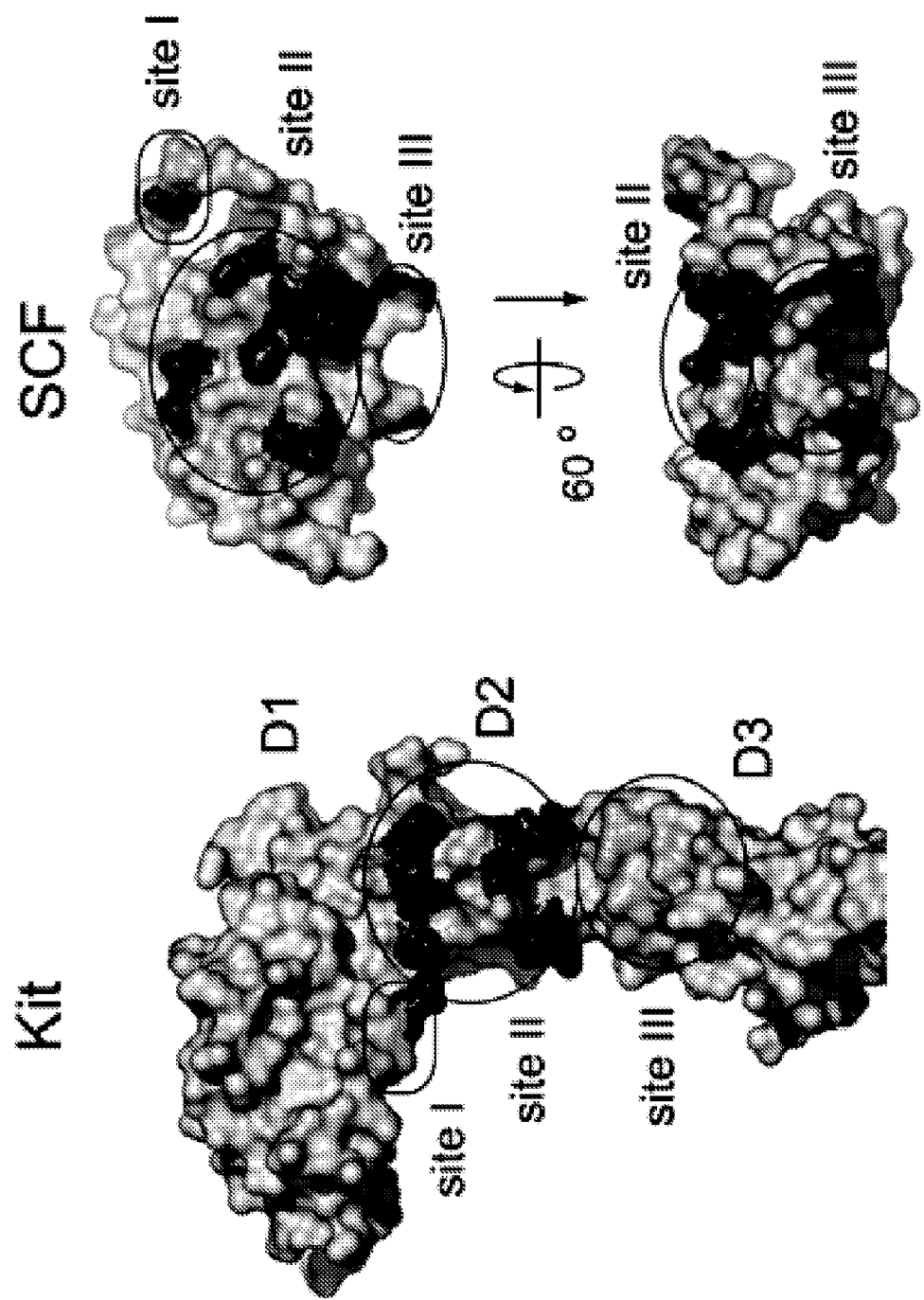
FIGS. 3A-E depict SCF recognition by Kit.
Figure 3B:
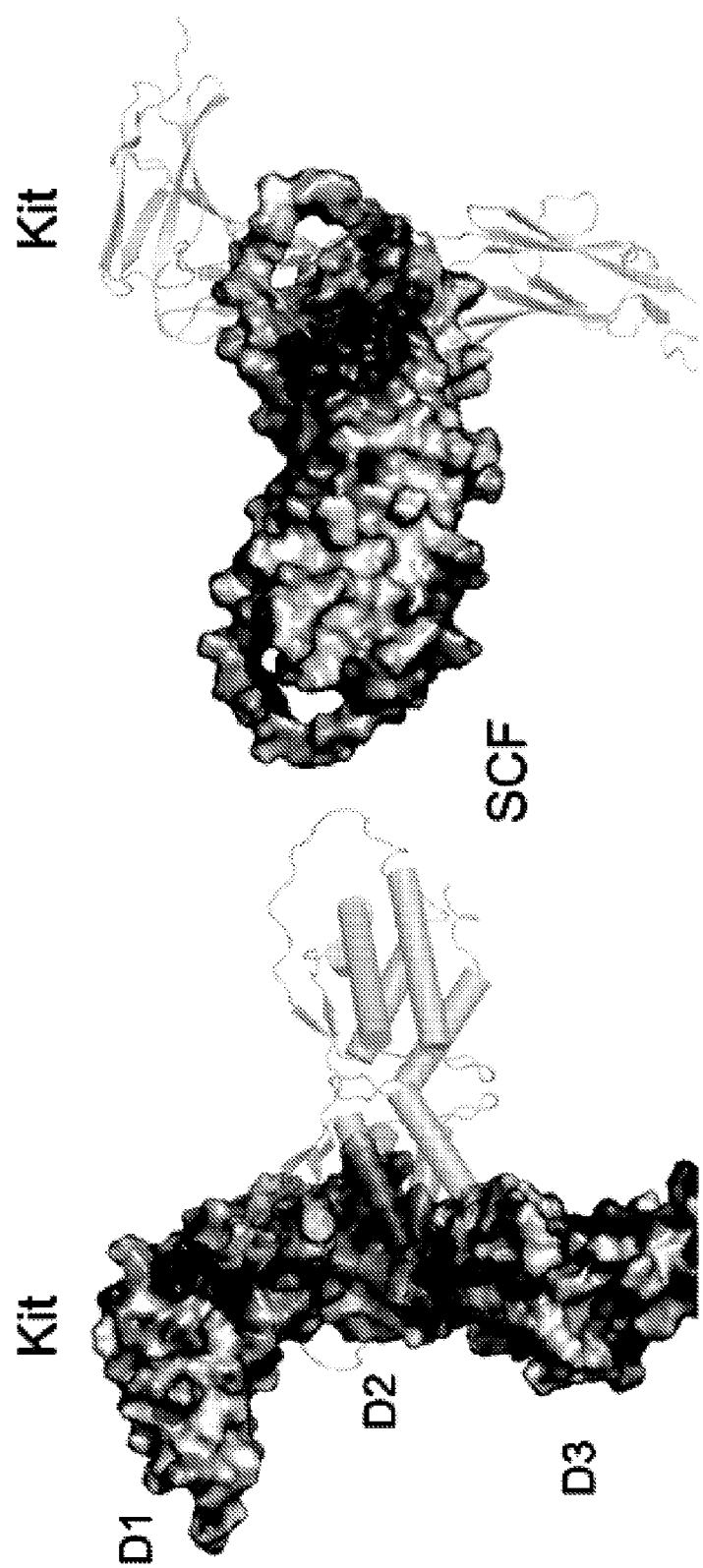
Figure 3C:
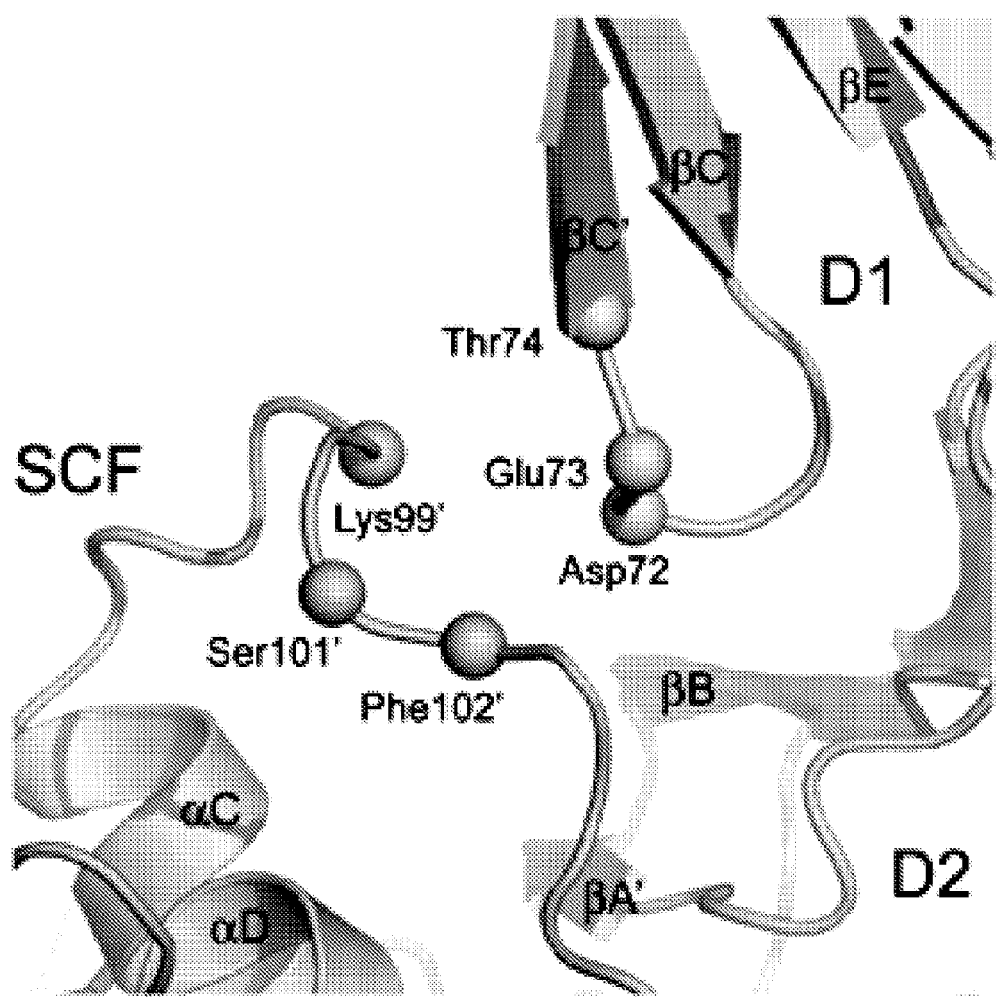

The αC-β2 loop of SCF is aligned perpendicularly to strand C' of D1, as presented in FIG. 3C. Asp72, Glu73 and Thr74 of D1 and Lys99', Ser101' and Phe102' of SCF are closely located at a Cα distance of 6-8 Å, indicating that these residue could participate in the interactions between D1 and SCF. Due to poor side chain electron density of the αC-β2 loop, specific interactions could not be defined.

Site-II

Figure 3D:
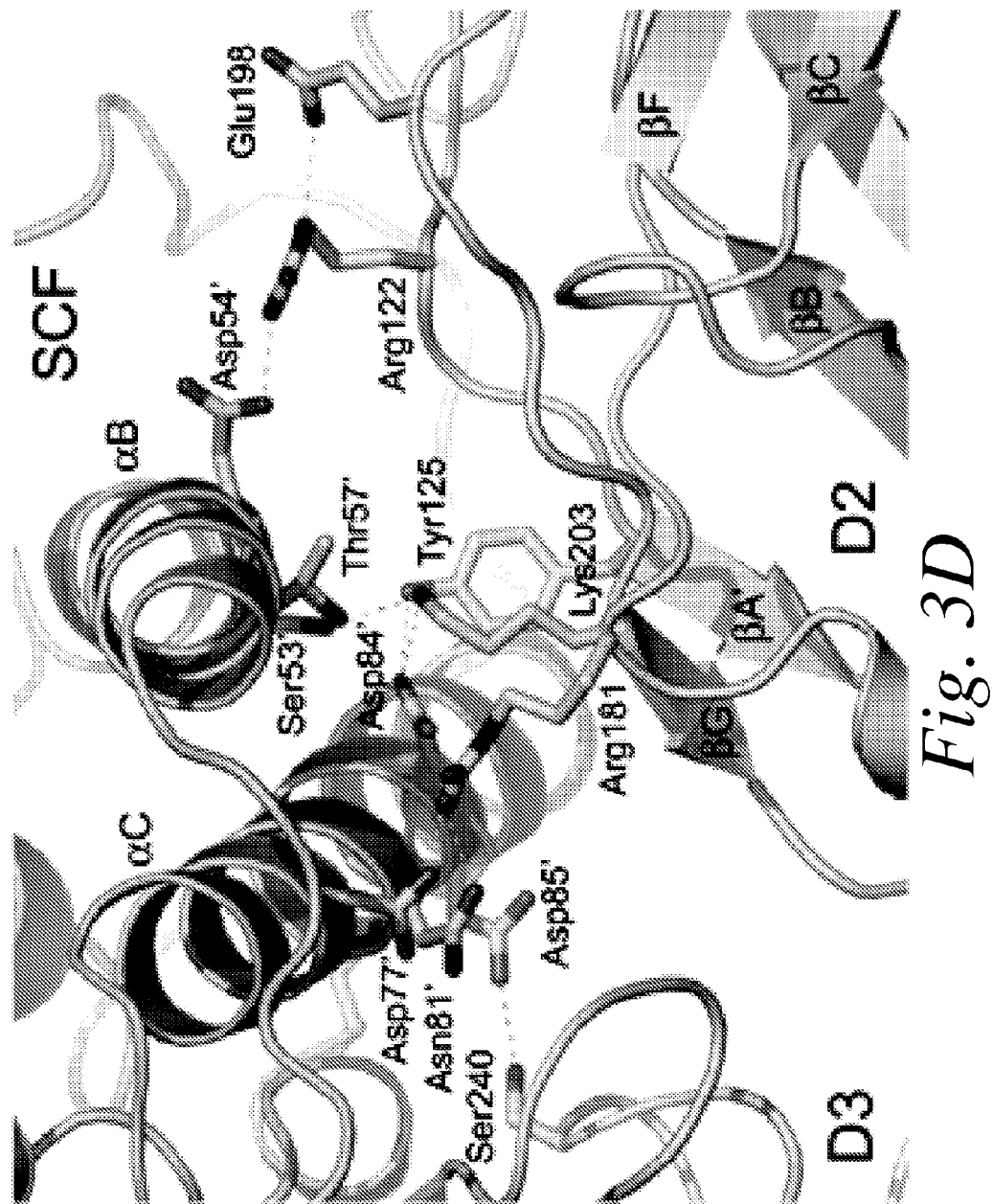
Figure 3E:
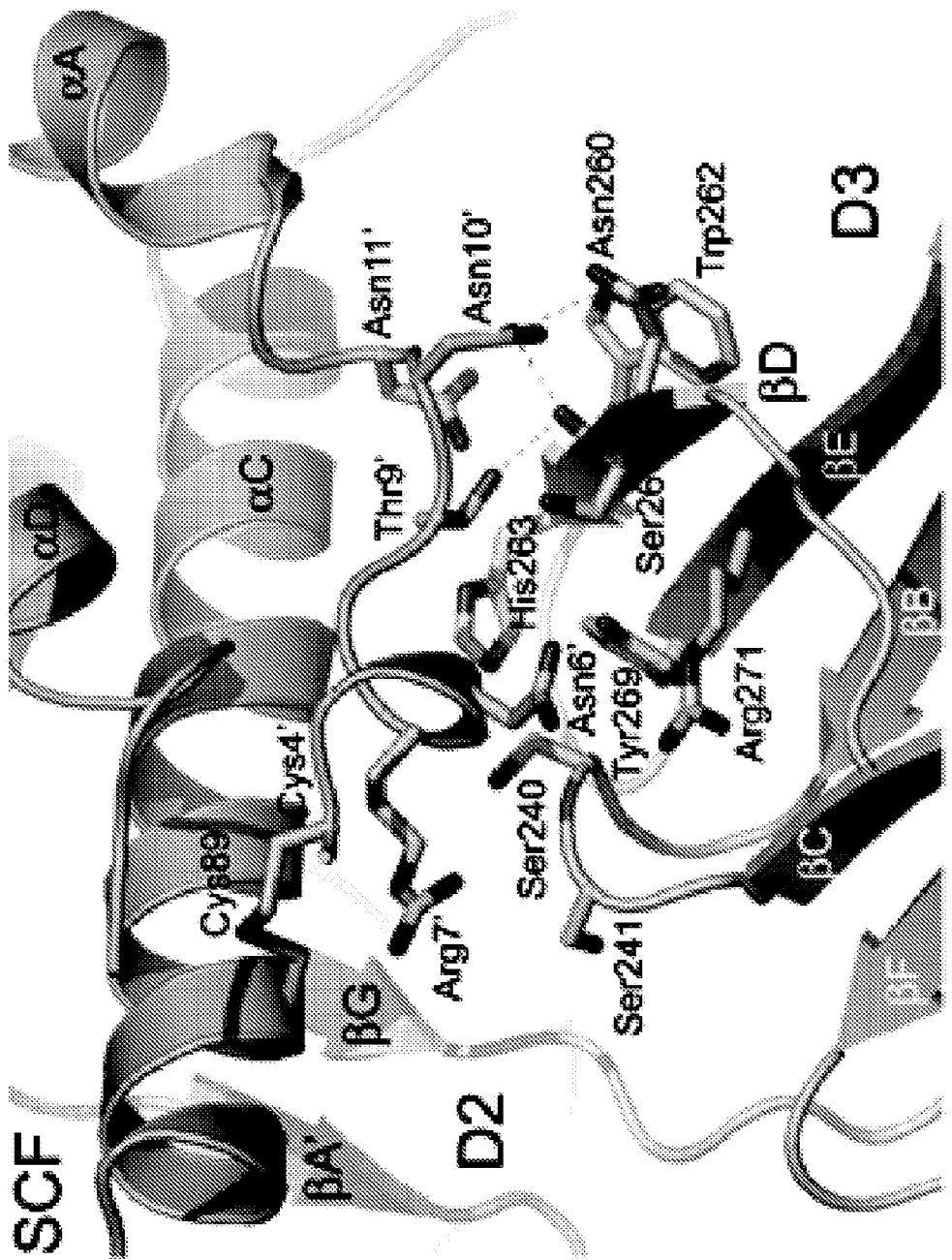
Figure 8A:
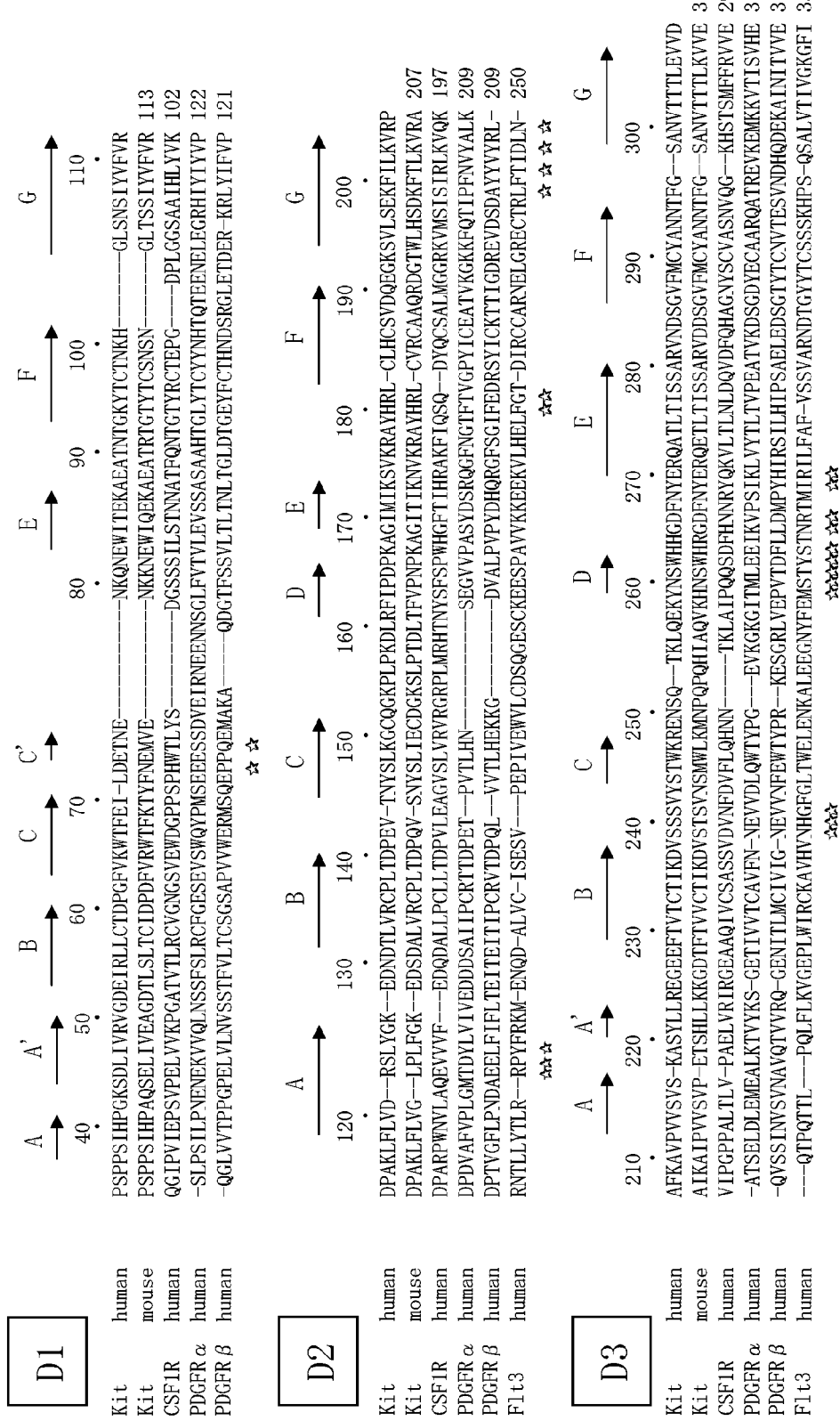
FIG. 8 depicts a structure based sequence alignment of type-III RTKs, based on Kit ectodomain structure, and structure based alignment of ligands for the type-III family RTKs. Each row shows alignment of an individual Ig-like domain. Amino acid sequences were manually aligned based on the IgSF fold characteristics, as determined by (Harpaz et al. (1994) J Mol Biol 238: 528-539) and within agreement with the secondary structure prediction of family members as calculated by Jpred (Cuff et al. (1998) Bioinformatics 14: 892-893). Amino acids marked in red represent IgSF fold determining amino acids. β strands are labeled by arrows and α-helices by springs above the sequence, along with numbering for human Kit and human SCF. Residues of the ligand binding site showing reduced solvent accessibility upon ligand binding are marked by asterisks. Site-I is colored in black, site-II in red and site-III in green. The same color code is used for labeling interacting amino acid residues in SCF. The D4 EF loop that is responsible for D4-D4 interaction is boxed in cyan. The sequences used for the alignment are: Kit human (AAC50969), Kit mouse (AAH75716), CSFR1 human (P07333), PDGFRα human (P16234), PDGFRβ human (P09619) and Flt3 human (P36888). For ligand structure alignment, the PDB entries of SCF (1EXZ), CSF (1HMC), Flt3L (1ETE) were superimposed using Lsqman (Kleywegt and Jones, 1995), while the sequence of SCF mouse (NP_038626) was aligned to the human SCF using ClustalW. Figure discloses SEQ ID NOS 112-147, respectively, in order of appearance.
Figure 8B:
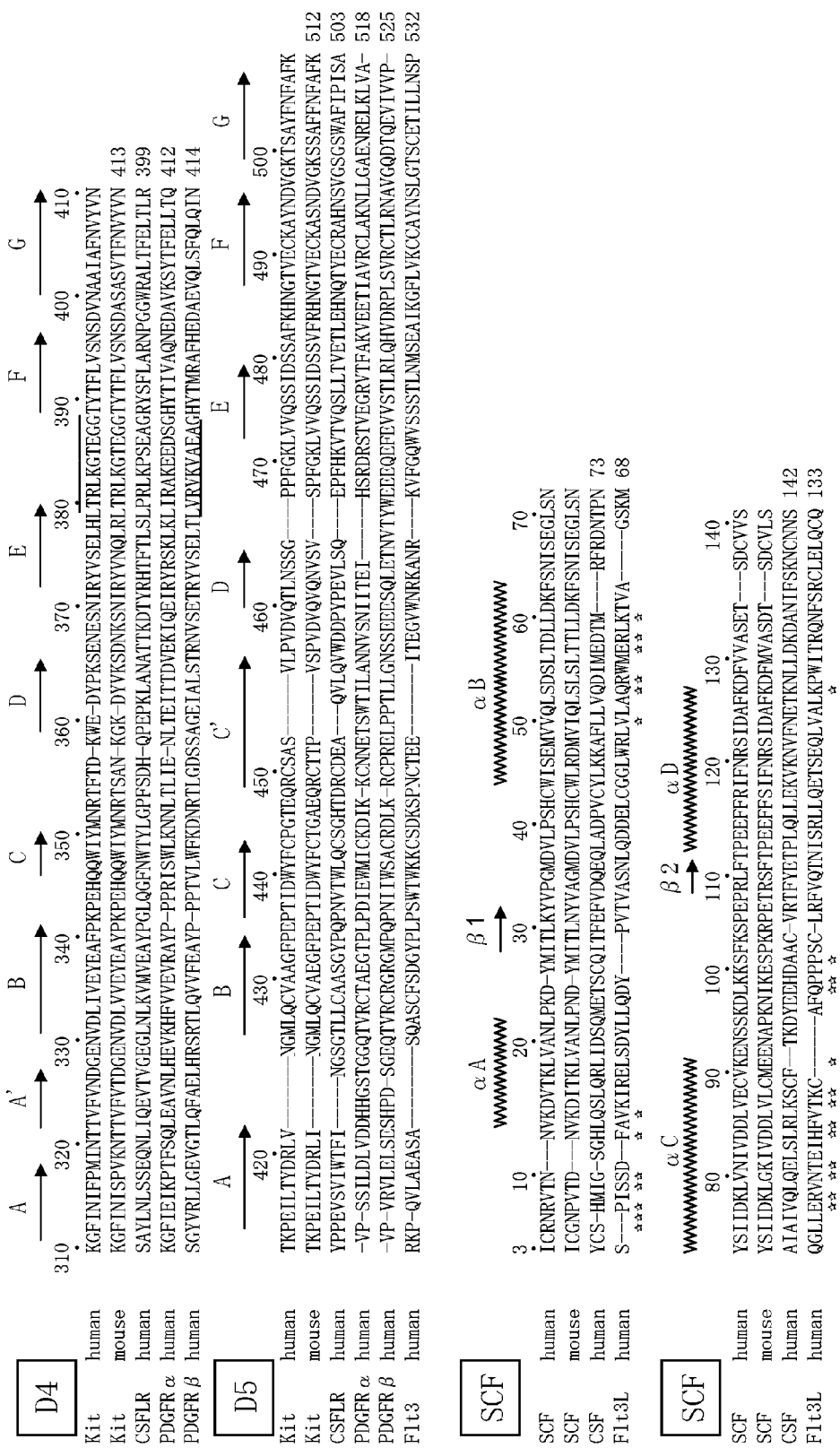
Figure 10:
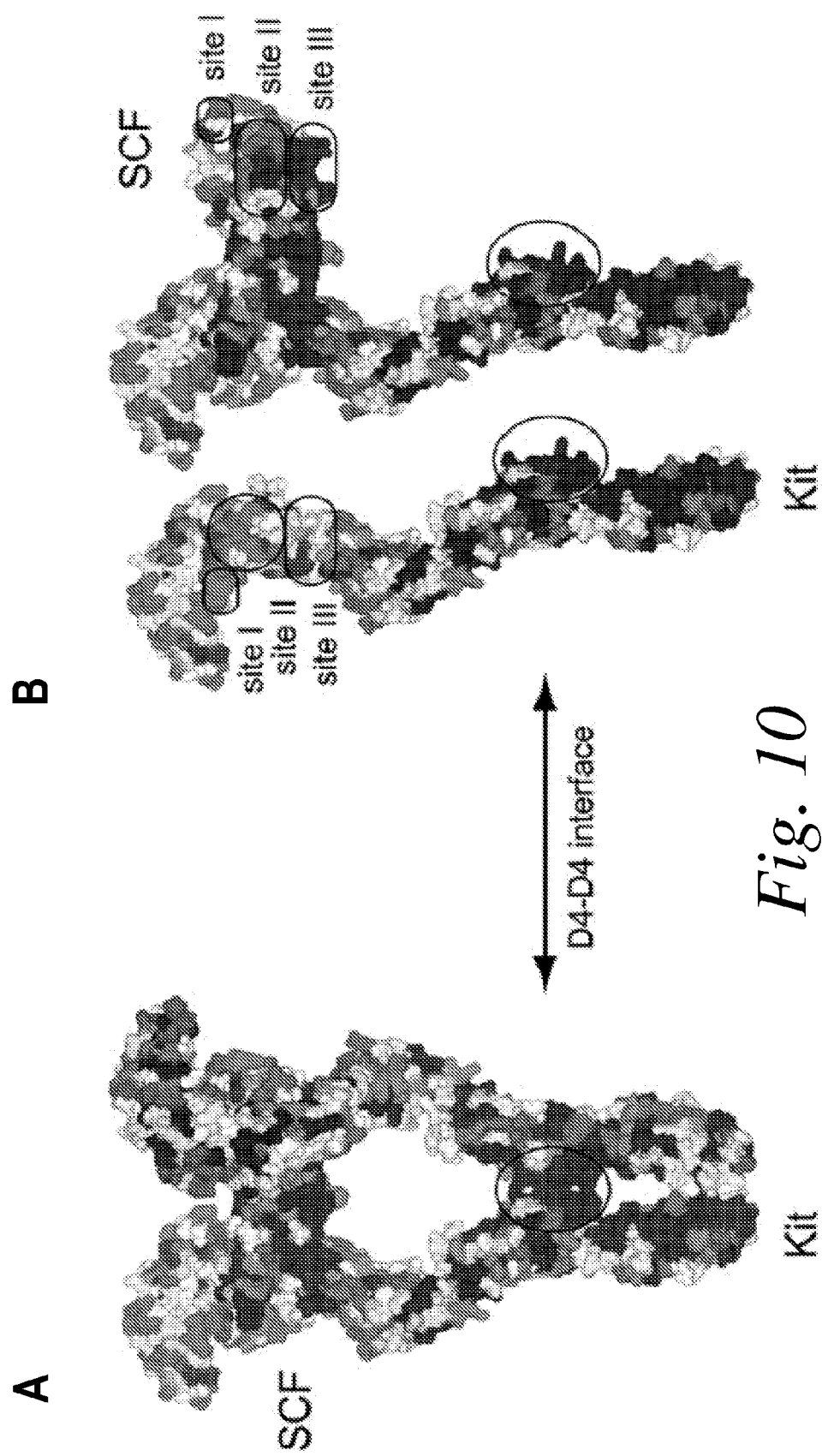
FIGS. 10A-B depict the amino acid conservation at the surface of SCF-Kit complex.

SCF binding is mediated, for the most part, by complimentary electrostatic interactions of charged surfaces on Kit (FIG. 3A, B, D). Salt bridges are formed between the basic amino acids Arg122, Arg181, Lys203 and Arg205 of Kit with the acidic amino acids Asp54', Asp77', Asp84' and Glu88' on SCF. The conformation of Arg122 is stabilized by a salt bridge between Glu198 of Kit and Asp54' of SCF. FIG. 3D shows that three of the major interacting residues Tyr125, Arg181 and Lys203 on D2 are aligned on the same plane and form hydrogen bonds with Asp77', Asn81', Asp84', Ser53' and Thr57' of αB and αC of SCF. The van-der-Waals contacts between Ser123 and Ile201 of D2 and Val50', and Thr57' of SCF also contribute towards the formation of ligand-receptor complex. However, there are notable differences in the residues of Site-II in Kit and SCF from other species (FIG. 3, FIG. 8 and FIG. 10). While Arg181 and Lys203 are invariant as basic amino acids in mammals, Tyr125 is substituted by a phenylalanine in the mouse and rat which most likely results in loss of a hydrogen bond. Arg205 of Kit is a highly conserved amino acid while Glu88' is substituted by a leucine and alanine residues in the mouse and rat, respectively. Furthermore, Arg122 of Kit and Asp54' of SCF in human are substituted by a leucine or valine in the mouse and rat, respectively. These substitutions may account for the reduced affinity of rodent SCF towards human Kit (Lev et al. (1992b) J Biol Chem 267: 15970-15977).

Site-III

The N-terminal segment of SCF interacts with strand D of D3 (FIG. 3A, E). Hydrogen bonds are formed between the side chain of Asn10' of SCF, and the main chain amide and carbonyl group of Ser261, as well as with the side chain of Asp260 and Trp262 on D3. In addition, Thr9' and Asn11' of SCF bind to the side chain and main chain amide of Ser261, and His263 of Kit, respectively. Mutational analysis of SCF has shown that substitution of Asn10' with alanine or glutamic-acid residues reduces the binding affinity of SCF towards Kit by approximately 10 fold and that Asn10' (or Asp in other species) is necessary for biological activity (Hsu et al. (1998) Biochemistry 37: 2251-2262). Comparison of the receptor binding interface in SCF from different species shows that Asn10' (or Asp) is a highly conserved residue (FIG. 8). Additional important interactions are mediated by Asn6' and Arg7' of SCF via van-der-Waals contacts with Tyr259, Thr269, Ser240, Val242, Ser241 Ser244 on D3 of Kit.

TABLE 3

SCF-Kit Interactions and Homophilic Interaction between two Kit protomers

| SCF-KIT interactions 1 Hydrogen bonds and salt bridges[1] | | | | SCF-KIT interactions 2 Hydrogen bonds and salt bridges[1] | | | | KIT D4-D4 interactions Hydrogen bonds and salt bridges[1] | | | |
|---|---|---|---|---|---|---|---|---|---|---|---|
| Kit (molA) | | SCF (molC) | | Kit (molB) | | SCF (molD) | | Kit (molA) | | KIT (molB) | |
| Arg122 | Nη1 | Asp54 | Oδ1 | Arg122 | Nη1 | Asp54 | Oδ1 | Arg381 | O | Arg381 | Nη1 |
| Tyr125 | OH | Asp84 | Oδ1 | Tyr125 | OH | Asp84 | Oδ1 | Arg381 | Nη1 | Thr380 | O |
| Arg181 | Nη1 | Asp77 | Oδ2 | Arg181 | Nη1 | Asp77 | Oδ2 | Arg381 | Nη2 | Glu386 | Oε1 |
| Arg181 | Nη2 | Asn81 | Oδ1 | Arg181 | Nη2 | Asn81 | Oδ1 | Glu386 | Oε1 | Arg381 | Nη2 |
| Lys203 | Nζ | Asp84 | Oδ1 | Lys203 | Nζ | Ser53 | Oγ | | | | |
| Lys203 | Nζ | Ser53 | Oγ | Ser240 | Oγ | Asp85 | Oδ2 | | | | |
| Ser240 | Oγ | Asp85 | Oδ2 | Ser261 | O | Thr9 | Oγ1 | | | | |
| Ser261 | O | Thr9 | Oγ1 | Ser261 | O | Asn10 | Oδ1 | | | | |
| Ser261 | O | Asn10 | Oδ1 | Trp262 | Nε1 | Asn10 | Oδ1 | | | | |

| van der waals contact[2] | | van der waals contact[2] | | van der waals contact[2] | |
|---|---|---|---|---|---|
| Asp72 | Phe102 | Asp72 | Lys99 | Thr380 | Thr380, Arg381 |
| Tyr125 | Val87, Ser53 | Thr74 | Lys99 | Arg381 | Leu382, Lys383 |
| Arg181 | Leu60, Val80 | Tyr125 | Val87, Ser53 | Leu382 | Arg381 |
| Ile201 | Thr57 | Arg181 | Leu60, Val80 | Lys383 | Arg381 |
| Lys203 | Thr57 | Ile201 | Thr57 | | |
| Arg205 | Glu88 | Lys203 | Thr57, Asp84 | | |
| Ser240 | Arg7 | Arg205 | Glu88 | | |

TABLE 3-continued

SCF-Kit Interactions and Homophilic Interaction between two Kit protomers

| Trp262 | Thr9, Asn10, Asn11 | Ser240 | Arg7 |
| His263 | Thr9, Asn11, Lys78, Asn81, Asp85 | Trp262 | Thr9, Asn11 |
| Gly265 | Lys78, Asn81 | His263 | Thr9, Asn11, Lys78 |
| Asp266 | Asn81 | Gly265 | Lys78, Asn81 |
| Tyr269 | Asn6 | Tyr269 | Asn6 |

[1]Hydrogen bond and salt bridge and
[2]van der waals contact have distance range of 2.5-3.5 and within 4.0 Å, respectively.

Example 7

Figure 11A:
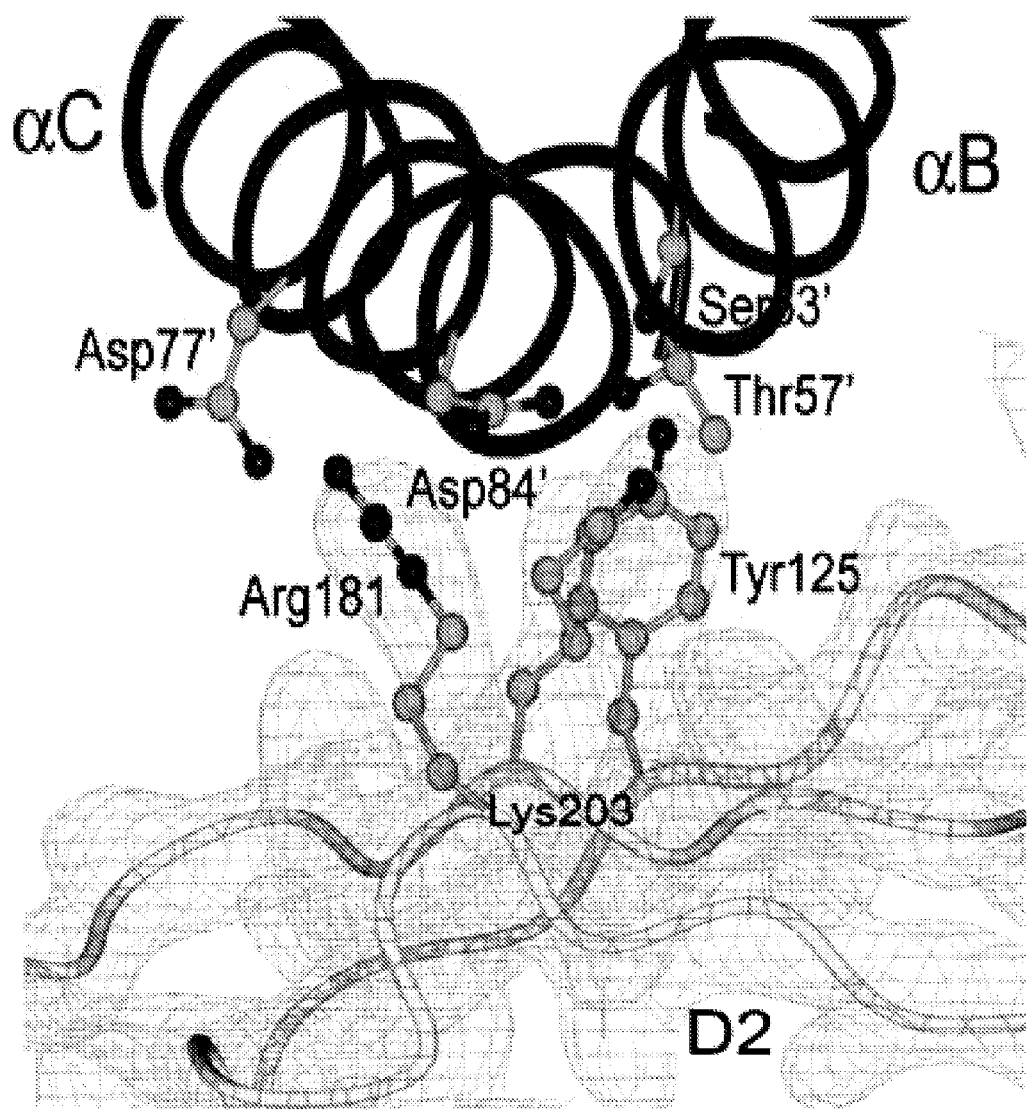
FIGS. 11A-B depict the electron densities of the SCF-Kit interface.
Figure 11B:
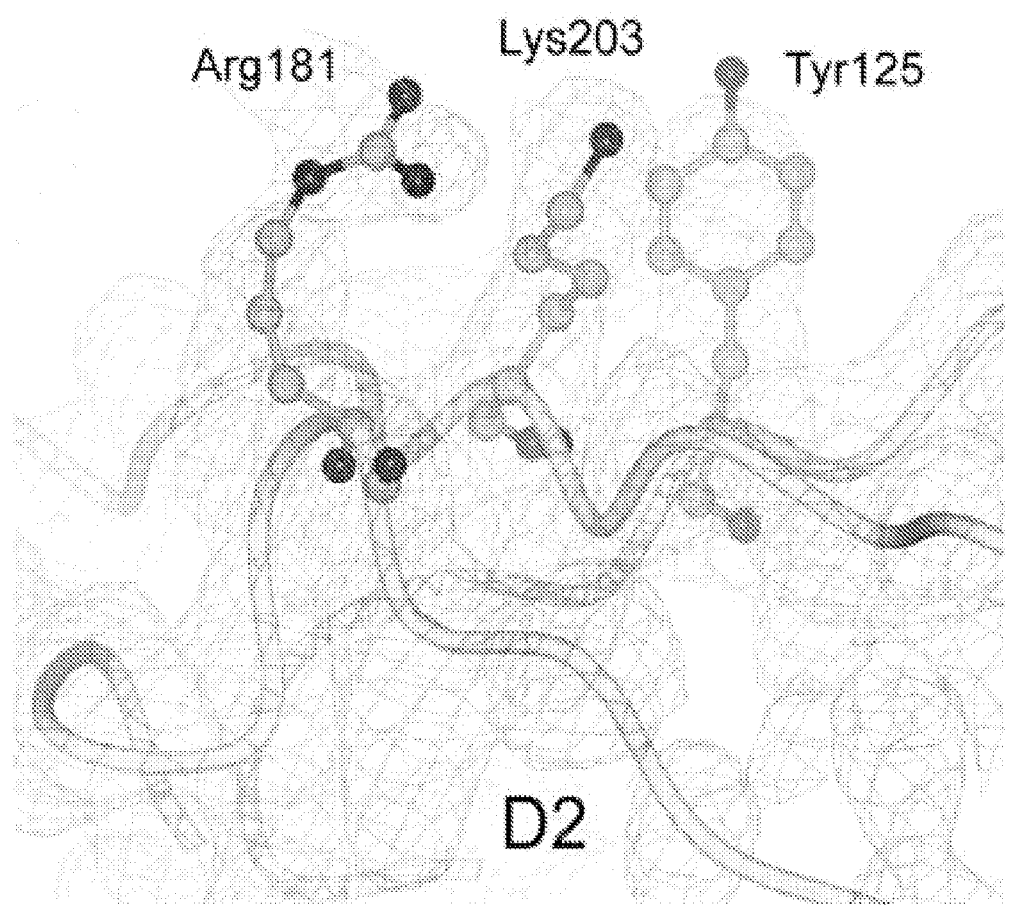
Figure 12A:
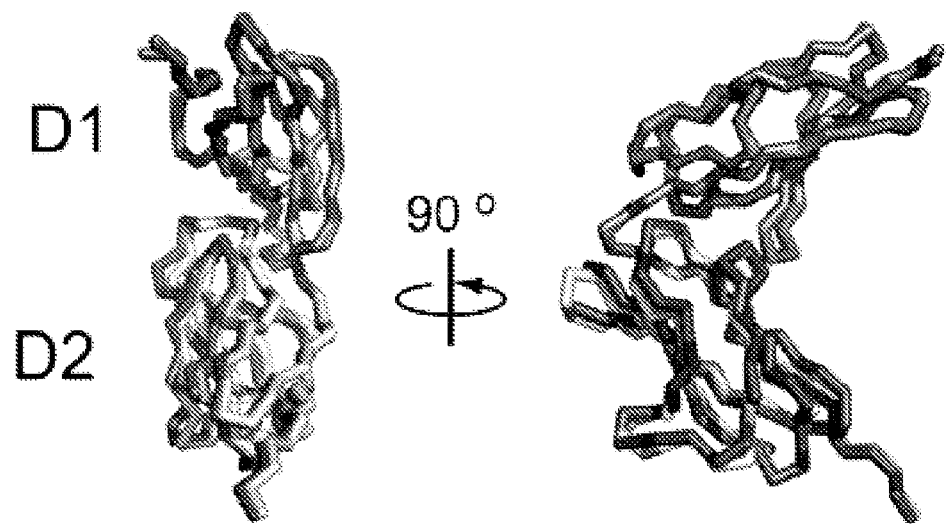
FIGS. 12A-D depict views of superimposed pairs of Ig-like domains from free and SCF bound Kit. Individual D1, D2, D3, and D4 from free and SCF bound Kit are superimposed.
Figure 12B:
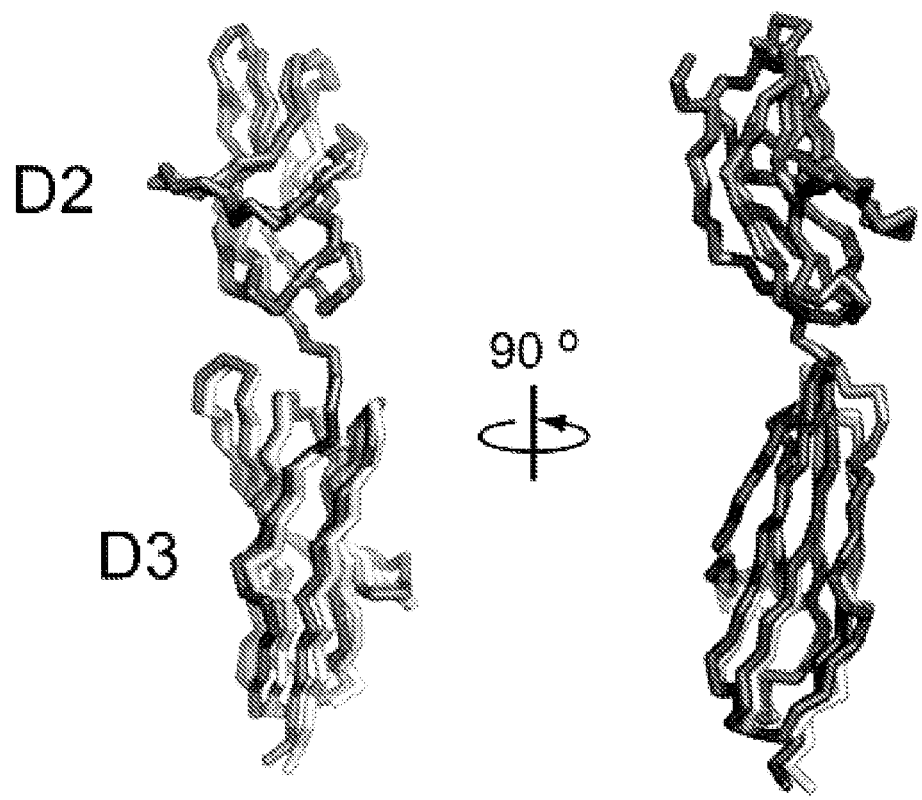
Figure 12C:
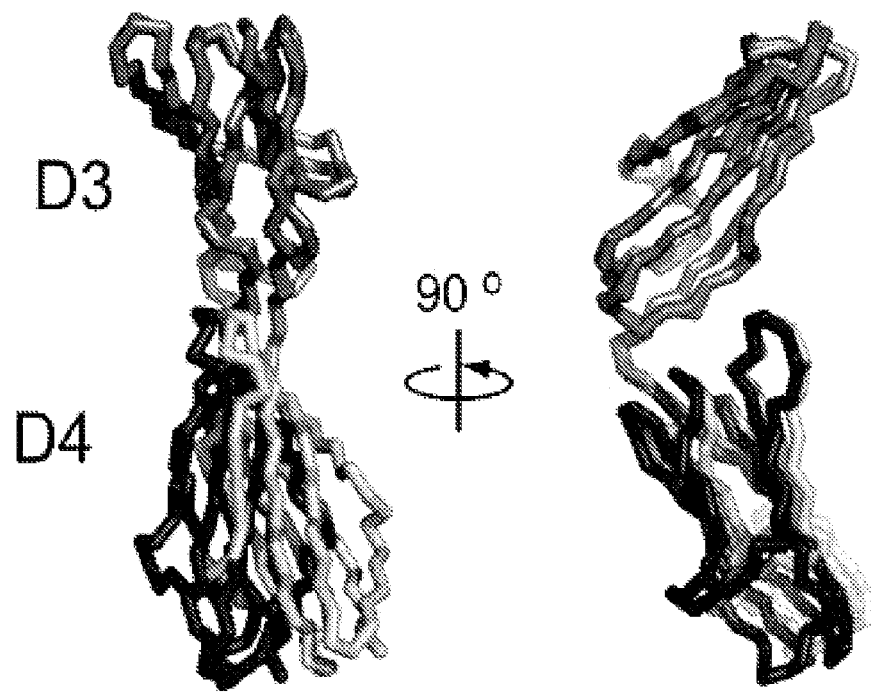
Figure 12D:
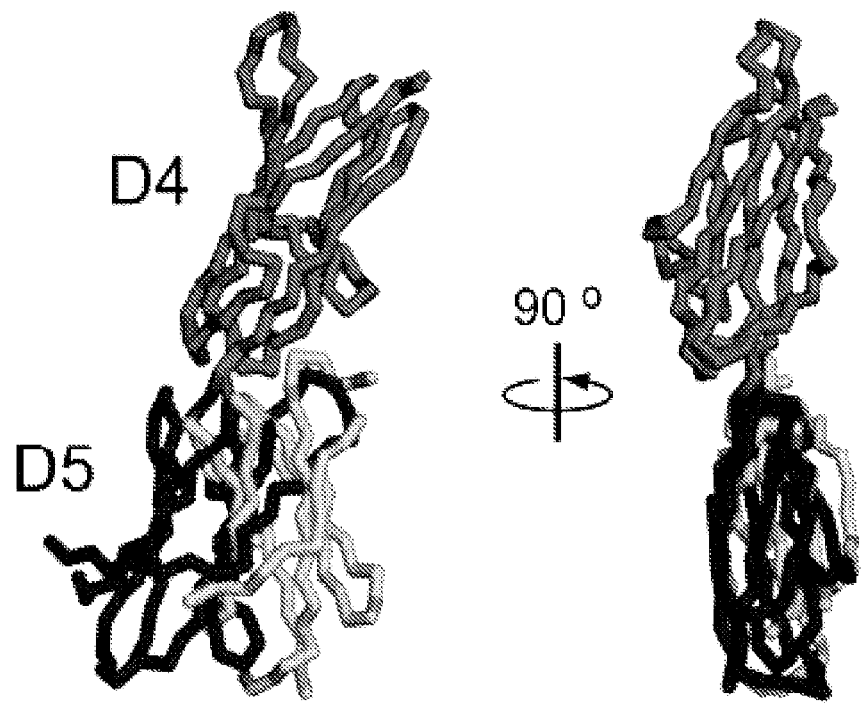

Analysis of the Kit/SCF Structure and the Conformational Changes Associated with Binding The Ligand Binding Domain of Kit is Poised for SCF Binding Superimposition of the structures of individual D1, D2, and D3 of Kit monomeric form with corresponding structures of the SCF-induced homodimeric form reveals r.m.s.d. values of 0.5, 0.8, and 1.1 Å for 82, 92, and 100 aligned Cα residues in D1, D2, and D3, respectively. Similarly, superimposition of the structure of the entire D1-D2-D3 region of Kit monomers with the corresponding structures in the SCF-Kit 2:2 complex reveals r.m.s.d. of 1.1 Å for 274 aligned Cα residues of the D1-D2-D3 region. Remarkably, there are no significant backbone changes in the structures of the SCF binding pocket of Kit (FIG. 3 and FIG. 11). However, several minor structural changes were detected in the SCF binding cleft upon SCF binding. A structural change is seen in the top half of strands G, F, and C (amino acids 167-187 and 143-166) of D2 following SCF binding (FIG. 1A, 2A). These strands are located at the side opposite to the SCF binding interface and are not involved in mediating any direct contacts with SCF. Overall, comparison of the structures of Kit monomers to those of SCF-occupied Kit dimers show that the D1-D2-D3 region of Kit may be viewed as a functional unit that is poised for SCF binding followed by subsequent Kit dimerization driven by dimeric SCF molecules.

Conformational Changes in SCF Molecules Bound to Kit

Figure 4A:
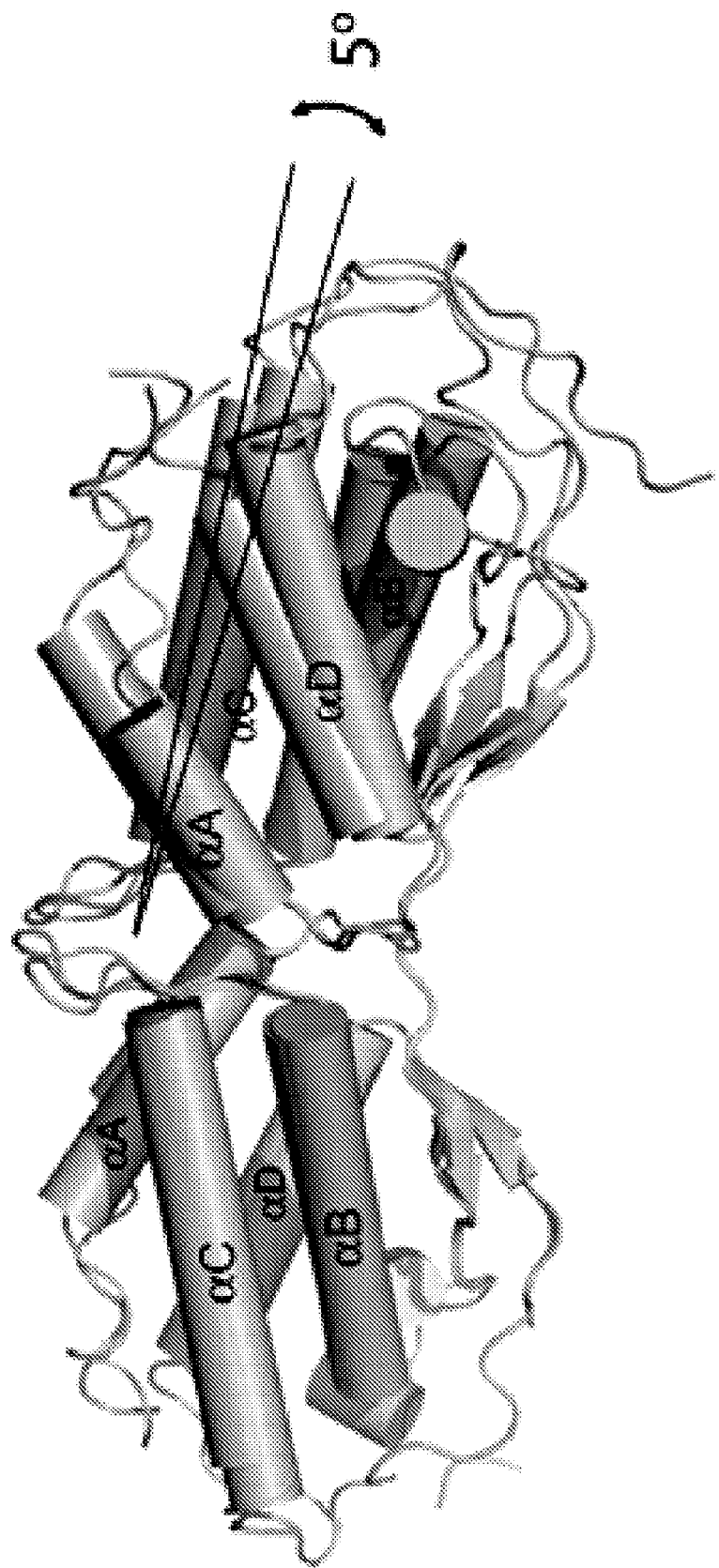
FIGS. 4A-C depict conformational changes in SCF upon binding to Kit.

While the overall structure of SCF bound to Kit is similar to the structure of free SCF, there are notable differences in the angle between the two protomers, in the conformations of the connecting loops and in the structures of the flexible N terminus of the molecule (FIG. 4). Comparison of the published structures of SCF dimers (Accession codes 1EXZ and 1 SCF in the Protein Data Bank) shows that the angle between the two protomers (the angles between αC helices) of free SCF homodimers may vary by 2° to 6° in the different structures, suggesting that a certain degree of flexibility exists in the SCF dimer. The range of differences in the angles between Kit bound SCF protomers to those of free SCF was increased by 3-9°. FIG. 4 shows a Kit bound SCF structure in which the angle between SCF protomers is increased by 5°.

Figure 4B:
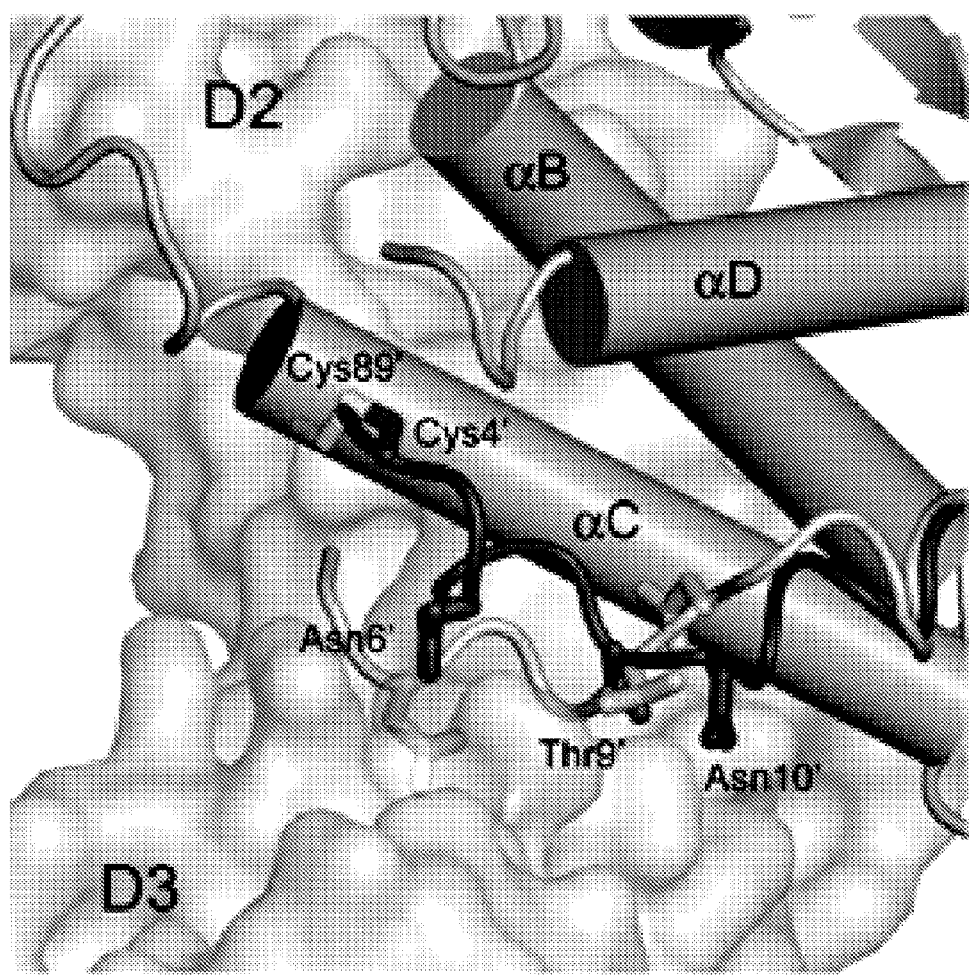
Figure 4C:
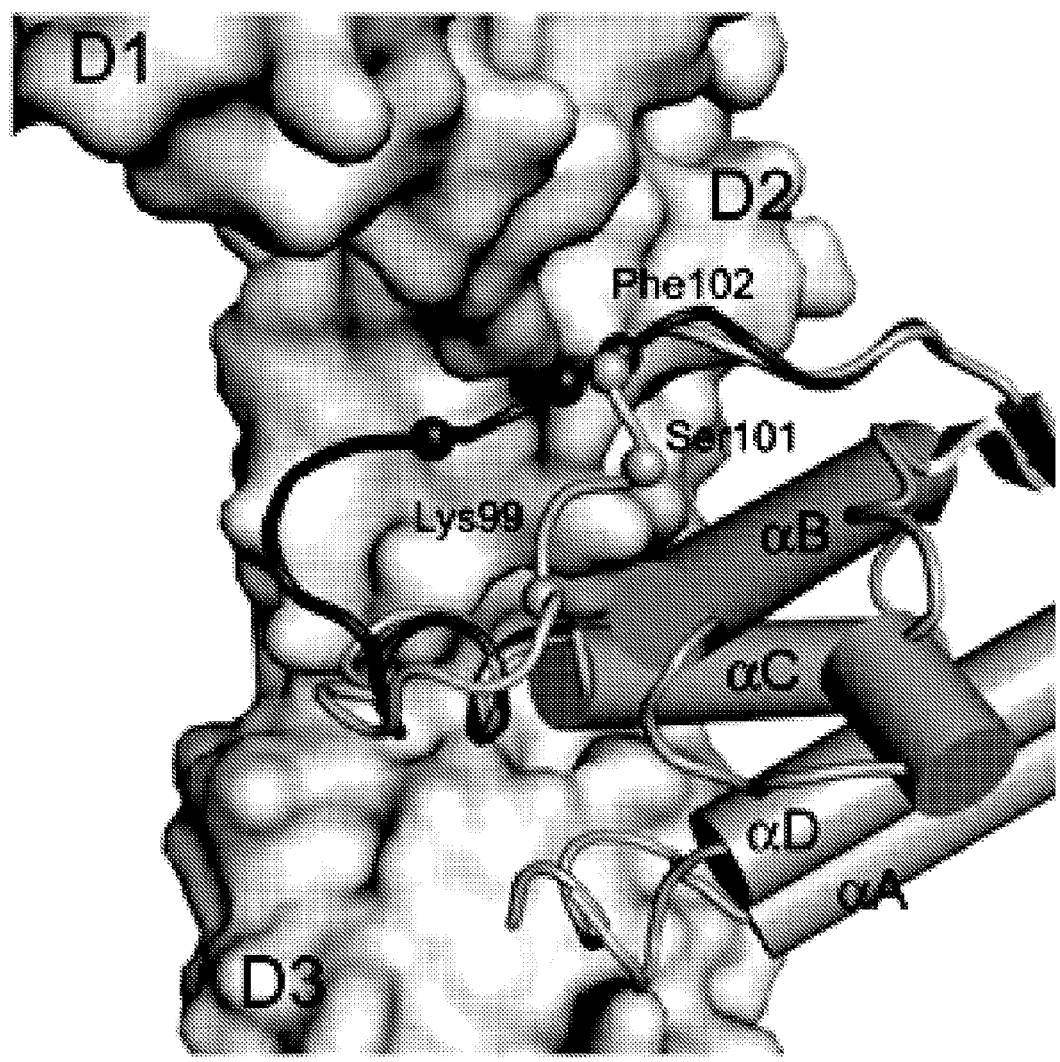

FIG. 4B shows that the N-terminus of free SCF from Cys4' to Asn11' has a random-coil configuration (Zhang et al. (2000) Proc Natl Acad Sci USA 97: 7732-7737). It was also shown that deletion of the first four amino acids leads to an approximately 25% reduction in the binding affinity of SCF to Kit, suggesting that the disulfide bridge between Cys4' and Cys89' plays a role in maintaining the functional integrity of SCF (Langley et al. (1994) Arch Biochem Biophys 311: 55-61). FIG. 4B also shows that Thr9' and Asn10' of the N-terminus region of SCF bound to Kit undergo a conformational change in which their Cα positions become displaced by 3 to 5 Å upon receptor binding (FIG. 4B). The disulfide bridge between Cys4' at the N-terminus and Cys89' at the αC helix appears to play an important role in mediating the conformational change that takes place in the N-terminus of SCF. The position of Cys24' in free SCF is not altered upon receptor occupancy as revealed by root mean square deviation (r.m.s.d.) of 1.2 Å of Cα positions. Finally, the αC-β2 of free SCF is either disordered or has a different structure from the structure of the αC-β2 loop in SCF bound to Kit. FIG. 4C shows that the αC-β2 loop of SCF undergoes a large conformational change upon receptor binding; a change critical for establishment of Site-I of the SCF-Kit interface.

A Large Rearrangement in D4 and D5 Orientations in SCF Bound Kit

Figure 5A:
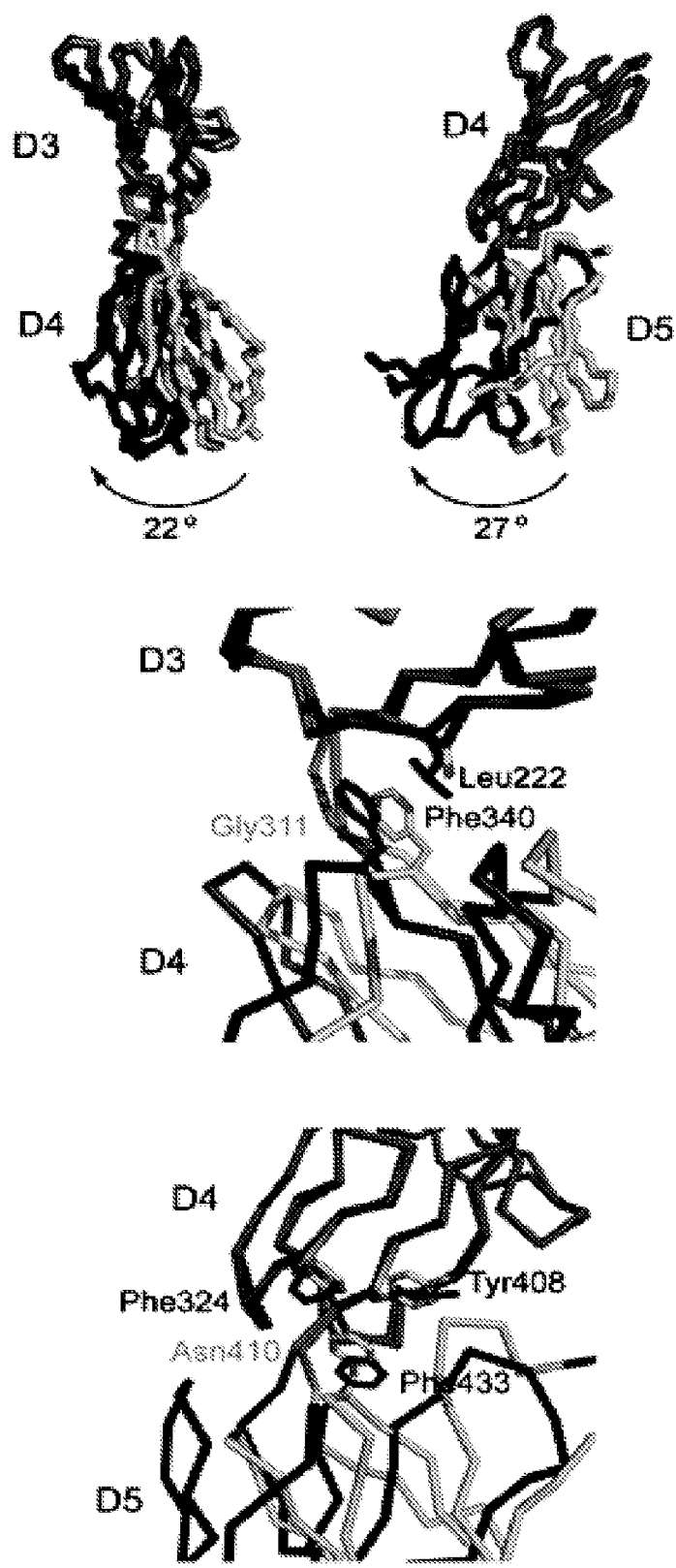
FIGS. 5A-B depict the reconfiguration of Kit D4 and D5 upon SCF binding.
Figure 5B:
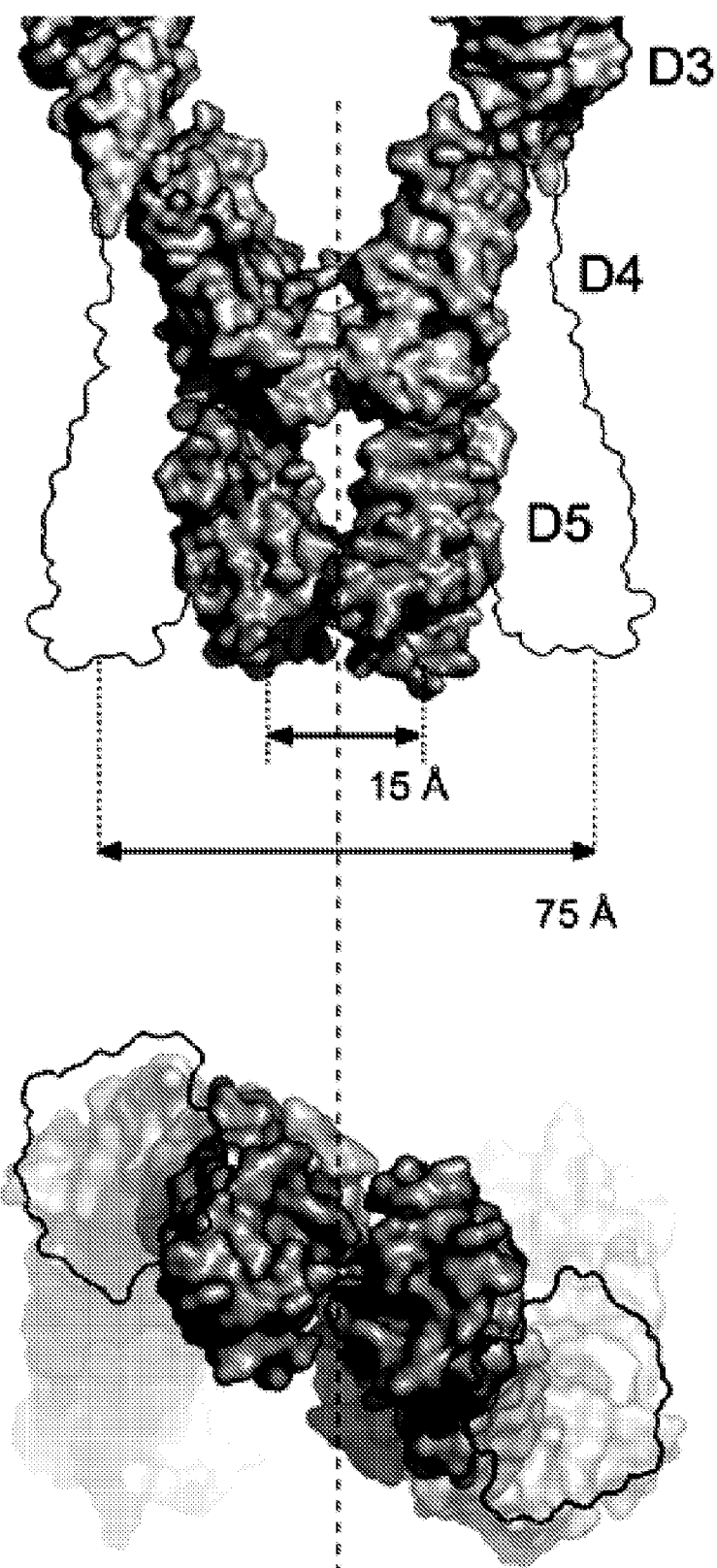

Superimposition of the structures of individual D1, D2, D3, D4, and D5 of Kit monomeric form with corresponding individual Ig-like domains in the SCF-induced homodimeric form reveals minor changes in the structure of Kit Ig-like domains following SCF binding. By contrast, superimposition of the D3-D4-D5 region of Kit monomeric form with the corresponding region in the homodimeric form reveals a large structural change in the orientation of D4 and D5 relative to each other and relative to the ligand binding region of Kit (FIG. 5A and FIG. 12). Each of the individual domains D3, D4, and D5 of monomeric Kit can be superimposed with their counterparts in the SCF-occupied Kit with r.m.s.d. values of 0.9, 0.9 and 1.9 Å for 98, 101, and 85 Cα atoms of D3, D4, and D5, respectively. However, superimposition of the D3 structure of Kit monomers with the D3 structure in ligand-occupied homodimeric form reveals a dramatic movement in the orientation of D4 and D5 in the SCF bound Kit (FIG. 5A). The re-orientations of D4 and D5 relative to the ligand binding region occurs by a rotation along an axis in the linker connecting D3 to D4, and a rotation along an axis in the linker connecting D4 to D5 running through the D3-D4 and D4-D5 interfaces (FIG. 5A), respectively. Comparison of the free and ligand-bound Kit shows that D4 of ligand occupied Kit rotates relative to D3 by 22°, and D5 of ligand occupied Kit rotates relative to D4 by 27° (FIG. 5A). The rearrangements of D4 and D5 in SCF occupied Kit result in receptor-receptor interactions that are mediated by D4-D4 and D5-D5 interactions of two neighboring Kit molecules (FIG. 5B). The conformation of the DE loop of D5 is altered in the SCF occupied ectodomain. Reorientation of D4 and D5 driven by receptor dimerization imposes upon the DE loop of D5 a new configuration (FIG. 5A).

D4:D4 Interactions in Kit Homodimers

Figure 6A:
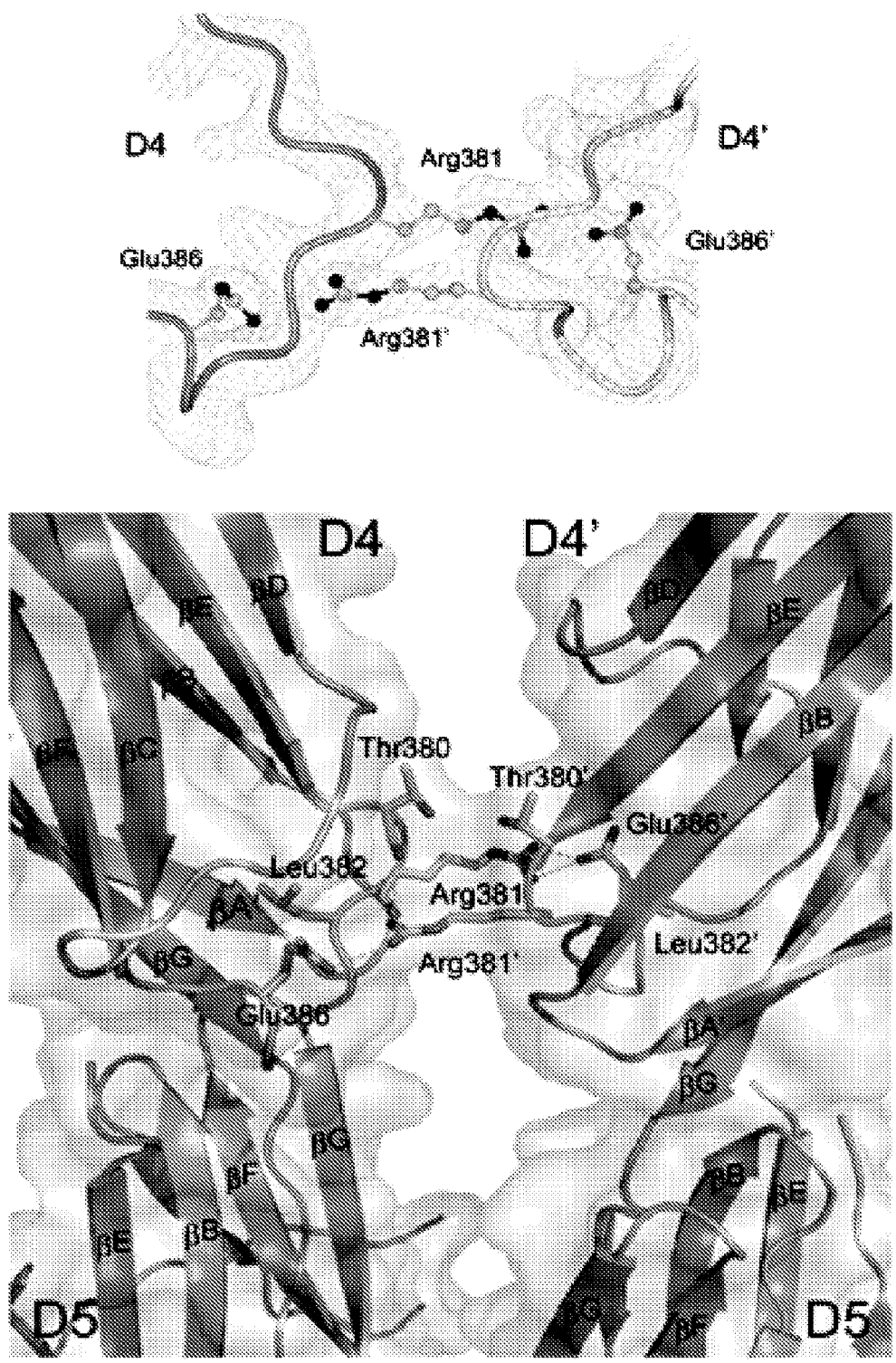

Homotypic interactions between D4 of two neighboring Kit molecules are mediated by the D4-D4 interface in the SCF-Kit 2:2 complex. The D4-D4 interface is mediated by two β sheets formed by the ABED strands of D4 of each Kit protomer to form a nearly planar arrangement in which Arg381 of each protomer points toward each other resulting in a buried surface area of 360 Å$^2$. FIG. 6A shows that Arg381 and Glu386 form salt bridges and van-der-Waals contacts across the two-fold axis of the Kit dimer. In addition, the side chains of Arg381 of each protomer form hydrogen bonds with the main chain carbonyl of the corresponding residue of the neighboring Kit molecules.

Structure based sequence analysis has shown that the D4-D4 interface is conserved in most type-III RTKs including CSF1R, PDGFRα and PDGFRβ (FIG. 6B and FIG. 8). In PDGFRα Glu386 is replaced by an aspartic acid; a residue that could also function as a salt bridge partner. A pair of basic (Arg381) and acidic (Glu386) residues are strictly conserved in type-III RTKs of different species. The sequence motif found in the D4-D4 interface is also conserved in the membrane proximal 7$^{th}$ Ig-like domain (D7) of all members of type-V RTK (VEGFR family) including VEGFR-1 (Flt1), VEGFR-2(Flk1) and VEGFR-3(Flt4). In VEGFR, the basic (Arg) and acidic (Asp) residues are located in the EF loop. Although the core sequence motif that is responsible for the type-III RTK D4-D4 interface is located in a different Ig-like domain of VEGFR (i.e., D7 versus D4 of type III) it is possible that receptor-receptor interactions similar to those seen in the D4-D4 interface of Kit will also take place through a similar D7-D7 interface (FIG. 6A) in all members of the VEGFR family of RTKs (Ruch et al. (2007) Nature. Struct. Mol. Biol. 14: 249-250).

D5-D5 Interactions in Kit Homodimers

Figure 6C:
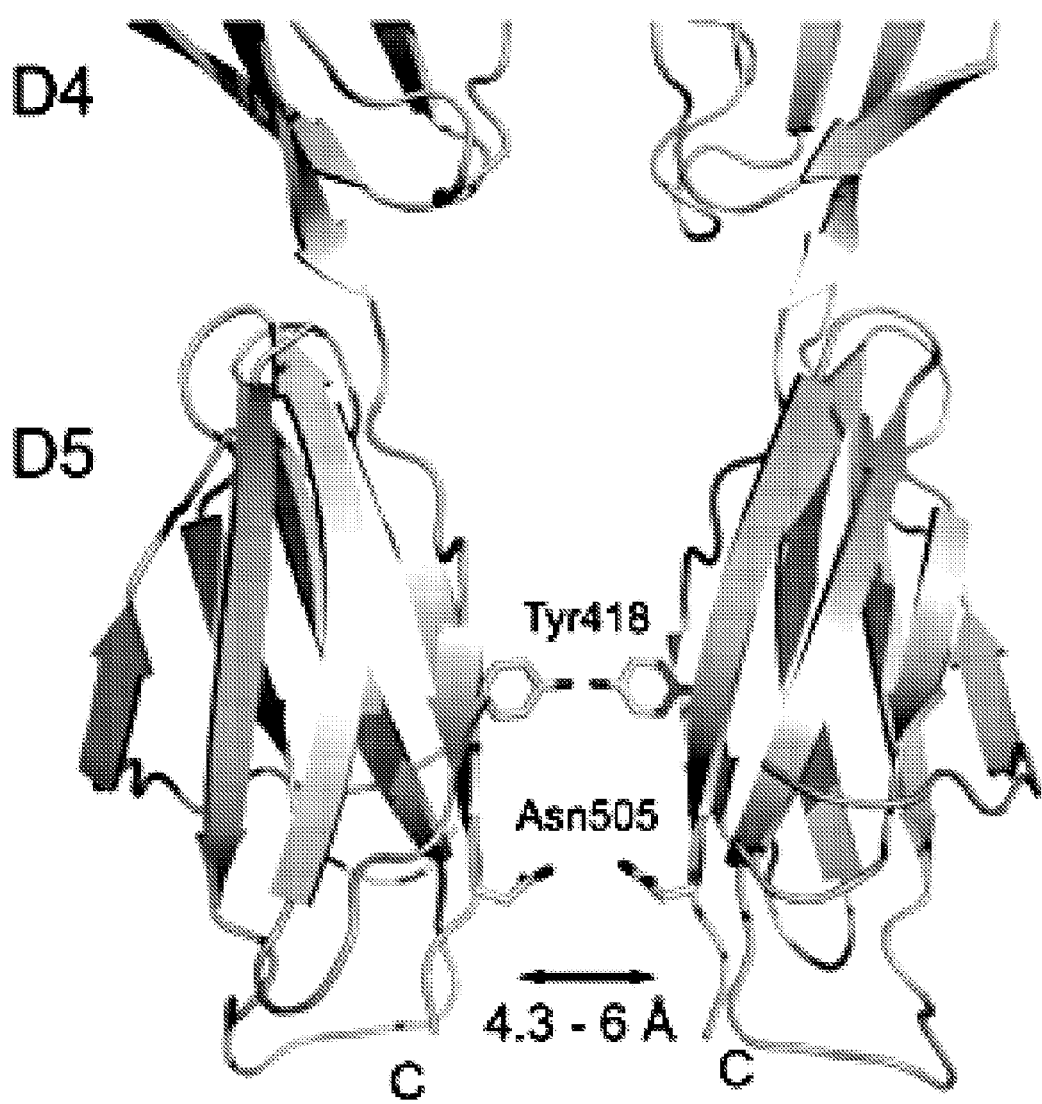

FIG. 2B and FIG. 5B, 6C show that in the SCF-Kit 2:2 complex neighboring D5 protomers are parallel and in a close proximity to each other as well as in an orientation likely to be perpendicular to the cell membrane. The β-sheet topology of D5 follows an atypical arrangement that is different from most I-set IgSF in which strand A is split into strand A and A'. Strand-A of D5 is paired with strand B resulting in the βsheet topology of ABED/CFG. Consequently, strands A and G that are located at the edge of two β sheets (ABED/CFG) are nearly parallel at a distance of 6.5-11.5 Å in the Cα from each other. Moreover, strands A and G of one protomer face strands A and G of neighboring D5 in a two-fold symmetry. The side chains of Asn505 of two neighboring Kit protomers are approximately 4.2 Å from each other but water or metal ions that may mediate indirect interactions between the two asparagines could not be detected in this area of weak electron density. Additional D5-D5 interactions are mediated by Tyr418 of two neighboring Kit molecules (FIG. 6C). The interaction between hydroxyl groups of neighboring Tyr418 side chains could be mediated by water molecules. It also suggests that the relative positions of neighboring D5 domains are mediated by indirect interactions formed by Tyr418 and Asn505 of the neighboring protomers. The G-strand of D5 is connected via a short linker to the transmembrane domain of Kit.

Example 8

Mechanism of Receptor Activation

The structures of Kit ectodomain monomers and SCF induced dimers provide novel insights concerning the mechanism of ligand-induced activation of Kit and other RTKs containing five or seven Ig-like domains in their extracellular domains. Comparison of the structures of D1, D2 and D3 of Kit ectodomain monomers to the corresponding region in the SCF-induced ectodomain dimers shows very few structural alterations in the SCF-binding pocket and in other parts of D1, D2 and D3 following SCF binding. On the basis of their distinct biochemical functions, we have divided the ectodomain of Kit into three independent functional units. The first unit is composed of the three membrane distal Ig-like domains D1, D2, and D3. The D1-D2-D3 region acts as a separate module that functions as a specific SCF binding unit. The SCF-binding unit is connected by a flexible joint (D3-D4 interface) to D4; a second independent unit that is connected by an additional flexible joint (D4-D5 interface) to D5, defined as a third independent unit. The function of D4 and D5 is to mediate, respectively, lateral D4-D4 and D5-D5 interactions that bring together and stabilize interactions between membrane proximal region of two neighboring Kit ectodomains.

According to this view, dimerization of Kit is driven by bivalent SCF binding whose sole function is to bind SCF and to bring together two Kit molecules. SCF-induced Kit dimerization is followed by a large change in D4 and D5 orientations relative to the position of the D1-D2-D3 SCF-binding unit. The data presented herein demonstrates that the flexible joints at the D3-D4 and D4-D5 interfaces enable lateral interactions that result in a large conformational change upon receptor dimerization. Rather than inducing a conformational change in Kit, dimerization may select particular conformations in a transition from a flexibly jointed monomer to a rigid dimer. This culminates in complex formations between two neighboring D4 and two neighboring D5 of Kit, bringing the C-termini of D5 to a point at the cell membrane in which the transmembrane domains of two neighboring Kit molecules are within 15 Å of each other. Indeed, SCF-induced tyrosine autophosphorylation of Kit (FIG. 7B) and stimulation of a downstream signaling pathways are strongly compromised by a point mutation in either Arg381 or Glu386 within D4 of Kit. PDGF-receptor activation and stimulation of downstream signaling pathways are also compromised by similar point mutations in D4 of PDGFR. The data presented herein demonstrates that the homotypic interactions between membrane proximal regions of Kit are mediated primarily by the D4-D4 interface and that the D5-D5 interface plays a cooperative secondary role by facilitating exact positioning of two Kit ectodomains at the cell surface interface.

Figure 6D:
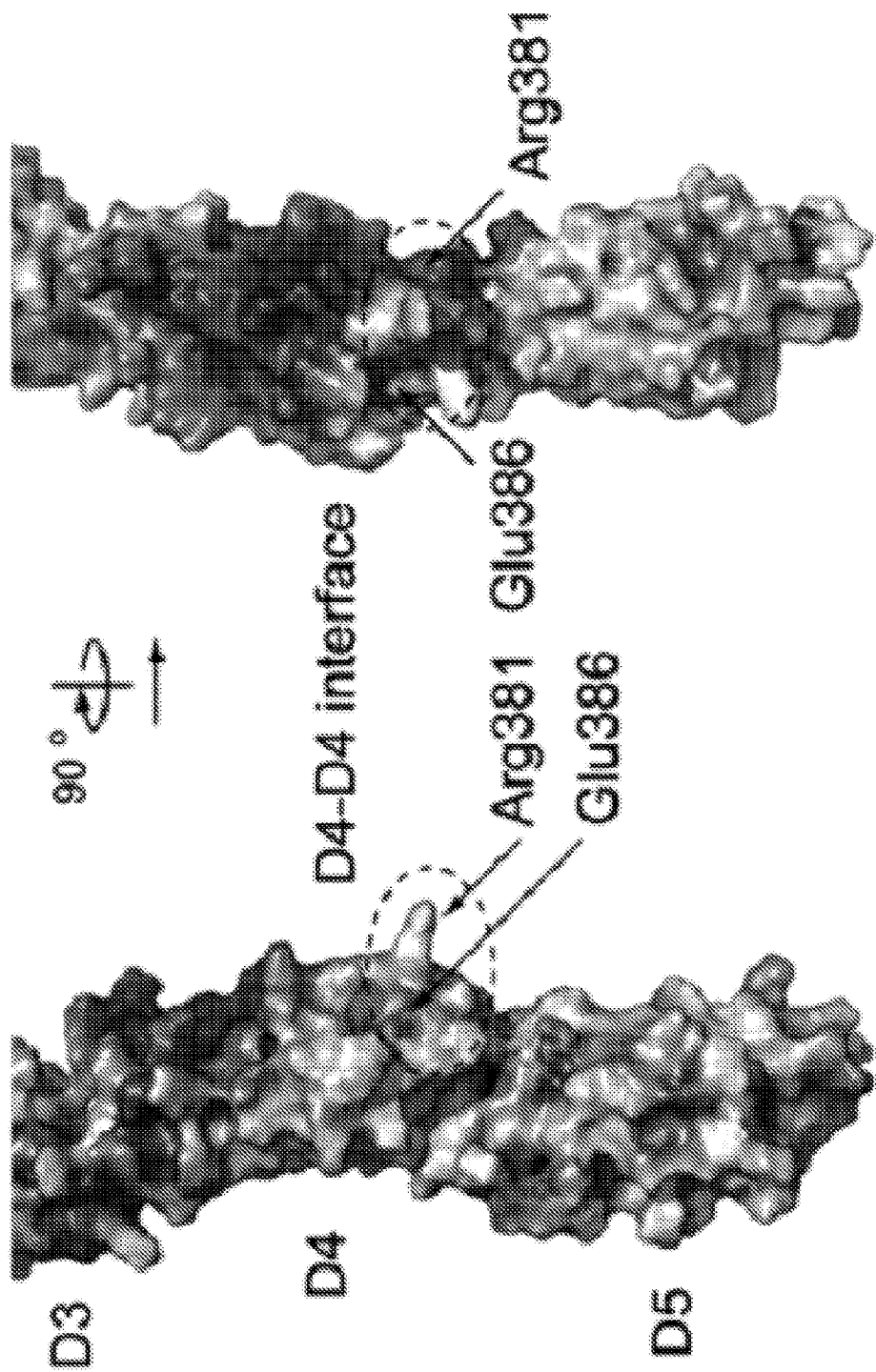
Figure 13:
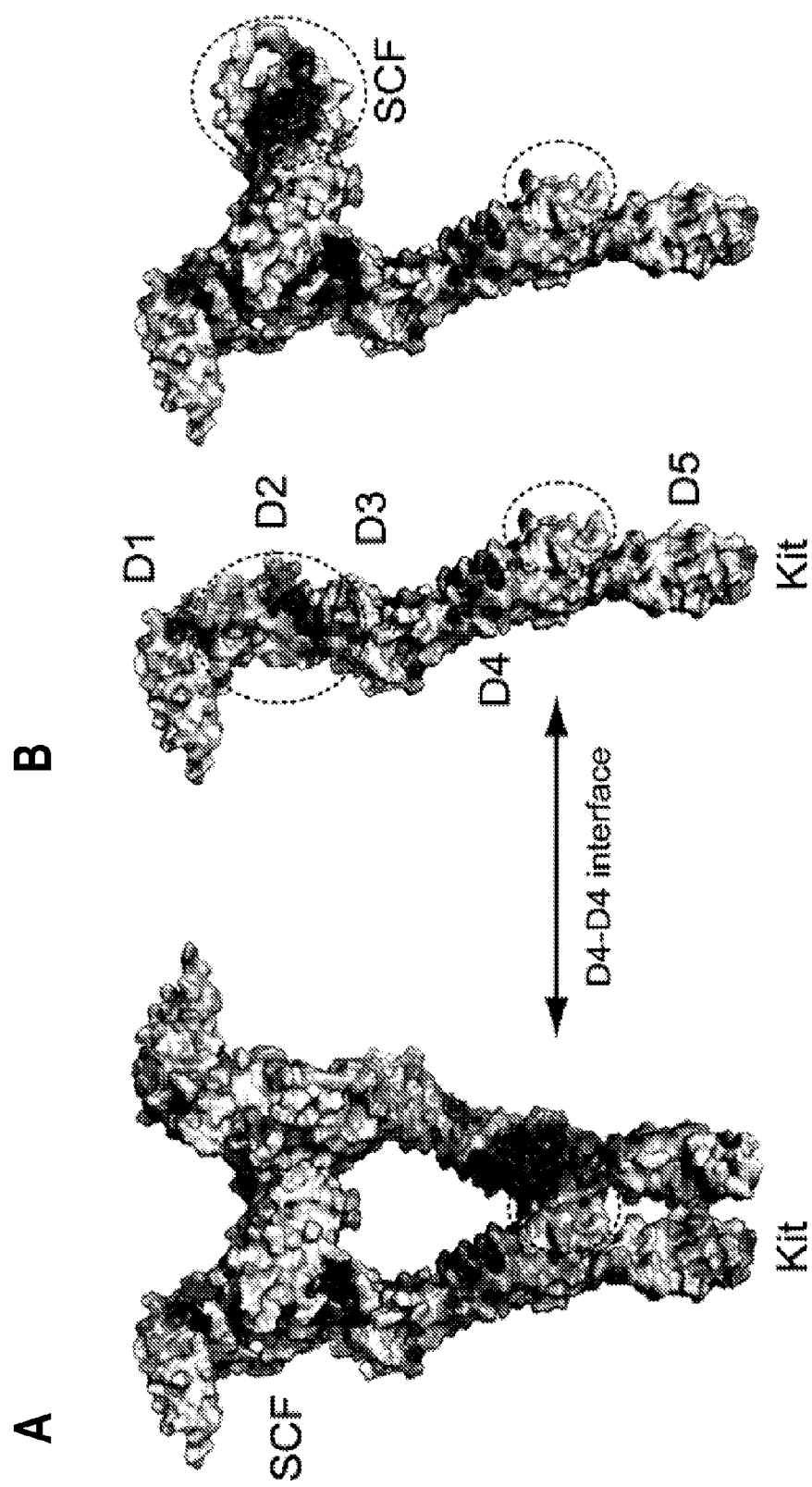

The SCF-Kit complex exhibits a strong polarization of the electrostatic field with the following characteristic: (i) an overall negatively charged surface; (ii) complementarity between SCF (negative), and the ligand binding D1-D2-D3 unit (positive); and (iii) a strongly negatively polarized surface right above and around the D4-D4 interface (FIG. 6D, 3B and FIG. 13). This data demonstrates that the binding of SCF to Kit occurs in at least two steps: First, the electrostatic attraction between SCF and D1-D2-D3 will align SCF along the opposing ligand binding region on Kit. The electrostatic attraction may also lead to a faster association rate of SCF due to a Steering effect (Muellera et al. (2002) Biochina and Biophysica Acta. 1592: 237-250). Subsequently, SCF-Kit complex formation will be stabilized by additional interactions including those mediated by a conformational change in bound SCF molecules. The strongly polarized electrostatic surface on D4 may also play a role in maintaining Kit in a monomeric inactive configuration by inducing repulsion between D4 domains of neighboring Kit receptors (FIG. 6D). The binding affinities of D4 towards D4 and D5 towards D5 of neighboring receptors are probably too low to facilitate Kit ectodomain dimerization before the local receptor concentration on the cell surface is increased by SCF-driven receptor dimerization and by the effect of dimensionality. Once such a threshold of local concentration is reached, the attraction between neighboring D4 will overcome the electrostatic repulsion to the extent that two neighboring D4 units will be able to bind to each other. Interestingly, the main interactions that maintain the D4-D4 interface, i.e. double salt bridges between Arg381 and Glu386 in neighboring Kit molecule are also mediated by electrostatic interactions.

The ectodomains of Kit and C-cadherin (Boggon et al. (2002) Science 296: 1308-1313), are each composed of five tandem Ig-like domains and both exhibit a similar elongated topology; 170 Å for Kit and 185 Å for C-cadherin. Moreover, the bacterial adhesion molecule invasin exhibits a remarkably similar elongated architecture and inter-Ig-like domain topologies (Hamburger et al. (1999) Science 286: 291-295). Kit ectodomains may have evolved from a common ancestral gene that coded for a protein that mediates cell-cell interactions. While classical-cadherins utilize their most membrane distal Ig-like domain for homotypic binding that mediate cell-cell interactions, the ectodomain of Kit has evolved to function as a cell signaling receptor that binds membrane anchored or soluble SCF isoforms to induce receptor dimerization and activation (FIG. 7C).

Figure 7A:
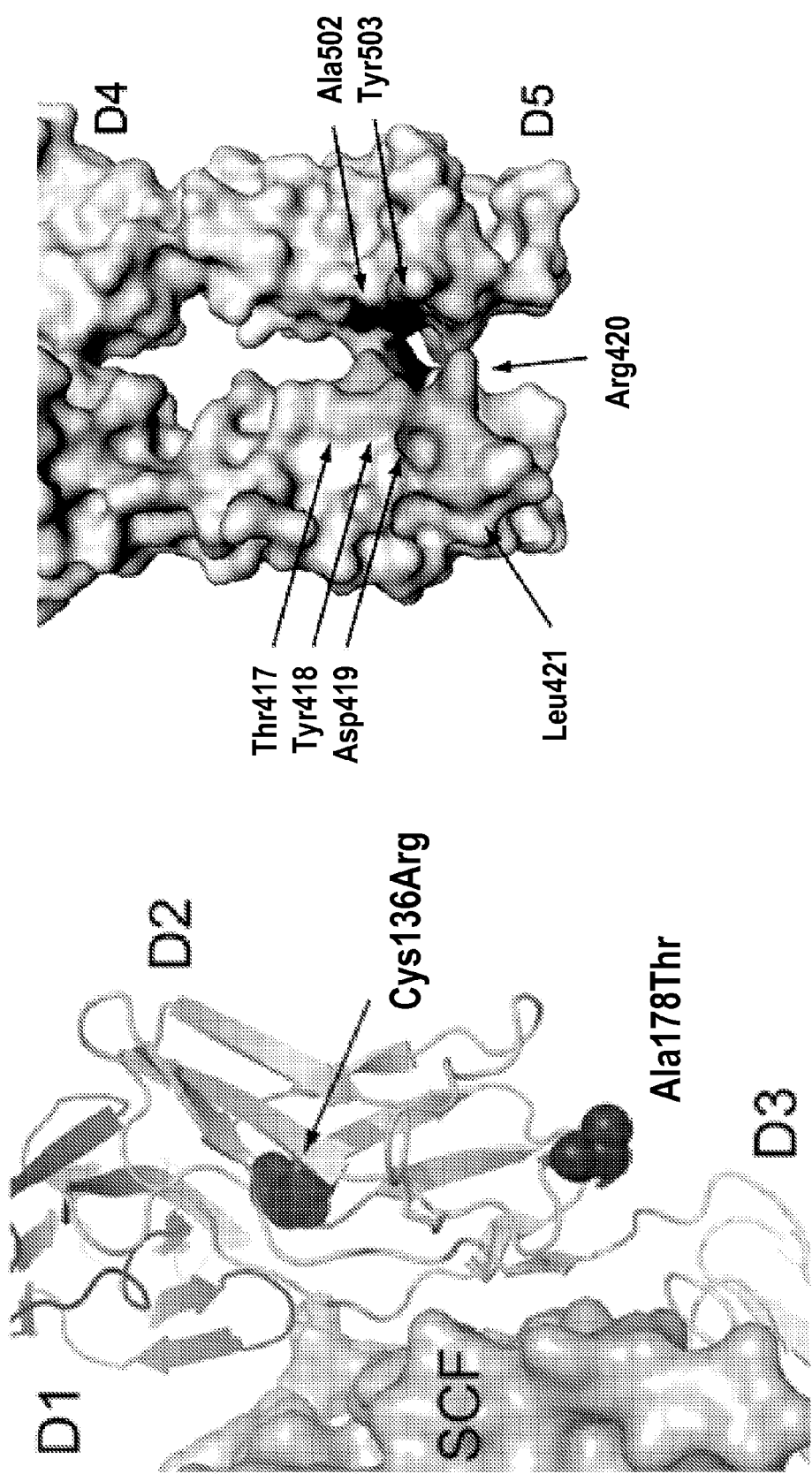
FIGS. 7A-C depict Kit ectodomain mutations implicated in cancer and other diseases and mechanism of Kit and other RTK activation.
Figure 7B:
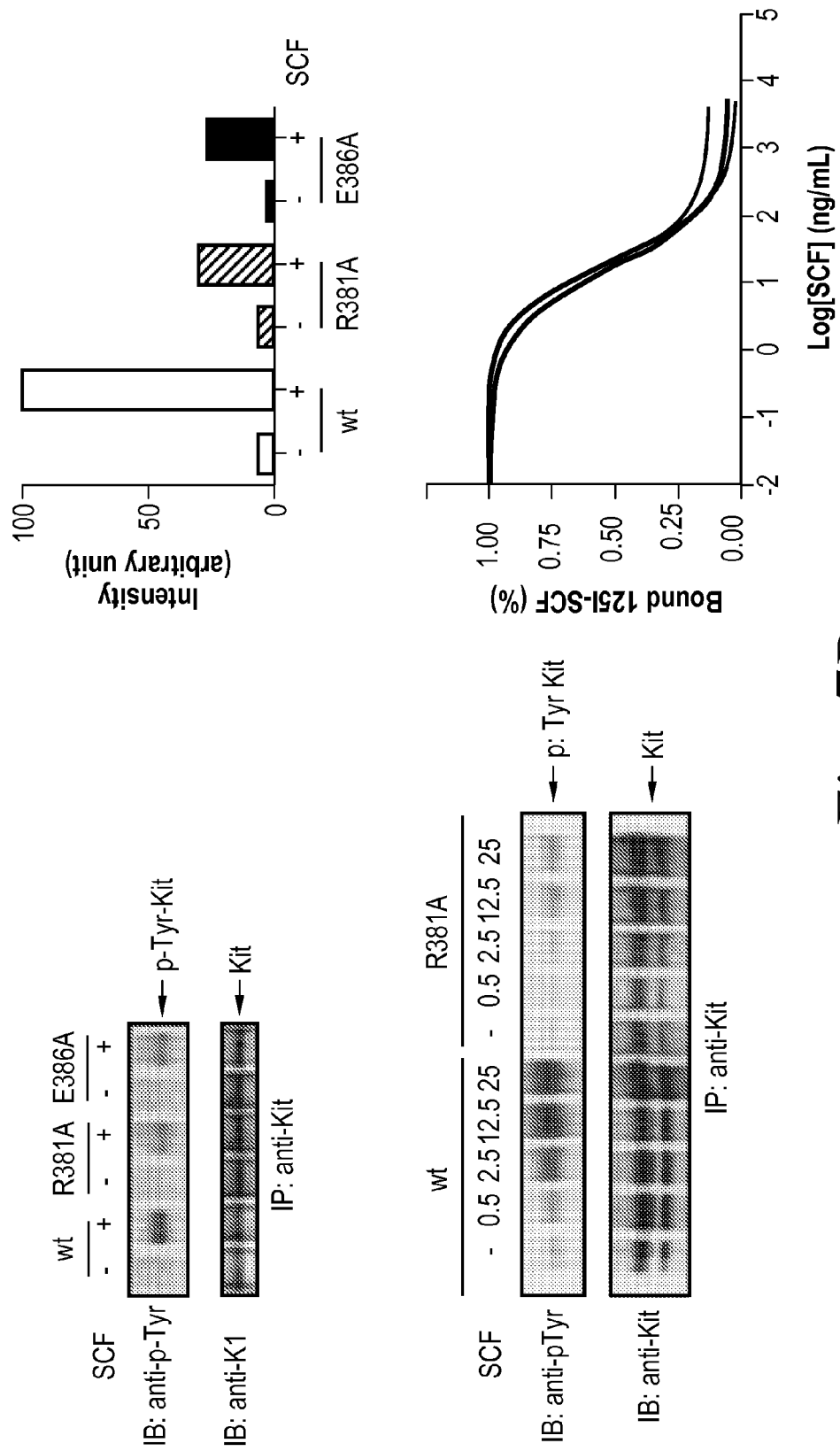
Figure 7C:
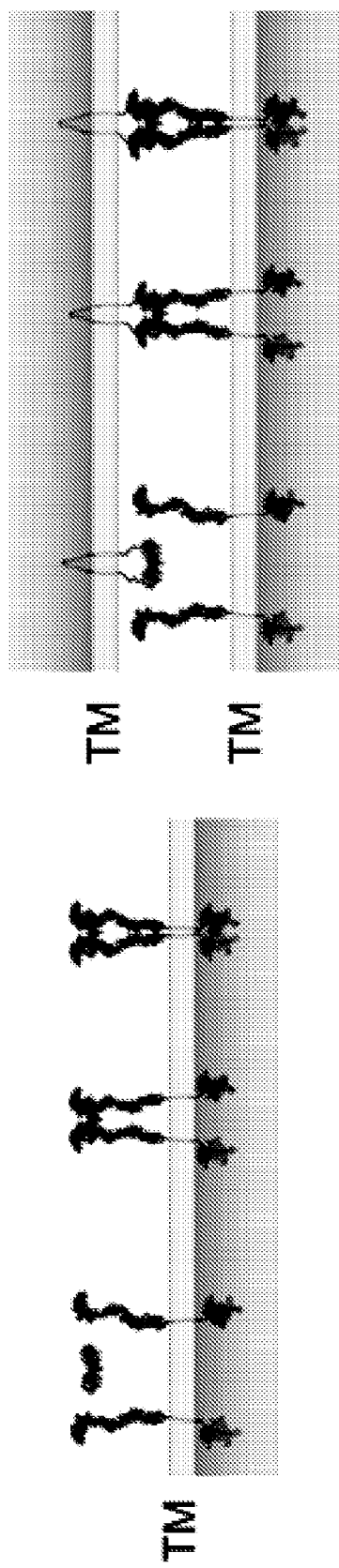

Since the hallmarks of Kit structure, ligand binding and receptor dimerization are conserved in other receptors, the mechanism described here for Kit activation may be a general mechanism for activation of many receptors (FIG. 7C). Moreover, the structural information described here could be applied to design novel therapeutic interventions for treatment of cancers and other diseases driven by activated receptors.

Example 9

Analysis of Kit Mutations in Human Diseases

A variety of human diseases are caused by mutations in the Kit gene. In humans, loss of function mutations in the ectodomain of Kit cause the piebald trait (Fleischman et al. (1996) J Invest Dermatol 107: 703-706; Murakami et al. (2005) J Invest Dermatol. 124: 670-672). These exon-2 and exon-3 point mutations in the Kit locus result in Cys136 being replaced by an arginine residue and Ala178 being substituted by a threonine residue. Both mutations take place in D2, a critical component of the SCF binding site on Kit (FIG. 7A). The piebald Cys136Arg mutation will cause the loss of an important disulfide bond that plays a critical role in maintaining the structural and functional integrity of D2 and hence its capacity to recognize SCF. Ala178 is located in the EF loop of D2 in close proximity to the D2-D3 interface (FIG. 7A). The piebald Ala178Thr mutation may disrupt interactions that are essential for maintaining the integrity of the D2-D3 interface and interactions that are required for D2 and/or D3 binding to SCF (FIG. 7A).

A variety of gain of function mutations in the Kit locus were found in different cancers including GIST, AML and SCLC (see Forbes et al. (2006) COSMIC 2005. BR J. CANCER, 94: 318-22. Somatic mutation database: Catalogue of Somatic Mutations in Cancer http://www.sanger.ac.uk/genetics/CGP/cosmic/). Many oncogenic mutations were identified in the JM and in the PTK domains of Kit. A variety of oncogenic mutations were also found in Kit ectodomain (FIG. 7A) including in-frame deletions, point mutations, in-frame duplications and insertions that collectively lead to formation of activated forms of Kit. In frame deletion and insertional mutations at exon-8 involving either a loss or substitution of Asp419 were described in patients with AML, while duplications of Ala502-Tyr503 and Ala502-Phe506 sequences were identified in GIST (FIG. 7A). Asp419 is located in a region connecting strand A and AB loop of D5 and Ala502-Tyr503 are located on strand G of D5 of Kit. Interestingly, virtually all the activating oncogenic mutations that were found in Kit ectodomain were mapped to the D5-D5 interface (FIG. 7A). The most plausible interpretation of the mode of action of the oncogenic D5 mutations is that these mutations enhance the binding affinity and homotypic interactions between neighboring D5 domains by increasing the on-rate or decreasing the off-rate or altering the rates of both processes in a fashion that facilitates enhanced D5-D5 interactions.

The analyses above demonstrate that the D4 and D5 regions are good candidates against which to target therapeutics. Drugs, pharmaceuticals, or biologics may be used to bind Kit in order to encourage Kit dimerization/activation or, more preferably, to prevent dimerization/activation.

Example 10

Expression, Purification and Partial Deglycosylation of Kit Ectodomain

A DNA construct coding for amino acids 1-519, of human Kit (Lemmon et al. (1997) J Biol Chem 272: 6311-6317) containing additional five histidine residues at the C terminus was ligated into pFastBacl (Invitrogen, Inc.). Baculoviruses expressing the ectodomain Kit proteins were prepared according to procedures described in the Bac-to-Bac instruction manual (Invitrogen). Insect Sf9 cells were grown in 15 L culture of Grace's insect medium supplemented with 10% heat inactivated fetal bovine serum with a Wave Bioreactor (Wave Biotech, LLC, System 20/50) to $2\sim3\times10^6$ cells/ml and were then infected with recombinant baculovirus carrying the Kit ectodomain genes. Although the ectodomain Kit contained the signal sequence from human Kit, the protein was accumulated in the insect cells rather than being secreted out. After 72 hours the cells were harvested and lysed in 1.4 liter of 50 mM of potassium phosphate buffer pH 8 containing 200 mM NaCl, 10% glycerol 1% NDP-40 and 2 mM PMSF for 20 minutes on ice. After centrifugation and filtration, the ectodomain of Kit was purified using affinity chromatography with Ni-NTA beads, followed by gel filtration using Superdex 200. The purified Kit ectodomain in 25 mM Tris buffer pH8.5 containing 25 mM NaCl and 1% glycerol was treated for 12 hours at 4° C. with recombinant endoglycosylase F1 that was added to the Kit solution at a final ratio of 10:1 w/w. The endonuclease F1 treated ectodomain of Kit was then loaded onto a pre-equilibrated 16/10 Mono Q column and eluted with a shallow gradient of Tris buffer pH 8.5 containing 400 mM NaCl and 1% glycerol. Fractions of deglycosylated Kit ectodomain were pooled and concentrated to 35 mg/ml using a spin concentrator. The purified, partially deglycoslyated Kit ectodomain preparation was split into aliquots and flash-frozen in liquid N2. Using this approach, ~10 mg of partially deglycosylated Kit ectodomain was purified from 15 liters of cultured cells. SCF (1-141) was expressed, refolded and purified as previously described (Zhang et al. (2000) Proc Natl Acad Sci USA 97: 7732-7737). The ectodomain of Kit (amino acids 1-514) was also expressed as a secreted form in Sf9 insect cell using the baculovirus system and purified as previously described (Lemmon et al. (1997) J Biol Chem 272: 6311-6317).

Example 11

Structure Determinations and Refinements

Experimental phases were determined using a combination of multi-wavelength anomalous diffraction (MAD) and multiple isomorphous replacement with anomalous scattering (MIRAS) of crystals of Kit ectodomain monomers. Heavy atom search and phasing were carried out using the CNS (Brunger et al. (1998) Acta Crystallogr D Biol Crystallogr 54: 905-921) and SHARP (Bricogne et al. (2003) Acta Crystallogr D Biol Crystallogr 59: 2023-2030) program suites. One major and two minor sites were detected for platinum derivative (K2Pt(NO2)4) and one major and five minor sites were detected for iodine soaked crystals. MAD phases were calculated up to 3.3 Å resolution for platinum derivatives at three wavelengths using CNS. MIRAS phases were calculated up to 3.0 Å resolution for platinum and iodine derivatives using CNS and SHARP. Solvent flipping density modification resulted in electron density maps of interpretable quality with continuous electron density and very clear solvent-protein boundaries. Regions of poor electron density quality, including the top half of stands F, G and C as well as CD loop in D2 and CD loop, strand D, DE loop and EF loop and bottom half of stand F in D5, were confirmed by comparing electron density maps calculated by MIRAS, and MAD phasing. The data collection and phasing statistics are summarized in Tables 1A and 1B. The molecular model of Kit was built manually into the experimental electron density maps using COOT (Emsley, and Cowtan (2004) Acta Crystallogr D Biol Crystallogr 60: 2126-2132). For the calculation of the free R-factor, 5% of the data were omitted during refinement. Refinements were carried out using CNS to 3.0 Å resolution against native data. At the final stage of the refinements, translation/liberation/screw (TLS) refinements were carried out by Refmac5 (Murshudov et al. (1997) Acta Crystallogr D Biol Crystallogr 53: 240-255) in the CCP4 program suite with three TLS group generated using the TLSMD web server (Painter et al. (2006) J Appl Cryst 39: 109-111).

The structure of SCF-Kit complex was solved by molecular replacement using PHASER (McCoy et al., (2005) Acta Crystallogr D Biol Crystallogr 61: 458-464). A clear molecular replacement solution for D1D2D3D4 of the Kit ectodomain and SCF was found using D1D2D3 and D4 of Kit and SCF as search models against native data set, respectively, using PHASER. The Kit (D1D2D3D4)-SCF complex structures were subjected to rigid body refinement from 20 to 4 Å, resulting in an Rcryst of 43.8%. Model rebuilding and refinement was performed using CNS to an Rcryst and Rfree values of 31.6% and 34.0%, respectively. Continuous electron density in the region of D5 was found in the 2σ 2Fo-Fc and 3σ Fo-Fc map. The strands for D5 were traced manually into the map using COOT, followed by application of refinements after each step. Throughout the initial refinement, non-crystallographic symmetry (NCS) constraints were imposed on the residues. Further refinements were performed to 3.5 Å resolution against native X-ray diffraction data. After building almost the entire SCF-Kit complex molecule, NCS constraints were released resulting in reduced values of R and Rfree and improved electron density. At the final stage of refinements, the NCS constraints were completely released. The stereochemistry of the models was analyzed with PROCHECK (Laskowski et al. (1993) J Appl Cryst 26: 283-291). A summary of the refinement statistics is shown in Table 1B.

Example 12

Radiolabeling of SCF and Ligand Displacement Assay

Human SCF (10 µg) was labeled with 1 mCi of $^{125}$I (PerkinElmer) using Iodo-Gen Iodination Tubes (Pierce) following the manufacturer's instructions. For the displacement binding assay, 3T3 cells expressing WT Kit or Kit mutants were grown in DMEM containing 10% FCS. Cells were washed three times with DMEM containing 10 mM HEPES PH7.4 and 0.1% BSA (DMEM-BSA), and then incubated for 1 hour at room temperature with 2 ng of $^{125}$I-labeled-SCF in the presence of increasing concentrations of native SCF. Cells were then washed three times with cold DMEM-BSA, lysed in 0.5 ml of 0.5M NaOH for 1 hour at room temperature, and 100 µl of the cell lysate were applied to 10 ml of Opti-Fluor scintillation solution (Perkin Elmer) to measure cell associated radioactivity using a LS6500 Scintillation Counter (Beckman Coulter).

Example 13

Conservation Analysis

Amino acid sequences of human SCF and Kit were used as queries to search the non-redundant database (nr) for homologous sequences, using PSI-BLAST (Altschul et al. (1990) J Mol Biol 215: 403-410). Sequence alignment was performed using ClustalW (Higgins (1994) Methods Mol Biol 25: 307-318) on SCF sequences or Kit sequences and then, manually adjusted based on the IgSF fold restrains for 20 key residues in Kit Ig-like domains. The alignment of amino acid sequences revealed by the SCF-Kit complex crystal structure was submitted to the Consurf 3.0 server (Landau et al. (2005) Nucleic Acids Res 33: W299-302) to generate maximum-likelihood normalized evolutionary rates for each position of the alignment where low rates of divergence correspond to high sequence conservation. As with the Consurf output, the continuous conservation scores are partitioned into a discrete scale of 9 bins for visualization, such that bin 9 contains the most conserved (maroon) positions and bin 1 contains the most variable (cyan) positions.

Example 14

Protein Expression, Purification and Generation of Antibodies

DNA encoding for the fourth Ig-like domain of human Kit (residues 309-413; Kit D4) was amplified from the cDNA of full length human Kit using a PCR reaction. BL21 (DE3) *E. Coli* codon plus cells were transformed with a bacterial expression vector (pET-NusA histidine tagged) that directs the synthesis of Kit D4 followed by overnight incubation at 16° C. The Kit D4-NusA fusion protein was purified from BL21 lysates using a metal chelating affinity column (Ni-NTA; QIAGEN) followed by further purification using anion-exchange chromatography (Source Q column; GE Healthcare). Kit D4-NusA was then incubated overnight at 4° C. with TEV protease in order to cleave NusA and the histidine tag from D4. An additional step of purification of Kit D4 was carried out using gel filtration chromatography (Superdex 200 column; GE Healthcare).

The fifth Ig-like domain of human Kit (residues 410-519; Kit D5) was expressed in the *E. coli* strain BL21 (DE3) cells and purified from bacterial inclusion bodies using a refolding step using 10 mM Tris buffer, pH 8.0 containing 6.0 M guanidine hydrochloride. Refolded Kit D5 was further purified using anion-exchange chromatography (Q sepharose column; GE Healthcare) followed by a purification using gel filtration chromatography (Superdex 200 column; GE Healthcare) and by an additional step of purification using anion-exchange chromatography (Source Q column; GE Healthcare).

Rabbit polyclonal antibodies against isolated D4, D5, or against the entire Kit ectodomain (amino acids 1-519; Kit EC) or against a GST-fusion protein containing a fragment from the C-terminal region of human Kit (residues 876-976) were generated using techniques well known in the art such as the method recited in Example 1. For example, polyclonal antibodies against the Kit ectodomain may be generated by immunizing a rabbit with a purified Kit ectodomain and collecting the produced antibodies by standard methods. The experiments in which the effect of antibodies on Kit activation were tested, such as in Example 15 and FIG. 14, were performed using antibody preparations subjected to purification with protein-A affinity chromography.

Example 15

Inhibition of SCF-Induced Kit Activation Using Antibodies Against the D5 Domain of Kit 3T3 cells expressing human Kit were incubated with buffer solutions containing increasing concentrations of polyclonal rabbit antibodies generated against isolated recombinant D5 of Kit (FIG. 14). As a control, the cells were treated with rabbit polyclonal antibodies against SCF or rabbit polyclonal antibodies directed against the entire Kit ectodomain that was produced in insect cells using a baculovirus expression system. Cell lysates were subjected to immunoprecipitation with anti-Kit antibodies followed by SDS-PAGE and immunoblotting with either anti-Kit or anti-pTyr antibodies (FIG. 14).

This experiment shows that anti-D5 antibodies block the SCF-induced tyrosine autophosphorylation of Kit.

Example 16

Inhibition of SCF-Induced Kit Activation by Isolated Recombinant Kit D4 Domain

3T3 cells expressing Kit were incubated for 10 minutes at 23° C. with increasing concentrations of purified recombinant D4 that was expressed in *E. Coli* followed by SCF incubation. Lysates of unstimulated or stimulated cells were subjected to immunoprecipitation with anti-Kit antibodies followed by SDS-PAGE and immunoblotting with either anti-Kit or anti-pTyr antibodies (FIG. 15).

This experiment shows that the presence of isolated D4 interferes with SCF-induced tyrosine autophosphorylation of Kit.

Example 17

SCF-Induced Kit Stimulation Experiments

3T3 cells expressing human Kit were grown in DMEM containing 10% Calf Serum. Prior to SCF stimulation, cells were starved overnight in serum free medium as described by Yuzawa et al (2007) Cell, 130: 323. The starved cells were washed three times with cold DMEM containing 10 mM HEPES at pH 7.4 and 0.1% BSA, followed by incubation with increasing concentration of antibodies or with Kit-D4 for 10 minutes at 23 C.° as indicated in FIG. 14 or FIG. 15. Cells were stimulated with 100 ng/mL SCF for 10 minutes at 23 C.° and washed three times with cold PBS. Lysates of unstimulated or SCF-stimulated cells were subjected to immunoprecipitation with anti-Kit antibodies followed by SDS-PAGE and immunoblotting with anti-Kit or anti-p-Tyr antibodies.

Example 18

PDGF-Induced Activation of Pdgf-Receptor β and Signaling Via PDGFRβ are Prevented by Point Mutations in Critical Amino Acids in D4 of PDGFRβ

Mouse embryonic fibroblasts (MEFs) derived from PDGFR−/− mice expressing either WT PDGFRβ or point mutants in critical amino acids in D4 (on the basis of sequence similarity with the D4-D4 interface in Kit ectodomain x-ray crystal structure) were used to demonstrate that mutations of R385 or E390 prevent PDGF-induced receptor activation (FIG. 16A), or PDGF-induced MAP kinase response and Akt stimulation (FIG. 16B). Moreover, using cross linking experiments with a covalent cross linking agent we demonstrate that an E390A point mutation does not interfere with PDGF-induced receptor dimerization. However, unlike the WT PDGFRβ covalently cross linked dimers that exist on the cell surface in an activated state, the covalently cross linked dimers of the E390A mutants are inactive (FIG. 16C). This experiment shows that mutation of a critical E390 residue in D4 prevents D4-D4 interactions that are essential for PDGFR activation. However, PDGF-induced dimerization of PDGFR is not affected by a point mutation in D4 that prevents receptor activation indicating that D4-D4 play an important role in mediating the positioning of the membrane proximal region of the ectodomain to enable activation of the tyrosine kinase domain of PDGFR.

Thus, one embodiment of the present invention includes moieties which bind to, or target the residues R385 or E390 in PDGFR. The moieties may be employed to inactivate the receptor while preserving receptor dimerization. This example also demonstrates that information based on the crystal structure of one RTK, in this case the Kit ecodomain crystal structure, can be easily transferred to other RTKs. Here, knowledge of the Kit D4 domain was correct in identifying the amino acids which were important to activation of the PDGF receptor. A more detailed set of experiments involving PDGFR is described in Examples 22-25.

Example 19

Molecular Surface Analysis of Kit Ectodomain

The determination of the crystal structures of the entire ectodomain of Kit before and after SCF binding described herein has demonstrated that SCF-induced receptor dimerization is followed by homotypic lateral interactions between membrane proximal Ig-like domains D4 and D5 of two neighboring Kit molecules. The homotypic D4 and D5 interactions position the cytoplasmic tyrosine kinase domains of two neighboring receptors at a distance and orientation that enable tyrosine autophosphorylation and kinase activation. It is also demonstrated herein that mutation of a single amino acid residue critical for D4 homotypic interactions compromised SCF-induced Kit activation and PDGF-induced PDGF-receptor activation (see Examples 22-25).

The structural analyses described herein provide new insights into how to design inhibitory moieties such as monoclonal antibodies that bind to conformational or non-contiguous epitopes in shallow regions of the cavities formed by the ectodomain of RTKs (e.g., the D3, D4, or D5 regions) or small molecule inhibitors that bind to the D3-D4 and D4-D5 hinge regions of the ectodomain of Kit and other type-III RTKs. Four regions in the ectodomain were initially targeted: (A) Moieties of the invention may be created that bind to the D3-D4 hinge regions and function as a molecular wedge that prevents the motion required for positioning of the membrane proximal region at a distance and orientation that enables tyrosine kinase activation (see FIG. 17); (B) Moieties may be created that bind to the D4-D5 hinge regions and function as a molecular wedge that prevents the motion required for positioning of the membrane proximal region at a distance and orientation that enables tyrosine kinase activation (see FIG. 18); (C) Moieties may be created that bind to the D4:D4 interface preventing homotypic D4 receptor interactions (see FIG. 19), (D) Moieties may be created that bind to a concave surface at the D2-D3 hinge region resulting in destabilization of ligand-receptor interactions (see FIG. 20); and (E) Moieties may be created that bind to peptide regions forming various contiguous and non-contiguous epitopes on the surface of Kit (Table 5).

The molecular surfaces of the ectodomain of Kit and SCF-Kit complex (PDB code: 2EC8 and 2E9W) were analyzed using the Computed Atlas of Surface Topography of proteins (CASTp) server to provide information about the location, and to enable delineation and measurements, of concave surface regions on three-dimensional structures of proteins (Dundas et al., (2006) Nucl Acids Res, 34: W116-W118). The identified cavities were visualized and inspected using Pymol (DeLano. (2002) DeLano Scientific, San Carlos, Calif., USA).

(A) Cavities in D3-D4 Hinge Region (FIG. 17)

Several cavities are scattered on the D3-D4 interface in the ectodomain monomer structure. The amino acids involved in defining the cavities are summarized in Table 4. Upon formation of homotypic interaction between two Kit receptors, the D3-D4 hinge region is altered resulting in the formation of a shallow cavity created by the following residues: K218, S220, Y221, L222 from D3 and F340, P341, K342, N367, E368, S369, N370, I371, Y373 from D4. FIG. 17 shows a ribbon diagram of the D3-D4 hinge region of unoccupied monomers (FIG. 17A) and SCF-bound dimers (FIG. 17B) and a mesh representation of the D3-D4 pocket.

(B) Cavities in the D4-D5 Hinge Region (FIG. 18)

Small cavities are formed by the AB loop and the EF loop of D4, the D4-D5 connecting linker and part of the DE loop and the FG loop of D5 in the Kit monomer. Residues defining the foregoing cavities are summarized in Table 4. The shape and size of the cavities are changed in the Kit ectodomain dimeric structure. The major cavities formed by the EF loop and strand G of D4, the D4-D5 linker and stand B and DE loop of D5 are located beneath the EF loop of D4; a region critical for formation of D4 homotypic interface. Note that the DE loop of D5 that is located close to the cavities may have higher flexibility as revealed by the lower quality of electron densities from both unbound and occupied Kit structures. FIG. 18 shows a ribbon diagram of unoccupied monomers (FIG. 18A) and SCF-dimers (FIG. 18B) and a mesh representation of a shallow cavity around the D4-D5 hinge region.

(C) Cavity at the Region Mediating D4 Homotypic Interactions

A concave surface formed by the CD loop and the EF loop of Kit D4 is located right above the D4 homotypic interface. Residues Y350, R353, F355, K358, L379, T380, R381, L382, E386 and T390 from D4 provide a surface area of approximately 130 $A^2$ for the concave surface in the ectodomain dimeric structure. The side chain of Glu386 plays an important role in the D4 homotypic interface projects toward the center of the surface. A characteristic feature of the concave surface is a small hydrophobic patch surrounded by charged residues (Glu386 and Lys358). The size and accessibility of the surface is altered upon homotypic D4:D4 interactions with changes taking place in the conformation of the CD loop that becomes folded upwards to the top of the domain The residues involved in the formation of the concave surface are summarized in Table 4. FIG. 19A depicts a ribbon diagram of the unoccupied D4 domain of Kit (gold) overlaid onto a ligand-occupied Kit D4 (not shown) with different conformations of the CD and EF loops between ligand-occupied (green) and unoccupied ectodomain structures (red). The critical residues for the D4:D4 interaction are shown in the stick model form. FIGS. 19B and 19C show a ribbon diagram of unoccupied Kit (FIG. 19B) and SCF-occupied Kit structures (FIG. 19C) and a mesh representation of a shallow cavity above the D4 homotypic interface.

(D) Concave Surface at the Ligand-Binding D2 and D3 Regions

A shallow concave surface is located on part of the ligand-binding surface of the D2 and the D3 domains. Residues involved in the small pocket are Y125, G126, H180, R181, K203, V204, R205, P206 and F208 from D2 and V238, S239, 5240, 5241, H263, G265, D266, F267, N268 and Y269 from the D3 domain of Kit. The pocket is created by a small hydrophobic patch surrounded by hydrophilic residues. There is no major alteration between unoccupied and SCF-occupied Kit structures with an overall buried surface area of approximately 500 $A^2$. FIGS. 20A and 20B show ribbon diagrams of unoccupied Kit (A) and SCF-bound Kit (B) and a mesh representation of the D2-D3 pocket.

TABLE 4

| No | Interface | Pocket/cavity | Area (Å$^2$) | | Residues |
|---|---|---|---|---|---|
| | | | Kit free | | |
| 84 | D2-D3 | 1 | 226 | D2 | Y125, H180, R181, K203, V204, R205, P206 |
| | | | | D3 | V238, S239, S240, H263, G265, D266, F267, N268, Y269 |
| 30 | | 2 | 32 | D2 | P206, F208 |
| | | | | D3 | V238, S239 |
| 22 | | 3 | 6 | D2 | K127, A207, F208 |
| | | | | D3 | T295 |
| 81 | D3-D4 | 1 | 102 | D3 | L222, |
| | | | | D4 | A339, F340, K342, E368, S369, N370, I371, Y373 |
| 80 | | 2 | 99 | D3 | L222, L223, E306, V308 |
| | | | | D4 | F312, E338, F340, I371 |
| 74 | | 3 | 57 | D3 | R224, V308, K310 |
| | | | | D4 | G311, F340, P341, D398 |
| 63 | | 4 | 49 | D3 | K218, A219, S220 |
| | | | | D4 | N367, E368, S369 |
| 59 | | 5 | 45 | D3 | K218, A220 |
| | | | | D4 | E368, S369 |
| 65 | D4-D5 | 1 | 41 | D4 | G384, T385, |
| | | | | D5 | T411, K412, E414, K471 |
| 61 | | 2 | 20 | D4 | Y408, |
| | | | | D5 | F433, G470, K471, L472 |
| 53 | | 3 | 14 | D4 | F324, V325, N326, N410 |
| | | | | D5 | |
| 24 | | 4 | 23 | D4 | D327, N410 |
| | | | | D5 | T411, K412, V497 |
| 18 | | 5 | 17 | D4 | G384, G387, V409 |
| | | | | D5 | K471 |
| 14 | | 6 | 25 | D4 | L382, G387, V407, V409 |
| | | | | D5 | |

TABLE 4-continued

| No | Interface | Pocket/cavity | Area (Å²) | | Residues |
|----|-----------|---------------|-----------|---|----------|
| | | SCF-Kit complex molA, C | | | |
| 60 | D2-D3 | 1 | 280 | D2 | Y125, G126, H180, R181, K203, V204, R205, P206, F208 |
| | | | | D3 | V238, S239, S240, S241, H263, G265, D266, F267, N268, Y269 |
| 47 | | 2 | 49 | D2 | P206, F208 |
| | | | | D3 | V238, S239 |
| 59 | D3-D4 | 1 | 175 | D3 | K218, S220, Y221, L222 |
| | | | | D4 | F340, P341, K342, N367, E368, S369, N370, I371, Y373 |
| 57 | D4-D5 | 1 | 126 | D4 | G384, G387, G388, Y408, V409 |
| | | | | D5 | T411, F433, F469, G470, K471 |
| 56 | | 2 | 95 | D4 | D327, |
| | | | | D5 | T411, K412, E414, A431, G432, K471 |

TABLE 4-continued

| No | Interface | Pocket/cavity | Area (Å²) | | Residues |
|----|-----------|---------------|-----------|---|----------|
| 55 | D4-D4 | 1 | 93 | D4 | Y350, F355, K358, L379, T380, R381, L382, E386, T390 |
| 7 | | 2 | 26 | D4 | Y350, R353, F355 |

(E) Structural Analysis of the Kit Tyrosine Kinase was Conducted as Described above. The analysis revealed both continuous and discontinuous epitopes which may be targets for the moieties of the invention. In Table 5, epitopes 1, 4, 5, 6, 8, 12-16, 19, 22-23, and 31-39 are continuous epitopes. These epitopes are composed of sequential amino acids in the KIT protein. Epitopes 2, 3, 7, 9-11, 17, 18, 20, 21, 24-30, and 40-43 in Table 5 are discontinuous conformational epitopes composed of at least 2 peptides of the KIT protein that are brought into proximity by the folding of the KIT protein.

TABLE 5

| # | Amino acids | sequence | Domain | Strand/loop | Amino acids | sequence | Domain | Strand/loop |
|---|-------------|----------|--------|-------------|-------------|----------|--------|-------------|
| 1 | Glu306-Ile313 | EVVDKGFIN (SEQ ID NO: 2) | D3-D4 linker | | | | | |
| 2 | Ala219-Leu222 | ASYL (SEQ ID NO: 3) | D3 | A | Thr304-Val308 | TLEVV (SEQ ID NO: 4) | D3 | G |
| 3 | Asp309-Gly311 | DKG | D3-D4 linker | | Arg224-Gly226 | REG | D3 | AB loop |
| 4 | Val213-Leu222 | VVSVSKASYLL (SEQ ID NO: 7) | D3 | A | | | | |
| 5 | Val301-Asp309 | VTTTLEVVD (SEQ ID NO: 8) | D3 | G | | | | |
| 6 | Arg224-Ile235 | REGEEFTVTCTI (SEQ ID NO: 9) | D3 | AB loop, B | | | | |
| 7 | Thr303-Glu306 | TTLE (SEQ ID NO: 10) | D3 | G | Ala219-Leu222 | ASYL (SEQ ID NO: 3) | D3 | A |
| 8 | Lys364-Arg372 | KSENESNIR (SEQ ID NO: 12) | D4 | D, DE loop | | | | |
| 9 | Asn367-Asn370 | NESN (SEQ ID NO: 13) | D4 | DE loop | Ser217-Tyr221 | SKASY (SEQ ID NO: 14) | D3 | A |
| 10 | Ala339-Pro343 | AFPKP (SEQ ID NO: 16) | D4 | BC loop | Asn396-Val399 | NSDV (SEQ ID NO: 17) | D4 | F |
| 11 | Ala339-Pro343 | AFPKP (SEQ ID NO: 16) | D4 | BC loop | Glu368-Arg372 | ESNIR (SEQ ID NO: 19) | D4 | DE loop |
| 12 | Asp357-Glu366 | DKWEDYPKSE (SEQ ID NO: 21) | D4 | D | | | | |
| 13 | Ile371-Leu379 | IRYVSELHL (SEQ ID NO: 22) | D4 | E | | | | |
| 14 | Leu379-Thr389 | LTRLKGTEGGT (SEQ ID NO: 23) | D4 | EF loop | | | | |
| 15 | Gly328-Glu338 | GENVDLIVEYE (SEQ ID NO: 24) | D4 | B | | | | |
| 16 | Met351-Glu360 | MNRTFTDKWE (SEQ ID NO: 25) | D4 | CD loop | | | | |
| 17 | Lys358-Tyr362 | KWEDY (SEQ ID NO: 26) | D4 | D | Val374-His378 | VSELH (SEQ ID NO: 27) | D4 | E |
| 18 | Asp357-Glu360 | DKWE (SEQ ID NO: 29) | D4 | CD loop | Leu377-Thr380 | LHLT (SEQ ID NO: 30) | D4 | E |
| 19 | His378-Thr389 | HLTRLKGTEGGT (SEQ ID NO: 32) | D4 | E, EF loop | | | | |
| 20 | Met351-Glu360 | MNRTFTDKWE (SEQ ID NO: 25) | D4 | CD loop | His378-Thr389 | HLTRLKGTEGGT (SEQ ID NO: 32) | D4 | E, EF loop |

TABLE 5-continued

| # | Amino acids | sequence | Domain | Strand/loop | Amino acids | sequence | Domain | Strand/loop |
|---|---|---|---|---|---|---|---|---|
| 21 | His378-Thr389 | HLTRLKGTEGGT (SEQ ID NO: 32) | D4 | E, EF loop | Val323-Asp332 | | D4 | A, AB loop |
| 22 | Val323-Asp332 | VFVNDGENVD (SEQ ID NO: 34) | D4 | A, AB loop | | | | |
| 23 | Val409-Ile415 | VNTKPEI (SEQ ID NO: 35) | D4-D5 linker | | | | | |
| 24 | Val409-Ile415 | VNTKPEI (SEQ ID NO: 35) | D4-D5 linker | | Ala493-Thr500 | AYNDVGKT (SEQ ID NO: 36) | D5 | FG loop |
| 25 | Val409-Ile415 | VNTKPEI (SEQ ID NO: 35) | D4-D5 linker | | Ala431-Thr437 | AGFPEPT (SEQ ID NO: 38) | D5 | B |
| 26 | Val409-Ile415 | VNTKPEI (SEQ ID NO: 35) | D4-D5 linker | | Phe469-Val473 | FGKLV (SEQ ID NO: 40) | D5 | DE loop |
| 27 | Val409-Ile415 | VNTKPEI (SEQ ID NO: 35) | D4-D5 linker | | Val325-Asn330 | VNDGEN (SEQ ID NO: 42) | D4 | A |
| 28 | Val409-Ile415 | VNTKPEI (SEQ ID NO: 35) | D4-D5 linker | | Arg381-Gly387 | RLKGTEG (SEQ ID NO: 44) | D4 | EF loop |
| 29 | Gly466-Leu472 | GPPFGKL (SEQ ID NO: 46) | D4 | DE loop | Gly384-Gly388 | GTEGG (SEQ ID NO: 47) | D4 | EF loop |
| 30 | Val325-Glu329 | VNDGE (SEQ ID NO: 49) | D4 | A | Tyr494-Lys499 | YNDVGK (SEQ ID NO: 50) | D5 | FG loop |
| 31 | Thr411-Leu421 | TKPEILTYDRL (SEQ ID NO: 52) | D5 | A | | | | |
| 32 | Asp419-Cys428 | DRLVNGMLQC (SEQ ID NO: 53) | D5 | AB loop | | | | |
| 33 | Gly498-Lys509 | GKTSAYFNFAFK (SEQ ID NO: 54) | D5 | G | | | | |
| 34 | Cys443-Ser453 | CPGTEQRCSAS (SEQ ID NO: 55) | D5 | C | | | | |
| 35 | Cys450-Gln460 | CSASVLPVDVQ (SEQ ID NO: 56) | D5 | C | | | | |
| 36 | Asp479-Thr488 | DSSAFKHNGT (SEQ ID NO: 57) | D5 | EF loop | | | | |
| 37 | Gly487-Tyr496 | GTVECKAYND (SEQ ID NO: 58) | D5 | F | | | | |
| 38 | Leu462-Leu472 | LNSSGPPFGKL (SEQ ID NO: 59) | D5 | DE loop | | | | |
| 39 | Phe506-Ile515 | FAFKGNNKEQI (SEQ ID NO: 60) | D5 | C tail | | | | |
| 40 | Thr411-leu416 | TKPEIL (SEQ ID NO: 61) | D5 | A | Val497-Ala502 | VGKTSA (SEQ ID NO: 62) | D5 | FG loop |
| 41 | Ile415-Leu421 | ILTYDRL (SEQ ID NO: 64) | D5 | A | Ala502-Ala507 | AYFNFA (SEQ ID NO: 65) | D5 | G |
| 42 | Ala502-Ala507 | AYFNFA (SEQ ID NO: 65) | D5 | G | Lys484-Thr488 | KHNGT (SEQ ID NO: 67) | D5 | EF loop |
| 43 | Ala502-Ala507 | AYFNFA (SEQ ID NO: 65) | D5 | G | Gly445-Cys450 | GTEQRC (SEQ ID NO: 69) | D5 | C |

Example 20

RTK Activity Assay

Cells containing an RTK of interest are exposed to the activating ligand for the receptor and a moiety of the invention. The RTK of interest may be isolated by standard molecular biology methods (e.g., antibody purification). After purification, an antibody which binds to the RTK (not a moiety of the invention but simply a structural binder, as used in purification) is pre-coated onto a 96-well mictrotiter plate. The RTK and calibrated standards are then added to separate wells wherein the RTK protein is captured. A detection antibody is added next, which may be phospho-site specific (e.g., c-Kit pY823 or other residue of Kit which is phosphorylated upon activation; the phosphoELISA™ system uses rabbit antibody). The antibody-Kit complex is detected using a secondary antibody (e.g., anti-rabbit Ab to detect a rabbit derived primary antibody) which is conjugated to a label or enzyme (e.g., horseradish peroxidase is used in the phosphoELISA™ system) followed with a colorimetric substrate. Stop solution is then added and the plate is read (e.g., using a 450 nm light source and detector). Detailed protocols for the phosphoELISA™ are available from Invitrogen (invitrogen.com/content.cfm?pageid=11655; invitrogen.com/downloads/F1027_BN_pELISA1006.pdf; invitrogen.com/downloads/F1028_BN_pELISA1006.pdf C-KIT [pY823] ELISA KIT, HU (BioSource™) Catalog Number—KH00401; c-KIT [TOTAL] ELISA KIT, HU (BioSource™) Catalog Number—KH00391).

Example 21

Receptor Internalization Assay

Cells expressing the RTK of interest are first incubated with an appropriate ligand (e.g., Kit expressing cells are incubated with SCF), inducing receptor internalization. The process of receptor internalization is stopped by washing the cells in cold PBS. The remaining surface bound ligand is then removed by washing the cells in a solution having a salt concentration and/or pH level sufficient to dissociate the ligand. The cells are then resuspended in the appropriate buffer. The cells at this point will contain internalized receptor, and, thus, a lessened amount of receptor remaining on the cell surface.

Another set of similar experiments is run wherein the cells are exposed to an appropriate ligand and a test moiety of the invention. If the test moiety prevents the activation of the target RTK, then receptor internalization will be inhibited. When compared to the cells described in the experiment above (wherein receptor activation occurred), these cells show decreased internalization and a greater amount of receptor on the cell surface. Control groups are also set up in which cells are treated only with buffer or ethanol solution, a common vehicle for solubilization of drugs.

Determination of the amount of receptor on the cell surface in the above experiments may be accomplished by incubating the cells with mouse antibodies specific for the receptor, followed by and incubation with anti-mouse antibodies which are conjugated to a fluorophore such as Green Fluorescent Protein (GFP). Fluorescence microscopy techniques may then be used to visualize and quantitate the amount of receptor on the cell surface.

Alternative techniques for the quantitation or visualization of cell surface receptors are well known in the art and include a variety of fluorescent and radioactive techniques. For example, one method involves incubating the cells with a radiolabeled anti-receptor antibody. Alternatitively, the natural ligand of the receptor may be conjugated to a fluorescent molecule or radioactive-label and incubated with the cells. Additional receptor internalization assays and are well known in the art and described in, for example: Jimenez et al. (1999) Biochemical Pharmacology. 57(10):1125-1131; Bernhagen et al. (2007) Nature Medicine. 13(5):587-596; and Conway et al. (2001) J. Cell Physiol. 189(3):341-55, the entire contents of each of which are incorporated herein by reference.

Introduction to Examples 22-25

The generally accepted mechanism of receptor tyrosine kinase (RTK) activation is that ligand-induced receptor dimerization facilitates trans-autophosphorylation of critical regulatory tyrosine residues in the activation loop of the catalytic core; a step essential for tyrosine kinase activation. This is followed by autophosphorylation of multiple tyrosine residues in the cytoplasmic domain that serve as binding sites for SH2 (Src homology 2) or PTB (phosphotyrosine binding) domains of a variety of signaling proteins, which upon recruitment and/or tyrosine phosphorylation transmit signals to variety of intracellular compartments in a regulated manner (Schlessinger, J. (2000) Cell 103, 211-225; Pawson, T. & Nash, P. (2003) Science 300, 445-452; and Hunter, T. (2000) Cell 100, 113-127).

While all RTKs are activated by dimerization, different RTK families have evolved to utilize different molecular strategies for ligand-induced receptor dimerization and activation (Burgess, A. W, et al. (2003) Mol Cell 12, 541-552; Schlessinger, J., et al. (2000) Molecular Cell 6, 743-750). All ligands of type-III RTKs including PDGFs, SCF, CSF and Flt3L are dimeric molecules capable of crosslinking their cognate receptors by bivalent binding to equivalent sites of two neighboring receptor molecules. The PDGF protomer is composed of a central four-stranded β-sheet with the characteristic cysteine-knot at one end of the molecule. Two PDGF protomers are arranged in antiparallel manner and are linked to each other by two inter-chain disulfide bridges (Oefner, C., et al. (1992) EMBO J. 11, 3921-3926). By contrast, each SCF, CSF or Flt3L protomer is composed of short helical fold and is connected to each other by non-covalent interactions (Jiang, X., et al. (2000) Embo J 19, 3192-3203; Zhang, Z., et al. (2000) Proc Natl Acad Sci USA 97, 7732-7737; Pandit, J., et al. (1992) Science 258, 1358-62; and Savvides, S. N., et al. (2000) Nat Struct Mol Biol 7, 486-491). Despite their diverse folds, the two growth factor subtypes bind to and activate their cognate RTKs in a virtually identical manner resulting in formation of activated ligand/RTK 2:2 complexes (Savvides, S. N., et al. (2000) Nat Struct Mol Biol 7, 486-491). All type-III RTKs are composed of extracellular ligand binding region containing five tandem Ig-like domains followed by a single transmembrane helix and a cytoplasmic tyrosine kinase domain with a large kinase-insert region flanked by regulatory regions that are subject to autophosphorylation and to phosphorylation by heterologous protein kinases (Hubbard, S. R. (1999) Prog Biophys Mol Biol 71, 343-358).

The mechanism of PDGF-receptor β (PDGFRβ) activation was explored by analyzing the properties of mutant receptors that were designed based upon the crystal structure of the extracellular region of the related receptor tyrosine kinase Kit. Based on these experiments it was demonstrated that PDGF-induced activation of a PDGFRβ mutated in Arg385 or Glu390 in D4 (the 4th Ig-like domain of the extracellular region) was compromised resulting in impairment of a variety of PDGF-induced cellular responses. These experiments also demonstrate that homotypic D4 interactions, likely mediated by salt bridges between Arg385 and Glu390, play an important role in activation of PDGFRβ and all type-III RTKs. A chemical crosslinking agent was also used to covalently crosslink PDGF-stimulated cells to demonstrate that a Glu390Ala mutant of PDGFRβ undergoes typical PDGF-induced receptor dimerization. However, unlike WT PDGFR that is expressed on the surface of ligand-stimulated cells in an active state, PDGF-induced Glu390Ala dimers are inactive. While the conserved amino acids that are required for mediating D4 homotypic interactions are crucial for PDGFRβ activation (and similar interactions in type-III RTKs), these interactions are dispensable for PDGFRβ dimerization. Moreover, PDGFRβ dimerization is necessary but not sufficient for tyrosine kinase activation.

Similar to the D4 domain of Kit, the D4 domain of PDG-FRα and PDGFRβ lack a characteristic disulfide bond that bridges cysteine residues located in B5 and F5 in Ig-like domains. The amino acid sequence alignment presented in FIG. 21 shows that 13 out of 20 finger-print residues of the Iset IgSF fold are conserved in the D4 domain of PDGFRs and that the number and length of strands corresponding to the finger-print residues are highly conserved in the D4 domain of Kit, PDGFRα, PDGFRβ and CSF1R. This indicates that the inhibitors of the invention may be designed to inhibit a variety of receptor molecules including all Type III RTKs.

The D4 domain of Kit is composed of two β sheets, each containing four strands with the arrangement ABED/A'GFC and the homotypic D4 contacts are mediated by the EF loop of D4 projecting from two neighboring Kit molecules. The Kit structure disclosed herein demonstrates that Arg381 and Glu386 in the EF loop form salt bridges and van-der-Waals contacts across a two-fold axis of the Kit dimer. In addition, the side chains of Arg381 of each protomer form hydrogen bonds with the main chain carbonyl of the corresponding residue of neighboring Kit molecules. Structure based sequence alignment has shown that the size of the EF loop, and the critical amino acids comprising the D4-D4 interface are conserved in Kit, PDGFRα, PDGFRβ, and CSF1R. In PDGFRα, Glu386 is replaced by an aspartic acid, a residue that may also function as a salt bridge partner. In addition, a pair of basic and acidic (Glu/Asp) residues is strictly conserved in PDGFRα and PDGFRβ of different species ranging from Takifugu rubripes to Homo sapien (FIG. 21), providing further support for the functional importance of this region. As such, moieties of the invention targeted to RTKs, e.g. Type III RTKs, with different amino acid sequences or to variant domains of similar function to those described herein also fall within the scope of the present invention.

Methods Related to Examples 22-25

Sequence Alignment and Homology Modeling

Amino acid sequence alignment was performed using the CONSEQ server (Berezin, C., et al. (2004) Bioinformatics 20, 1322-1324), as well as according to the IgSF fold characteristics (Harpaz, Y. & Chothia, C. (1994) Journal of Molecular Biology 238, 528-539) and according to the core residues of the Ig-fold of D4 of human Kit structure (Yuzawa, S., et al. (2007) Cell 130, 323-334). The accession codes of each sequence are: PDGFRα human (P16234), mouse (P26618), chicken (Q9PUF6), frog (P26619) and fugu (Q8AXC7); PDGFRβ human (P09619), dog (Q6QNF3), mouse (P05622), fugu (P79749) and Kit human (Q96RW7). A homology model of D4 of PDGFRβ was generated on the basis of D4 Kit structure (PDB code: 2E9W) using the WHAT IF server (Rodriguez, R., et al. (1998) Bioinformatics 14, 523-528). Figures were generated using PyMOL (Delano, W. L.; pymol.org).

Reagents and Antibodies

L-histidinol and anti-flag antibodies were purchased from Sigma. Antibodies against MAPK, phospho-MAPK, Akt, phospho-Akt, and phospholipase Cγ were purchased from Cell Signaling Technology. Anti-phosphotyrosine (4G10) antibodies was from Upstate Technology. Antiubiquitin antibodies (P4D1) was from Santa Cruze. Antibodies against PDGFRβ were produced by immunization of rabbit with synthetic peptides from the cytoplasmic domain of PDGFRβ. PDGF BB cDNA was obtained from Stuart Aaronson. PDGF BB was purchased from Invitrogen, and produced in bacteria as previously described (Hoppe, J., et al. (1990) European Journal of Biochemistry 187, 207-214). $^{125}$I radionuclide was purchased from Perkin Elmer. Bolton-Hunter reagent and IODO-GEN pre-coated iodination tubes were from Piece. FITC-phalloidin was purchased from Invitrogen.

Cell Lines and Retroviral Infection

Fibroblasts derived from mouse embryos deficient in both PDGFRα and PDGFRβ (PDGFRα/β) were provided by Philip Sariano and Andrius Kazlauskas. PDGFRβ cDNA was provided by Daniel DeMaio. PDGFRβ cDNA was subcloned into pLXSHD retroviral vector, and a flag-tag was added to the C terminus of the receptor. All mutants in D4 were generated by site-directed mutagenesis according to the manufacturer's instructions (Stratagen). Retrovirus encoding WT and mutant PDGFRβ were produced in 293GPG cells (Ory, D. S., et al. (1996) Proc. Nat. Acad. Sci. 93, 11400-11406). Following infection, cells were selected with L-histidinol, and pools of selected cells were used in the experiments.

Immunoprecipitation and Immunoblotting

Unstimulated or PDGF-stimulated cells were lysed in a buffer solution containing 50 mM Hepes, 150 mM NaCl, 1 mM EDTA, 1% Triton X-100, 25 mM sodium fluoride, 1 mM orthovanadate, 1 mM phenyl-methylsulfonyl fluoride, 5 μg of aprotinin and leupeptin (pH 7.5). Equal amount of cell lysates were immunoprecipitated with indicated antibodies, immunopellets were resolved by SDS-PAGE and transferred to nitrocellulose membrane. Membranes were immunoblotted with different antibodies. Films were scanned using densitometer (Amersham) and quantitated with Imagequant software (Molecular dynamics).

In Vitro Phosphorylation Assay for PDGFR

Cells were serum-starved for 16 hours and solubalized in lysis buffer containing 150 mM NaCl, 50 mM Hepes (pH 7.4), 1 mM EDTA, 25 mM NaF, 0.1 mM sodium orthovanadate, 5 μg/ml leupeptine and aprotinin, 1 mM PMSF and 1% NP40. Lysates were immunoprecipitated with anti-PDGFRβ antibodies, and immunopelletes were incubated in reaction buffer containing 50 mM Hepes (pH7.4), 1 mM ATP and 10 mM $MgCl_2$ at room temperature for 5 minutes. After incubation, pellets were analyzed by SDS-PAGE followed by immunoblotting with antiphosphotyrosine antibodies. The membrane was stripped off and re-blotted with anti-Flag tag antibodies for determination of total PDGFRβ level.

Chemical Crosslinking of Receptor Dimers

Cells were grown in 150 mm plates until an 80% confluency was reached and were serum-starved for 16 hours prior to incubation with the indicated concentration of PDGF in DMEM containing 50 mM Hepes (pH 7) at 4° C. After 90 minutes, the cells were extensively washed with PBS (pH 7.4). Plates were transferred to room temperature and disuccinimidyl suberate (DSS) was added to a final concentration of 0.5 mM. The crosslinking reaction was quenched after 30 minutes by incubation with 10 mM Tris buffer for 15 minutes, followed by extensive wash with PBS. Cell lysates in 50 mM Hepes, 150 mM NaCl, 1 mM EDTA, 1% Triton X-100, 25 mM sodium fluoride, 1 mM sodium orthovanadate, 1 mM phenylmethylsulfonyl fluoride, 5 μg/ml aprotinin and 5 μg/ml leupeptin (pH 7.4) were immunoprecipitated with anti-PDGFR antibodies and resolved by SDS-PAGE. Nitrocellulose membrane was immunoblotted with antibodies against flag-tag or antiphosphotyrosine (4G10) antibodies to detect the total receptor and phosphorylated receptor level respectively.

PDGF-Induced Actin Cytoskeletal Reorganization

MEFs were plated to subconfluency on glass coverslips for 24 hours, followed by overnight serum-starvation. Cells were either treated with 50 ng/ml PDGF for 2,5,10, or 30 minutes or left untreated. Cells were fixed in 4% paraformaldehyde in PBS, permeablized with 0.1% Triton in PBS and stained with FITC-phalloidin (Sigma) in PBS containing 1% BSA for 30 min. Coverslip were mounted with Prolong Antifade mounting medium (Invitrogen), and images were acquired with Nikon fluorescence microscope. About 400 cells on each coverslip were analyzed, and the percentage of cells showing actin ring formation was calculated and presented linearly.

PDGF Binding and Internalization Experiments

PDGF was labeled using Bolton-Hunter reagent (Pierce) prior to iodination using Iodo-gen Iodination tubes (Pierce) according to the manufacturer's instructions. Cells were plated on 24-well plates and allowed to grow to 80% confluency in DMEM supplemented with 10% fetal bovine serum. Cells were washed twice in cold DMEM containing 20 mM Hepes (pH7.4) and 0.1% BSA. Triplicate wells were incubated with 5 ng/ml of $^{125}$I-PDGF in the presence of increasing amounts of native PDGF. Binding was allowed to proceed at 25° C. for 1 hour. Cells were then washed in cold PBS and solubilized in 0.5 M NaOH. The radioactive content of the samples was determined using a LS6500 scintillation counter (Beckman Coulter), and data were analyzed using PRISM software (GraphPad).

For internalization experiments, cells were seeded in 24-well plates, allowed to grow to 80% confluency and starved overnight. Cells were incubated with 5 ng/ml $^{125}$I-PDGF in DMEM/0.1% BSA/50 mM Hepes, pH7.4 for 90 min at 4° C. Unbound ligand was removed by washing with ice cold PBS (pH 7.4). Pre-warmed DMEM/0.1% BSA/50 mM Hepes was added to the cells and incubated at 37° C. for the time indicated. Cell surface-associated ligand was collected with ice-cold acidic buffer containing PBS (pH 3) and 0.1% BSA for 10 minutes. Internalized ligands were collected by solubilization with 0.5 M NaOH. The amount of degraded $^{125}$I-PDGF was determined by precipitation of the incubation medium with 10% trichloroacetic acid (TCA), and counting the supernatant for the TCA soluble fraction. Cell-surface-associated internalized and released radioactivities were determined by liquid scintillation counter. The amounts of surface bound, intracellular and degraded PDGF were expressed as a percent of total cell associated radioactivity after a 90 minute incubation on ice (t=0 minutes). Each time point was performed in triplicate, and the results were expressed as mean±SE.

Example 22

PDGF-Induced PDGF-Receptor Activation is Compromised by Mutations in the D4 Domain The amino acid sequence alignment presented in FIG. 21A demonstrates that Arg385 and Glu390 in the EF loop of PDGFR may mediate homotypic D4 interactions similar to the salt bridges formed between Arg381 and Glu386 of Kit that are responsible for mediating homotypic D4 interactions between neighboring Kit receptors. To investigate whether a similar mechanism is employed by PDGFRβ, Arg385 and Glu390, each alone (R385A, E390A) or in combination (R385E390/AA) were substituted by alanine residues. An additional conserved Lys387 residue in the loop region was also substituted by an alanine (R385K387E390/AAA) residue in order to examine its potential role in control of PDGF-induced PDGFRβ activation. Wild-type and mutant PDGFRβs were stably expressed in fibroblasts derived from mouse embryos (MEFs) deficient in both PDGFRα and PDGFRβ (Soriano, P. (1994) Genes Dev. 8, 1888-1896; Soriano, P. (1997) Development 124, 2691-2700; and Andrews, A., et al. (1999) Invest. Ophthalmol. Vis. Sci. 40, 2683-2689). MEFs expressing wild type or mutant PDGFRβs that were matched for expression level were used in the experiments described below. Cell lysates from unstimulated or PDGF-stimulated cells were subjected to immunoprecipitation with anti-PDGFR antibodies, followed by immunoblotting with anti-phosphotyrosine antibodies.

The membranes were subsequently stripped off, and re-blotted with anti-PDGFR antibodies for quantitation of PDGFR expression. The experiment presented in FIG. 22A shows that PDGF-induced tyrosine autophosphorylation of PDGFRβ is strongly compromised in cells expressing the E390A, R385A, (R385E390/AA), and (R385K387E390/AAA) mutants of PDGFRβ; both the magnitude and kinetics of tyrosine autophosphorylation were reduced and attenuated, respectively. These experiments demonstrate that Arg385 and Glu390 in the EF loop of D4 play an important role in PDGF-induced stimulation of PDGFRβ, which demonstrates that a similar pair of salt bridge to those identified in the Kit structure exists in activated PDGFRs and other Type III RTKs. Direct interaction between the D4 domain of a neighboring receptor within the ligand-receptor complex may represent a common mechanism utilized for ligand induced activation of type-III RTKs. It has consistently and reproducibly been observed that PDGF-induced receptor autophosphorylation is more strongly compromised in cells expressing the E390A in comparison to cells expressing the R385A, (R385E390/AA) or the (R385K387E390/AAA) mutants. While the precise mechanism responsible for the difference between these mutants is not clear, it is possible that the positive local surface charge at the D4 interface may cause electrostatic repulsion to maintain D4 of neighboring receptors apart prior to ligand stimulation. Whereas substitution of Arg385 by an alanine residue will prevent salt bridge formation, this change may also decrease the net positive charge in the D4-D4 interface resulting in weaker inhibition of PDGFR activation.

In order to examine the possibility of whether mutation in the D4 domain of PDGFR may have affected cell membrane expression and ligand binding affinity of mutant PDGFRβs, quantitative PDGF binding experiments to cells expressing wild type or mutant PDGFRβs were performed next. Cells expressing wild type, R385A, E390A or the (R385E390/AA) PDGFRβ mutants were incubated with a buffer solution containing $^{125}$I-PDGF for 90 minutes at 4° C. in the presence of increasing concentration of native PDGF. Cell bound radioactivity was measured using a scintillation counter. The EC50 values of the displacement curves of wild type and mutant PDGFRβs were analyzed by curve fitting with Prism4 (FIG. 22B). The amounts of wild type and mutant PDGFRβs that are expressed in the transfected MEFs were also compared by immunoblotting of total cell lysates with antibodies against PDGFR or anti-tag antibodies (FIGS. 22A and C). Taken together, these experiments demonstrate that similar amounts of wild type or mutant PDGFRβs are expressed on the cell surface of the transfected cells. Moreover, similar IC50 values (PDGF concentration that displaces 50% of $^{125}$I-PDGF binding) were obtained for cells expressing wild type (3.7 nM), R385A (6.0 nM), E390A (2.8 nM) or the RE/AA (3.0 nM) mutants. The possibility of whether the intrinsic tyrosine kinase activity of mutant PDGFRβs was adversely affected by comparing the in vitro tyrosine kinase activities of wild type and mutant receptors was also examined. In this experiment, cell lysates from serum-starved cells were subjected to immunoprecipitation with anti-PDGFR antibodies, and the immobilized PDGFRs were subjected to in vitro kinase assays in the presence of 1 mM ATP and 10 mM magnesium chloride. After incubation, the samples were analyzed by immunoblotting with anti-phosphotyrosine antibodies. The experiment presented in FIG. 22C demonstrates that the R385A, E390A or RE/AA mutations do not influence the intrinsic tyrosine kinase activity of PDGFR. Altogether, these experiments demonstrate that the mutations in D4 that affect PDGF-induced stimulation of PDGFRβ do not alter the expression of PDFGRβ on the cell surface, do not influence the ligand binding affinity of PDFGRβ and do not alter the intrinsic tyrosine kinase activities of mutant PDGFRβ.

Example 23

PDGF Receptor D4 Point Mutants are Expressed on the Surface of PDGF-Stimulated Cells in the Form of Inactive Dimmers Since receptor dimerization has been established as a critical mechanism underlying receptor tyrosine kinase activation, we investigated whether reduced tyrosine autophosphorylation of mutant PDGFRβ in response to PDGF stimulation is caused by deficiency in receptor dimerization. Chemical crosslinking agents have previously been used to monitor and follow ligand-induced dimerization of several cell membrane receptors including wild type and a variety of EGF receptor mutants on the cell surface of living cells (Cochet, C., et al. (1988) J Biol Chem 263, 3290-3295). In this experiment, cells expressing wild type PDGFRβ or the E390A mutant were serum starved overnight, followed by PDGF incubation for 90 minutes at 4° C. Several washes were used to remove unbound PDGF and the cells were incubated with 0.5 mM disuccinimidyl suberate (DSS) in PBS for 30 minutes at 25° C. Cell lysates from unstimulated or PDGF-stimulated cells were subjected to immunoprecipitation with anti-PDGFR antibodies followed by SDS-PAGE and immunoblotting with either anti-flag antibodies to monitor the status of PDGFR dimerization or with antiphosphotyrosine antibodies to monitor the status of PDGFR activation (FIG. 23).

The experiment depicted in FIG. 23 demonstrates that in lysates of unstimulated cells a band that migrates on an SDS gel with an apparent molecular weight of 180 kDa corresponding to PDGFR monomers was detected in lysates from cells expressing either wild type PDGFRβ or the E390A mutant. Upon PDGF stimulation, an additional band that migrates on an SDS gel with an apparent molecular weight of 360 kDa corresponding to PDGFR dimers was detected in cells expressing both wild type PDGFRβ and the E390A mutant. However, immunoblotting of the samples with antiphosphotyrosine antibodies demonstrates that while the band corresponding to dimers of wild type PDGFR is strongly tyrosine phosphorylated, very weak tyrosine phosphorylation of the band corresponding to the dimers of E390A mutant is detected (FIG. 23).

This experiment shows that impaired ligand-induced tyrosine autophosphorylation of the E390A mutant is not caused by a deficiency in ligand-induced receptor dimerization. This experiment also demonstrates that the covalently crosslinked wild type PDGFRβ are displayed on the cell surface of PDGF-stimulated cells in the form of active dimers while the E390A mutant is displayed on the surface of PDGF-stimulated cells in the form of inactive dimers. The foregoing data demonstrate that the D4 homotypic interactions in PDGFR are dispensable for receptor dimerization and that PDGF-induced receptor dimerization is necessary but not sufficient for tyrosine kinase activation.

Example 24

Figure 24A:
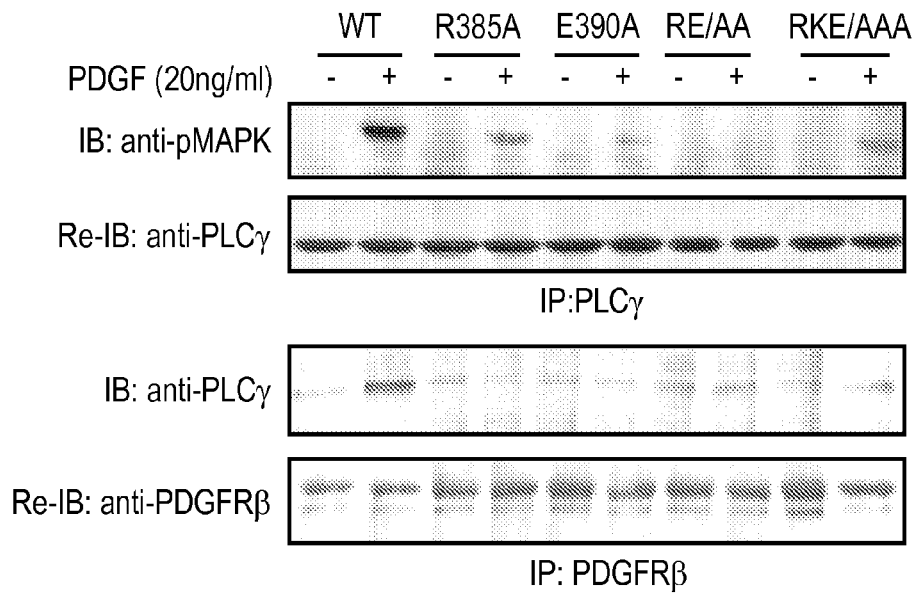
Figure 24B:
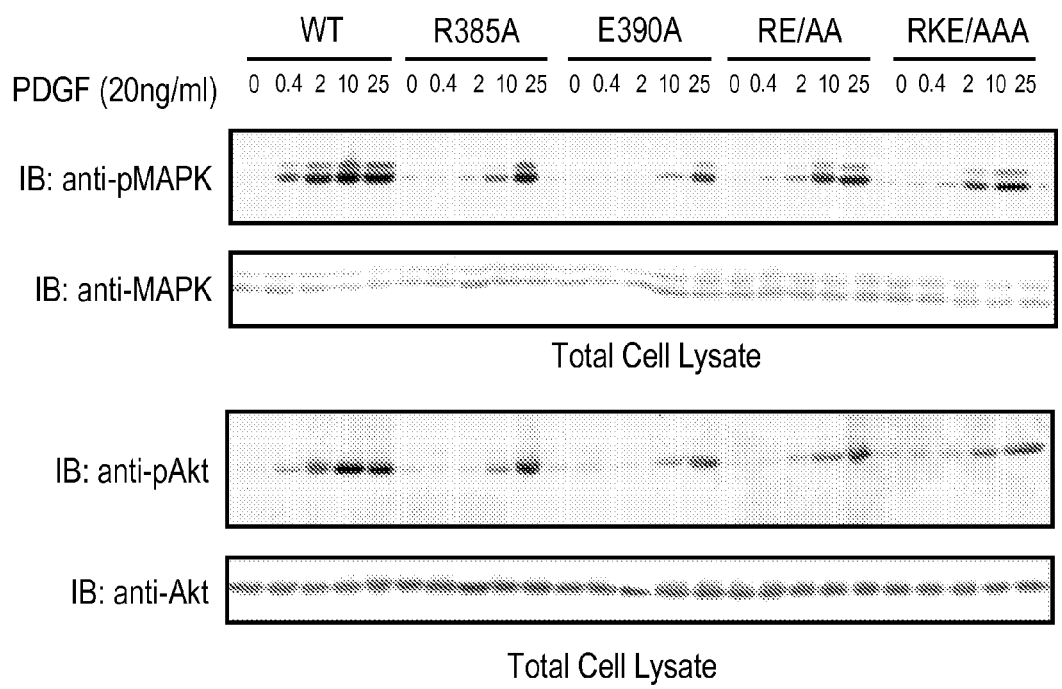

Impaired Stimulation of Cells Signaling in Cells Expressing D4 PDGF-Receptor Mutants The impact of PDGFR D4 mutations on cell signaling in response to PDGF stimulation was examined. Lysates from unstimulated or PDGF-stimulated cells expressing either WT or PDGFR D4 mutants were subjected to immunoprecipitation with anti-phospholipase Cγ (anti-PLCγ) antibodies followed by SDS-PAGE and immunoblotting with either anti-PLCγ or antipTyr antibodies. The experiment presented in FIG. 24A shows that tyrosine phosphorylation of PLCγ is severely compromised in cells expressing the R385A, E390A, RE/AA or the RKE/AAA PDGFR mutants. Impaired stimulation of additional PDGF induced cellular responses are observed in cells expressing PDGFR D4 mutants. The experiment presented in FIG. 24B shows that MAP-kinase response and Akt stimulation were strongly compromised in cells expressing the R385A, E390A, R385E390/AA or R385K387E390/AAA PDGFR mutants, as compared to similar responses induced by PDGF in MEFs expressing WT PDGFRs. Overall, approximately 10-fold higher concentrations of PDGF were required for a similar level of MAP kinase response and Akt stimulation in cells expressing the E390A, R385E390/AA (i.e., RE/AA) or R385K387E390/ AAA (i.e, RKE/AAA) PDGFR mutants.

One of the hallmarks of PDGF stimulation of cultured fibroblasts is a typical formation of membrane ruffles and circular actin ring structures on the dorsal surface of PDGF-stimulated cells. The experiment presented in FIG. 25 shows that PDGF stimulation of actin ring formation is compromised in MEFs expressing PDGFR D4 mutants. While approximately 83% of MEFs expressing WT PDGFR exhibited circular actin ring formation, only 5% of PDGFR D4 mutant cells showed similar circular actin ring formation after a 2 minute stimulation with 50 ng/ml of PDGF. Furthermore, the transient circular actin ring formation that peaks in MEFs expressing WT PDGFR after 2-5 minutes of PDGF stimulation, was weakly detected in cells expressing the R385A, E390A or the RE/AA PDGFR mutants.

Example 25

Reduced Internalization and Degradation of D4 PDGF Receptor Mutants

The effect of PDGFR D4 mutations on PDGF internalization, PDGFR degradation and PDGFR ubiquitination was also examined. MEFs expressing WT PDGFR or the PDGFR D4 mutants were treated with 5 ng/ml of $^{125}$I labeled PDGF for 90 minutes at 4° C. followed by brief washes with PBS (pH7.4) to remove the excess ligand in the medium. Prelabeled cells were warmed to 37° C. to initiate the endocytosis of ligand-receptor complex for various time intervals up to 4 hours. Cell surface-bound, intracellular and degraded $^{125}$I-PDGF in medium were collected, quantitated using a scintillation counter, and presented as percent of total cell-associated $^{125}$IPDGF radioactivity after a 90 minute incubation (t=0) at 4° C. (mean±SD). The experiment presented in FIG. 26A shows that the kinetics of internalization of $^{125}$I labeled PDGF bound to MEFs expressing WT PDGFR is much faster than the kinetics of internalization of $^{125}$I labeled PDGF bound to cells expressing the E390A, R385A or the R385E390/AA PDGFR mutants. After 30 minutes, ~75-80% of $^{125}$I-PDGF was removed from cell surface and accumulated inside the cells expressing WT receptors compared to less than 50% in cells expressing mutant receptors.

The low molecular weight degradation product of $^{125}$I-PDGF became detectable after 30 minutes. The release of degraded $^{125}$I-PDGF was much slower in E390A mutant cells than in WT cells (FIG. 26A). Reduced PDGF internalization and degradation were reflected in reduced degradation of PDGFR D4 mutants. Cells expressing WT or the R385A, E390A or R385E390/AA PDGFR mutants were first incubated for 30 minutes with cycloheximide, in order to prevent the biosynthesis of new PDGFR molecules during the degradation experiment. Lysates of unstimulated or PDGF stimulated cells were subjected to immunoprecipitation with anti-PDGFR antibodies followed by SDS-PAGE and immunoblotting with antibodies directed against a tag attached to the C-termini of WT or PDGFR D4 mutants. The experiment presented in FIG. 26B shows that the kinetics of degradation of R385A, E390A or the R385E390/AA PDGFR mutants was strongly attenuated; while half of WT PDGFRs were degraded within 1.5 hour of PDGF stimulation, the half-life for PDGFR D4 mutants was extended to approximately 4 to 6 hours. The experiment presented in FIG. 26C shows that PDGF induced stimulation of ubiquitination of the E390A PDGFR was also strongly reduced as compared to WT PDGFR under similar conditions. Taken together these experiments demonstrate that PDGFR internalization and ubiquitin-mediated PDGFR degradation are compromised by mutations in D4 of PDGFR.

Discussion of Examples 22-25

The extracellular domains of all members of type-III RTKs, including PDGFRα, PDGFRβ, CSF1R, Flt3 and Kit are composed of five Ig-like domains of which the first three function as binding site for dimeric ligand molecule which, upon binding, stimulates receptor dimerization and activation. As the molecular architecture, ligand binding characteristics and mechanism of receptor dimerization of type-III RTKs are highly conserved, the mechanism of SCF induced Kit activation revealed by the crystal structures of the complete extracellular domain of Kit before and after SCF stimulation represents a general mechanism of activation of all type-III RTKs. Moreover, phylogenic analysis of RTKs containing Ig-like domains in their extracellular domains indicates a common evolutionary origin for type-III and type-IV RTK; a family including VEGFR1 (Flt1), VEGFR2 (KDR) and VEGFR3 (Flt4). Moreover, both VEGF and PDGF belong to the same cystein-knot family; homodimeric growth factors, sharing similar topology, size and receptor binding strategy. The salient features of Kit activation revealed by the x-ray structural analysis of its extracellular domain (disclosed for the first time herein) may, therefore, also apply for ligand-induced activation of type-V RTKs.

The structural analysis of Kit has shown that a pair of salt bridges formed between Glu386 and Arg381 of two neighboring D4 domains, are responsible for mediating homotypic D4 interactions that are essential for SCF-induced Kit activation. Comparison of the amino acid sequences of type-III RTKs demonstrates that an identical sequence motif exists in the EF loop region of D4 of PDGFRα, PDGFRβ and CSF1R (FIG. 21), providing evidence that a similar salt bridge is also formed between D4 of type-III RTKs. Indeed, substitution of Arg385 or Asp390 in the D4 domain of PDGFRβ by alanines has compromised PDGF stimulation of PDGFRβ activation resulting in impairment of a variety of cellular responses that are stimulated by PDGF in cells expressing WT PDGFRβ. The mechanism of ligand induced Kit activation revealed by analysis of Kit structure applies for the activation of all type-III RTKs. A sequence motif identical to the sequence motif responsible for D4 homotypic interactions was also identified in the EF loop of the membrane proximal $7^{th}$ Ig-like domain (D7) of all three members of VEGFR family (type-IV) of RTK. Although the conserved sequence motif that is responsible for mediating homotypic D4 interactions in Kit and other type-III RTK is located in the D7 domain of type-IV RTKs, D7 of VEGFRs likely plays a role similar to D4 in mediating homotypic interactions between membrane proximal regions of type-IV RTKs. Indeed, an electron microscopic analysis of the structure of the extracellular domain of VEGFR2 has revealed a direct contact between D7 in VEGF-bound VEGFR2 dimers (Ruch, C., et al. (2007) Nat Struct Mol Biol 14, 249-250). Direct contacts between membrane proximal Ig-like domains represents a general mechanism employed by both type-III and type-IV RTKs.

Studies exploring a variety of receptor mutants or employing monoclonal antibodies that bind specifically to individual Ig-like domains of Kit (Blechman, et al. (1995) Cell 80, 103-113), PDGF-receptors (Miyazawa, K., et al. (1998) J. Biol. Chem. 273, 25495-25502) and other type-III RTKs have proposed that D4 plays a role in mediating receptor dimerization even when Kit is stimulated by monovalent SCF ligands (Lev, S., et al. (1992) J Biol Chem 267, 15970-15977). However, quantitative analyses employing microcalorimetry of SCF binding and SCF stoichiometry towards the purified extracellular domain of Kit composed of either the first three Ig-like domains (D1-D3) or all five Ig-like domains (D1-D5) have shown that D4 and D5 are dispensable for SCF stimulation of Kit dimerization. In other words these reports have shown that Kit dimerization is primarily driven by the dimeric nature of SCF binding to Kit (Lemmon, M. A., et al. (1997) J. Biol. Chem. 272, 6311-6317).

However, the work presented herein demonstrates that, rather than playing a role in receptor dimerization, the homotypic D4 (and also homotypic D5) interactions between neighboring receptors are required for precise positioning of the membrane proximal regions of two receptors at a distance and orientation that enable interactions between their cytoplasmic domains resulting in tyrosine kinase activation. Therefore, rather than interfering with receptor dimerization, the moieties, e.g., monoclonal antibodies, of the invention exert their inhibitory effect on receptor activation by preventing critical homotypic interactions between membrane proximal regions of type-III RTK that are essential for positioning the cytoplasmic domain at a distance and orientation essential for tyrosine kinase activation.

The experiments presented herein demonstrate that dimerization of PDGFRβ, Kit and other type-III RTKs is entirely driven by ligand binding and that the sole role of ligand binding is to crosslink two receptor molecules in order to increase their local concentration in the cell membrane. The two salt bridges (with interface of a buried surface area of 360 Å$^2$) responsible for mediating homotypic D4 interactions are too weak to support receptor interactions without the support of ligand mediated receptor dimerization which in the case of Kit is mediated by a variety of strong interactions with a total buried surface area of 2060 Å$^2$ for each SCF protomer. The apparent concentration of a receptor in the cell membrane of an unstimulated cell expressing 20,000 receptors per cell has been estimated to be approximately 1-3 µM (Klein, P., et al. (2004) Proc Natl Acad Sci USA 101, 929-934; Chandrasekhar, S. (1943) Reviews of Modern Physics 15, 1). Upon binding a dimeric ligand such as SCF, two occupied receptors are held together at a distance of 75 Å. Under these conditions, the apparent receptor concentration in the cell membrane calculated using the average distance to nearest neighbor approach is increased by more than two orders of magnitude to 4–6×10$^{-4}$ M. This calculation shows that even weak interactions with a dissociation constant in the range of 10$^4$-10$^{-5}$M, such as those mediated by the two salt bridges, could mediate association and direct contacts between membrane proximal regions of two neighboring receptors. The high local concentration in the cell membrane together with the flexibility of the joints connecting D4 and D5 to the rest of the receptor molecule enable movement and formation of homotypic D4 as well as homotypic D5 contacts that position the membrane proximal region of the receptor at a precise orientation and distance (15 Å in the case of Kit) that enable interactions between neighboring cytoplasmic domains, tyrosine autophosphorylation, and stimulation of tyrosine kinase activity.

Finally, applying a chemical crosslinking agent to covalently crosslink WT or mutant receptors on unstimulated or PDGF-stimulated cells it has been demonstrated herein that an E390A PDGFRβ mutant undergoes PDGF-induced dimerization similar to PDGF-induced dimerization of WT receptors. However, by contrast to WT PDGFRβ that is expressed on the cell surface of PDGF-stimulated cells in the form of activated dimers, the E390A mutant is expressed on the surface of PDGF-stimulated cells in the form of inactive dimers. This experiment demonstrates that homotypic D4-D4 interactions are dispensable for PDGFRβ dimerization and that PDGFRβ dimerization is necessary but not sufficient for receptor activation.

Example 26

Disruption of the D4-D4 Interface Overcomes Oncogenic Kit Activation

Murine 3T3 cells stably expressing wild type (WT) KIT, an oncogenic KIT mutant in which Ala502 and Tyr503 of D5 were duplicated (D5-Repeat mutant), or a KIT mutant in which Ala502 and Tyr503 of D5 (D5-Repeat) were duplicated together with an additional point mutation in which Glu386 of D4 was substituted by an Ala residue (D5-Repeat/E386A mutant) were stimulated with 1, 5 or 10 ng/ml of SCF for 5 minutes at 37° C.

Lysates of unstimulated or SCF stimulated cells were subjected to immunoprecipitation with anti-KIT antibodies followed by SDS-PAGE and immunoblotting with either anti-KIT or anti-phosphotyrosine (anti-pY) antibodies.

The experiment presented in FIG. 27 demonstrates that SCF stimulation of wild type KIT leads to enhancement of KIT activation revealed by enhanced tyrosine autophosphorylation of KIT in response to SCF stimulation. The experiment also shows that an oncogenic D5-Repeat mutant of KIT is constitutively tyrosine autophosphorylated (i.e., it is activated in the absence of SCF stimulation). By contrast, the D5-Repeat/E386A mutant which carries an additional point mutation in D4 (which was shown to impair SCF activation of KIT in a background of normal receptor protein) blocks constitutive tyrosine autophosphorylation of KIT mediated by the oncogenic D5-repeat mutation.

This experiment provides a genetic validation for the importance of D4-D4 homotypic interactions in mediating KIT activation by an oncogenic mutation in D5 and presumably by other oncogenic mutations in different parts of the-KIT molecule. Furthermore, this experiment provides further validation to the notion that disruption of the D4-D4 interface by pharmacological intervention by a moiety of the invention, e.g., an antibody, or antigen binding portion thereof, a small molecule or a peptidic molecule, will block the activity of oncogenic mutations in D5, oncogenic mutations in other parts of KIT molecule and in oncogenic type-III and type-IV RTKs.

Example 27

Antibodies Directed Against a Synthetic Peptide Corresponding to the Signature Motif of KIT, Involved in Mediating D4 Homotypic Interactions, Recognize Intact KIT Protein In this example, rabbit polyclonal antibodies were raised against three different KIT antigens:
1. The full-length extracellular domain of human KIT (amino acids 1-510).
2. KIT Ig-like domain 4 (D4) composed of amino acids 308-411 (KIT-D4)
3. A 17-mer peptide corresponding to amino acids 375-391 including the signature motif of KIT D4 (SELHLTRLKGTEGGTYT) (SEQ ID NO: 159) conjugated to KLH.

Rabbits were immunized in two week intervals with each of the three antigens, and test bleeds were analyzed. The results presented are from a serum sample that was collected after the third immunization.

Lysates of 3T3 cells expressing wild type human KIT were incubated with 30 µls of serum containing one of the following antibodies: 1. Anti-KIT, directed against the full-length KIT extracellular domain. 2. Anti-D4, directed against KIT-D4 and 3. Anti-peptide, directed against a peptide corresponding to amino acids 375-391 of KIT D4. Lysates of 3T3 cells expressing wild type KIT, with each of the antibodies, were incubated together with protein A Sepharose for 2 hours at 4° C. and then washed three times with washing buffer containing 20 mM Hepes, 150 mM NaCl, 0.1% TritonX-100 and 5% glycerol. Immunoprecipitates were separated on SDS-PAGE, transferred to nitrocellulose and immunoblotted with each of the antibodies as described in FIG. 28. The data presented in FIG. 28 show that each of the antibodies, including the anti-peptide antibodies directed against the homotypic interaction region of D4 that is essential for positioning KIT dimers in its activated configuration, recognize intact native KIT in the immunoprecipitation and the immunoblotting steps of the experiment.

Remarkably, this experiment shows that the anti-peptide antibodies recognize wild type KIT as efficiently as antibodies directed against the intact extracellular or the D4 regions of KIT.

Equivalents

Those skilled in the art will recognize, or be able to ascertain using no more that routine experimentation, many equivalents to the specific embodiments of the invention described herein. Such equivalents are intended to be encompassed by the following claims.

We claim:

1. An antibody, or antigen-binding portion thereof, that binds to the human KIT receptor (SEQ ID NO:92), wherein said antibody, or antigen-binding portion thereof, is a humanized antibody or antigen-binding portion thereof, a human antibody or antigen-binding portion thereof, or a chimeric antibody or antigen-binding portion thereof, and wherein said antibody, or antigen-binding portion thereof, binds to a sequence consisting of amino acid residues 375-391 of the human KIT receptor (SEQ ID NO:92).

2. The An antibody, or antigen-binding portion thereof, that binds to the human KIT receptor (SEQ ID NO:92), wherein the antibody, or antigen-binding portion thereof, is a humanized antibody or antigen-binding portion thereof, a human antibody or antigen-binding portion thereof, or a chimeric antibody or antigen-binding portion thereof, and wherein the antibody, or antigen-binding portion thereof, binds to a sequence consisting of $LX_1RX_2X_3X_4X_5X_6X_7G$ (SEQ ID NO:158) wherein L is Leucine, R is Arginine, G is Glycine; $X_1$ is Threonine; X2 is Leucine; $X_3$ is Lysine; $X_4$ is Glycine; $X_5$ is Threonine; $X_6$ is Glutamic Acid; and $X_7$ is Glycine.

3. The antibody, or antigen-binding portion thereof, of claim 1 or claim 2, wherein said antibody, or antigen-binding portion thereof, comprises a heavy chain constant region selected from the group consisting of IgG1, IgG2, IgG3, IgG4, IgM, IgA and IgE constant regions.

4. The antibody, or antigen-binding portion thereof, of claim 3, wherein the antibody heavy chain constant region is IgG1.

5. The antibody, or antigen-binding portion thereof, of claim 1 or claim 2, wherein said antibody, or antigen-binding portion thereof, is selected from the group consisting of a Fab fragment, a F(ab')$_2$ fragment, a single chain Fv fragment, an SMIP, an affibody, an avimer, a nanobody, and a single domain antibody.

6. The antibody, or antigen-binding portion thereof, of claim 1 or claim 2, wherein said antibody, or antigen-binding portion thereof, binds to the human KIT receptor (SEQ ID NO:92) with a KD selected from the group consisting of $1 \times 10^{-7}$ M or less, $5 \times 10^{-8}$ M or less, $1 \times 10^{-8}$ M or less, and $5 \times 10^{-9}$ M or less.

7. The antibody, or antigen-binding portion thereof, of claim 1 or claim 2, wherein the antibody, or antigen-binding portion thereof, binds to all of the amino acid residues recited therein.

8. The antibody, or antigen-binding portion thereof, of claim 1 or claim 2, wherein the antibody, or antigen-binding portion thereof, is a humanized antibody, or antigen-binding portion thereof.

9. A pharmaceutical composition comprising the antibody, or antigen-binding portion thereof, of claim 1 or claim 2 and a pharmaceutically acceptable carrier.

* * * * *

UNITED STATES PATENT AND TRADEMARK OFFICE
CERTIFICATE OF CORRECTION

PATENT NO. : 9,273,134 B2  Page 1 of 1
APPLICATION NO. : 12/602235
DATED : March 1, 2016
INVENTOR(S) : Joseph Schlessinger et al.

It is certified that error appears in the above-identified patent and that said Letters Patent is hereby corrected as shown below:

In the Claims:

In claim 2 (column 215, line 11), delete "The An Antibody" and replace with --An antibody--.

Signed and Sealed this
Nineteenth Day of July, 2016

Michelle K. Lee
*Director of the United States Patent and Trademark Office*